(12) United States Patent
Tang et al.

(10) Patent No.: US 7,202,265 B2
(45) Date of Patent: Apr. 10, 2007

(54) INDOLINONE COMBINATORIAL LIBRARIES AND RELATED PRODUCTS AND METHODS FOR THE TREATMENT OF DISEASE

(75) Inventors: Peng Cho Tang, Moraga, CA (US); Connie Li Sun, Foster City, CA (US); Gerald McMahon, San Francisco, CA (US); Klaus Peter Hirth, San Francisco, CA (US); Laura Kay Shawver, San Francisco, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 10/784,917

(22) Filed: Feb. 24, 2004

(65) Prior Publication Data

US 2005/0197382 A1    Sep. 8, 2005

Related U.S. Application Data

(60) Division of application No. 10/076,621, filed on Feb. 19, 2002, now abandoned, which is a continuation of application No. 09/617,529, filed on Jul. 13, 2000, now abandoned, which is a division of application No. 08/915,366, filed on Aug. 20, 1997, now Pat. No. 6,147,106.

(51) Int. Cl.
*A61K 31/404* (2006.01)
*C07D 403/06* (2006.01)

(52) U.S. Cl. ...................................... 514/414; 548/468
(58) Field of Classification Search .............. 548/468; 514/414
See application file for complete search history.

(56) References Cited

U.S. PATENT DOCUMENTS

| | | |
|---|---|---|
| 2,872,372 A | 2/1959 | Hull |
| 2,968,557 A | 1/1961 | Burgardt et al. |
| 4,002,749 A | 1/1977 | Rovnyak |
| 4,053,613 A | 10/1977 | Rovnyak et al. |
| 4,376,110 A | 3/1983 | David et al. |
| 4,642,309 A | 2/1987 | Michel et al. |
| 4,826,847 A | 5/1989 | Michel et al. |
| 4,853,403 A | 8/1989 | Shiraishi et al. |
| 4,868,304 A | 9/1989 | Larock et al. |
| 4,966,849 A | 10/1990 | Vallee et al. |
| 4,971,996 A | 11/1990 | Shiraishi et al. |
| 5,051,417 A | 9/1991 | Nadler et al. |
| 5,057,538 A | 10/1991 | Shiraishi et al. |
| 5,089,516 A | 2/1992 | Shiraishi et al. |
| 5,124,347 A | 6/1992 | Connor et al. |
| 5,202,341 A | 4/1993 | Shiraishi et al. |
| 5,206,261 A | 4/1993 | Kawaguchi et al. |
| 5,217,999 A | 6/1993 | Levitzki et al. |
| 5,302,606 A | 4/1994 | Spada et al. |
| 5,322,950 A | 6/1994 | Sircar et al. |
| 5,330,992 A | 7/1994 | Eissenstat et al. |
| 5,374,652 A | 12/1994 | Buzzetti et al. |
| 5,382,593 A | 1/1995 | Le Baut |
| 5,397,787 A | 3/1995 | Buzzetti et al. |
| 5,409,949 A | 4/1995 | Buzzetti et al. |
| 5,463,052 A | 10/1995 | Haga et al. |
| 5,786,488 A | 7/1998 | Tang et al. |
| 5,792,783 A | 8/1998 | Tang |
| 5,834,504 A | 11/1998 | Tang et al. |
| 5,840,745 A | 11/1998 | Buzzetti et al. |
| 5,849,710 A | 12/1998 | Battistini et al. |
| 5,880,141 A | 3/1999 | Tang et al. |
| 5,883,113 A | 3/1999 | Tang et al. |
| 5,883,116 A | 3/1999 | Tang et al. |
| 5,886,020 A | 3/1999 | Tang et al. |
| RE36,256 E | 7/1999 | Spada et al. |

(Continued)

FOREIGN PATENT DOCUMENTS

AU    286870    5/1967

(Continued)

OTHER PUBLICATIONS

Abramovitch and Hey, "Internuclear cyclisation. Part VIII. Naphth[3:2:1-cd]oxindoles," *J. Chem. Soc.* pp. 1697-1703 (1954).

(Continued)

*Primary Examiner*—Laura L. Stockton
(74) *Attorney, Agent, or Firm*—Foley & Lardner LLP

(57) ABSTRACT

The present invention relates to organic molecules capable of modulating, regulating and/or inhibiting protein kinase signal transduction. Such compounds are useful for the treatment of diseases related to unregulated protein kinase signal transduction, including cell proliferative diseases such as cancer, atherosclerosis, arthritis and restenosis and metabolic diseases such as diabetes. The present invention features indolinone compounds that potently inhibit protein kinases and related products and methods. Inhibitors specific to the FLK protein kinase can be obtained by adding chemical substituents to the 3-[(indole-3-yl)methylene]-2-indolinone, in particular at the 1' position of the indole ring. Indolinone compounds that specifically inhibit the FLK and platelet derived growth factor protein kinases can harbor a tetrahydroindole or cyclopentano-b-pyrrol moiety. Indolinone compounds that are modified with substituents, particularly at the 5 position of the oxindole ring, can effectively activate protein kinases. This invention also features novel hydrosoluble indolinone compounds that are tyrosine kinase inhibitors and related products and methods.

6 Claims, 41 Drawing Sheets

U.S. PATENT DOCUMENTS

| | | | |
|---|---|---|---|
| 6,130,238 A | 10/2000 | Tang et al. | |
| 6,147,106 A | 11/2000 | Tang et al. | |
| 6,486,185 B1 * | 11/2002 | McMahon et al. | 514/359 |
| 6,531,502 B1 * | 3/2003 | Tang et al. | 514/414 |
| 6,906,093 B2 * | 6/2005 | Tang et al. | 514/414 |
| 2004/0067531 A1 * | 4/2004 | Tang et al. | 435/7.1 |

FOREIGN PATENT DOCUMENTS

| | | |
|---|---|---|
| CA | 2012634 A1 | 9/1991 |
| DE | 878539 | 6/1953 |
| DE | 2159360 A | 6/1973 |
| DE | 2159361 A | 6/1973 |
| DE | 2159362 | 6/1973 |
| DE | 2159363 A | 6/1973 |
| DE | 2321656 A | 11/1973 |
| DE | 3426419 A | 1/1986 |
| EP | 0 252 713 B1 | 1/1988 |
| EP | 0 351 213 A2 | 1/1990 |
| EP | 0 525 472 A2 | 2/1993 |
| EP | 0 566 226 B1 | 10/1993 |
| EP | 0 580 502 B1 | 1/1994 |
| EP | 0 626 377 B1 | 11/1994 |
| EP | 0 632 102 A1 | 1/1995 |
| EP | 0 662 473 A1 | 7/1995 |
| EP | 0 788 890 A1 | 8/1997 |
| FR | 1.398.224 | 5/1965 |
| FR | 2.689.397 A1 | 10/1993 |
| GB | 809691 | 3/1959 |
| GB | 835473 | 5/1960 |
| HU | 65452 | 6/1994 |
| JP | 62-29570 A | 2/1987 |
| JP | 62-39564 A | 2/1987 |
| JP | 63-141955 A | 6/1988 |
| JP | 5-58894 A | 3/1993 |
| WO | WO 88/07035 A1 | 9/1988 |
| WO | WO 91/13055 A2 | 9/1991 |
| WO | WO 91/15495 A1 | 10/1991 |
| WO | WO 92/03736 A1 | 3/1992 |
| WO | WO 92/07830 A2 | 5/1992 |
| WO | WO 92/20642 A1 | 11/1992 |
| WO | WO 92/21660 A1 | 12/1992 |
| WO | WO 93/01182 A1 | 1/1993 |
| WO | WO 93/23040 A1 | 11/1993 |
| WO | WO 94/03427 A1 | 2/1994 |
| WO | WO 94/10202 A1 | 5/1994 |
| WO | WO 94/14808 A1 | 7/1994 |
| WO | WO 95/01349 A1 | 1/1995 |
| WO | WO 95/14667 A1 | 6/1995 |
| WO | WO 95/17181 A1 | 6/1995 |
| WO | WO 95/24190 A2 | 9/1995 |
| WO | WO 96/00226 A1 | 1/1996 |
| WO | WO 96/16964 A1 | 6/1996 |
| WO | WO 96/22976 A1 | 8/1996 |
| WO | WO 96/32380 A1 | 10/1996 |
| WO | WO 96/40116 A1 | 12/1996 |
| WO | WO 97/25986 A1 | 7/1997 |
| WO | WO 97/36867 A1 | 10/1997 |
| WO | WO 98/07695 A1 | 2/1998 |
| WO | WO 98/07835 A2 | 2/1998 |
| WO | WO 98/45708 A1 | 10/1998 |
| WO | WO 98/50356 A1 | 11/1998 |
| WO | WO 98/56376 A1 | 12/1998 |
| WO | WO 99/10325 A1 | 3/1999 |

OTHER PUBLICATIONS

Abramovitch et al., "A Novel Synthesis of a Cyclic Hydroxamic Acid Involving a Molecular Rearrangement," *Chemistry and Industry* 44:1871 (1967).

Abramovitch, Beilstein Reg. No. 236050, *J. Chem. Soc.*, pp. 1697, 1700 (1954).

Akbasak and Suner-Akbasak et al., "Oncogenes: cause or consequence in the development of glial tumors," *J. Neurol. Sci.* 111:119-133 (1992).

Andreani et al., "In Vivo Cardiotonic Activity of Pyridylmethylene-2-indolinones," *Arzneimittel-Forschung Drug Research* 48 (II): 727-729(1998).

Andreani et al., "Potential antitumor agents. 25[1]. Synthesis and cytotoxic activity of 3-(2-chloro-3-indolylmethlene) 1,3-Dyhydroindol-2-ones," *AntiCancer Research* 16:3585-3588 (1996).

Andreani et al., "Synthesis and cardiotonic activity of 2-indolinones," *Chemical Abstracts*, vol. 113, abstract No. 78106 (1990).

Andreani et al., "Synthesis and cardiotonic activity of 2-indolinones bearing pyridyl groups," *Eur. J. Med. Chem.* 28:653-657 (1993).

Andreani et al., "Synthesis and cardiotonic activity of pyridylmethylene-2-indolinones," *Eur. J. Med. Chem.* 27:167-170 (1992).

Andreani et al., "Synthesis of lacatams with potential cardiotonic activity," *Eur. J. Med. Chem.* 28:825-829 (1993).

Arteaga et al., "Blockade of the type I somatomedin receptor inhibits growth of human breast cancer cells in athymic mice," *J. Clin. Invest.* 84:1418-1423 (1989).

Arvidsson et al., "Tyr-716 in the Platelet-Derived Growth Factor β-Receptor Kinase Insert is Involved in GRB2 Binding and Ras Activation," *Molecular and Cellular Biology* 14:6715-6726 (1994).

Autrey and Tahk, "The Synthesis and Sterochemistry of Some Isatylideneacetic Acid Derivatives," *Tetrahedron* 23:901-917 (1967).

Bahner et al., "Benzylideneindenes with Oxygen Attached to the Indene Ring," *J. Med. Chem.* 12:721-722 (1969).

Bamfield et al., "Diels-Alder Reactions of Oxindolylideneacetone," *J. Chem. Soc. (C)* pp. 1028-1030 (1966).

Baserga, "The insulin-like growth factor I receptor: a key to tumor growth?" *Cancer Res.* 55:249-252 (1995).

Beilstein Reg. No. 235647 (1997).

Beilstein Reg. No. 252929 (1923).

Blake and Jaques, "Anistropic Effects in alpha-substituted methoxystilbenes," *J. Chem. Soc. Perkin II* pp. 1660-1663 (1973).

Blake and Jacques, "Anistropic Effects in alpha-substituted methoxystilbenes," *Chemical Abstracts*, vol. 80, abstract No. 266692 (1974).

Bolen, "Nonreceptor tyrosine protein kinases," *Oncogene* 8:2025-2031 (1993).

Bolen et al., "The Src family of tyrosine protein kinases in hemopoietic signal transduction," *FASEB J.* 6:3403-3409 (1992).

Bonner et al., "Structure and Biological Activity of Human Homologs of the *raf/mil* Oncogene," *Molecular and Cellular Biology* 5:1400-1407 (1986).

Buzzetti et al., "Cinnamamide Analogs as Inhibitors of Protein Tyrosine Kinases," II *Farmaco* 48(5):615-636 (1993).

Cance et al., "Novel Protein Kinases Expressed in Human Breast Cancer," *Int. J. Cancer* 54:571-577 (1993).

Canoira and Rodriguez, "Synthesis of Oxindole Derivatives from N-Alkenyl-o-Chloroanilides with Zero-Valent Nickel Complex," *J. Heterocyclic Chem.* 22:1511-1518 (1985).

Carpenedo et al., "Identification and Measurement of Oxindole (2-Indolinone) in the Mammalian Brain and Other Rat Organs," *Analytical Biochemistry* 244:74-79 (1997).

Chao, "Growth Factor Signaling: Where is the Specificity?" *Cell* 68:995-997 (1992).

Chatten et al., "Substituted Oxindoles. Part VI. Polarographic Reduction of Substituted trans-3-Benzylideneindol-2(3H)-ones," *J. Chem. Soc. Perkin II* pp. 469-473 (1973).

Chen et al., "Effects of 3,3-Dipyridylmethyl-1-Phenyl-2-Indolinone on γ-Aminobutyric Acid Elicited Chloride Current of Snail Central Neuron," *Chinese Journal of Physiology* 40(3):149-156 (1997).

Claesson-Welsh, "Signal Transduction by the PDGF Receptors," *Progress in Growth Factor Research* 5:37-54 (1994).

Coda et al., "(Z)- and (E)-Arylidene-1,3-dihydroindol-2-ones: Configuration, Conformation and Infrared Carbonyl Stretching Frequencies," *J. Chem. Soc. Perkin II* pp. 615-619 (1984).

Coda et al., "3-(4-methylbenzilidene)-1-,3-dihydroindol-2-one," *J. Chem. Soc. Perkin II*, Database Crossfire, Beilstein Ref. No. 6-21, 4: 615-620 (1984).

Coppola et al., "A Functional Insulin-Like Growth Factor I Receptor is Required for the Mitogenic and Transforming Activities of the Epidermal Growth Factor Receptor," *Molecular and Cellular Biology* 14:4588-4595 (1994).

Daisley, "Thin-layer chromatographic separation of some substituted 3-benzylidine-indol-2(3H)-ones," *J. Chromatography* 100:240-242 (1974).

Damiani et al., "Inhibition of Cooper-Mediated Low Density Lipoprotein Peroxidation by Quinoline and Indolinone Nitroxide Radicals," *Biochemical Pharmacology* 48(6):1155-1161 (1994).

Dati et al., "Inhibition of c-erbB-2 oncogene expression by estrogens in human breast cancer cells," *Oncogene* 5:1001-1006 (1990).

Davis et al., "Synthesis and Microbiological Properties of 3-Amino-1-Hydroxy-2-Indolinone and Related Compounds," *Journal of Medicinal Chemistry* 16(9):1043-1045 (1973).

Decker and Lohmann-Matthes, "A quick and simple method for the quantitation of lactate dehydrogenase release in measurements of cellular cytotoxicity and tumor necrosis factor (TNF) activity," *J. Immunol. Methods* 15:61-69 (1988).

De Vries et al., "The *fms*-Like Tyrosine Kinase, a Receptor for Vascular Endothelial Growth Factor," *Science* 255:989-991 (1992).

Dickson et al., "Tyrosine kinase receptor-nuclear protooncogene interactions in breast cancer," *Cancer Treatment Res.* 61:249-273 (1992).

Elliot, "1-methyl-2-(3-oxindolidenmethyl)-pyridinium," Database Crossfire, Beilstein Ref. No. 5-24, Mar. 19, 1991, XP 002049951.

Elliott and Rivers, "Reduction of some oxindolylidene derivatives to 3-substituted oxindoles by sodium borohydride," *J. Organic Chem.* 29:2438-2440 (1964).

Fantl et al., "Distinct Phosphotyrosines on a Growth Factor Receptor Bind to Specific Molecules That Mediate Different Signaling Pathways," *Cell* 69:413-423 (1992).

Fendly et al., "Characterization of Murine Monoclonal Antibodies Reactive to Either the Human or Epidermal Growth Factor Receptor or HER2/*neu* Gene Product" *Cancer Research* 50:1550-1558 (1990).

Ferrara and Henzel, "Pituitary Follicular Cells Secrete a Novel Heparin-Binding Growth Factor Specific for Vascular Endothelial Cells," *Biochemical and Biophysical Research Communications* 161:851-858 (1989).

Fingl and Woodbury, Chapter 1, pp. 1-46 in *The Pharmacological Basis of Therapeutic*(5$^{th}$ edition), eds. Goodman et al., MacMillan Publishing Co., Inc., New York (1975).

Floege et al., "Factors involved in the regulation of mesangial cell proliferation *in vitro in vivo*," *Kidney International* 43S:47-54 (1993).

Floege et al., "Heparin suppresses mesangial cell proliferation and matrix expansion in experimental mesangioproliferative glomerulonephritis," *Kidney International* 43:369-380 (1993).

Folkman and Shing, "Angiogenesis," *J. Biol. Chem.* 267:10931-10934 (1992).

Folkman, "What is the Evidence that Tumors are Angiogenesis Dependent?" *Journal of the National Cancer Institute* 82:4-6 (1990).

Folkman, "Ch. 24. Angiogenesis, "*Congress of Thrombosis and Haemostasis* (Verstraete et al., eds.) Leuven University Press, Leuven pp. 583-596 (1987).

Folkman, "Tumor Angiogenesis: Therapeutic Implications" *New England J. Medicine* 285:1182-1186 (1971).

Gazit et al., "Tyrphostins. 2. Heterocyclic and alpha-substituted benzylidenemalononitrile tyrphostins as potent inhibitors of EGF receptor and ErbB2-neu tyrosine-kinases," *J. Med. Chem.* 34(6):1896-1907 (1991).

Gennaro (editor), *Remington's Pharmaceutical Sciences* (1990)(Table of Contents Only).

Goldring and Goldring, "Cytokines and cell growth control," *Critical Reviews in Eukaryotic Gene Expression* 1:301-326 (1991).

Gottardis et al., "Estradiol-Stimulated Growth of MCF-7 Tumors Implanted in Athymic Mice: A Model to Study the Tumoristatic Action of Tamoxifen," *J. Steroid Biochem.* 30(1-6):311-314 (1988).

Graziani et al., "Hepatocyte Growth Factor/Scatter Factor Stimulates the Ras-Guanine Nucleotide Exchanger," *The Journal of Biological Chemistry* 268(13):9165-9168 (1993).

Hewgill and Stewart, "Phenanthrene-4,5-quinones: a Synthesis of Morphenol," *J. Chem. Soc. Perkin Trans. I* pp. 1305-1311 (1988).

Hodges et al., "Chemical and biological properties of some oxindolidyl-3-methines," *Canadian J. Chemistry* 46:2189-2194 (1968).

Honegger et al., "Point Mutation at the ATP Binding Site of EGF Receptor Abolishes Protein-Tyrosine Kinase Activity and Alters Cellular Routing," *Cell* 5:199-209 (1987).

Houck et al., "Dual Regulation of Vascular Endothelial Growth Factor Bioavailability Genetic and Proteolytic Mechanisms," *J. Biol. Chem.* 267:26031-26037 (1992).

Howard et al., U.S. Appl. No. 60/015,134, filed Mar. 29, 1996 for "Lactam Derivatives".

Howard et al., "Synthesis and aldose reductase inhibitory activity of substituted 2(1*H*)-benzimidazolone-and oxindole-1-acetic acids," *Eur. J. Med. Chem.* 27:779-789 (1992).

Hu et al., "Interaction of Phosphatidylinositol 3-Kinase-Associated p85 with Epidermal Growth Factor and Platelet-Derived Growth Factor Receptors," *Molecular and Cellular Biology* 12(3):981-990 (1992).

Ijaz et al., "The Conversion of o,β-Dinitrostyrenes into Indoles and the Preparation of Oxindole Quinones," *J. Chem. Res. (S)* pp. 116 (1990).

Ijaz et al., "The Conversion of o,β-Dinitrostyrenes into Indoles and the Preparation of Oxindole Quinones," *Chemical Abstracts*, vol. 113, abstract No. 93739 (1990).

Jellinek et al., "Inhibition of Receptor Binding by High-Affinity RNA Ligands to Vascular Endothelial Growth Factor," *Biochemistry* 33:10450-10456 (1994).

Kashishian and Cooper, "Phosphorylation Sites at the C-terminus of the Platelet-Derived Growth Factor Receptor Bind Phospholipase Cγ1," *Molecular Biology of the Cell* 4:49-57 (1993).

Kashishian et al., "Phosphorylation Sites in the PDGF receptor with Different Specificities for Binding GAP and P13 Kinase *in vivo*," *The EMBO Journal* 11(4):1373-1382 (1992).

Kato et al., "Simultaneous Determination of Amfenac Sodium and its Metabolite (7-Benzoyl-2-Oxindole) in Human Plasma by High-Performance Liquid Chromatography," *Journal of Chromatography* 616:67-71 (1993).

Katritzky et al., "Color and Constitution, Part 8[1]. Some Novel Dyestuffs Containing Indoxyl Residues," *J. Heterocyclic Chem.* 25:1287-1292 (1988).

Kazlauskas et al., "The 64-kDa Protein That Associates with the Platelet-Derived Growth Factor Receptor β Subunit via Tyr-1009 Is The SH2-Containing Phosphotyrosine Phosphatase Syp," *Proc. Natl. Acad. Sci. USA* 90:6939-6942 (1993).

Kendall and Thomas, "Inhibition of vascular endothelial cell growth factor activity by an endogenously encoded soluble receptor," *Proc. Natl. Acad. Sci. USA* 90:10705-10709 (1993).

Khalil and Abdel-Rahman, "Synthesis of New Mero- and Asymmetrical Pyrazolo-Monomethine Cyanine Dyes," *J. Indian Chem. Soc.*, 54:904-907 (1977).

Kim et al., "Inhibition of Vascular endothelial growth factor-induced angiogenesis suppresses tumor growth *in vivo*," *Nature* 362:841-844 (1993).

Kinsella et al., "Protein Kinase C Regulates Endothelial Cell Tube Formation on Basement Membrane Matrix, Matrigel," *Exp. Cell Research* 199:52-62 (1992).

Klagsburn and Soker, "VEGF/VPF: the angiogenesis factor found?" *Current Biology* 3:699-702 (1993).

Kobayashi et al., "Anti-tumor Activity of Indole Derivatives," *Yakugaku Zasshi* 97(9):1033-1039 (1977).

Koch et al., "SH2 and SH3 Domains: Elements that Control Interactions of Cytoplasmic Signalling Proteins," *Science* 252:668-674 (1991).

Köhler and Milstein, "Continuous cultures of fused cells secreting antibody of predefined specificity," *Nature* 256:495-497 (1975).

Komada et al., "The cell dissociation and motility triggered by scatter factor/hepatocyte growth factor are mediated through the cytoplasmic domain of the c-Met receptor," *Oncogene* 8:2381-2390 (1993).

Korc et al., "Overexpression of the epidermal growth factor receptor in human pancreatic cancer is associated with concomitant increases in the levels of epidermal growth factor and transforming growth factor alpha," *J. Clin. Invest.* 90:1352-1360 (1992).

Korzeniewski and Callewaert, "An Enzyme-Release Assay for Natural Cytotoxicity[1]," *J. Immunol. Methods* 64:313-320 (1983).

Kovac and Stetinova, "Furan derivatives LXXX. Synthesis and properties of substituted furfurylidenoxindoles," *Chem. rvesu* 30:484-492 (1976).

Krueger and Saito, "A human transmembrane protein-tyrosine-phosphatase, PTP, is expressed in brain and has an N-terminal receptor domain homologous to carbonic anhydrases," *Proc. Natl. Acad. Sci. USA* 89:7417-7421 (1992).

Kumbae et al., "Amplification of α-platelet-derived growth factor receptor gene lacking an exon coding for a portion of the extracellular region in a primary brain tumor of glial origin," *Oncogene* 7:627-633 (1992).

Larock and Babu, "Synthesis of Nitrogen Heterocycles via Palladium-catalyzed Intramolecular Cyclization," *Tetrahedron Letters* 28:5291-5294 (1987).

Lee and Donoghue, "Intracellular retention of membrane-anchored v-*sis* protein abrogates autocrine signal transduction," *Journal of Cell Biology* 118:1057-1070 (1992).

Levitzki and Gazit, "Tyrosine kinase inhibition: An approach to drug development," *Science* 267:1782-1788 (1995).

Maas et al., "Viral resistance to the thiazolo-iso-indolinoes, a new class of nonnucleoside inhibitors of human immunodeficiency virus type 1 reverse transcriptase," *Antimicrobial Agents and Chemotherapy* 37(12):2612-2617 (1993).

Macauley et al., "Autocrine function for insulin-like growth factor I in human small cell lung cancer cell lines and fresh tumor cells," *Cancer Research* 50:2511-2517 (1990).

Mariani et al., "Inhibition of angiogenesis by FCE 26806, a potent tyrosine kinase inhibitor," *Experimental Therapeutics—Proceedings of the American Association for Cancer Research* 35:381 at abstract No. 2268 (1994).

Martin-Leòn et al., "On the Cyclization to the Elusive Amino-*4H*-pyran Ring," *Liebigs Ann. Chem.* pp. 101-104 (1990).

Millauer et al., "High Affinity VEGF Binding and Developmental Expression Suggest Flk-1 as a Major Regulator of Vasculorgenesis and Angiogenesis," *Cell* 72:835-846 (1993).

Mirand et al., "A Synthetic Entry in the *Aristotelia* Alkaloids," *J. Org. Chem.* 47:4169-4170 (1982).

Mohammad et al., "Structures of the tyrosine kinase domain of fibroblast growth factor receptor in complex with inhibitors," *Science* 276:955-960 (1997).

Moreto et al., "3,3-Bis-(4-Hydroxyphenyl)-7-Methyl-2-Indolinone (BHMI), the Active Metabolite of the Laxative Sulisatin," *Arzneimittel-Forschung Drug Research* 29(II):1561-1564 (1979).

Moreto et al., "Study of the Laxative Properties of the Disodium Salt of the Sulfuric Diester of 3,3 Bis-(4-Hydroxyphenyl)-7-Methyl-2-Indolinone (Dan-603) in the Rat," *European Journal of Pharmacology* 36:221-226 (1976).

Morrison et al., "Signal transduction from membrane to cytoplasm: Growth factors and membrane-bound oncogene products increase Raf-1 phosphorylation and associated protein kinase activity," *Proc. Natl. Acad. Sci. USA* 85:8855-8859 (1988).

Mosmann, "Rapid Colorimetric Assay for Cellular Growth and Survival: Application to Proliferation and Cytotoxicity Assays," *J. Immunol. Methods* 65:55-63 (1983).

Neber and Rocker, "Ueber die einwirkung vbon benzaldehyden auf die freie o-aminophenyl-essigsaure," *Chem. Ber.* 56:1710-1717 (1923) (with translation).

Nishimura et al., "Two Signaling Molecules Share a phosphotyrosine-Containing Binding Site in the Platelet-Derived Growth Factor Receptor," *Molecular and Cellular Biology* 13:6889-6896 (1993).

Nodiff et al., "Antimalarial Phenanthrene Amino Alcohols. 3. Halogen-containing 9-phenanthrenemethanols," *Chemical Abstracts*, vol. 83, abstract No. 188214 (1975).

Nodiff et al., "Antimalarial Phenanthrene Amino Alcohols. 1. Fluorine-Containing 3- and 6-Substituted 9-Phenanthrenemethanols," *J. Med. Chem.* 14:921-925 (1971).

O'Sullivan and Rothery, "The Preparation and Possible Clinical Significance of 4'-Dialkylaminoisoindogenides," *Clinica Chimica Acta* 62:181-182 (1975).

Osborne et al., "Effect of Estrogens and Antiestrogens on Growth of Human Breast Cancer Cells in Athymic Nude Mice," *Cancer Research* 45:584-590 (1985).

Ozzello and Sordat, "Behavior of Tumors Produced by Transplantation of Human Mammary Cell Lines in Athymic Nude Mice," *Eur. J. Cancer* 16:553-559 (1980).

Pavlenko et al., "Introduction of aminomethyl groups into heterocyclic CH-acid molecules," *Dopov. Akad. Nauk Ukr, RSR* 7:64-66 (1980).

Plate, "Vascular endothelial growth factor is potential tumor angiogenesis factor in human gitomas *in vivo*," *Nature* 359:845-848 (1992).

Plowman et al., "Receptor Tyrosine Kinases as Targets for Drug Intervention," *DN&P* 7(6):334-339 (1994).

Quinn et al., "Fetal Liver Kinase 1 is a Receptor for Vascular Endothelial Growth Factor and is Selectively Expressed in Vascular Endothelium," *Proc. Natl. Acad. Sci. USA* 90:7533-7537 (1993).

Rozakis-Adcock et al., "Association of the Shc and Grb2-Sem5 SH2-containing proteins is implicated in activation of the Ras pathway by tyrosine kinases," *Nature* 360:689-692 (1992).

Ruveda and Gonzalez, "Geometric isomerism in benzylideneoxindoles," *Spectrochimica Acta* 26A:1275-1277 (1970).

Rygaard and Povlsen, "Heterotransplantation of a Human Malignant Tumour to 'Nude' Mice," *Acta path. microbiol. scand.* 77:758-760 (1969).

Saito and Streuli, "Molecular Characterization of Protein Tyrosine Phosphatases," *Cell Growth & Differentiation* 2:59-65 (1991).

Sandberg-Nordqvist et al., "Characterization of insulin-like growth factor 1 in human primary brain tumors," *Cancer Res.* 53:2475-2478 (1993).

Schlessinger and Ullrich, "Growth Factor Signalling by Receptor Tyrosine Kinases," *Neuron* 9:383-391 (1992).

Schnierle et al., "Vilsmeier-Reaktion mit Pyrrol- und Pyrrolon-Derivaten," *Liebigs Ann. Chem.* 715:90-97 (1968).

Schuchter et al., "Successful Treatment of Murine Melanoma With Bryostatin 1," *Cancer Research* 51:682-687 (1991).

Seibert et al., "Clonal Variation of MCF-7 Breast Cancer Cells *in Vitro* and in Athymic Nude Mice," *Cancer Research* 43:2223-2239 (1983).

Shafie and Grantham, "Role of Hormones in Growth and Regression of Human Breast Cancer Cells (MCF-7) Transplanted into Athymic Nude Mice," *J. Natl Cancer Institute* 67(1):51-56 (1981).

Shibuya et al., "Nucleotide sequence and expression of a novel human receptor-type tyrosine kinase gene (*flt*) closely related to the *fms* family," *Oncogene* 5:519-524 (1990).

Shiraishi et al., "Specific Inhibitors of Tyrosine-specific Protein Kinases: Properties of 4- Hydroxycinnamamide Derivatives in Vitro," *Cancer Research* 49:2374-2378 (1989).

Shiraishi, "Specific inhibitors of Tyrosine-Specific Protein Kinase, Synthetic 4- Hydroxycinnamamide Derivatives," *Biochemical and Biophysical Research Communications* 147:322-328 (1987).

Shweiki et al., "Vascular endothelial growth factor induced by hypoxia may mediate hypoxia-initiated angiogenesis," *Nature* 359:843-845 (1992).

Singh et al., "Indolinone Derivatives as Potential Antimicrobial Agents," *Zentralbl. Mikrobiol.* 144:105-109 (1989).

Singh et al., "Synthesis and Anticonvulsant Activity of New 1-Substituted 1'-Methyl-3-Chloro-2-Oxosprio (Azetidin-3', 4-Indol-2'Ones)," *Bollettino Chimico Farmaceutico* 133:76-79 (1994).

Skehan et al., "New Colorimetric Cytotoxicity Assay for Anticancer-Drug Screening," *J. Natl. Cancer. Inst.* 82:1107-1112 (1990).

Slamon et al., "Studies of the HER/2-*neu* Proto-oncogene in Human Breast and Ovarian Cancer," *Science* 244:707-712 (1989).

Soldi et al., "Platelet-Activating Factor (PAF) Induces the Early Tyrosine Phosphorylation of Focal Adhesion Kinase (p125$^{FAK}$) in Human Endothelial Cells," *Oncogene* 13(3):515-525 (1996).
Songyang et al., "SH2 Domains Recognize Specific Phosphopeptide Sequences," *Cell* 72:767-778 (1993).
Songyang et al., Specific motifs recognized by the SH2 domains of Csk, 3BP2, fps/fes, GRB-2, HCP, SHC, Syk and Vav, *Molecular and Cellular Biology* 14:2777-2785 (1994).
Spada and Myers, "Small molecule inhibitors of tyrosine kinase activity," *Expert Opinion on Therapeutic Patents* 5(8):805-817 (1995).
Stolle, Beilstein Reg. No. 273650, *J. Prakt. Chem.*, vol. 2, p. 128 (1930).
Sun et al., "Synthesis and biological evaluations of 3-substituted indolin-2-ones: A novel class of tyrosine kinase inhibitors that exhibit selectivity toward particular receptor tyrosine kinsases," *J. Med. Chem.* 41:2588-2603 (1998).
Superti-Furga et al., "A functional screen in yeast for regulators and antagonizers of heterologous protein tyrosine kinases," *Nature Biotech* 14:600-605 (1996).
Superti-Furga et al., "Csk inhibition of c-Src activity requires both the SH2 and SH3 domains of Src," *EMBO J.* 12:2625-2634 (1993).
Tacconi and Marinone, "Preparazione e caratteristiche di alcuni 3-ossindolidenderivati," *Ricerca Scientifica* 38:1239-1244 (1968).
Tacconi et al., "(Z)- and (E)-3-Alkylidene-1 ,3-dihydroindol-2-ones: Influence of Configuration on the Transmission of the Inductive Effect to the Carbonyl Group," *J.C.S. Perkin II* pp. 150-154 (1976).
Takano et al., "Inhibition of angiogenesis by a novel diaminoanthraquinone that inhibits protein kinase C," *Mol. Bio. Cell* 4:358A (1993), at abstract No. 2076.
Terrett et al., "Combinatorial synthesis- the design of compound libraries and their application to drug discovery," *Tetrahedron* 51(30):8135-8173 (1995).
Thompson et al., "Facile Dimerisation of 3-Benzylideneindoline-2-thiones," *J. Chem. Soc. Perkin Trans.* (*I*) pp. 1835-1837 (1993).
Torp et al., "Expression of the epidermal growth factor receptor gene in human brain metastases," *AMPIS* 100:713-719 (1992).
Traxler, "Protein tyrosine kinase inhibitors in cancer treatment," *Expert Opinion on Therapeutic Patents* 7(6):571-588 (1997).
Treibs et al., "Uber isoindigoide Farbstroffe der Pyrrol-Reihe," *Liebigs Ann. Chem.* 702:112-130 (1967).
Trost et al. (ed.), "*Comprehensive Organic Synthesis," Selectivity, Strategy & Efficiency in Modern Organic Chemistry* 4:478 (1991).
Tsai et al., "The Effect of 3,3-Di-Pyridyl-Methyl-1-Phenyl-2-Indolinone on the Nerve Terminal Currents of Mouse Skeletal Muscles," *Neuropharmacology* 31(9):943-947 (1992).
Tuzi et al., "Expression of growth factor receptors in human brain tumours," *Br. J. Cancer* 63:227-233 (1991).
Twamley-Stein et al., "The Src Family Tyrosine Kinases are Required for Platelet-Derived Growth Factor-Mediated Signal Transduction in NIH-3T3 Cells," *Proc. Natl. Acad. Sci.* 90:7696-7700 (1993).
Ullrich and Schlessinger, "Signal Transduction by Receptors with Tyrosine Kinase Activity," *Cell* 61:203-212 (1990).
Vaisman et al., "Characterization of the Receptors for Vascular Endothelial Growth Factor," *J. Biol. Chem.* 265:19461-19466 (1990).
Varma and Gupta, "Nucleophilic Reactions of 2-Methyl-3-(4'-carbomethoxyphenyl)-4-quinazolinones with 2-Indolinones," *J. Indian Chem. Soc.* 66:804-805 (1989).
Voller et al., "Enzyme-Linked Immunosorbent Assay," in *Manual of Clinical Immunology*, 2$^{nd}$ edition, Rose and Friedman editors, American Society of Microbiology, Washington D.C., pp. 359-371 (1980).
Wahl et al., "Chimie Organique—Sur les iso-indogenides," *C.R. Hebd. Seancest Acad. Sci.* 149:132-134 (Jul. 1909).
Wahl, "3-benzilidene-5-methyl-1,3-dihydroindol-2-one," Ann. Chim. Database Crossfire, Beilstein Ref. No. 2-21-00-00290, p. 350 (1926).
Walker, "Synthesis of a α-(p-Aminophenyl)- and α-(p-Chlorophenyl)-β-aryl-propionitriles by Catalytic Reduction of Stilbenenitriles," *J. Med. Chem.* 8(5):583-588 (1965).
Walker, "Synthesis of New 3-(Pyridylmethylene)-, 3-(Pyridylmethyl)-,3-(Piperidylmethyl)- and 3-(β-Alkylaminoethyl)-2-indolinones. The Reduction of Isoindogenides, Nitro Compounds, and Pyridines in a Series of 2-Indolinones," *J. Med. Chem.* 8(5):626-637 (1965).
Warri et al., "Estrogen Suppression of *erb*B2 Expression is Associated with Increased Growth Rate of ZR-75-I Human Breast Cancer Cells *in Vitro* and in Nude Mice," *Int. J. Cancer* 49:616-623 (1991).
Weidner et al., "Tumor Angiogenesis and Metastasis—Correlation in Invasive Breast Carcinoma," *New England J. Medicine* 324:1-7 (1991).
Wright et al., "Cyclic Hydroxamic Acids Derived from Indole," *J. Amer. Chem. Soc.* 78:221-224 (1956).
Wright et al., "Inhibition of Angiogenesis in Vitro and In Ovo With an Inhibitor of Cellular Protein Kinases, MDL 27032," *J. Cellular Physiology* 152:448-457 (1992).
Young and Babbitt, "2-(2-Methyl-3-indolyl)-1,4-benzoquinone, A Reversible Redox Substrate at the Carbon Paste Electrode in Acidic Aqueous-Ethanolic Media," *J. Org. Chem.* 47:1571-1572 (1982).
Zaman et al., "Tyrosine Kinase Activity of Purified Recombinant Cytoplasmic Domain of Platelet-Derived Growth Factor β-Receptor (β-PDGFR) and Discovery of a Novel Inhibitor of Receptor Tyrosine Kinases," *Biochemical Pharmacology* 57(1):57-64 (1999).
Zhang et al., "Microtubule Effects of Welwistatin, a Cyanobacterial Indolinone that Circumvents Multiple Drug Resistance," *Molecular Pharmacology* 49:288-294 (1996).
Zhungietu et al., "Reaction of Indoles and 2-Ketoindolines With Some Aldehydes," *Chemical Abstracts*, vol. 78, abstract No. 111201 (1973).
Andreani et al., "Synthesis and cardiotonic activity of 2-indolinones," *Eur. J. Med. Chem.* 25:187-190 (1990) (*Abstract considered by examiner, best available full reference attached*).
Andreani et al., "Synthesis and potential coanthracyclinic activity of substituted 3-(5-imidazo [2, 1-b]thiazolymethylene)-2-indolinones," *Eur. J. Med. Chem.* 32:919-924 (1997).
Baserga, "Oncogenes and the strategy of growth factors," *Cell* 79:927-930 (1994).
Borsche et al., "Über nielkernige kondersierte systeme mit heterocyclischen ringen," *Liebigs Ann. Chem.* 550:160-174 (1941).
Coda et al., "(Z)- and (E)-Arylidene-1,3-dihydroindol-2-ones: Configuration, Conformation and Infrared Carbonyl Stretching Frequencies," *Chemical Abstracts*, vol. 101, abstract No. 37875 (1984).
Daisley, "Thin-layer chromatographic separation of some substituted 3-benzylidine-indol-2(3H)-ones," *Chemical Abstracts* vol. 82, abstract No. 72891 (1975).
Houben-Weyl., "Substance Index," *Cyclic Compounds V Bicyclic Compounds 1* E23i:834-1018 (1999).
Howard et al., "Synthesis and aldose reductase inhibitory activity of substituted 2(1*H*)-benzimidazolone-and oxindole-1 acetic acids" *Chemical Abstracts*, vol. 118, abstract No. 254813 (1993).
Nodiff et al., "Antimalarial Phenanthrene Amino Alcohols. 1. Fluorine-Containing 3- and 6-Substituted 9- Phenanthrenemethanols," *Chemical Abstracts*, vol. 76, abstract No. 21121 (1972).
Schindler et al., "Dibenz[*b,f*]-azocin-Derivate," *Helvetica Chimica Acta* 49:985-989 (1966).
Stetinova et al., "Stereochemistry and Photoisomerisation of Furfurylideneoxindoles," *Collection Czecholslov. Chem. Commun.* 42:2201-2206 (1977).
Wahl, Beilstein Reg. No. 191439, *Bull. Soc. Chim. Fr.*, p. 1038 (1909).
Wahl, *Bull. Soc. Chim. Fr.*, pp. 1035-1038 (1909) (*see C21, partial duplicate*).
Winkelmann et al., "Chemotherapeutically Active Nitro Compounds: 4. 5-Nitroimidazoles (Part I)," *Arzneim.-Forsch./Drug Res.* 27(II):2251-2263 (1977).
Wright, Beilstein Reg. No. 235900, *J. Amer. Chem. Soc.* 78:221-224 (1956).
Zhungietu et al., "Reaction of Indoles and 2-Ketoindolines With Some Aldehydes," *Institute of Chemistry, Academy of Science of the Moldavian SSR*, Kishinev pp. 34-37 translated from *Khimiya Geterotsiklicheskikh Soedinenii* 1:40-44 (1973) (*Abstract considered by examiner, full document enclosed, not in English*).

* cited by examiner

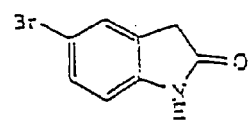
c1
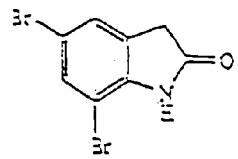
c2
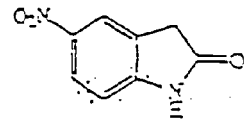
c3
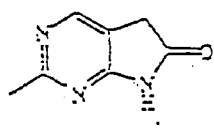
c4
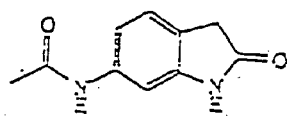
c5
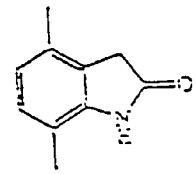
c6
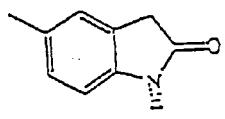
c7
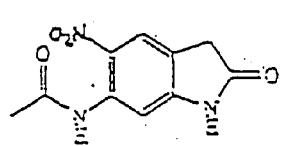
c8
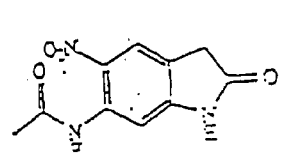
c9
Fig 1. Sheet 1 of 12

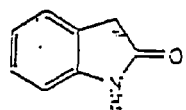
O10
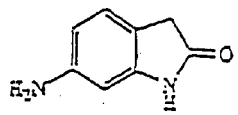
O11
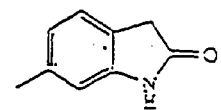
O12
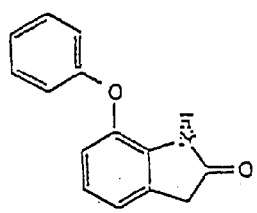
O13
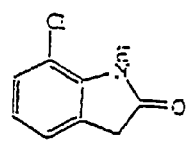
O14
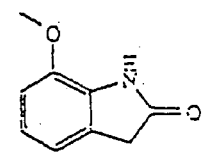
O15
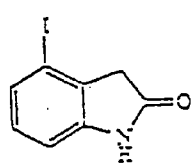
O16
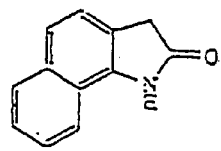
O17
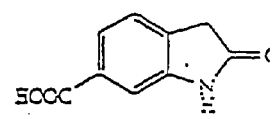
O18
Fig 1. Sheet 2 of 12

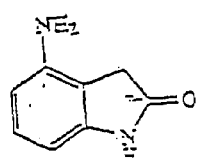
019
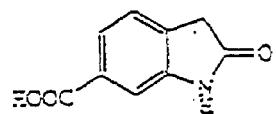
020
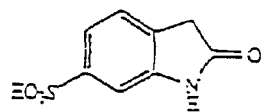
021
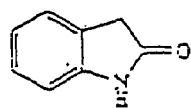
022
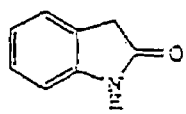
023
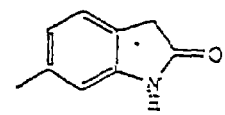
024
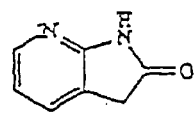
025
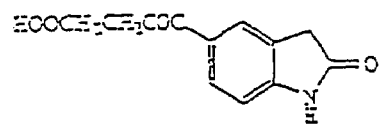
026
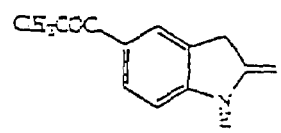
027
Fig 1. Sheet 3 of 12

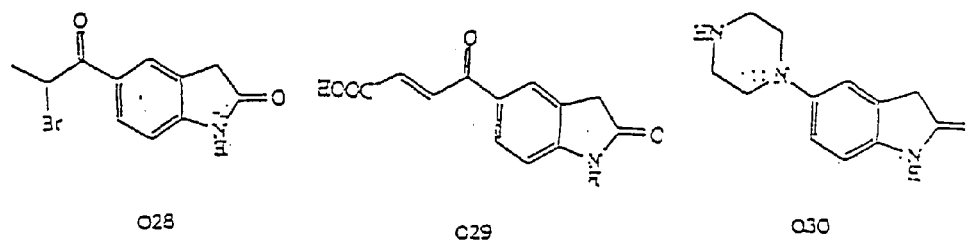
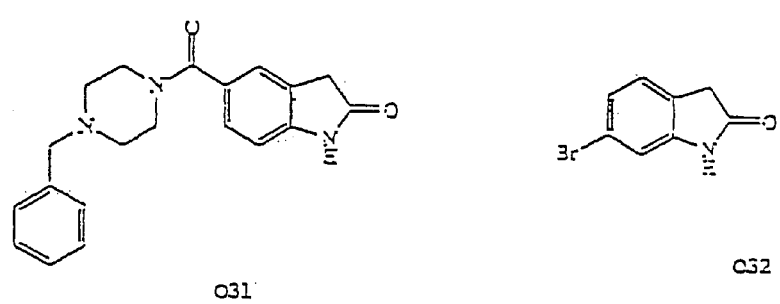
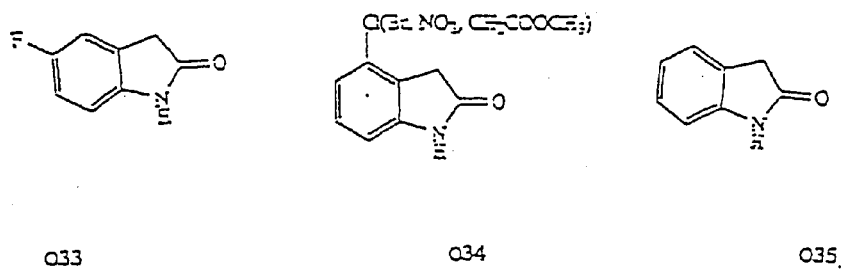
Fig 1. Sheet 4 of 12

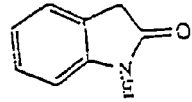
C36
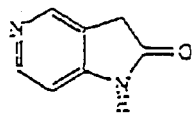
C37
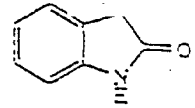
C38
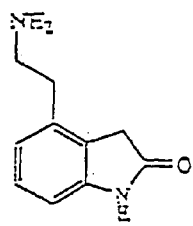
C39
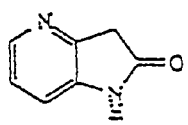
C40
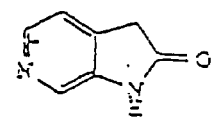
C41
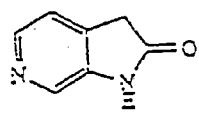
C42
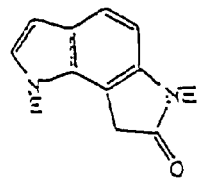
Oxindole[4,5-b]pyrrole
C44
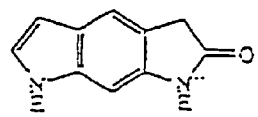
Oxindole[6,5-b]pyrrole
C45
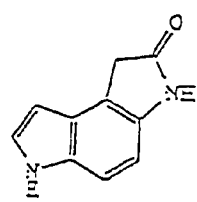
Oxindole[5,4-b]pyrrole
C47
Fig 1. Sheet 5 of 12

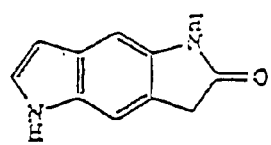
C48
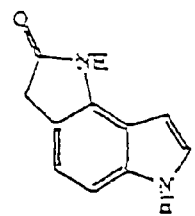
C50
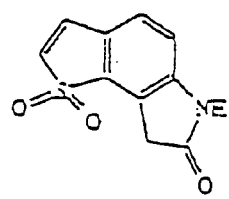
C52
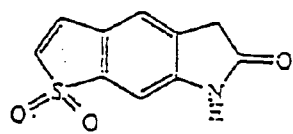
O53
Fig 1. Sheet 6 of 12

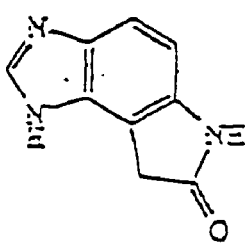
O55
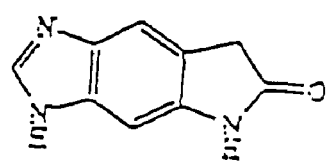
O56
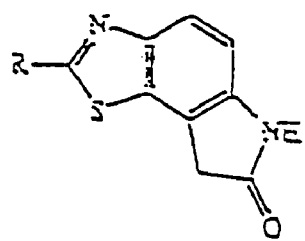
O58
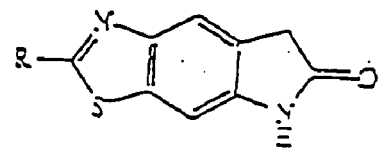
O59
Fig 1. Sheet 7 of 12

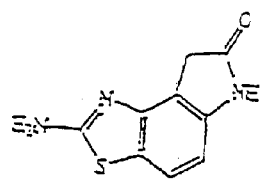
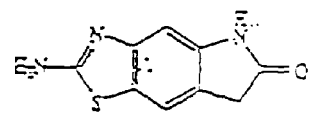
C61  C62
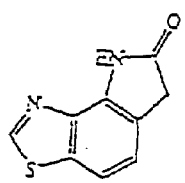
C64
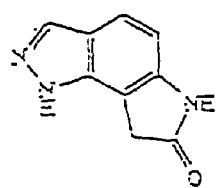
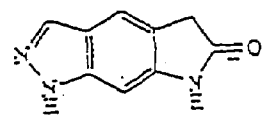
C66  C67
Fig 1. Sheet 8 of 12

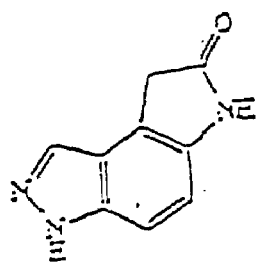
C69
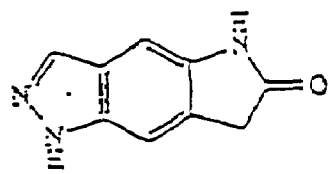
O70
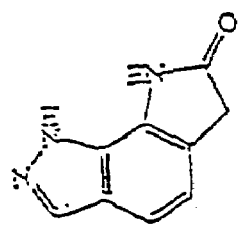
O73
Fig 1. Sheet 9 of 12

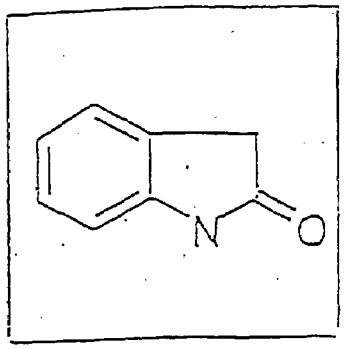
074
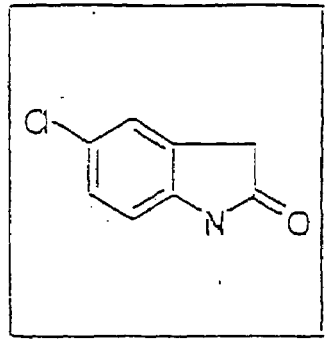
075
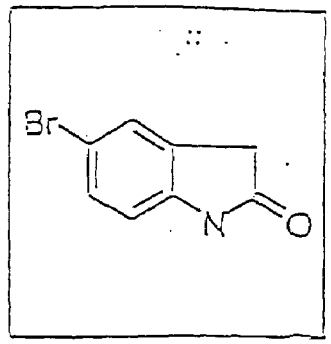
076
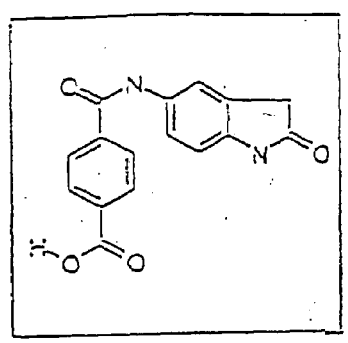
077
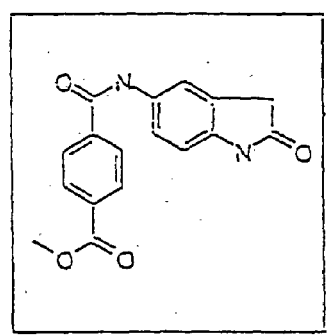
078
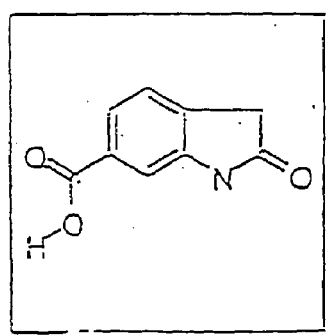
079
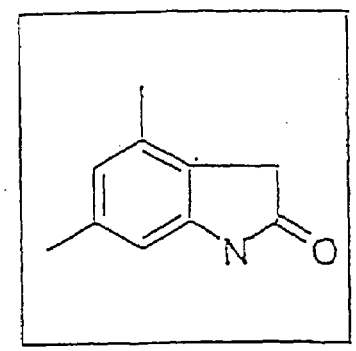
080
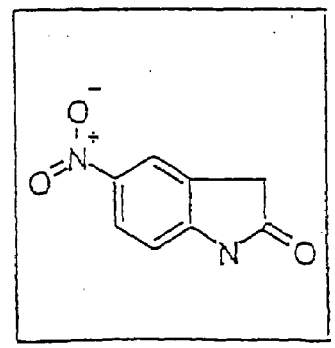
081
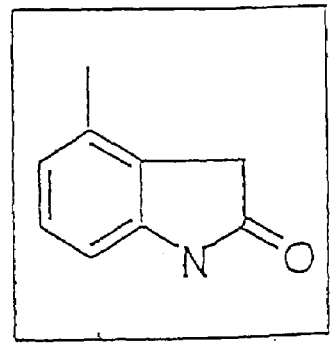
082
Fig 1. Sheet 10 of 12

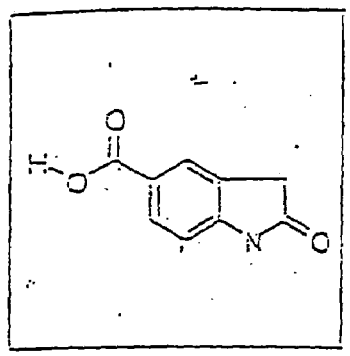
C83
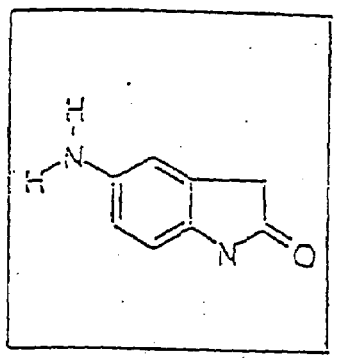
C84
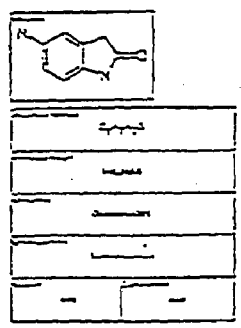
C85
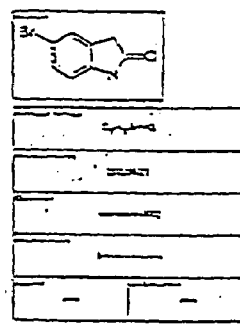
C86
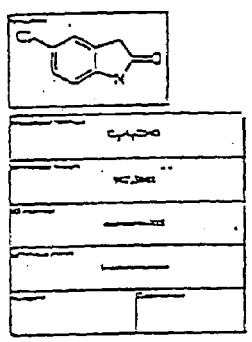
C87
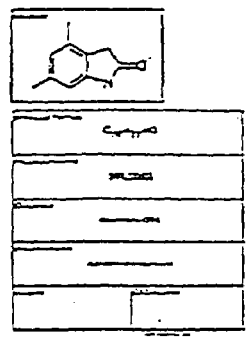
C88
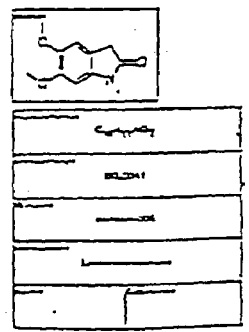
C89
Fig 1. Sheet 11 of 12

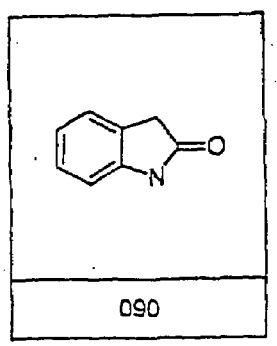
090
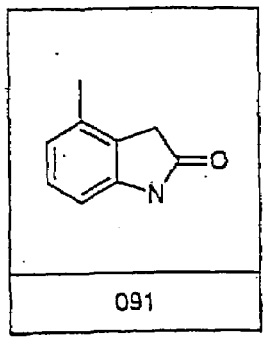
091
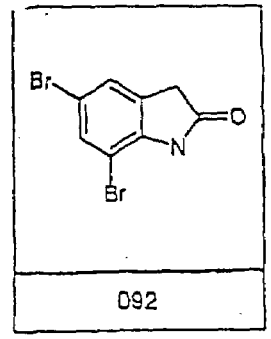
092
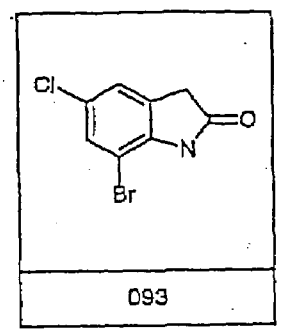
093
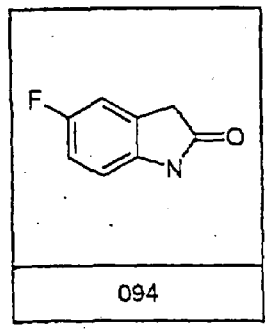
094
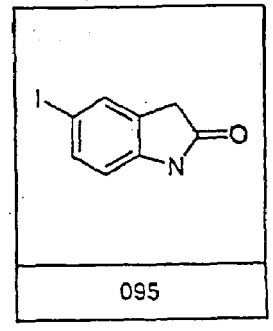
095
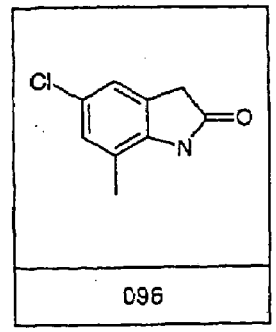
096
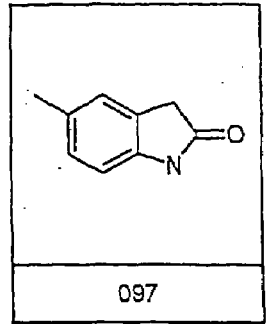
097
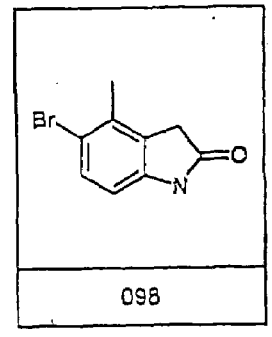
098
Figure 1, Sheet 12 of 12

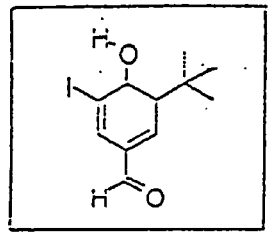
A1
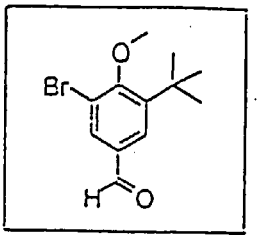
A2
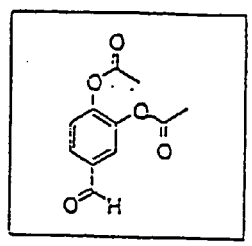
A3
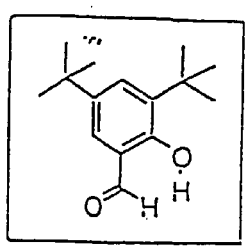
A4
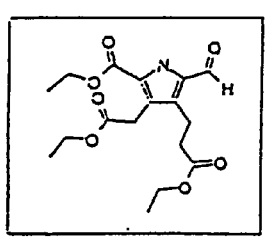
A5
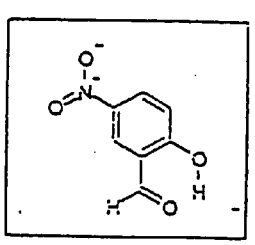
A6
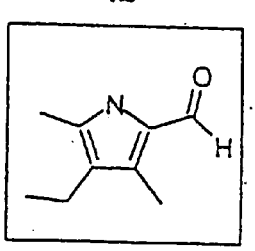
A7
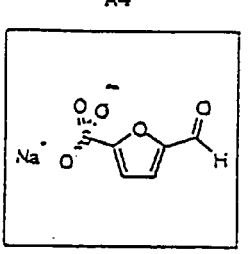
A8
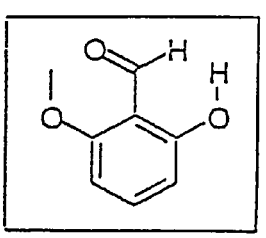
A9
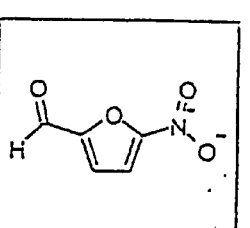
A10
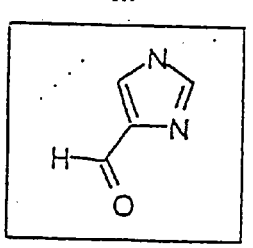
A11
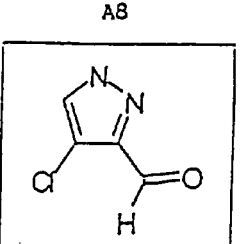
A12
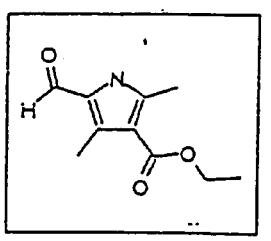
A13
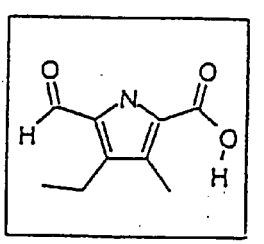
A14
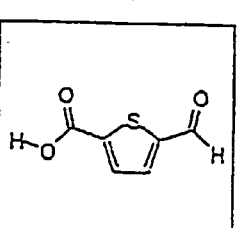
A15
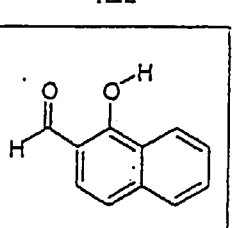
A16
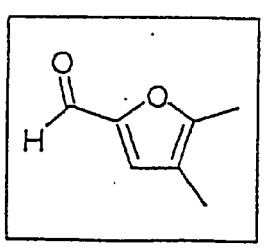
A17
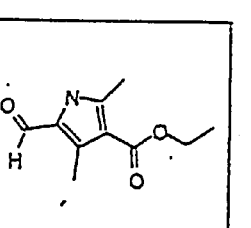
A18
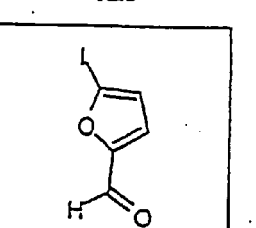
A19
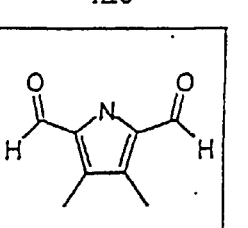
A20
Figure 2, Sheet 1 of 30

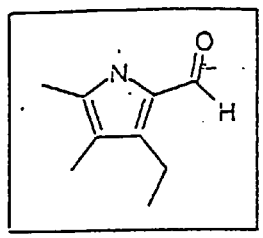
A21
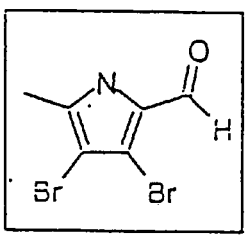
A22
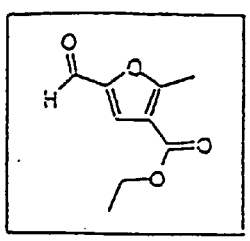
A23
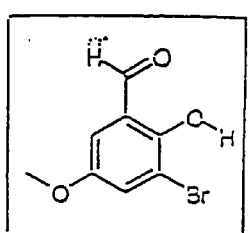
A24
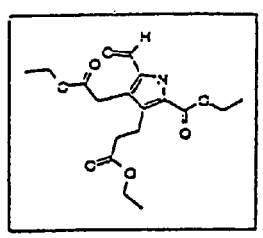
A25
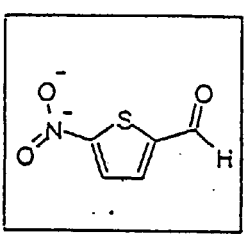
A26
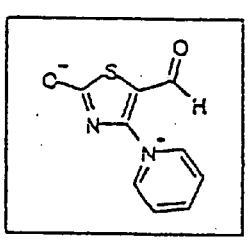
A27
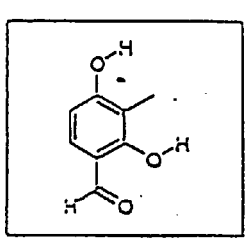
A28
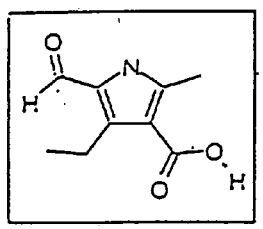
A29
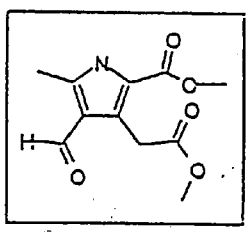
A30
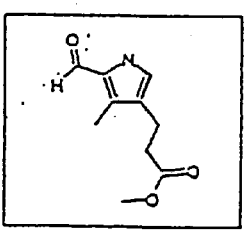
A31
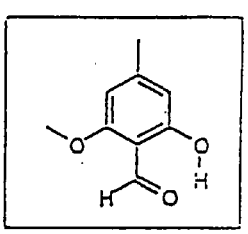
A32
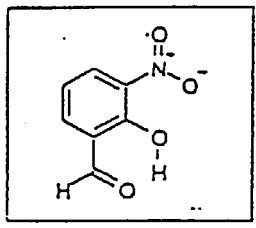
A33
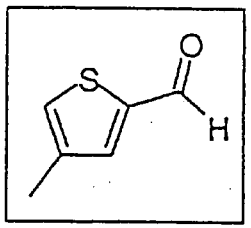
A34
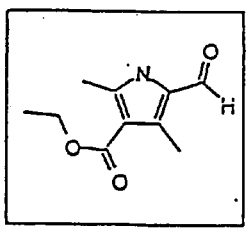
A35
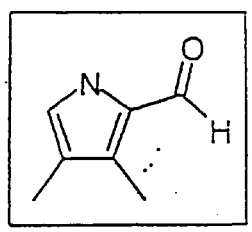
A36
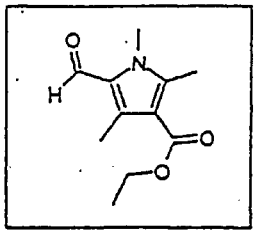
A37
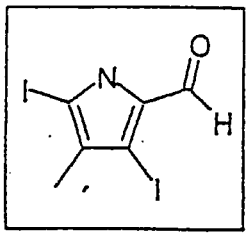
A38
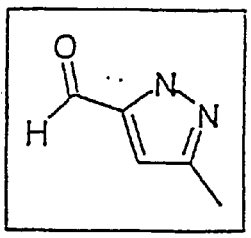
A39
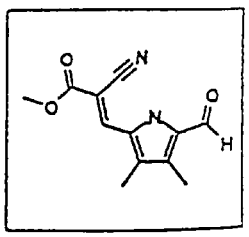
A40
Figure 2, Sheet 2 of 30

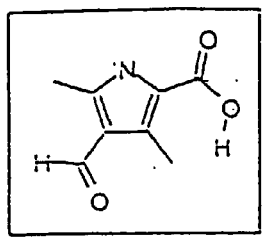
A41
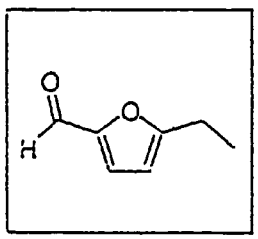
A42
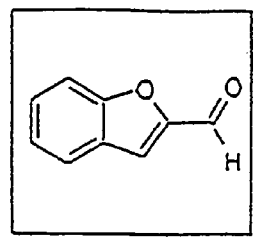
A43
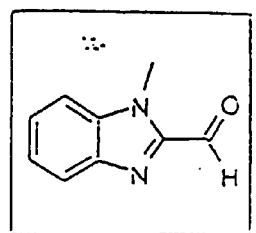
A44
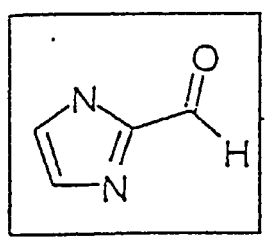
A45
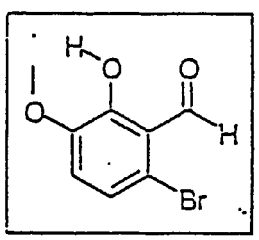
A46
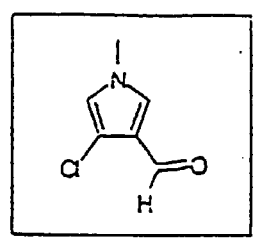
A47
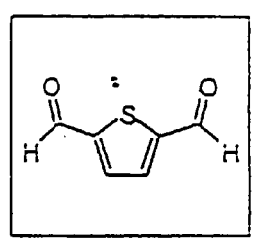
A48
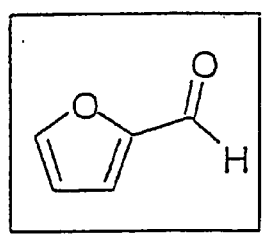
A49
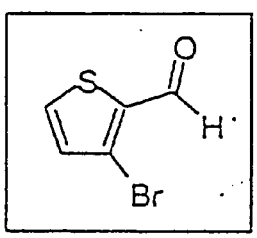
A50
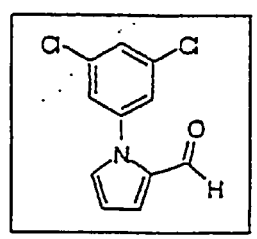
A51
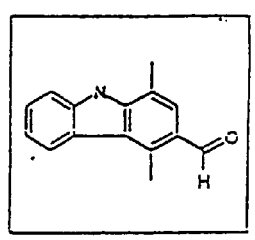
A52
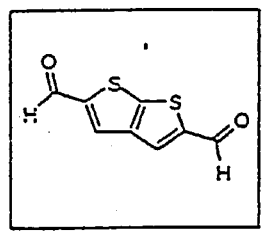
A53
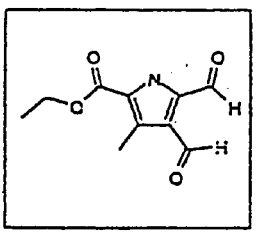
A54
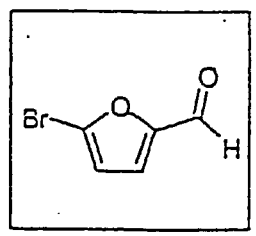
A55
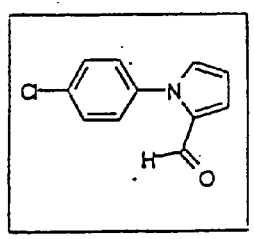
A56
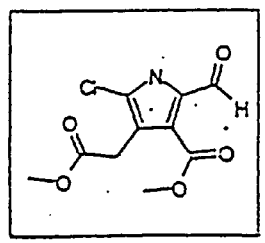
A57
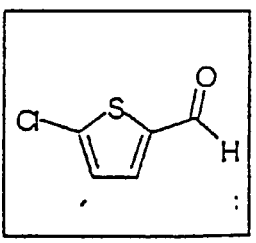
A58
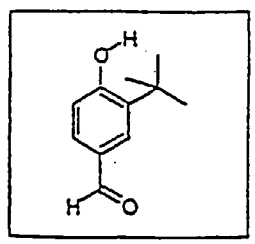
A59
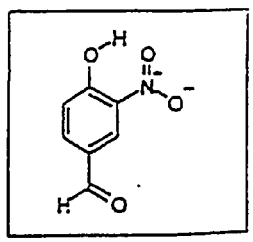
A60
Figure 2, Sheet 3 of 30

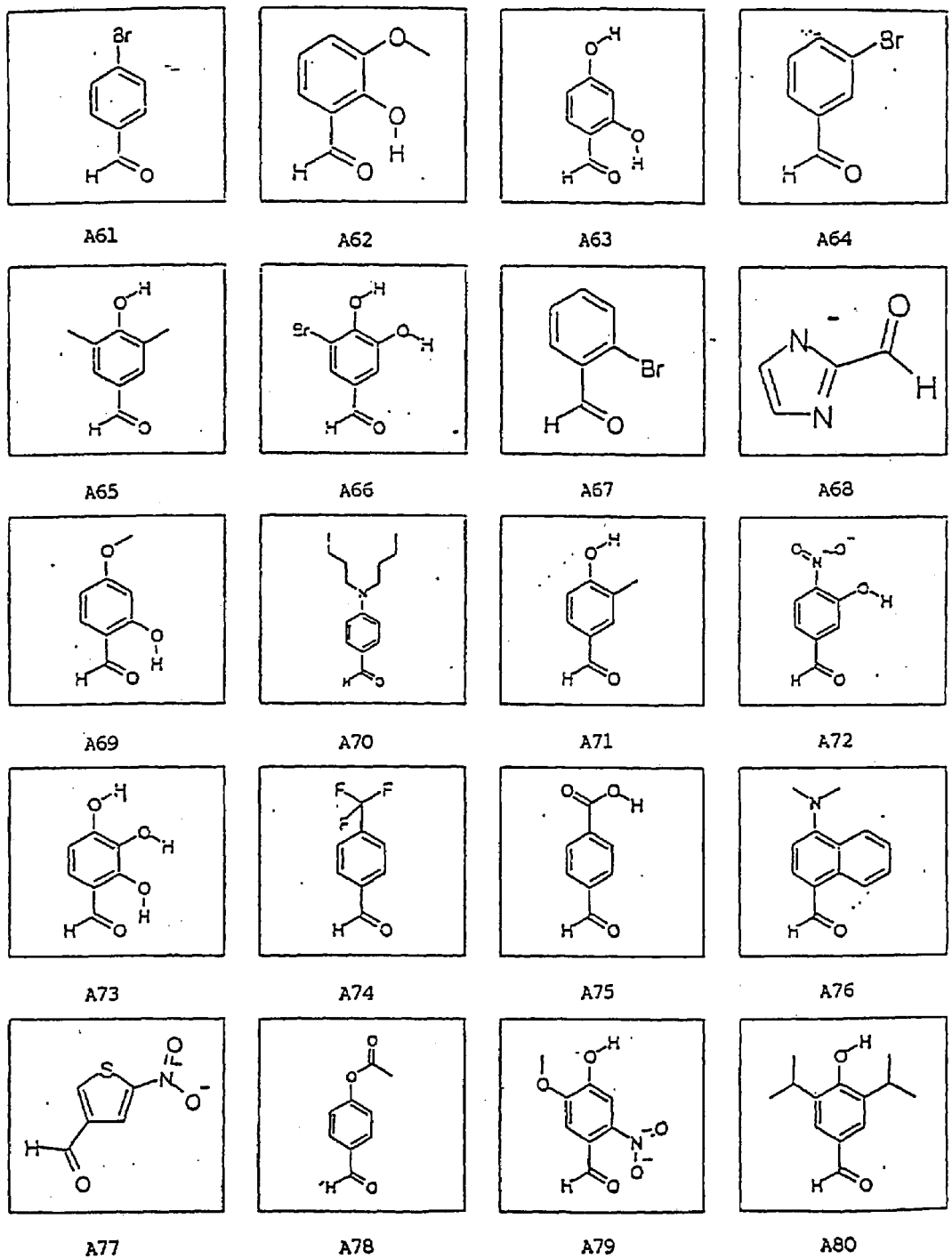
Figure 2, Sheet 4 of 30

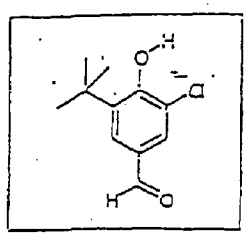
A81
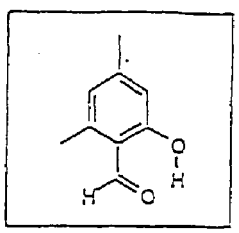
A82
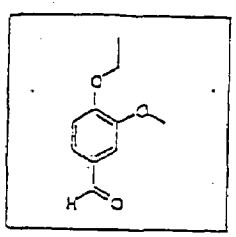
A83
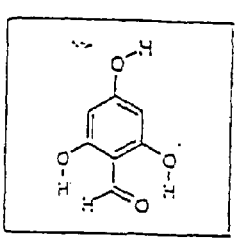
A84
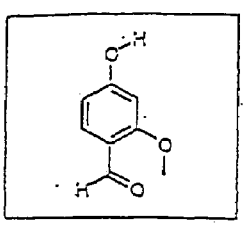
A85
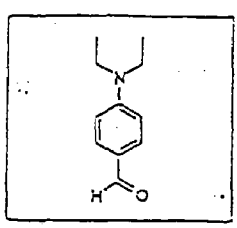
A86
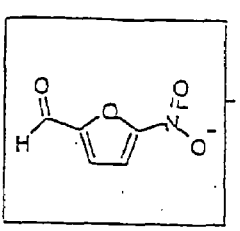
A87
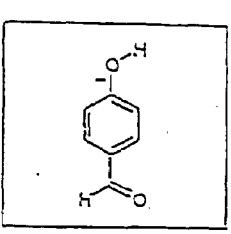
A88
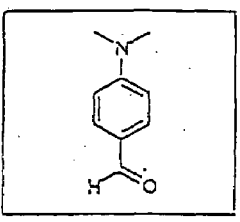
A89
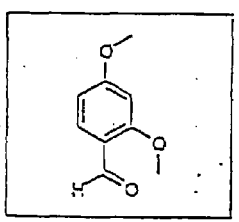
A90
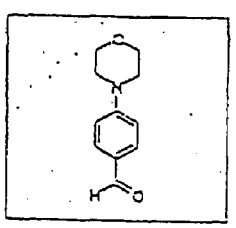
A91
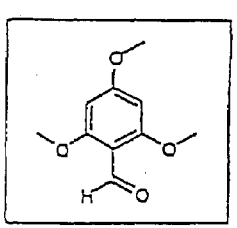
A92
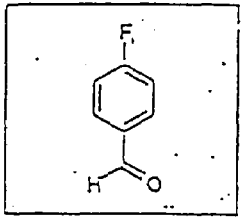
A93
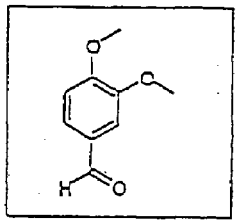
A94
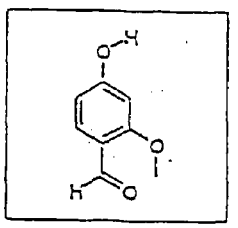
A95
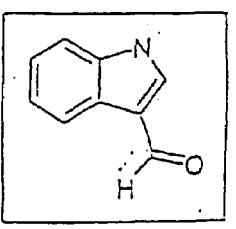
A96
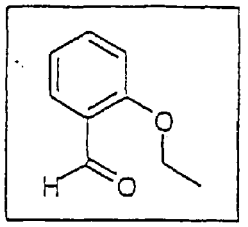
A97
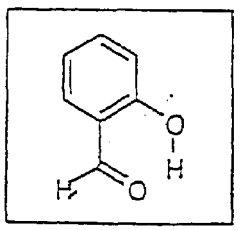
A98
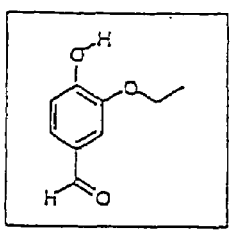
A99
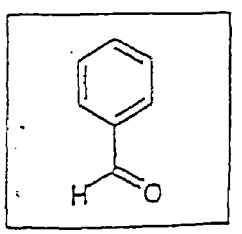
A100
Figure 2, Sheet 5 of 30

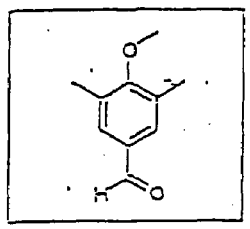
A121'
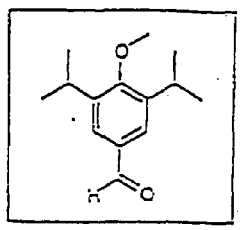
A122
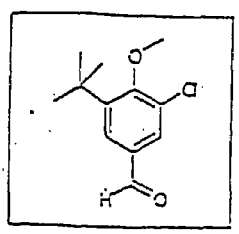
A123
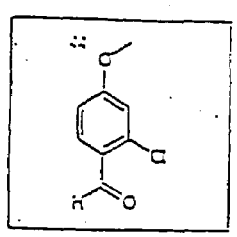
A124
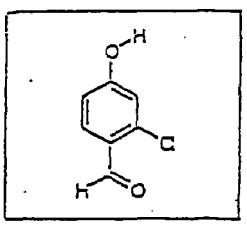
A125
Figure 2, Sheet 7 of 30

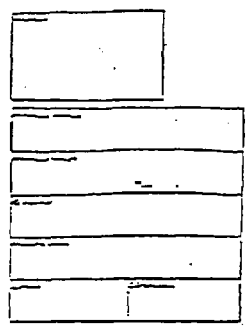 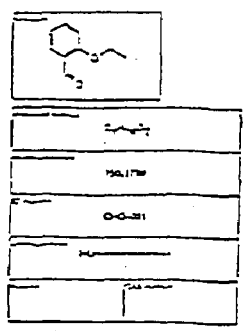 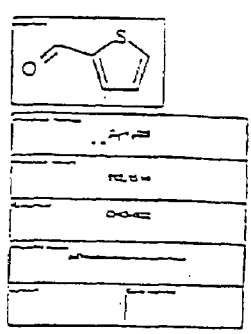
A125 A126 A127
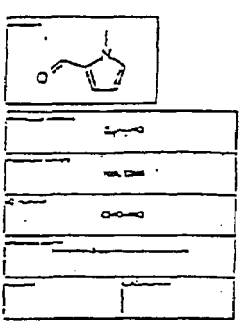 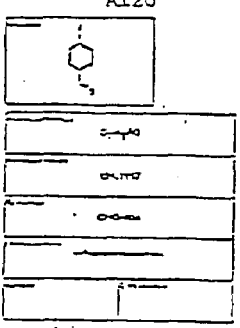 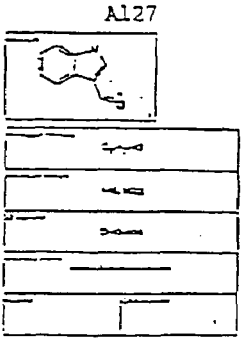
A128 A129 A130
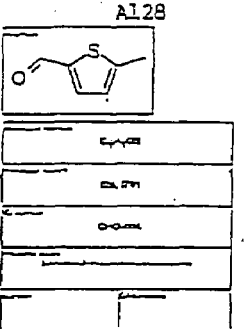 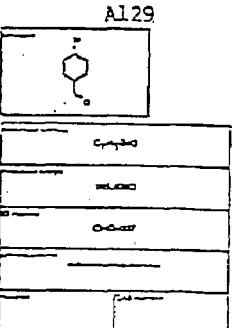 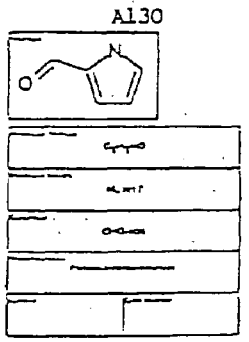
A131 A132 A133
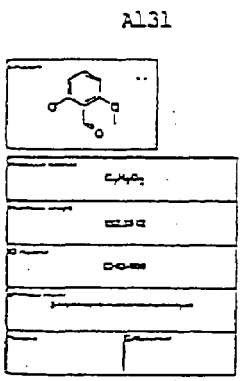 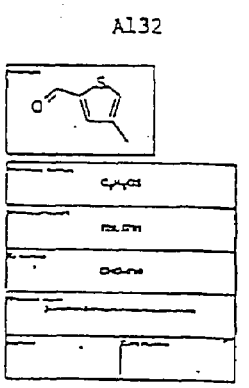 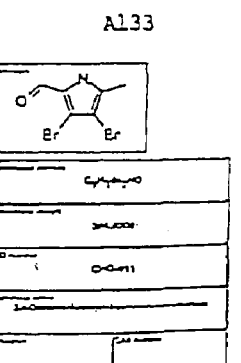
A134 A135 A136
Figure 2, Sheet 8 of 30

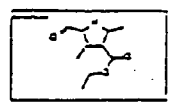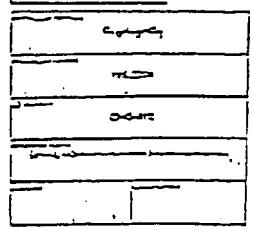
A137
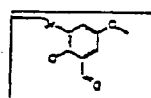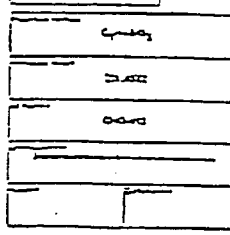
A138
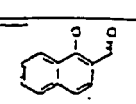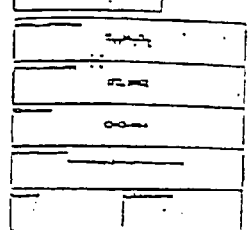
A139
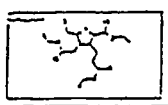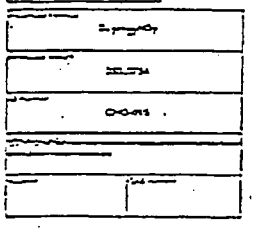
A140
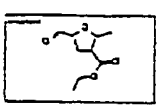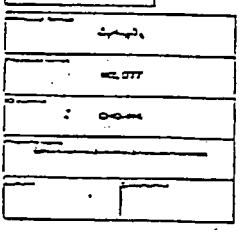
A141
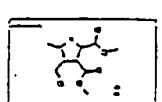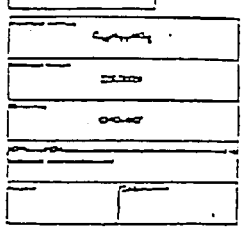
A142
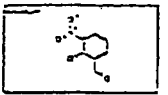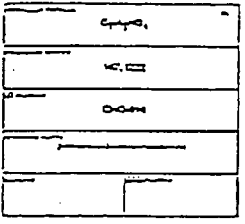
A143
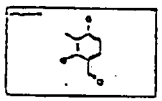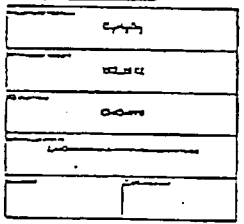
A144
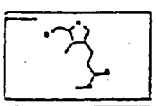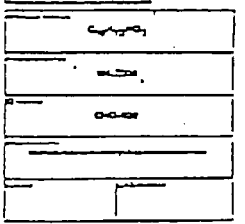
A145
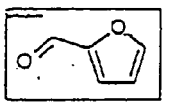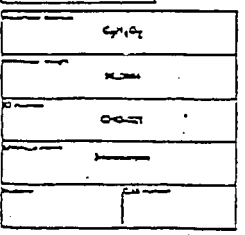
A146
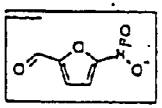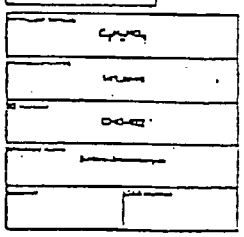
A147
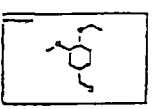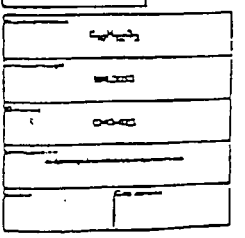
A148
Fig 2. Sheet 9 of 30

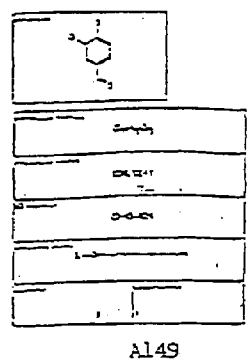
A149
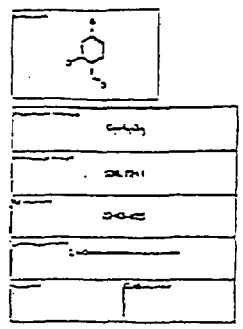
A150
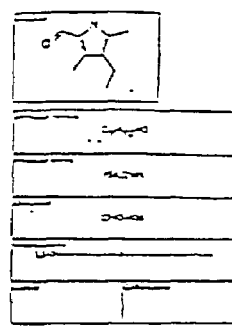
A151
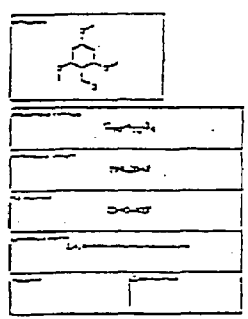
A152
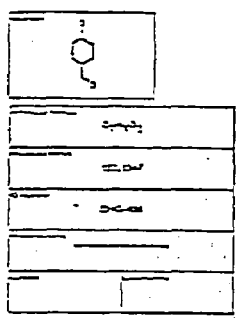
A153
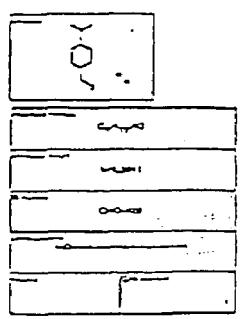
A154
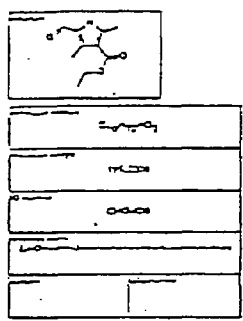
A155
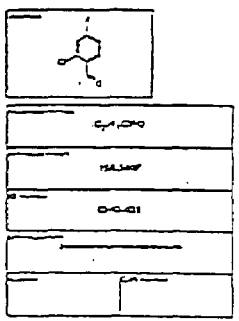
A156
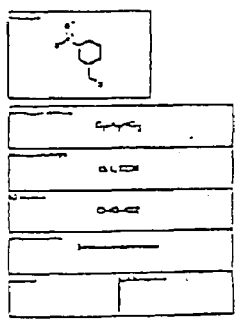
A157
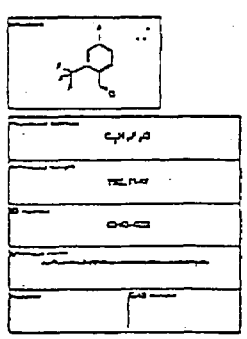
A158
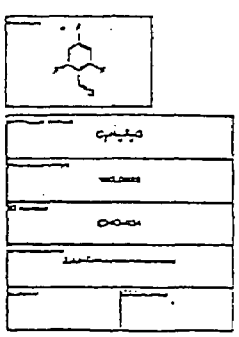
A159
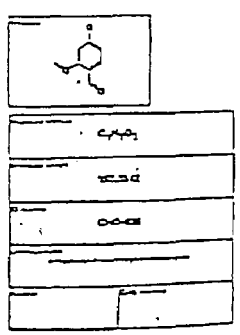
A160
Fig 2. Sheet 10 of 30

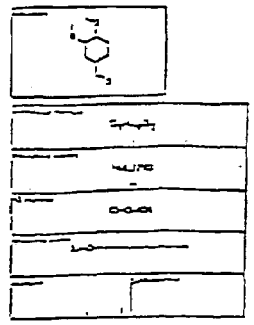
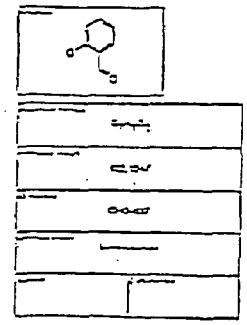
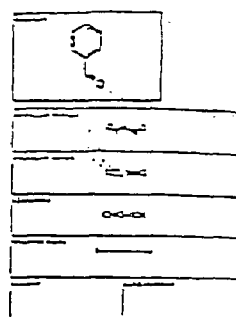
A161　　　　　　　　A162　　　　　　　　A163
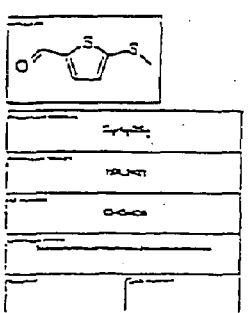
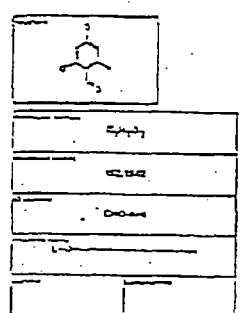
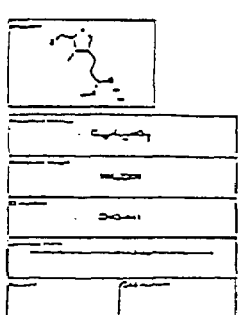
A164　　　　　　　　A165　　　　　　　　A166
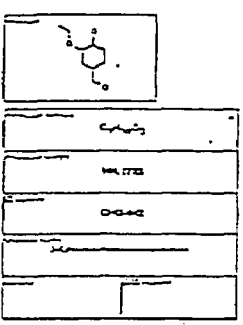
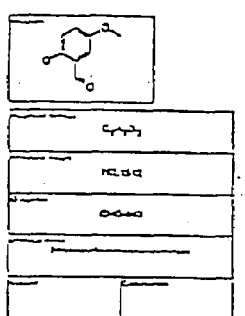
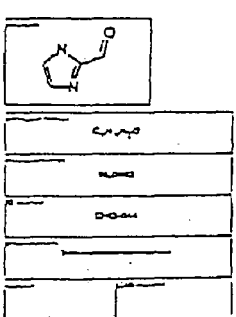
A167　　　　　　　　A168　　　　　　　　A169
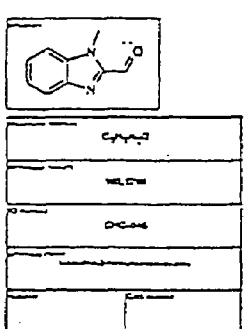
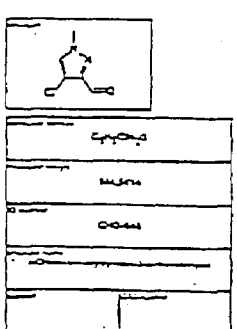
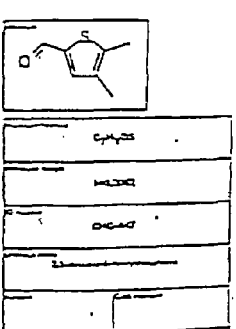
A170　　　　　　　　A171　　　　　　　　A172
Fig 2. Sheet 11 of 30

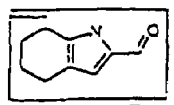
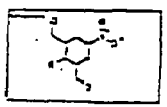
A173　　　　　　　　A174　　　　　　　　A175
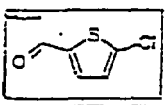
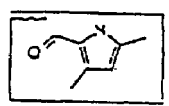
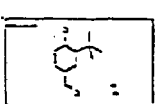
A176　　　　　　　　A177　　　　　　　　A178
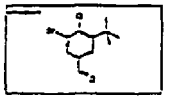
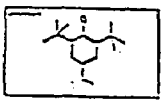
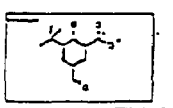
A179　　　　　　　　A180　　　　　　　　A181
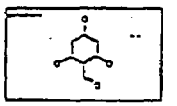
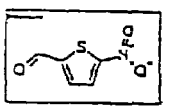
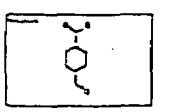
A182　　　　　　　　A183　　　　　　　　A184
Fig 2. Sheet 12 of 30

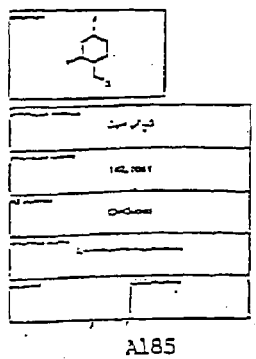
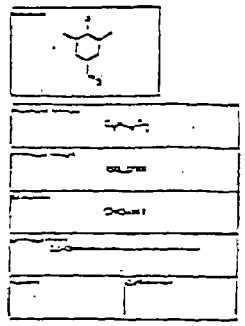
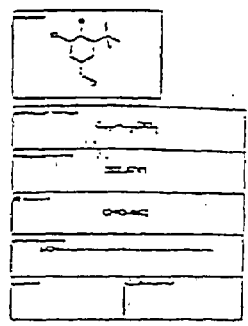
A185　　　　　　　　A186　　　　　　　　A187
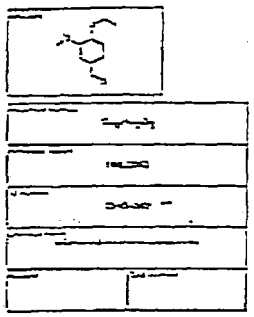
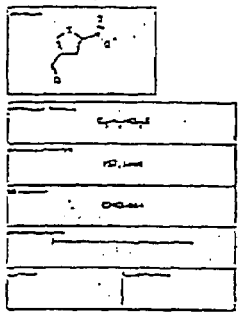
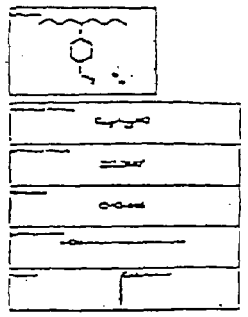
A188　　　　　　　　A189　　　　　　　　A190
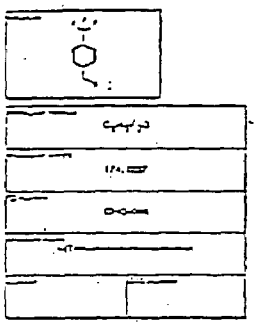
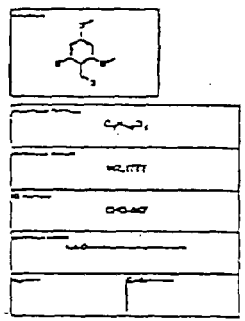
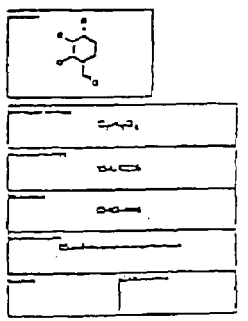
A191　　　　　　　　A192　　　　　　　　A193
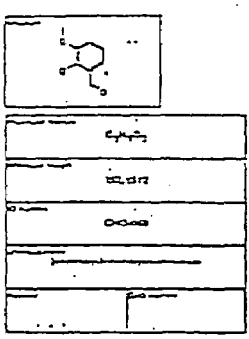
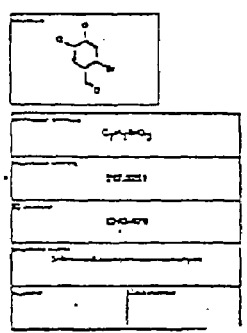
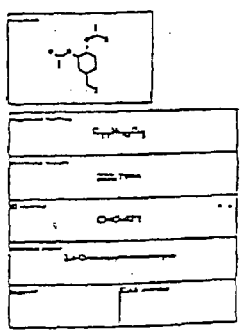
A194　　　　　　　　A195　　　　　　　　A196
Fig 2. Sheet 13 of 30

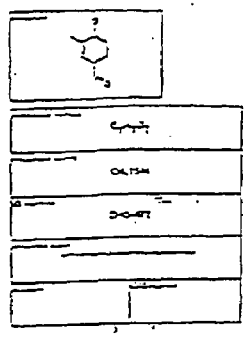
A197
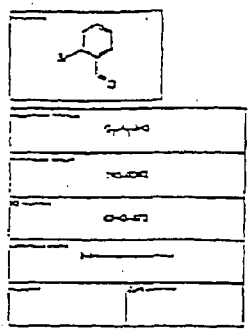
A198
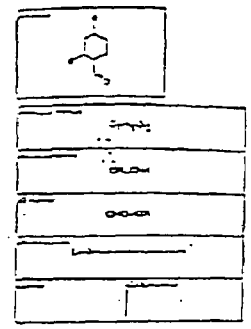
A199
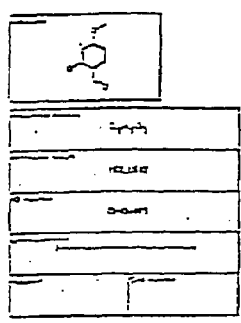
A200
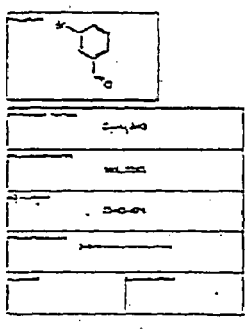
A201
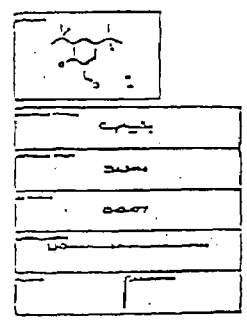
A202
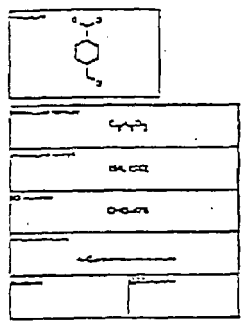
A203
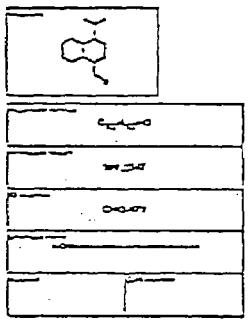
A204
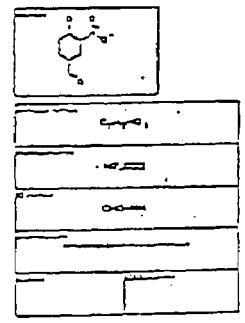
A205
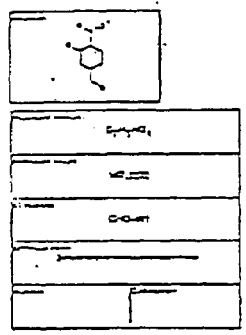
A206
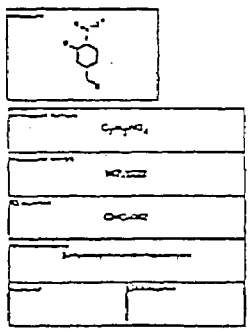
A207
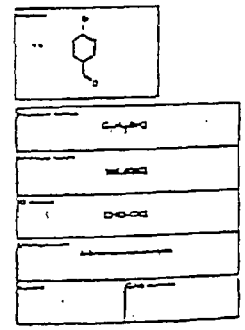
A208
Fig 2. Sheet 14 of 30

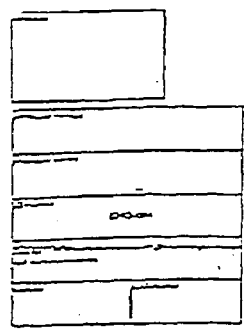
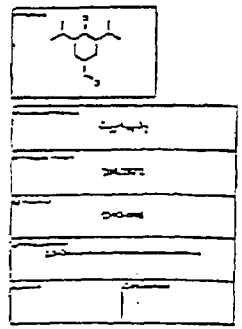
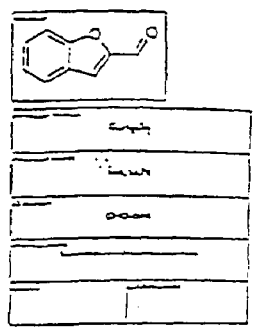
A209　　　　　　　A210　　　　　　　A211
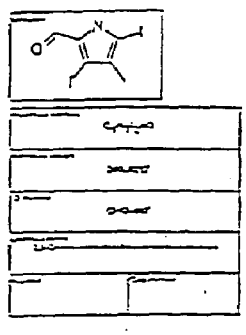
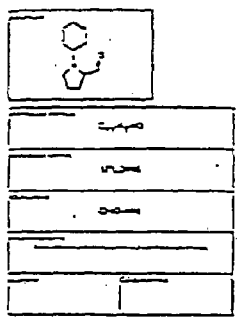
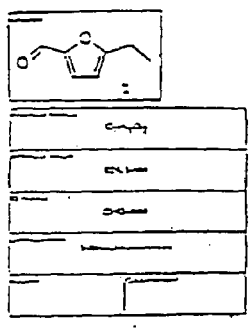
A212　　　　　　　A213　　　　　　　A214
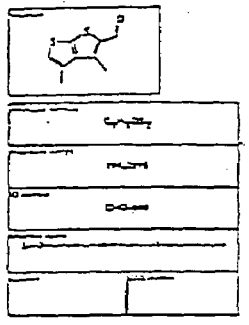
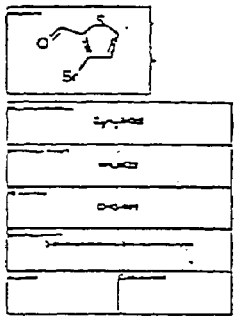
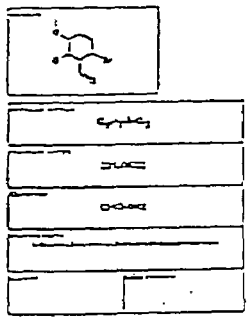
A215　　　　　　　A216　　　　　　　A217
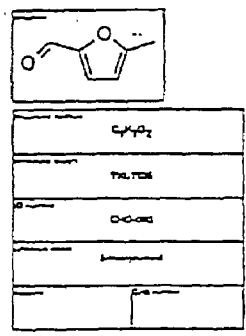
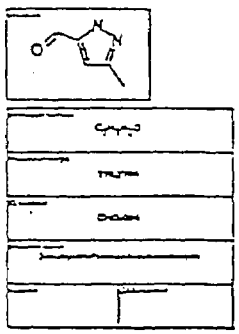
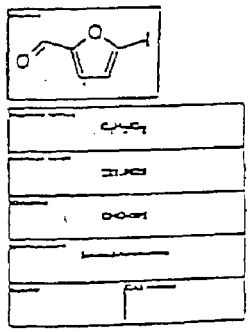
A218　　　　　　　A219　　　　　　　A220
Fig 2. Sheet 15 of 30

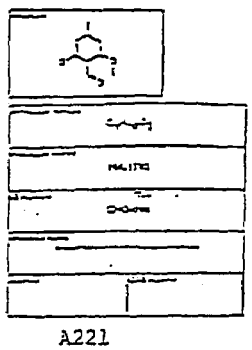
A221
A222
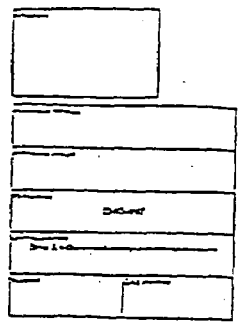
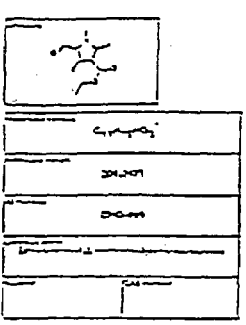
A223
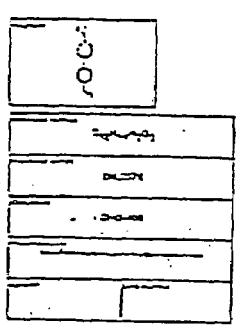
A224
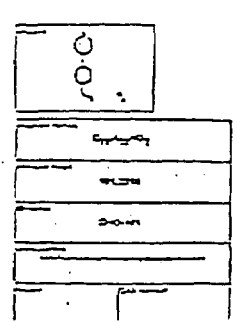
A225
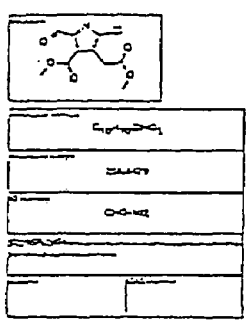
A226
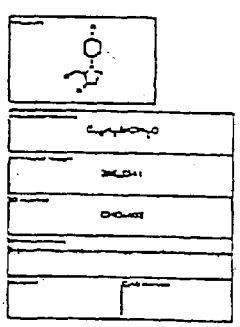
A227
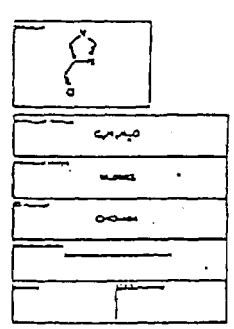
A228
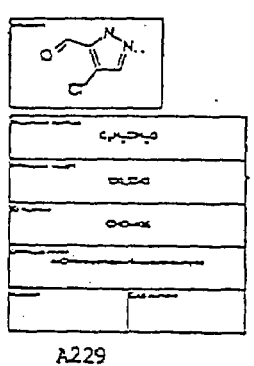
A229
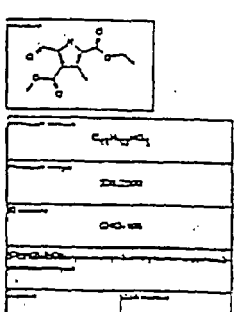
A230
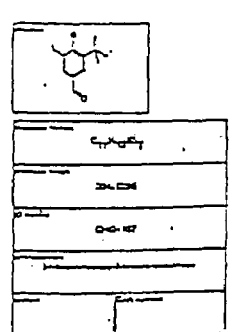
A231
Fig 2. Sheet 16 of 30

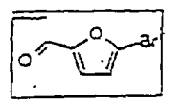
A232
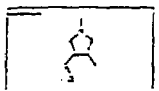
A233
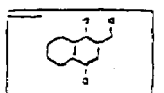
A234
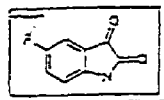
A235
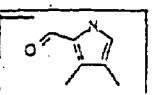
A236
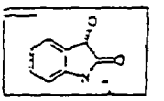
A237
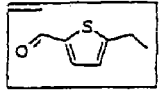
A238
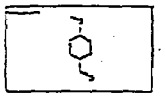
A239
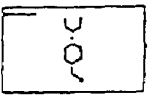
A240
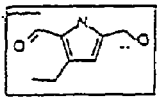
A241
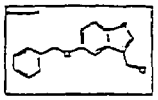
A242
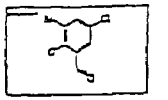
A243
Fig 2. Sheet 17 of 30

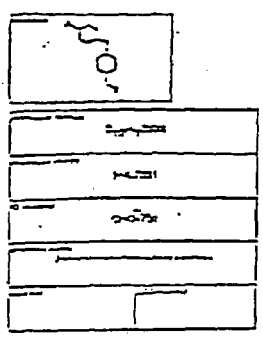
A244
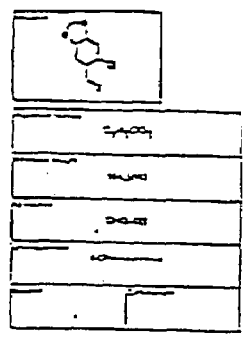
A245
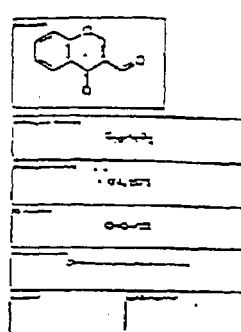
A246
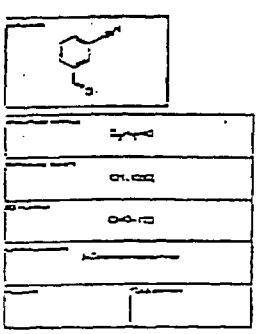
A247
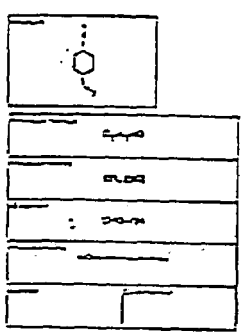
A248
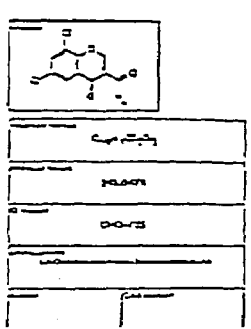
A249
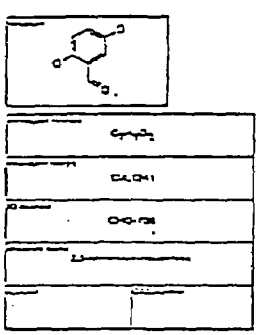
A250
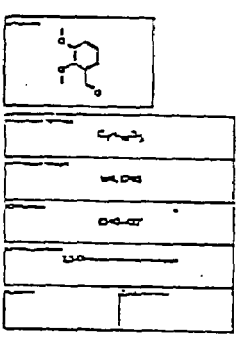
A251
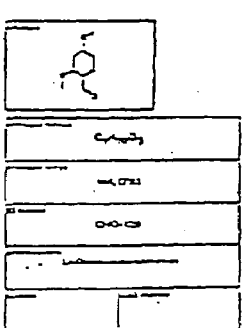
A252
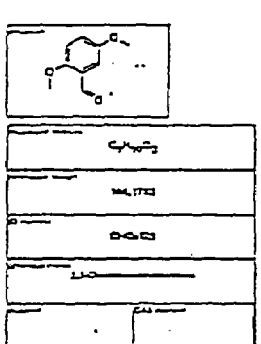
A253
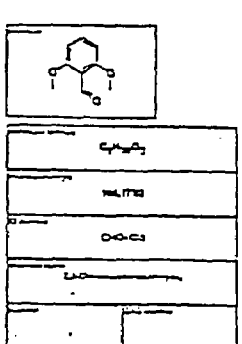
A254
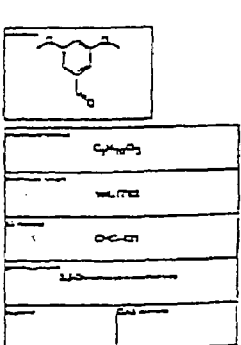
A255
Figure 2, Sheet 18 of 30

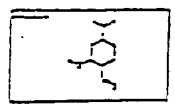 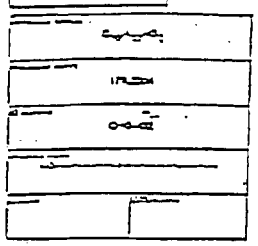
A256
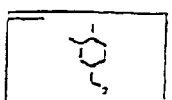 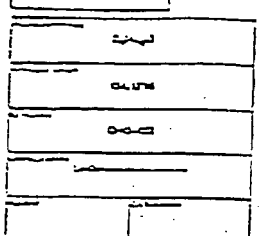
A257
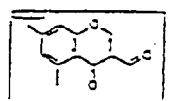 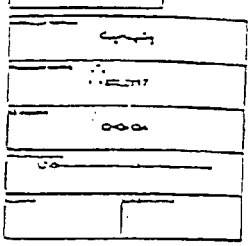
A258
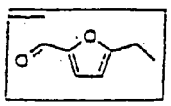 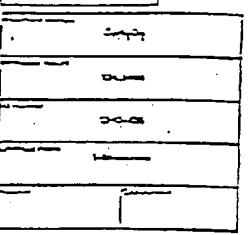
A259
 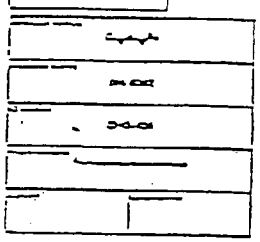
A260
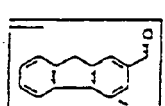 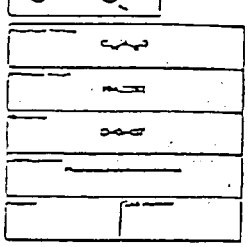
A261
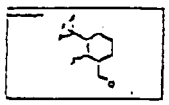 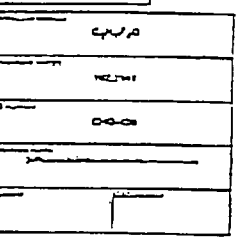
A262
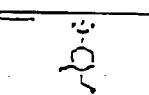 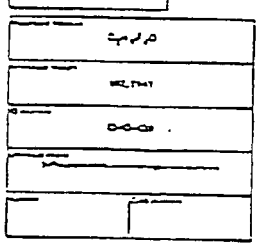
A263
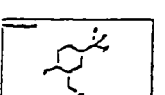 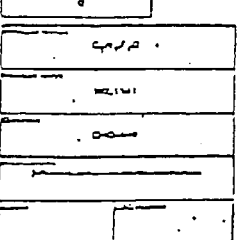
A264
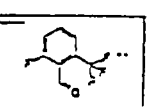 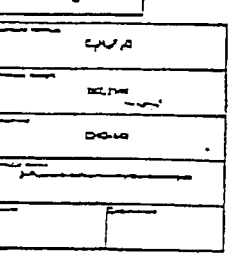
A265
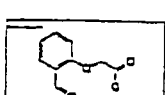 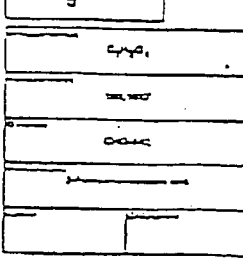
A266
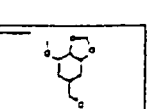 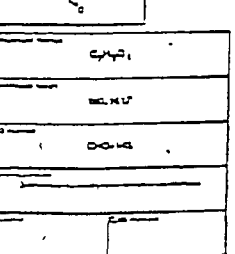
A267
Figure 2. Sheet 19 of 30

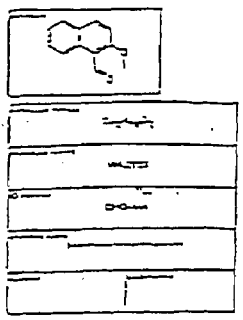
A268
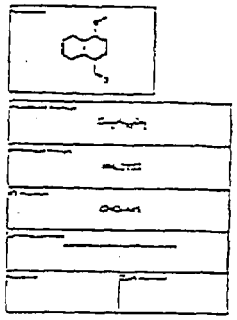
A269
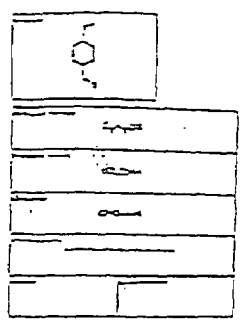
A270
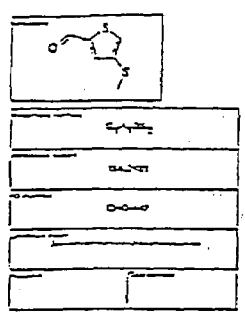
A271
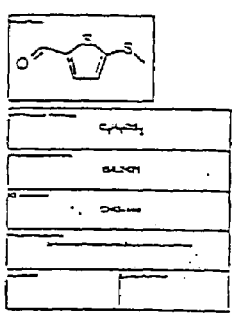
A272
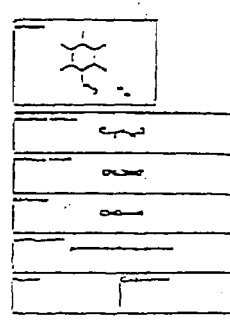
A273
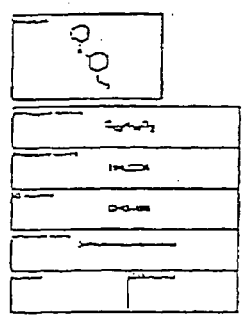
A274
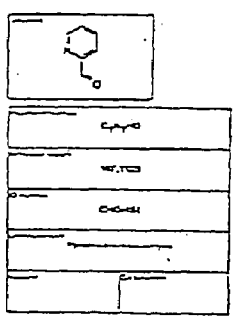
A275
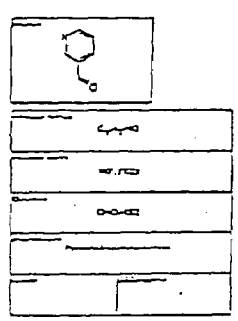
A276
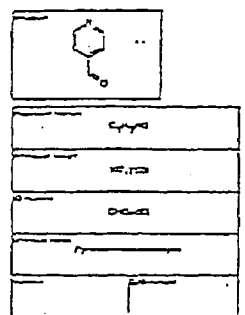
A277
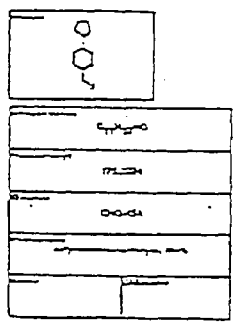
A278
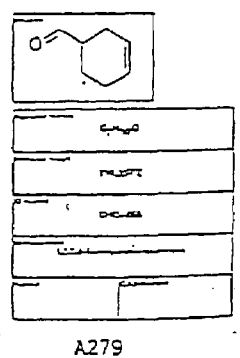
A279
Fig 2. Sheet 20 of 30

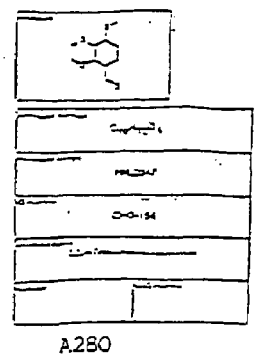
A280
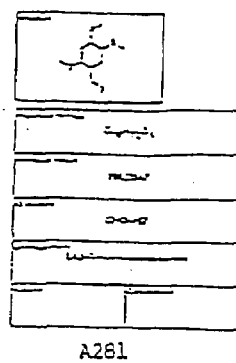
A281
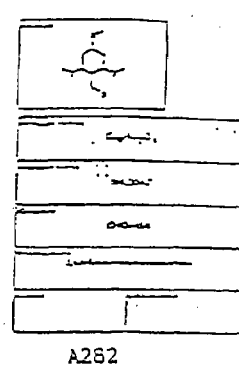
A282
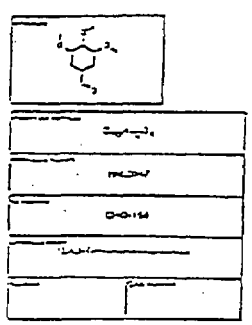
A283
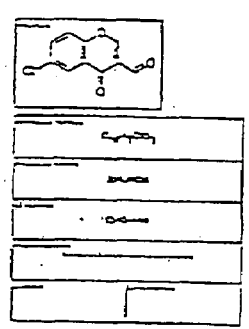
A284
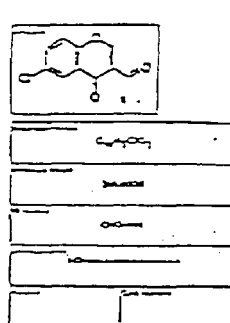
A285
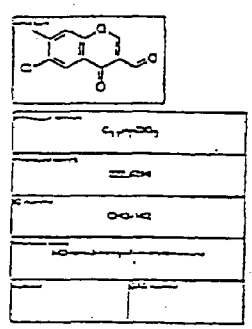
A286
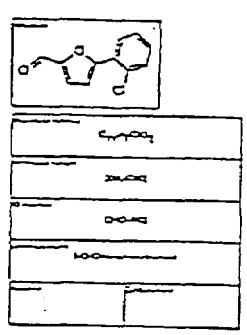
A287
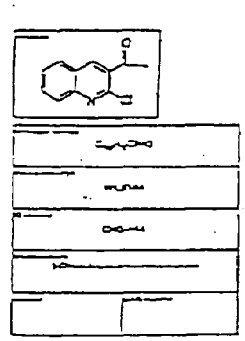
A288
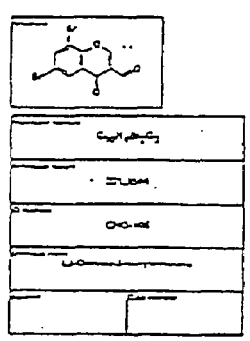
A289
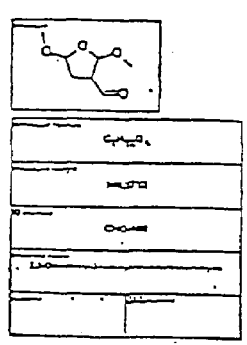
A290
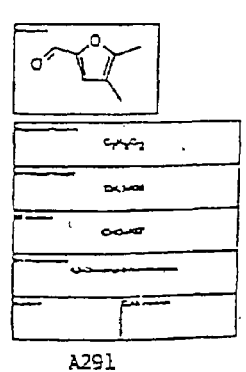
A291
Fig 2. Sheet 21 of 30

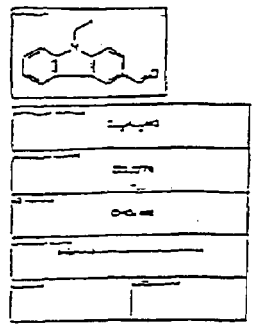
A292
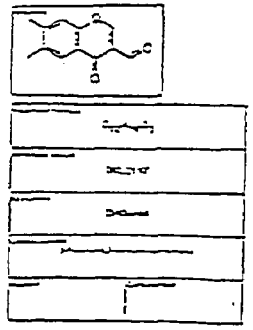
A293
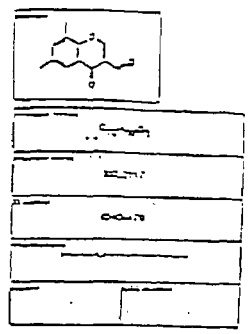
A294
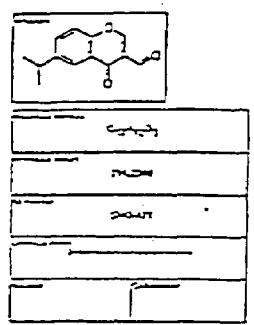
A295
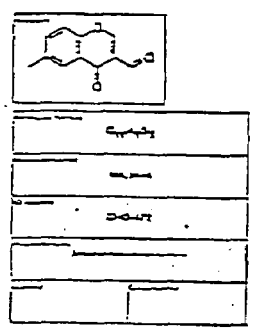
A296
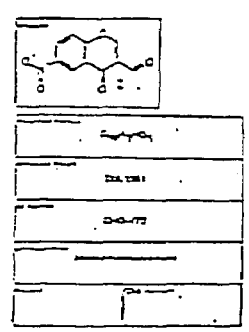
A297
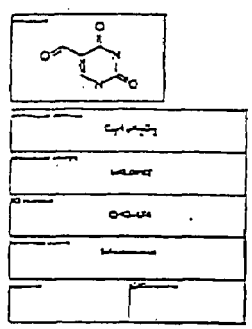
A298
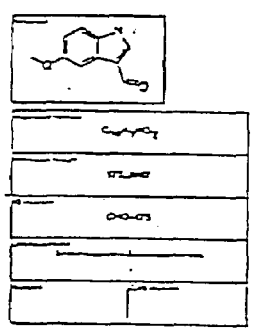
A299
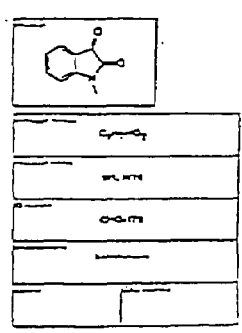
A300
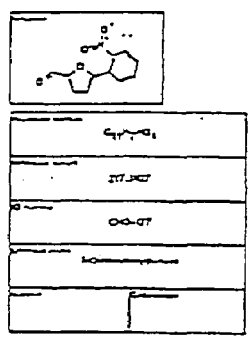
A301
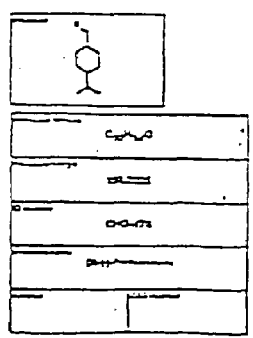
A302
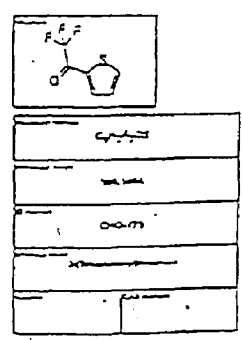
A303
Figure 2, Sheet 22 of 30

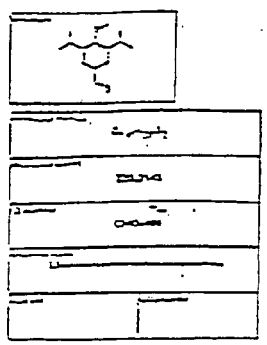
A304
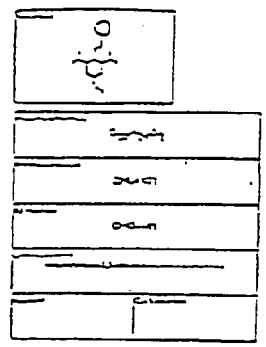
A305
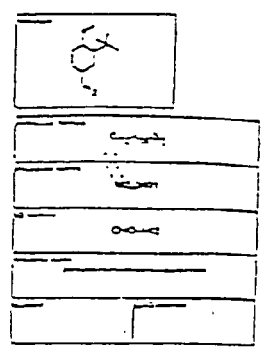
A306
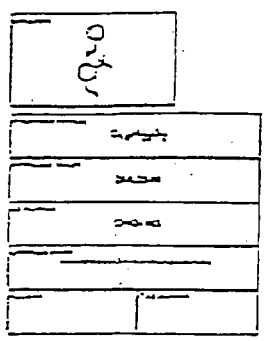
A307
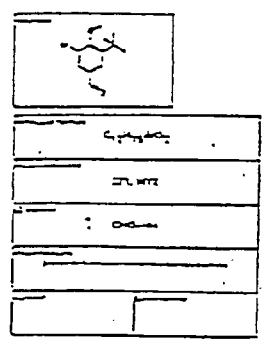
A308
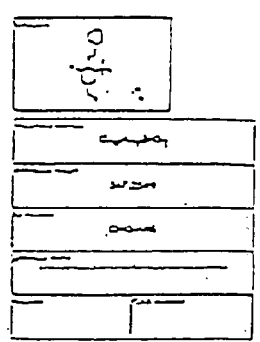
A309
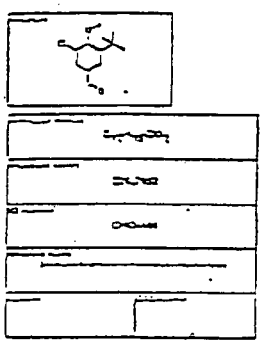
A310
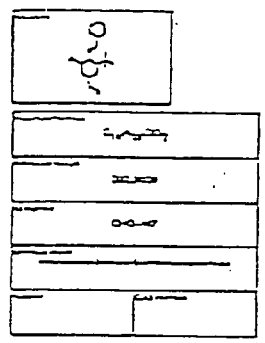
A311
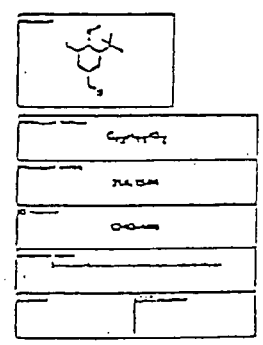
A312
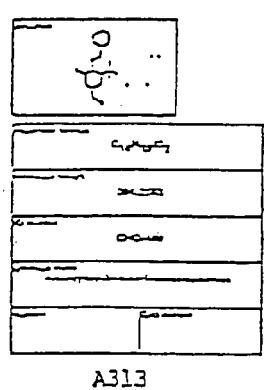
A313
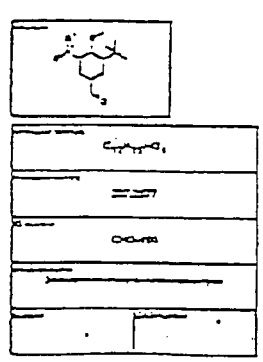
A314
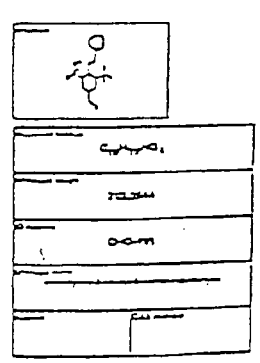
A315
Figure 2, Sheet 23 of 30

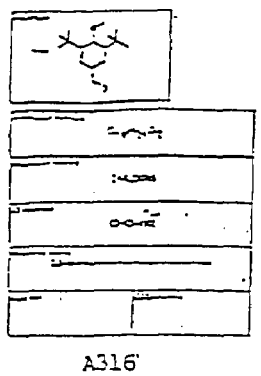
A316
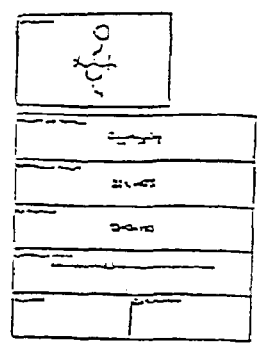
A317
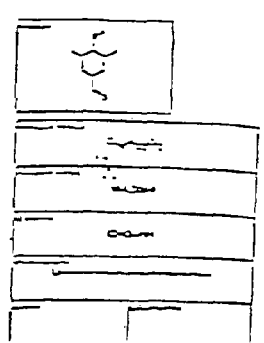
A318
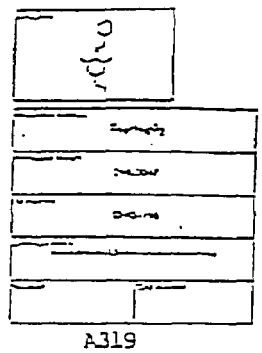
A319
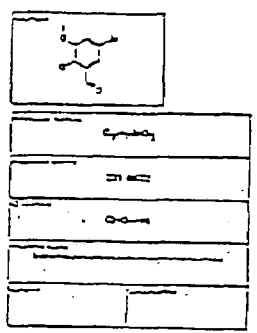
A320
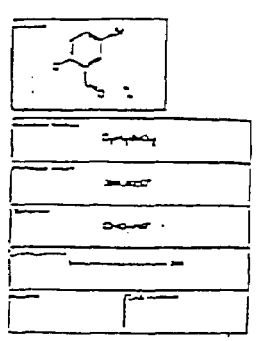
A321
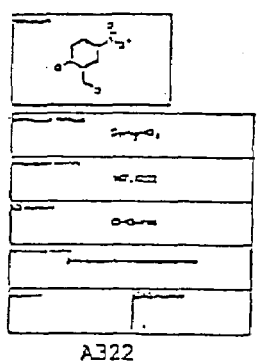
A322
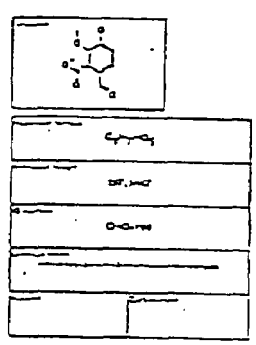
A323
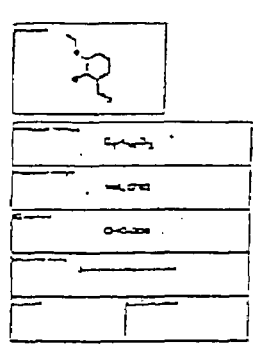
A324
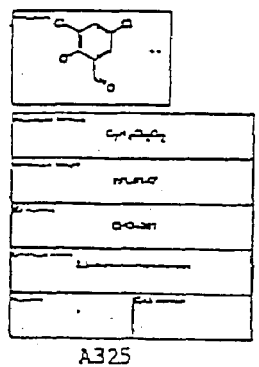
A325
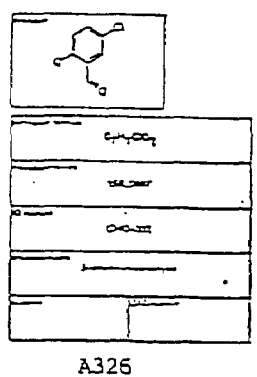
A326
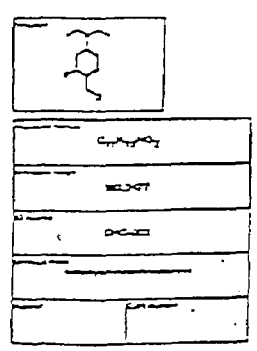
A327
Fig 2. Sheet 24 of 30

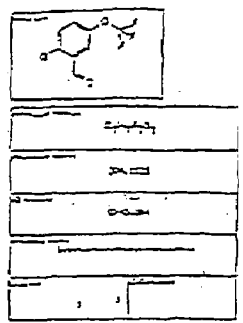
A328
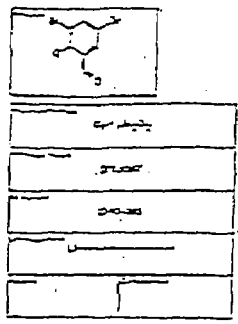
A329
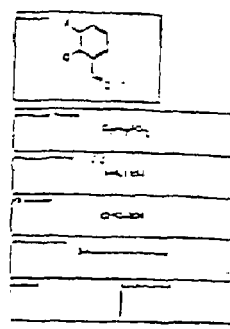
A330
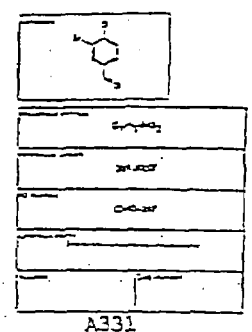
A331
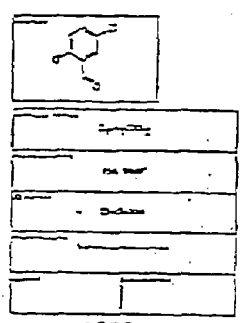
A332
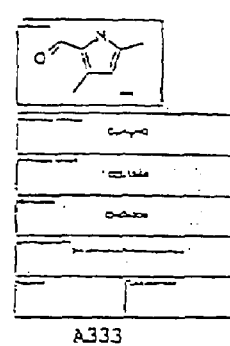
A333
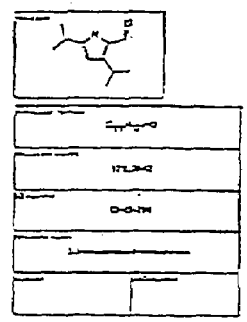
A334
Figure 2, Sheet 25 of 30

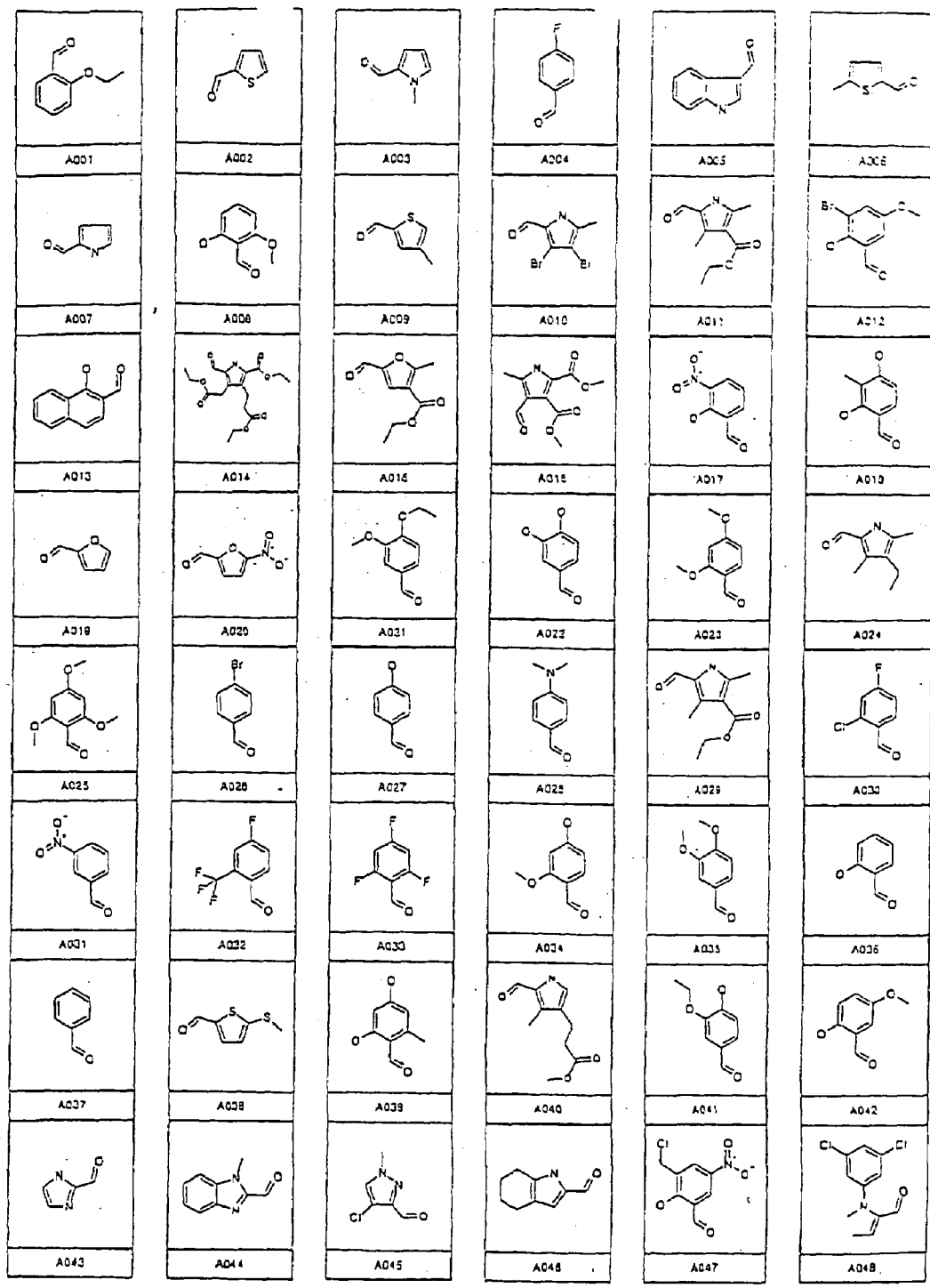
Figure 2, Sheet 26 of 30

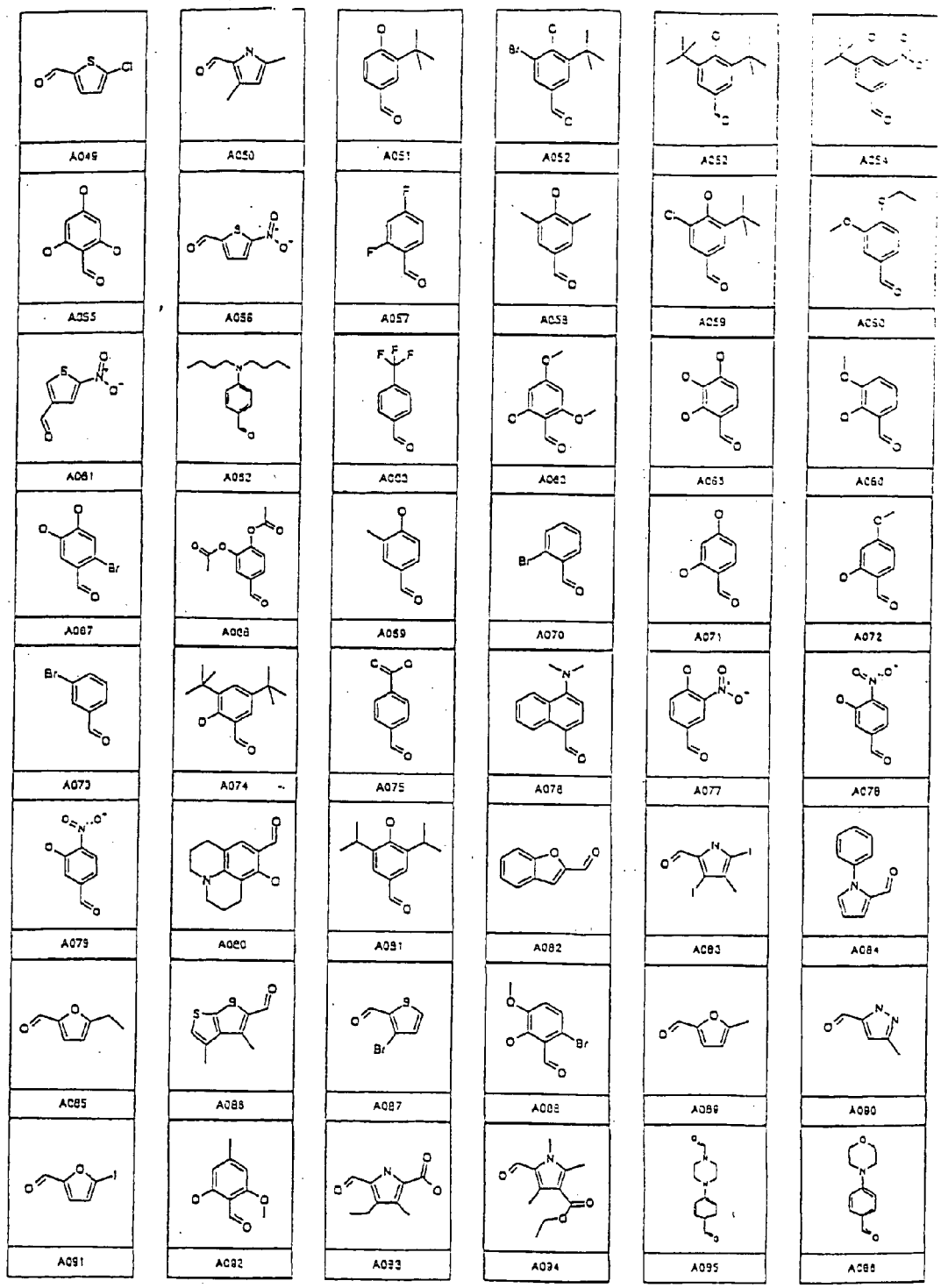
Figure 2, Sheet 27 of 30

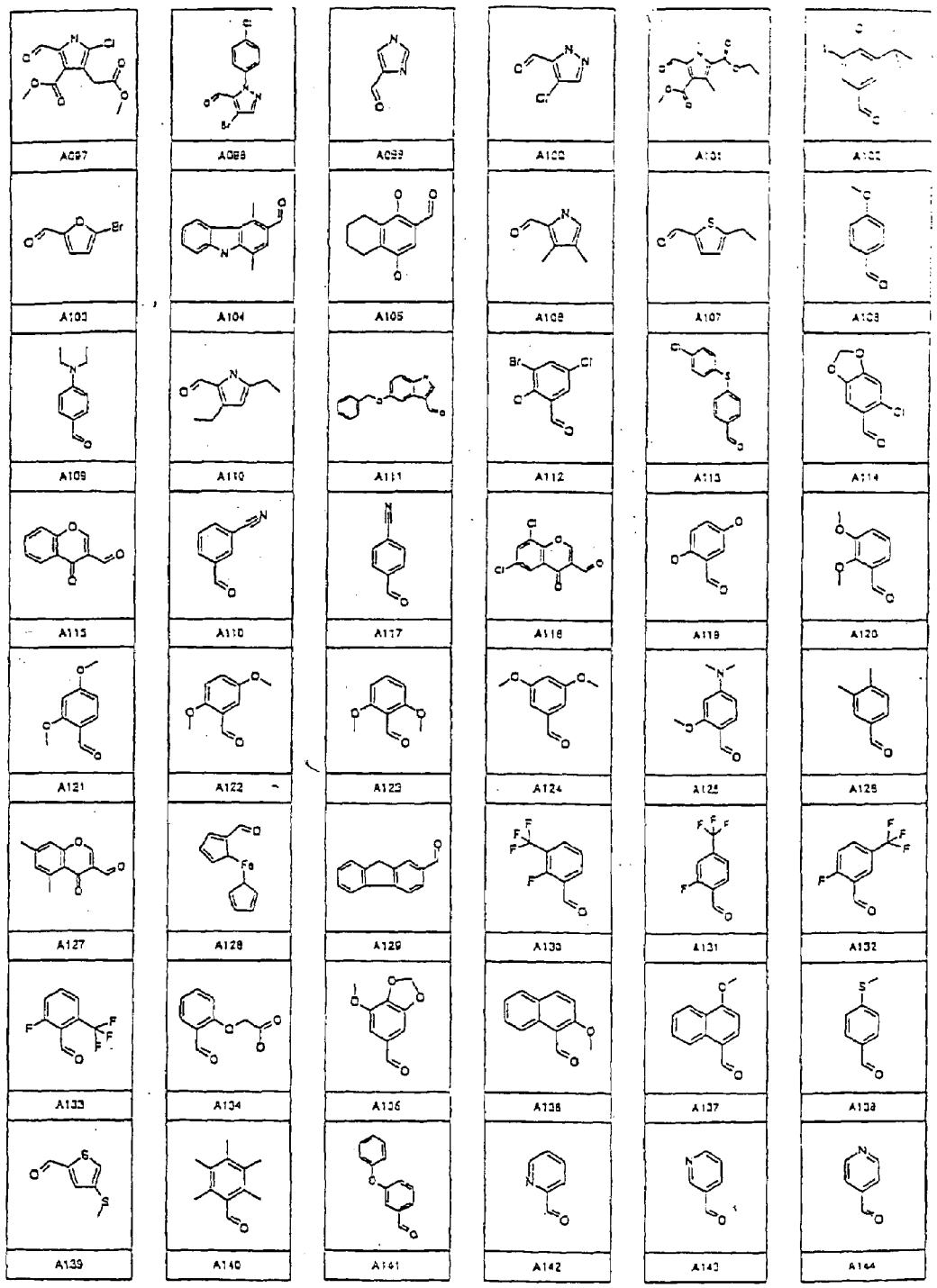
Figure 2, Sheet 28 of 30

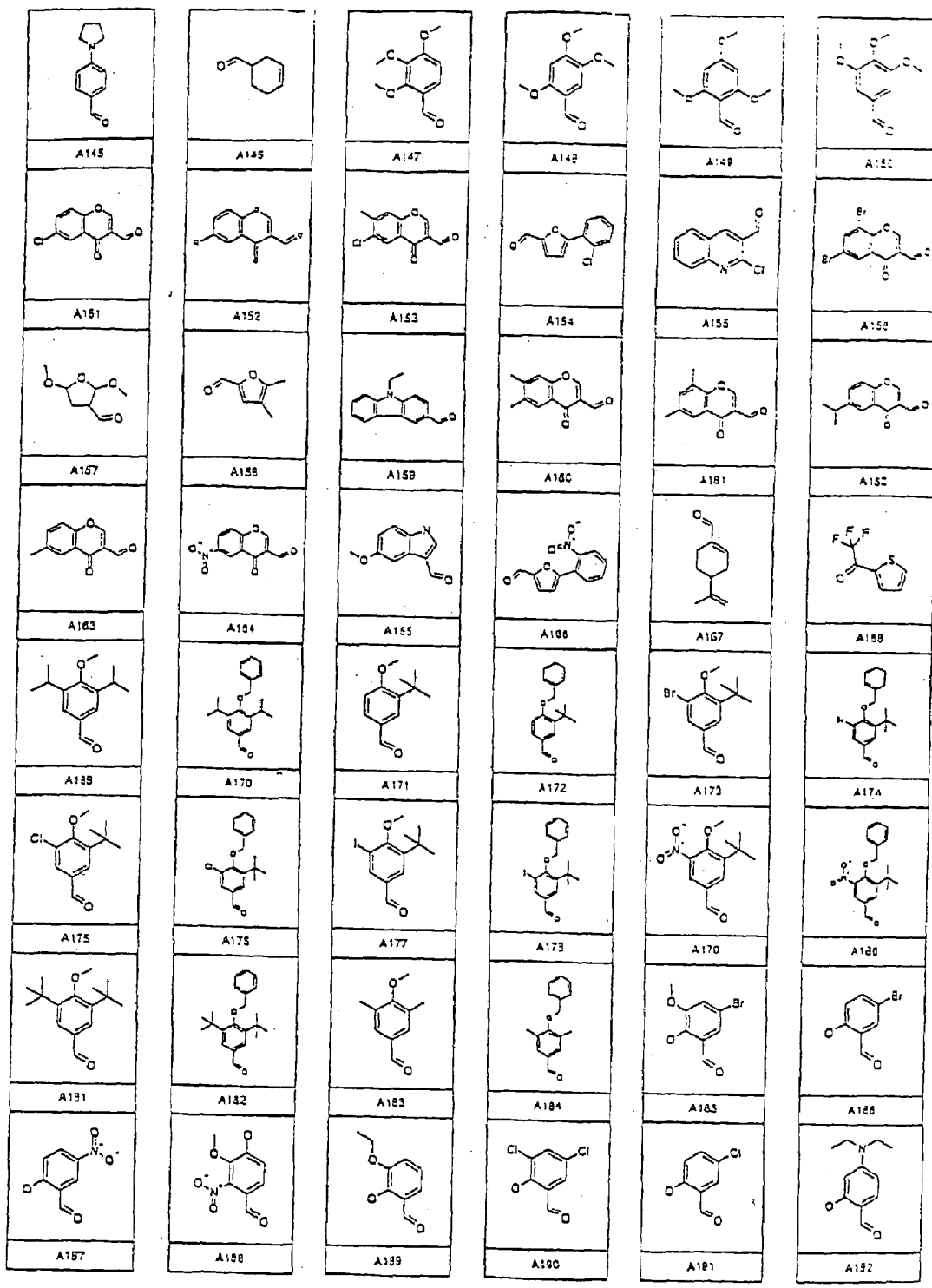
Fig 2. Sheet 29 of 30

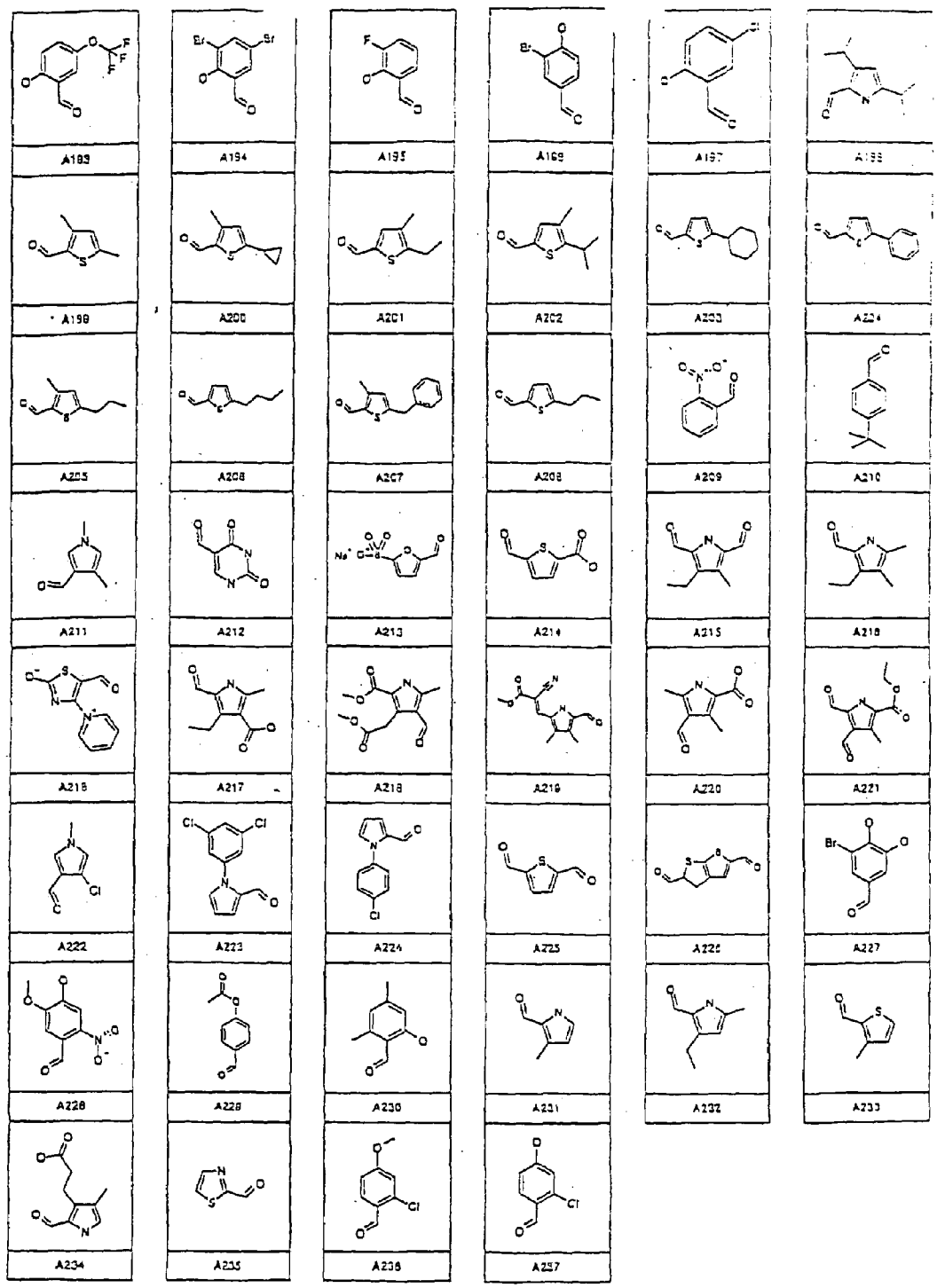
Figure 2, Sheet 30 of 30

INDOLINONE COMBINATORIAL LIBRARIES AND RELATED PRODUCTS AND METHODS FOR THE TREATMENT OF DISEASE

RELATED APPLICATIONS

This application relates to U.S. patent applications Ser. No. 60/031,586, filed Dec. 5, 1996, entitled "FLK Specific Indolinone Compounds and Related Products and Methods for the Treatment of Disease" by McMahon et al. Ser. No. 60/045,566, filed May 5, 1997, entitled "FLK Specific Indolinone Compounds and Related Products and Methods for the Treatment of Disease" by McMahon et al.; Ser. No. 60/032,546, filed Dec. 5, 1996, entitled "HYDROSOLUBLE INDOLINE TYROSINE KINASE INHIBITORS" by McMahon et al.; Ser. No. 60/045,715, filed Dec. 5, 1996, entitled "SUBSTITUTED 3-[(TETRAHYDROINDOLE-2-YL)METHYLENE]-2-INDOLINONE AND 3-[(CYCLOPENTANO-b-PYRROL-2-YL) METHYLENE]-2-INDOLINONE COMPOUNDS" by McMahon et al.; Ser. No. 60/031,588, filed Dec. 5, 1996, entitled "5-SUBSTITUTED INDOLINONE COMPOUNDS AS MODULATORS OF PROTEIN KINASE ACTIVITY" by McMahon et al.; Ser. No. 60/045,714, filed May 5, 1997, entitled "5-SUBSTITUTED INDOLINONE COMPOUNDS AS MODULATORS OF PROTEIN KINASE ACTIVITY" by McMahon et al.; Ser. No. 60/032,547, filed Dec. 5, 1996, entitled "SUBSTITUTED 3-[(TETRAHYDROINDOLE-2-YL)METHYLENE]-2-INDOLINONE AND 3-[(CYCLOPENTANO-b-PYRROL-2-YL) METHYLENE]-2-INDOLINONE COMPOUNDS" by McMahon et al.; Ser. No. 60/046,843, filed May 5, 1997, entitled "HYDROSOLUBLE INDOLINE TYROSINE KINASE INHIBITORS" by McMahon et al.; Ser. No. 60/031,585, filed Dec. 5, 1996, entitled "SUBSTITUTED 3-[(INDOLE-3-YL)METHYLENE])-2-INDOLINONE COMPOUNDS" by McMahon et al.; Ser. No. 60/031,565, filed May 5, 1997, entitled "SUBSTITUTED 3-[(INDOLE-3-YL)METHYLENE]-2-INDOLINONE COMPOUNDS" by McMahon et al. and this application also relates to U.S. patent application Ser. No. 08/702,232, filed Aug. 23, 1996, entitled "Indolinone Combinatorial Libraries and Related Products and Methods for the Treatment of Disease" by Tang et al. which is a continuation-in-part application of U.S. patent applications Ser. No. 08/655,225, filed Jun. 5, 1996, entitled "3-(2'Halobenzylidenyl)-2-Indoline Compounds for the Treatment of Disease" by Tang et al.; Ser. No. 08/655,226, filed Jun. 5, 1996, entitled "3-(4'-Dimethylaminobenzylidenyl)-2-Indolinone and Analogues Thereof for the Treatment of Disease" by Tang et al.; Ser. No. 08/655,223, filed Jun. 5, 1996, entitled "3-Heteroaryl-2-Indolinone Compounds for the Treatment of Disease" by Tang et al.; Ser. No. 08/655,224, filed Jun. 5, 1996, entitled "3-(2'-Alkoxybenzylidenyl)-2-Indolinone and Analogues Thereof for the Treatment of Disease" by Tang et al.; and, Ser. No. 08/659,191, filed Jun. 5, 1996, entitled "3-(4'Bromobenzylindenyl)-2-Indolinone and Analogues Thereof for the Treatment of Disease" by Tang et al., all of which are continuations-in-part of U.S. patent application Ser. No. 08/485,323, filed Jun. 7, 1995, entitled "Benzylidene-Z-Indoline Compounds for the Treatment of Disease" by Tang et al. all of which are incorporated herein by reference in their entirety, including any drawings.

INTRODUCTION

The present invention relates to novel compounds capable of modulating, regulating and/or inhibiting protein kinase signal transduction. The present invention is also directed to methods of regulating, modulating or inhibiting protein kinases, whether of the receptor or non-receptor class, for the prevention and/or treatment of disorders related to unregulated protein kinase signal transduction, including cell proliferative and metabolic disorders.

BACKGROUND OF THE INVENTION

The following description of the background of the invention is provided to aid in understanding the invention, but is not admitted to be or describe prior art to the invention.

Protein kinases and protein phosphatases regulate a wide variety of cellular processes including metabolism, cell proliferation, cell differentiation, and cell survival by participating in signal transduction pathways. Alterations in the cellular function of a protein kinase or protein phosphatase can give rise to various diseased states in an organism. For example, many types of cancer tumors are associated with increases in the activity of specific protein kinases. Cell and tissue degeneration can also be associated with decreases inthe activity of particular protein kinases.

Cellular signal transduction is a fundamental mechanism whereby extracellular stimuli are relayed to the interior of cells. One of the key biochemical mechanisms of signal transduction involves the reversible phosphorylation of proteins. Phosphorylation of amino acids regulates the activity of mature proteins by altering their structure and function.

Phosphate most often resides on the hydroxyl moiety of serine, threonine, or tyrosine amino acids in proteins. Enzymes that mediate phosphorylation of cellular effectors fall into two classes. While protein phosphatases hydrolyze phosphate moieties from phosphoryl protein substrates, protein kinases transfer a phosphate moiety from adenosine triphosphate to protein substrates. The converse functions of protein kinases and protein phosphatases balance and regulate the flow of signals in signal transduction processes.

Protein kinases are divided into two groups—receptor and non-receptor type proteins. Receptor protein kinases comprise an extracellular region, a transmembrane region, and an intracellular region. Part of the intracellular region of receptor protein kinases harbors a catalytic domain. While non-receptor protein kinases do not harbor extracellular or transmembrane regions, they do comprise a region similar to the intracellular regions of their receptor counterparts.

Protein kinases are divided further into three classes based upon the amino acids they act upon. Some incorporate phosphate on serine or threonine only, some incorporate phosphate on tyrosine only, and some incorporate phosphate on serine, threonine, and tyrosine.

In an effort to discover novel treatments for diseases, biomedical researchers and chemists have designed, synthesized, and tested molecules that inhibit the function of protein kinases. Some small organic molecules form a class of compounds that modulate the function of protein kinases.

The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules that potently inhibit only specific protein kinases. Indolinone synthesis, methods of testing the biological activity of indolinones, and inhibition patterns of some indolinone derivatives are described in International Patent Publication No. WO96/40116, published Dec. 19, 1996 entitled "Benzylidene-Z-Indolinone Compounds for the Treatment of Disease" by Tang et al. and International Patent Publication No. WO 96/22976, published Aug. 1, 1996 by Ballinari et al., both of which are incorporated herein by reference in their entirety, including any drawings.

Despite the significant progress that has been made in developing indolinone based pharmaceuticals, there remains a need in the art to identify the particular structures and substitution patterns that cause inhibition of particular protein kinases and other specified biological activities.

SUMMARY OF THE INVENTION

The present invention relates to organic molecules capable of modulating, regulating and/or inhibiting protein kinase signal transduction. Such compounds are useful for the treatment of diseases related to unregulated protein kinase signal transduction, including cell proliferative diseases such as cancer, atherosclerosis, arthritis and restenosis and metabolic diseases such as diabetes. The protein kinases effected include, but are not limited to Flk, FGFR, PDGFR, and raf.

The present invention features indolinone compounds that potently inhibit protein kinases and related products and methods. Inhibitors specific to the FLK protein kinase can be obtained by adding chemical substituents to the 3-[(indole-3-yl)methylene]-2-indolinone, in particular at the 1' position of the indole ring. Indolinone compounds that specifically inhibit the FLK and platelet derived growth factor protein kinases can harbor a tetrahydroindole or cyclopentano-b-pyrrol moiety. Indolinone compounds that are modified with substituents, particularly at the 5 position of the oxindole ring, can effectively activate protein kinases. This invention also features novel hydrosoluble indolinone compounds that are tyrosine kinase inhibitors and related products and methods.

The compounds of the invention represent a new generation of potential therapeutics for diseases caused by one or more non-functional protein kinases. Neuro-degenerative diseases fall into this class of diseases, including, but not limited to Parkinson's Disease and Alzheimers disease. The compounds can be modified such that they are specific to their target or targets and will subsequently cause few side effects and thus represent a new generation of potential cancer therapeutics. These properties are significant improvements over the currently utilized cancer therapeutics that cause multiple side effects and deleteriously weaken patients.

It is believed the compounds of the invention will minimize and obliterate solid tumors by specifically inhibiting the activity of the FLK protein kinase, or will at least modulate or inhibit tumor growth and/or metastases. The FLK protein kinase regulates proliferation of blood vessels during angiogenesis. Increased rates of angiogenesis accompany cancer tumor growth in cells as cancer tumors must be nourished by oxygenated blood during growth. Therefore, inhibition of the FLK protein kinase and the corresponding decreases in angiogenesis will starve tumors of nutrients and most likely obliterate them.

While a precise understanding of the mechanism by which compounds inhibit PTKs (e.g., the fibroblast growth factor receptor 1 [FGFR1]) is not required in order to practice the present invention, the compounds are believed to interact with the amino acids of the PTKs' catalytic region. PTKs typically possess a bi-lobate structure, and ATP appears to bind in the cleft between the two lobes in a region where the amino acids are conserved among PTKs; inhibitors of PTKs are believed to bind to the PTKs through non-covalent interactions such as hydrogen bonding, Van der Waals interactions, and ionic bonding, in the same general region that ATP binds to the PTKs. More specifically, it is thought that the oxindole component of the compounds of the present invention binds in the same general space occupied by the adenine ring of ATP. Specificity of an indolinone PTK inhibitor for a particular PTK may be conferred by interactions between the constituents around the oxindole core with amino acid domains specific to individual PTKs. Thus, different indolinone substitutents may contribute to preferential binding to particular PTKs. The ability to select those compounds active at different ATP (or other nucleotide) binding sites makes them useful in targeting any protein with such a site, not only protein tyrosine kinases, but also serine/threonine kinases and protein phosphatases. Thus, such compounds have utility for in vitro assays on such proteins and for in vivo therapeutic effect through such proteins. In one aspect the invention features a combinatorial library of indolinone compounds. The library includes a series of at least ten (preferably at least 50–100, more preferably at least 100–500, and most preferably at least 500–5,000) indolinones that can be formed by reacting an oxindole compound with an aldehyde. In preferred embodiments the indolinones in the library can be formed by reacting a type A oxindole with a type B aldehyde. Type A oxindoles and type B aldehydes are shown in FIGS. 1 and 2 respectively (and Tables 11 and 12 respectively), as explained in detail below. As can be seen, in the figures the oxindoles are labeled 01, 02, 03, . . . and the aldehydes are named A1, A2, A3, . . . . Thus, one can readily appreciate that the combinatorial library could include any and all combinations of oxindoles and aldehydes, including the indolinones resulting from 01 and A1, 01 and A2, 01 and A3, 02 and A1, 02 and A2, 02 and A3, 03 and A1, 03 and A2, 03 and A3 and so on. Similarly, the indolinones in the library can be formed by any combination of the oxindoles in Table 11 with any of the aldehydes listed in FIG. 2 or Table 12. Finally, the indolinones may also, of course, come from any combination of aldehydes listed in Table 12 with any oxindoles from FIG. 1 or Table 11.

The term "combinatorial library" refers to a series of compounds. In the present case, the combinatorial library contains a series of indolinone compounds that can be formed by reacting an oxindole and an aldehyde. A wide variety of oxindoles and aldehydes may be used to create the library of indolinones.

The term "indolinone" is used as that term is commonly understood in the art and includes a large subclass of substituted or unsubstituted compounds that are capable of being synthesized from analdehyde moiety and an oxindol moiety, such as the compounds shown below.

The term "type A oxindole" is meant to include any and all of the oxindoles set forth in FIG. 1 and Table 11. Oxindoles, as that term is used herein, typically have the structure set forth below:

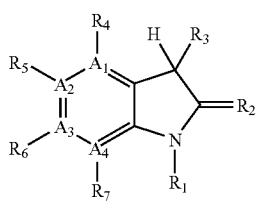

(I)

wherein, (a) $A_1$, $A_2$, $A_3$, and $A_4$ are independently carbon or nitrogen;

(b) $R_1$ is hydrogen or alkyl;

(c) $R_2$ is oxygen or sulfur;

(d) $R_3$ is hydrogen;

(e) $R_4$, $R_5$, $R_6$ and $R_7$ (i) are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' or (ii) any two adjacent $R_4$, $R_5$, $R_6$, and $R_7$ taken together form a fused ring with the aryl portion of the oxindole-based portion of the indolinone.

It is to be understood that when $A_1$, $A_2$, $A_3$, and $A_4$ is nitrogen or sulfur that the corresponding $R_4$, $R_5$, $R_6$, or $R_7$ is nothing and that the corresponding bond shown in structure I does not exist.

Examples of oxindoles having such fused rings (as described in (e) (ii) above) are shown in FIG. 1, compounds 044, 045, 047, 048, 050, 051, 052, 053, 055, 056, 058, 059, 061, 062, 064, 066, 067, 069, 070, and 073. Other examples of suitable fused rings include the following:

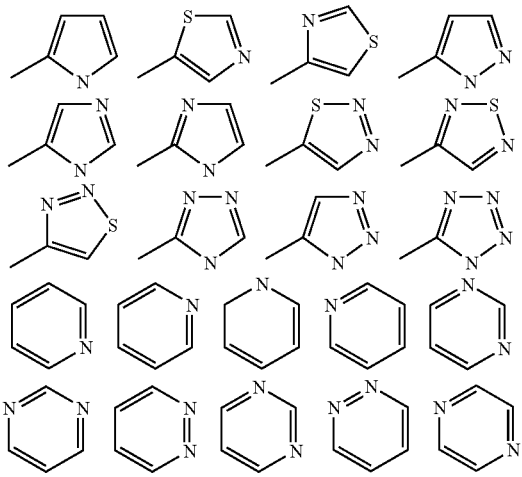

The six membered rings shown above also exemplify possible A rings in the structures II, III and IV.

The term "type B aldehyde" includes any and all of the aldehydes set forth in FIG. 2 and Table 11. The term "aldehyde" is used as is commonly understood in the art to include substituted and unsubstituted aldehydes of the structure $R_dCHO$ where $R_d$ can be a wide variety of substituted or unsubstituted groups such as alkyl and aryl.

In yet another aspect, the invention provides a method of synthesizing an indolinone by reacting a type A oxindole with a type B aldehyde. The method of making the indolinones of the present invention may involve creating a combinatorial library of compounds as described above, testing each compound in biological assays such as those described herein, selecting one or more suitable compounds and synthesizing the selected compound or compounds.

Also featured is an indolinone compound having formula II or III:

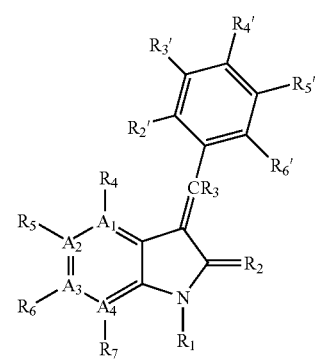

(II)

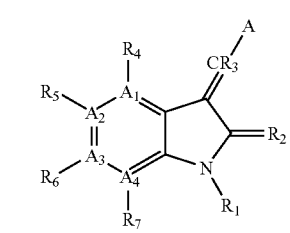

(III)

wherein:

(a) $A_1$, $A_2$, $A_3$, and $A_4$ are independently carbon or nitrogen;

(b) $R_1$ is hydrogen or alkyl;

(c) $R_2$ is oxygen or sulfur;

(d) $R_3$ is hydrogen;

(e) $R_4$, $R_5$, $R_6$, and $R_7$ (i) are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' or (ii) any two adjacent $R_4$, $R_5$, $R_6$, and $R_7$ taken together form a fused ring with the aryl ring of the oxindole-based portion of the indolinone;

(f) $R_2'$, $R_3'$, $R_4'$, $R_5'$, and $R_6'$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

(g) n is 0, 1, 2, or 3;

(h) R is hydrogen, alkyl or aryl;

(i) R' is hydrogen, alkyl or aryl; and (j) A is a five membered heteroaryl ring selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, optionally substituted at one or more positions with alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R or CONRR'.

As used herein, the term "compound" is intended to include pharmaceutically acceptable salts, esters, amides, prodrugs, isomers and metabolites of the base compound.

In preferred embodiments of structure III, the A substituent may be a five membered heterocycle of formula IV shown below:

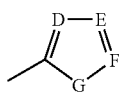

(IV)

wherein D, E, F, and G are nitrogen, carbon or sulfur atoms. The specific juxtaposition of groups D–G is limited to examples of heterocyclic groups known in the chemistry arts, such as the fused rings referred to above and all of which may be optionally substituted as described above in paragraph (j).

In preferred embodiments, the aryl ring ("the A ring") of the oxindole-derived portion of the indolinone (i.e., the ring shown in structures II and III with A$_1$, A$_2$, A$_3$, and A$_4$) has a polar substituent, preferably selected from the group consisting of NH$_2$, COOH, SO$_3$H, Br, Cl, I, F, COCH$_2$CH$_2$COOH, COCH$_2$Cl, piperazine, and CH$_2$CH$_2$NH$_2$ at the 4, 5, 6, and 7 carbon atom positions (identified by substituents R$_4$, R$_5$, R$_6$, and R$_7$ respectively in structures V and VI), most preferably hydrophilic groups such as NH$_2$, COOH, SO3, COCH$_2$CH$_2$COOH, piperazine and CH$_2$CH$_2$NH$_2$.

One approach to choosing target inhibitors of the FGFR (a protein kinase receptor linked to various disorders, such as Pfeiffer, Jackson-Weiss and Cruzon syndromes; dysplasias and hypochondroplasia; dwarfism; bone dysplasia; and developmental disorders involves selecting target compounds with a substituent on the A ring that mimics the triphosphate of ATP and thereby increases the affinity of target compounds for the active-site of the FGFR. Hydrophillic groups may act to mimic the triphosphate at ATP, and also to improve the solubility of the final inhibitor. Without being bound to any theory, it appears that the trans form of the indolinones is generally a more favorable form for FGFR inhibitors.

Amine-based substituents at positions 4, 5, and 6 at the A ring of structures II and III are a preferred class of substituents and an especially preferred class are amines of the structure:

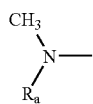

wherein R$_a$ is CO(CH$_2$)$_2$COOH, aryl, alkyl, or contains COOH, OH, or NH$_2$. These types of groups provide steric hindrance in order to force the isomer into a trans conformation which may be a favored property of FGFR inhibition and acts as a linker to a hydrophillic group.

Another favored class of substituents on the aryl ring of structures II and III includes piperazine type substituents of the structure:

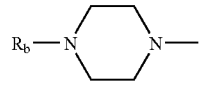

wherein R$_b$ is preferably a negatively charged group, such as a negatively charged alkyl or acyl.

Yet another preferred class of substituents for the aryl ring of structures II and III are C-COR groups of the formula:

wherein R$_c$ is a hydrophilic or negatively charged group, preferably at the 5 and/or 6 positions of the A ring of structures II and III, such as amide, ester, CH$_2$CH$_2$COOH, CH$_2$Cl, or piperazine. R$_c$ could also be linked to the aryl ring by a sp3 carbon or could be attached as R$_c$O$_3$S—.

Yet another preferred set of substituents on the aryl ring are fused heterocyclic rings which can be synthesized by acylation of the arylamine followed by alkylation of the heterocyclic ring systems. Examples of several such compounds are set forth in FIG. 1, compounds 044, 045, 047, 048, 050, 051, 052, 053, 055, 056, 058, 059, 061, 062, 064, 066, 067, 069, 070, and 073.

In another aspect, the invention features a 3-[(indole-3-yl)methylene]-2-indolinone compound having a substituent at the 1' position of the indole ring. The substituent at the 1' position of the indole ring is selected from the group consisting of (a) alkyl that is optionally substituted with a monocyclic or bicyclic five, six, eight, nine, or ten membered heterocyclic ring, where the ring is optionally substituted with one or more halogen, or trihalomethyl substituents;

(b) five, six, eight, nine, or ten membered monocyclic or bicyclic heterocyclic ring, where the ring is optionally substituted with one or more halogen or trihalomethyl substituents;

(c) an aldehyde or ketone of formula —CO—R12, where R12 is selected from the group consisting of hydrogen, alkyl, and a five or six membered heterocyclic ring;

(d) a carboxylic acid of formula —(R$_{13}$)$_n$—COOH or ester of formula —(R$_{14}$)$_m$—COO—R$_{15}$, where R$_{13}$, R$_{14}$, and R$_{15}$ are independently selected from the group consisting of alkyl and a five or six membered heterocyclic ring and m and n are independently 0 or 1;

(e) a sulfone of formula —(SO$_2$)—R$_{16}$, where R$_{16}$ is selected from the group consisting of alkyl and a five or six membered heterocyclic ring, where the ring is optionally substituted with an alkyl moiety;

(f) —(R$_{17}$)$_n$-(indole-1-yl) or —(R$_{18}$) m-CHOH—(R$_{19}$)$_p$-(indole-1-yl), where the indol moiety is optionally substituted where R$_{17}$, R$_{18}$, and R$_{19}$ are alkyl, and where m, n, and p are independently 0 or 1; and (g) taken together with a 2' substituent of the indole ring forms a five or six membered heterocyclic ring.

The term "alkyl" refers to a straight-chain, branched, or cyclic saturated aliphatic hydrocarbon. The alkyl group is preferably 1 to 10 carbons, more preferably a lower alkyl of from 1 to 7 carbons, and most preferably 1 to 4 carbons. Typical alkyl groups include methyl, ethyl, propyl, isopropyl, butyl, isobutyl, tertiary butyl, pentyl, hexyl and the like. The alkyl group may be substituted and some typical alkyl substituents include hydroxyl, cyano, alkoxy, oxygen, sulfur, nitroxy, halogen, —N(CH$_3$)$_2$, amino, and —SH.

The term "methyl" refers to a saturated alkyl moiety of one carbon. The term "ethyl" refers to a saturated alkyl moiety of two carbons. The term "propyl" refers to a saturated alkyl moiety of three carbons. The term "butyl" refers to a saturated alkyl moiety of four carbons. The term "pentyl" refers to a saturated alkyl moiety of five carbons.

The term "aryl" refers to an aromatic group which has at least one ring having a conjugated pi electron system and includes both carbocyclic aryl (e.g. phenyl) and heterocyclic aryl groups (e.g. pyridine). Aryl moieties include monocyclic, bicyclic, and tricyclic rings, where each ring has preferably five or six members. The aryl moiety may be substituted and typical aryl substituents include halogen, trihalomethyl, hydroxyl, —SH, —OH, —NO$_2$, amine, thioether, cyano, alkoxy, alkyl, and amino.

The terms "heterocycle" or "heterocyclic" refer to compounds that form a ring and contain up to four hetero atoms, the remainder of the atoms forming the ring being carbon. Thus, for example, each ring in the structure can contain zero, one, two, three, or four nitrogen, oxygen, or sulfur atoms within the ring. The ring can preferably be saturated with hydrogen atoms, more preferably harbor one or more unsaturations, and most preferably contain an aryl conjugated pi electron system. The rings are preferably eleven, twelve, thirteen, or fourteen membered rings, more preferably eight, nine, or ten membered rings, and most preferably five or six membered rings. Examples of such rings are furyl, thienyl, pyrrol, imidazolyl, indolyl, pyridinyl, thiadiazolyl, thiazolyl, piperazinyl, dibenzfuranyl, dibenzthienyl. The heterocyclic rings of the invention may be optionally substituted with one or more functional groups which are attached commonly to such rings, such as, e.g., hydroxyl, bromo, fluoro, chloro, iodo, mercapto or thio, cyano, cyanoamido, alkylthio, heterocycle, aryl, heteroaryl, carboxyl, oxo, alkoxycarbonyl, alkyl, alkenyl, nitro, amino, alkoxyl, amido, and the like. Structures of some preferred heterocyclic rings are the fused rings that have been shown above.

The term "aldehyde" refers to a chemical moiety with formula —(R)$_n$—CHO, where R is selected from the group consisting of alkyl or aryl and n is 0 or 1.

The term "ketone" refers to a chemical moiety with formula —(R)$_n$—CO—R', where R and R' are selected from the group consisting of alkyl or aryl and n is 0 or 1.

The term "carboxylic acid" refers to a chemical moiety with formula —(R)$_n$—COOH, where R is selected from the group consisting of alkyl or aryl and n is 0 or 1.

The term "ester" refers to a chemical moiety with formula —(R)$_n$—COOR', where R and R' are independently selected from the group consisting of alkyl or aryl and n is 0 or 1.

The term "sulfone" refers to a chemical moiety with formula —SO$_2$—R, where R is selected from the group consisting of alkyl or aryl.

The term "pharmaceutically acceptable salt" refers to a formulation of a compound that does not cause significant irritation to an organism and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic. acid, ethanesulfonic acid, p-toluenesulfonic acid, salicylic acid and the like.

The term "prodrug" refers to an agent that is converted into the parent drug in vivo. Prodrugs may be easier to administer than the. parent drug in some situations. For example, the prodrug may be bioavailable by oral administration but the parent is not, or the prodrug may improve solubility to allow for intravenous administration.

A preferred embodiment of the invention relates to compound of the following formula,

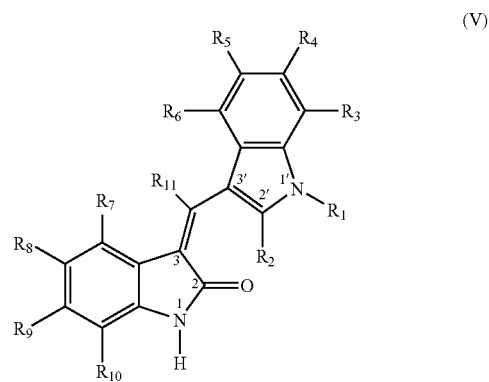

(V)

where (a) R$_1$ as is described above for the substituent at the 1' position of the indole ring;

(b) R$_2$, R$_3$, R$_4$, R$_5$, and R$_6$ are independently selected from the group consisting of, (i) hydrogen;

(ii) alkyl that is optionally substituted with a monocyclic or bicyclic five, six, eight, nine, or ten membered heterocyclic ring, where the ring is optionally substituted with one or more halogen, or trihalomethyl substituents;

(iii) five, six, eight, nine, or ten membered monocyclic or bicyclic heterocyclic ring, where the ring is optionally substituted with one or more halogen or trihalomethyl substituents;

(iv) a ketone of formula —CO—R$_{20}$, where R$_{20}$ is selected from the group consisting of hydrogen, alkyl, or a five or six membered heterocyclic ring (v) a carboxylic acid of formula —(R21)n-COOH or ester of formula —(R$_{22}$)—COO—R$_{23}$, where R$_{21}$, R$_{22}$, and R$_{23}$ and are independently selected from the group consisting of alkyl or a five or six membered heterocyclic ring and m and n are independently 0 or 1;

(vi) halogen;

(vii) an alcohol of formula (R24)m-OH or an ether of formula —(R$_{24}$)$_n$—O—R$_{25}$, where R$_{24}$ and R$_{25}$ are independently selected from the group consisting of alkyl and a five or six membered heterocyclic ring and m and n are independently 0 or 1;

(viii) —NR$_{26}$R$_{27}$, where R$_{26}$ and R$_{27}$ are independently selected from the group consisting of hydrogen, oxygen, alkyl, and a five or six membered heterocyclic ring;

(ix) —NHCOR$_{28}$, where R$_{28}$ is selected from the group consisting of hydroxyl, alkyl, and a five or six membered heterocyclic ring, where the ring is optionally substituted with alkyl, halogen, carboxylate, or ester;

(x) —SO$_2$NR$_{29}$R$_{30}$, where R$_{29}$ and R$_{30}$ are selected from the group consisting of hydrogen, oxygen, alkyl, and a five or six membered heterocyclic ring;

(xi) any two of $R_3$, $R_4$, $R_5$, or $R_6$ taken together form a bicyclic or tricyclic moiety fused to the six membered ring of the indole, where each ring in the multicyclic moiety is a five or six membered heterocyclic ring;

(c) $R_7$, $R_8$, $R_9$, and $R_{10}$ are independently selected from the group consisting of, (i) hydrogen;

(ii) alkyl that is optionally substituted with a monocyclic or bicyclic five, six, eight, nine, or ten membered heterocyclic ring, where the ring is optionally substituted with one or more halogen, aldehyde, or trihalomethyl substituents;

(iii) five, six, eight, nine, or ten membered monocyclic or bicyclic heterocyclic ring, where the ring is optionally substituted with one or more halogen or trihalomethyl substituents;

(iv) an aldehyde or ketone of formula —CO—$R_{31}$, where $R_{31}$ is selected from the group consisting of hydrogen, alkyl, or a five or six membered heterocyclic ring;

(v) a carboxylic acid of formula —(R32)n-COOH or ester of formula —$(R_{33})_m$—COO—$R_{34}$, where $R_{32}$, $R_{33}$, and $R_{34}$ and are independently selected from the group consisting of alkyl or a five or six membered heterocyclic ring and n and m are independently 0 or 1;

(vi) halogen;

(vii) an alcohol of formula $(R_{35})_m$—OH or an ether of formula —$(R_{35})$n-O—$R_{36}$, where $R_{35}$ and $R_{36}$ are independently chosen from the group consisting of alkyl or a five or six membered heterocyclic ring and m and n are independently 0 or 1;

(viii) —$NR_{37}R_{38}$, where $R_{39}$ and $R_{38}$ are independently selected from the group consisting of hydrogen, oxygen, alkyl, and a five or six membered heterocyclic ring;

(ix) —$NHCOR_{39}$, where $R_{39}$ is selected from the group consisting of hydroxyl, alkyl, and a five or six membered heterocyclic ring, where the ring is optionally substituted with alkyl, halogen, carboxylate, or ester;

(x) —$SO2NR_{40}R_{41}$, where $R_{40}$ and $R_{41}$ are selected from the group consisting of hydrogen, oxygen, alkyl, and a five or six membered heterocyclic ring;

(xi) any two of $R_7$, $R_8$, $R_9$, or $R_{10}$ taken together form a bicyclic or tricyclic heterocyclic moiety fused to the six membered ring of the indole, where each ring in the multicyclic moiety is a five or six membered heterocyclic ring; and (d) $R_{11}$ is hydrogen or alkyl; provided that at least one of $R_1$, $R_2$, $R_3$, $R_4$, $R_5$, $R_6$, $R_7$, $R_8$, $R_9$, or $R_{10}$ is alkyl or provided that at least four of $R_1$, $R_2$, $R_3$, $R_4$, $R_5$, $R_6$, $R_7$, $R_8$, $R_9$, or $R_{10}$ are not hydrogen.

In preferred embodiments of the invention as shown in structure V above, $R_1$ is preferably a lower alkyl, branched or unbranched, more preferably an unbranched lower alkyl (e.g., ethyl, propyl, isopropyl, butyl, tertiary butyl, pentyl), and most preferably a methyl moiety.

In other preferred embodiments one or more of $R_1$, $R_2$, $R_3$, $R_4$, $R_5$, $R_6$, $R_7$, $R_8$, $R_9$, and $R_{10}$ of structure V are a heterocyclic ring. The heterocycle is preferably selected from the group consisting of five, six, eight, nine, ten, eleven, twelve, thirteen, and fourteen membered aryl or non-aryl rings. The heterocycles can be furyl, thienyl, pyrrol, imidazolyl, indolyl, pyridinyl, thiadiazolyl, thiazolyl, piperazinyl, dibenzfuranyl, dibenzthienyl, 2-aminothiazol-4-yl, 2-amino-5-chlorothiazol-4-yl, 2-amino-thiadiazol-4-yl, 2,3-dioxopiperazinyl, 4-alkylpiperazinyl, 2-iodo-3-dibenzfuranyl, and 3-hydroxy-4-dibenzthienyl. $R_2$ preferably is lower alkyl, more preferably methyl, or phenyl or biphenyl preferably mono-substituted with halogen. $R_3$, $R_4$, $R_5$ and mono-$R_6$ preferably are selected from the group consisting of hydrogen, unsubstituted lower alkyls, halogen, methoxy, carboncyclic and ether. R11 is preferably hydrogen.

In especially preferred embodiments of structure V, $R_1$ is methyl and $R_2$, $R_3$, $R_4$, $R_5$, $R_6$, $R_7$, $R_8$, $R_9$, $R_{10}$, and $R_{11}$ are hydrogen, or $R_1$ and $R_7$ are methyl and $R_2$, $R_3$, $R_4$, $R_6$, $R_9$, $R_{10}$, and $R_{11}$ are hydrogen. Other especially preferred compounds are set forth in the tables and examples set forth herein.

In another aspect, the invention features a method of synthesizing an indolinone compound, where the method comprises the steps of:

(a) reacting an aldehyde of formula VI with an oxindol of formula VII,

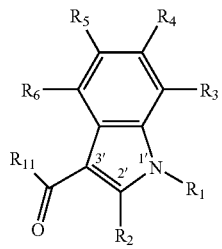

VI

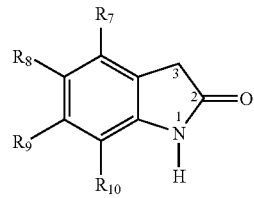

VII where $R_1$, $R_2$, $R_3$, $R_4$, $R_5$, $R_6$, $R_7$, $R_8$, $R_9$, $R_{10}$, and $R_{11}$ are described herein; and (b) separating the indolinone compound from the aldehyde and oxindol reactants.

The term "synthesizing" defines a method of combining multiple compounds together and/or chemically modifying the compound(s) in a controlled environment. A controlled environment preferably includes a glass vessel, a stirring rod or bar, a heating or cooling source, and specific organic solvents.

The term "reacting" refers to mixing two compounds together in a controlled environment. The compounds that are mixed together and reacted with one another are termed "reactants".

The term "separating" describes methods of segregating compounds from one or more other compounds. Compounds can be separated from one another by using techniques known in the art which include, but are not limited to, column chromatography techniques and solvent phase separation techniques.

In another aspect, the invention features optionally substituted 3-[(tetrahydroindole-2-yl)methylene]-2-indolinone and 3-[(cyclopentano-b-pyrrol-2-yl)methylene]-2-indolinone compounds.

The term "optionally substituted" refers, for example, to a benzene ring that either harbors a hydrogen at a particular position or optionally harbors another substituent at that position. The term "optionally substituted" refers to other molecules in addition to benzene. A ring structure, for example can be N-substituted or C-substituted.

The term "N-substituted" refers to a compound that harbors chemical substituents attached to a nitrogen atom in a ring of the indolinone.

The term "C-substituted" refers to a compound that harbors chemical substituents attached to a carbon atom in the indolinone.

The term "independently selected" refers to a molecule that harbors one substituent chosen from a group of substituents.

A preferred embodiment of the invention relates to an indolinone compound of the following formula,

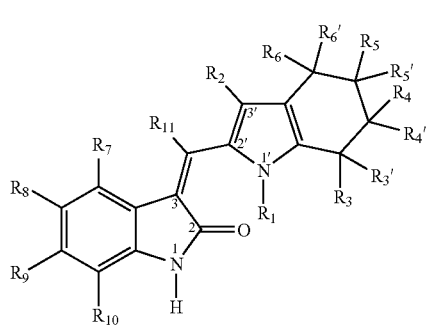

VIII

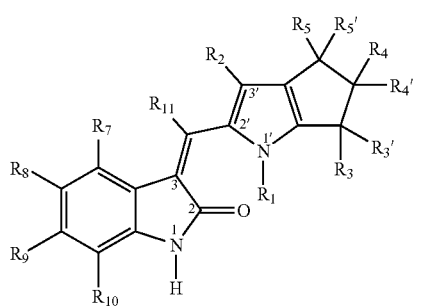

IX where (a) $R_1$ is selected from the group consisting of,
(i) hydrogen;
(ii) alkyl that is optionally substituted with a monocyclic or bicyclic five, six, eight, nine, or ten membered heterocyclic ring, where the ring is optionally substituted with one or more halogen, or trihalomethyl substituents;
(iii) five, six, eight, nine, or ten membered monocyclic or bicyclic heterocyclic ring, where the ring is optionally substituted with one or more halogen or trihalomethyl substituents;
(iv) ketone of formula —CO—$R_{11}$, where $R_{11}$ is selected from the group consisting of hydrogen, alkyl, or a five or six membered heterocyclic ring;
(v) a carboxylic acid of formula —$(R_{12})_n$—COOH or ester of formula —$(R_{13})_m$—COO—$R_{14}$, where $R_{12}$, $R_{13}$, and $R_{14}$ and are independently selected from the group consisting of alkyl or a five or six membered heterocyclic ring and n and m are independently 0 or 1;
(vi) a sulfone of formula —(SO2)-$R_{15}$, where $R_{15}$ is selected from the group consisting of alkyl or a five or six membered heterocyclic ring, where the ring is optionally substituted with an alkyl moiety;
(vii) —$(R_{16})_n$-(indole-1-yl) or —$(R_{17})_m$—CHOH—$(R_{18})$ p-(indole-1-yl), where the indole moiety is optionally substituted with an aldehyde and $R_{16}$, $R_{17}$, and $R_{18}$ are alkyl and n, m, and p are independently 0 or 1;
(viii) taken together with a 2' substituent of the indole ring form a tricyclic moiety, where each ring in the tricyclic moiety is a five or six membered heterocyclic ring;

(b) $R_2$, $R_3$, $R_{3'}$, $R_4$, $R_{4'}$, $R_5$, $R_{5'}$, $R_6$, and $R_{6'}$ are independently selected from the group consisting of,
(i) hydrogen;
(ii) alkyl that is optionally substituted with a monocyclic or bicyclic five, six, eight, nine, or ten membered heterocyclic ring, where the ring is optionally substituted with one or more halogen, aldehyde, or trihalomethyl substituents;
(iii) five, six, eight, nine, or ten membered monocyclic or bicyclic heterocyclic ring, where the ring is optionally substituted with one or more halogen or trihalomethyl substituents;
(iv) ketone of formula —CO—$R_{20}$, where $R_{20}$ is selected from the group consisting of hydrogen, alkyl, or a five or six membered heterocyclic ring;
(v) a carboxylic acid of formula —$(R_{21})_n$—COOH or ester of formula —$(R_{22})$—COO—$R_{23}$, where $R_{21}$, $R_{22}$, and $R_{23}$ and are independently selected from the group consisting of alkyl or a five or six membered heterocyclic ring and m and n are independently 0 or 1;
(vi) halogen;
(vii) an alcohol of formula $(R_{24})_m$—OH or an ether of formula —$(R_{24})_n$—O—$R_{25}$, where $R_{24}$ and $R_{25}$ are independently selected from the group consisting of alkyl and a five or six membered heterocyclic ring and m and n are independently 0 or 1;
(viii) —$NR_{26}R_{27}$ where $R_{26}$ and $R_{27}$ are independently selected from the group consisting of hydrogen, oxygen, alkyl, and a five or six membered heterocyclic ring;
(ix) —$NHCOR_{28}$, where $R_{28}$ is selected from the group consisting of hydroxyl, alkyl, and a five or six membered heterocyclic ring, where the ring is optionally substituted with alkyl, halogen, carboxylate, or ester;
(x) —$SO2NR_{29}R_{30}$, where $R_{29}$ and $R_{30}$ are selected from the group consisting of hydrogen, oxygen, alkyl, and a five or six membered heterocyclic ring;
(xi) any two of $R_3$, $R_{3'}$, $R_4$, $R_{4'}$, $R_5$, $R_{5'}$, $R_6$, or $R_{6'}$ taken together form a bicyclic or tricyclic hetercyclic moiety fused to the six membered ring of the indole, where each ring in the multicyclic moiety is a five or six membered heterocyclic ring;

(c) $R_7$, $R_8$, $R_9$, and $R_{10}$ are independently selected from the group consisting of,
(i) hydrogen;
(ii) alkyl that is optionally substituted with a monocyclic or bicyclic five, six, eight, nine, or ten membered heterocyclic ring, where the ring is optionally substituted with one or more halogen, or trihalomethyl substituents;
(iii) five, six, eight, nine, or ten membered monocyclic or bicyclic heterocyclic ring, where the ring is optionally substituted with one or more halogen or trihalomethyl substituents;
(iv) ketone of formula —CO—$R_{31}$, where $R_{31}$ is selected from the group consisting of hydrogen, alkyl, or a five or six membered heterocyclic ring;
(v) a carboxylic acid of formula —$(R_{32})_n$—COOH or ester of formula —$(R_{33})_m$—COO—$R_{34}$, where $R_{32}$, $R_{33}$, and $R_{34}$ and are independently selected from the group consisting of alkyl or a five or six membered heterocyclic ring and n and m are independently 0 or 1;

(vi) halogen;

(vii) an alcohol of formula $(R_{35})_m$—OH or an ether of formula —$(R_{35})_n$—O—$R_{36}$, where $R_{35}$ and $R_{36}$ are independently chosen from the group consisting of alkyl or a five or six membered heterocyclic ring and m and n are independently 0 or 1;

(viii) —$NR_{37}R_{38}$, where $R_{37}$ and $R_{38}$ are independently selected from the group consisting of hydrogen, oxygen, alkyl, and a five or six membered heterocyclic ring;

(ix) —$NHCOR_{39}$, where $R_{39}$ is selected from the group consisting of hydroxyl, alkyl, and a five or six membered heterocyclic ring, where the ring is optionally substituted with alkyl, halogen, carboxylate, or ester;

(x) —$SO2NR_{40}R_{41}$, where $R_{40}$ and $R_{41}$ are selected from the group consisting of hydrogen, oxygen, alkyl, and a five or six membered heterocyclic ring;

(xi) any two of $R_7$, $R_8$, $R_9$, or $R_{10}$ taken together form a bicyclic or tricyclic hetercyclic moiety fused to the six membered ring of the indole, where each ring in the multicyclic moiety is a five or six membered heterocyclic ring; and (d) $R_{11}$ is hydrogen or alkyl.

Another preferred embodiment of the invention relates to indolinone compounds of structures VIII and IX, where $R_1$, $R_2$, $R_3$, $R_{3'}$, $R_4$, $R_{4'}$, $R_5$, $R_{5'}$, $R_6$, $R_{6'}$, $R_7$, $R_8$, $R_9$, $R_{10}$, and $R_{11}$ are hydrogen.

In another preferred embodiment, the invention relates to oxidolinone compounds of structures VIII and IX, where $R_8$ is bromine, chlorine, or NH2 and $R_2$, $R_{2'}$, $R_3$ $R_{3'}$, $R_4$, $R_{4'}$, $R_5$, $R_{5'}$, $R_6$, $R_{6'}$, $R_7$, $R_9$, $R_{10}$, and $R_{11}$ are hydrogen.

In yet another preferred embodiment, the invention relates to indolinone compounds of structures VIII and IX, where $R_7$ is methyl and $R_1$, $R_2$, $R_3$, $R_{3'}$, $R_4$, $R_{4'}$, $R_5$, $R_{5'}$, $R_6$, $R_{6'}$, $R_7$, $R_9$, $R_{10}$, and $R_{11}$ are hydrogen.

In another aspect, the invention features a method of synthesizing an indolinone compound, where the method comprises the steps of:

(a) reacting an aldehyde of formula X or XI with an oxindol of formula XII,

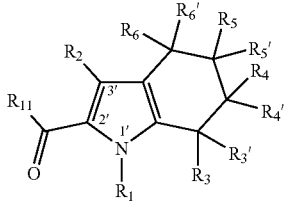

X

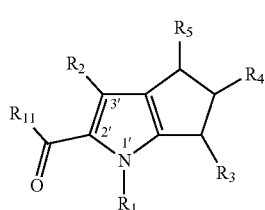

XI

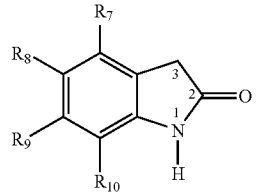

XII where $R_1$, $R_2$, $R_3$, $R_{3'}$, $R_4$, $R_{4'}$, $R_5$, $R_{5'}$, $R_6$, $R_{6'}$, $R_7$, $R_8$, $R_9$, $R_{10}$, and $R_{11}$ are described herein; and (b) separating the indolinone compound from the aldehyde and oxindole reactants.

In another aspect, the invention features an indolinone compound having a substituent at the 5 position of the oxindole ring, where the substituent at the 5 position of the oxindole ring is selected from the group consisting of:

(a) alkyl that is optionally substituted with a monocyclic or bicyclic five, six, eight, nine, or ten membered heterocyclic ring, where the ring is optionally substituted with one or more halogen, or trihalomethyl substituents;

(b) five, six, eight, nine, or ten membered monocyclic or bicyclic heterocyclic ring, where the ring is optionally substituted with one or more halogen or trihalomethyl substituents;

(c) a ketone of formula —CO—$R_{10}$, where $R_{10}$ is selected from the group consisting of hydrogen, alkyl, or a five or six membered heterocyclic ring;

(d) a carboxylic acid of formula —$(R_{11})$n-COOH or ester of formula —$(R_{12})$—COO—$R_{13}$, where $R_{11}$, $R_{12}$, and $R_{13}$ and are independently selected from the group consisting of alkyl or a five or six membered heterocyclic ring and m and n are independently 0 or 1;

(e) halogen;

(f) an alcohol of formula $(R_{14})_m$—OH or an ether of formula —$(R_{14})$n-O—$R_{15}$, where $R_{14}$ and $R_{15}$ are independently selected from the group consisting of alkyl and a five or six membered heterocyclic ring and m and n are independently 0 or 1;

(g) —$NR_{16}R_{17}$, where $R_{16}$ and $R_{17}$ are independently selected from the group consisting of hydrogen, alkyl, and a five or six membered heterocyclic ring;

(h) —$NHCOR_{18}$, where $R_{18}$ is selected from the group consisting of alkyl, and a five or six membered heterocyclic ring, where the ring is optionally substituted with alkyl, halogen, carboxylate, or ester;

(i) —$SO_2NR_{19}R_{20}$, where $R_{19}$ and $R_{20}$ are selected from the group consisting of hydrogen, alkyl, and a five or six membered heterocyclic ring;

(j) any two of $R_4$, $R_5$, $R_6$, or $R_7$ taken together form a bicyclic or tricyclic hetercyclic moiety fused to the six membered ring of the indole, where each ring in the multicyclic moiety is a five or six membered heterocyclic ring.

A preferred embodiment of the invention relates to a compound of the following formula,

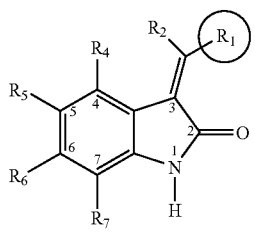

(XIII)

where (a) $R_5$ is selected from the group consisting of,
  (i) alkyl that is optionally substituted with a monocyclic or bicyclic five, six, eight, nine, or ten membered heterocyclic ring, where the ring is optionally substituted with one or more halogen, or trihalomethyl substituents;
  (ii) five, six, eight, nine, or ten membered monocyclic or bicyclic heterocyclic ring, where the ring is optionally substituted with one or more halogen or trihalomethyl substituents;
  (iii) a ketone of formula —CO—$R_{10}$, where $R_{10}$ is selected from the group consisting of hydrogen, alkyl, or a five or six membered heterocyclic ring;
  (iv) a carboxylic acid of formula —($R_{11}$)n-COOH or ester of formula —($R_{12}$)—COO—$R_{13}$, where $R_{11}$, $R_{12}$, and $R_{13}$ and are independently selected from the group consisting of alkyl or a five or six membered heterocyclic ring and m and n are independently 0 or 1;
  (v) halogen;
  (vi) an alcohol of formula $(R_{14})_m$—OH or an ether of formula —$(R_{14})_n$—O—$R_{15}$, where $R_{14}$ and $R_{15}$ are independently selected from the group consisting of alkyl and a five or six membered heterocyclic ring and m and n are independently 0 or 1;
  (vii) —$NR_{16}R_{17}$, where $R_{16}$ and $R_{17}$ are independently selected from the group consisting of hydrogen, alkyl, and a five or six membered heterocyclic ring;
  (viii) —$NHCOR_{18}$, where $R_{18}$ is selected from the group consisting of alkyl, and a five or six membered heterocyclic ring, where the ring is optionally substituted with alkyl, halogen, carboxylate, or ester;
  (ix) —$SO_2NR_{19}R_{20}$, where $R_{19}$ and $R_{20}$ are selected from the group consisting of hydrogen, alkyl, and a five or six membered heterocyclic ring;
  (x) any two of $R_4$, $R_5$, $R_6$, or $R_7$ taken together form a bicyclic or tricyclic hetercyclic moiety fused to the six membered ring of the oxindole, where each ring in the multicyclic moiety is a five or six membered heterocyclic ring;
(b) $R_1$ is selected from the group consisting of a five, six, eight, nine, and ten membered monocyclic or bicyclic heterocyclic ring, where the ring is optionally substituted with one or more substituents selected from the group consisting of
  (i) hydrogen and alkyl that is optionally substituted with a monocyclic or bicyclic five, six, eight, nine, or ten membered heterocyclic ring, where the ring is optionally substituted with one or more halogen, or trihalomethyl substituents;
  (ii) five, six, eight, nine, or ten membered monocyclic or bicyclic heterocyclic ring, where the ring is optionally substituted with one or more halogen or trihalomethyl substituents;
  (iii) a ketone of formula —CO—$R_{21}$, where $R_{21}$ is selected from the group consisting of hydrogen, alkyl, or a five or six membered heterocyclic ring;
  (iv) a carboxylic acid of formula —$(R_{22})_n$—COOH or ester of formula —$(R_{23})$—COO—$R_{24}$, where $R_{22}$, $R_{23}$, and $R_{24}$ and are independently selected from the group consisting of alkyl or a five or six membered heterocyclic ring and m and n are independently 0 or 1;
  (v) halogen;
  (vi) an alcohol of formula $(R_{25})$m-OH or an ether of formula —$(R_{25})_n$—O—$R_{26}$, where $R_{25}$ and $R_{26}$ are independently selected from the group consisting of alkyl and a five or six membered heterocyclic ring and m and n are independently 0 or 1;
  (vii) —$NR_{27}R_{28}$, where $R_{27}$ and $R_{28}$ are independently selected from the group consisting of hydrogen, alkyl, and a five or six membered heterocyclic ring;
  (viii) —$NHCOR_{29}$, where $R_{29}$ is selected from the group consisting of alkyl, and a five or six membered heterocyclic ring, where the ring is optionally substituted with alkyl, halogen, carboxylate, or ester;
  (ix) —$SO_2NR_{30}R_{31}$, where $R_{30}$ and $R_{31}$ are selected from the group consisting of hydrogen, alkyl, and a five or six membered heterocyclic ring;
(c) $R_4$, $R_6$, and $R_7$ are independently selected from the group consisting of,
  (i) hydrogen and alkyl that is optionally substituted with a monocyclic or bicyclic five, six, eight, nine, or ten membered heterocyclic ring, where the ring is optionally substituted with one or more halogen, or trihalomethyl substituents;
  (ii) five, six, eight, nine, or ten membered monocyclic or bicyclic heterocyclic ring, where the ring is optionally substituted with one or more halogen or trihalomethyl substituents;
  (iii) a ketone of formula —CO—$R_{32}$, where $R_{32}$ is selected from the group consisting of hydrogen, alkyl, or a five or six membered heterocyclic ring;
  (iv) a carboxylic acid of formula —$(R_{33})$n-COOH or ester of formula —$(R_{34})$—COO—$R_{35}$, where $R_{33}$, $R_{34}$, and $R_{35}$ and are independently selected from the group consisting of alkyl or a five or six membered heterocyclic ring and m and n are independently 0 or 1;
  (v) halogen;
  (vi) an alcohol of formula $(R_{36})$m-OH or an ether of formula —$(R_{36})_n$—O—$R_{37}$, where $R_{36}$ and $R_{37}$ are independently selected from the group consisting of alkyl and a five or six membered heterocyclic ring and m and n are independently 0 or 1;
  (vii) —$NR_{38}R_{39}$, where $R_{38}$ and $R_{39}$ are independently selected from the group consisting of hydrogen, alkyl, and a five or six membered heterocyclic ring;
  (viii) —$NHCOR_{40}$, where $R_{40}$ is selected from the group consisting of alkyl, and a five or six membered heterocyclic ring, where the ring is optionally substituted with alkyl, halogen, carboxylate, or ester;
  (ix) —$SO_2NR_{41}R_{42}$, where $R_{41}$ and $R_{42}$ are selected from the group consisting of hydrogen, alkyl, and a five or six membered heterocyclic ring; and
(d) $R_2$ is hydrogen or alkyl.

In preferred embodiments of the invention shown in structure XIII above one or more of $R_1$, $R_4$, $R_5$, $R_6$, or $R_7$ are a heterocyclic ring. Preferred heterocycles of the invention are described herein.

Another preferred embodiment of the invention shown in structure XIII above is an indolinone compound, where $R_1$ is (3,5-dimethylpyrrol)-2-yl, $R_5$ is —COOH, and $R_2$, $R_4$, $R_6$, and $R_7$ are hydrogen.

Another preferred embodiment of the invention shown in structure XIII above is an indolinone compound, where $R_1$ is (3,5-diethylpyrrol)-2-yl, $R_5$ is —COOH, and $R_2$, $R_4$, $R_6$, and $R_7$ are hydrogen.

Another preferred embodiment of the invention shown in structure XIII above is an indolinone compound, where $R_1$ is (3,5-diisopropylpyrrol)-2-yl, $R_5$ is —COOH, and $R_2$, $R_4$, $R_6$, and $R_7$ are hydrogen.

Another preferred embodiment of the invention shown in structure XIII above is an indolinone compound, where $R_1$ is (3,5-dimethylpyrrol)-2-yl, $R_5$ is —$(CH_2)_2COOH$, and $R_2$, $R_4$, $R_6$, and $R_7$ are hydrogen.

Another preferred embodiment of the invention shown in structure XIII above is an indolinone compound, where $R_1$ is (5-methylthiophene)-2-yl, $R_5$ is —COOH, and $R_2$, $R_4$, $R_6$, and $R_7$ are hydrogen.

In another aspect, the invention features a method of synthesizing an indolinone compound, where the method comprises the steps of:

(a) reacting an aldehyde of formula XIV with an oxindole of formula XV,

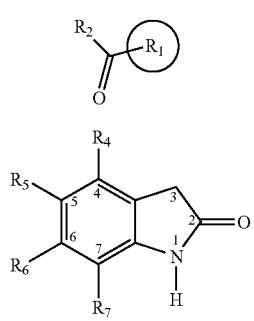

where $R_1$, $R_2$, $R_3$, $R_4$, $R_5$, $R_6$, $R_7$, $R_8$, $R_9$, $R_{10}$, and $R_{11}$ are as described herein; and (b) separating the indolinone compound from the aldehyde and oxindole reactants.

In another aspect, the invention features an indolinone compound having a substituent at the 3 position of the oxindole ring, where the substituent at the 3 position of the oxindole ring is selected from the group consisting of five-membered or six-membered heterocyclic rings. The oxindolonine is further substituted with groups enhancing hydrosolubility as set forth below.

A preferred embodiment of the invention relates to a compound of the following formula:

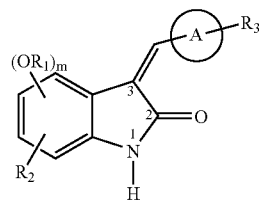

wherein (a) A is a five membered heterocyclic ring selected from the following group consisting of thiophene, pyrrole, pyrazole, imidazole, 1,2,3-triazole, 1,2,4-triazole, oxazole, isoxazole, thiazole, isothiazole, furan, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole (b) m is zero, 1, or 2;

(c) $R_1$ is hydrogen, $C_1$–$C_6$ alkyl or $C_2$–$C_6$ alkanoyl;

(d) one of $R_2$ and $R_3$ independently is hydrogen and the other is a substituent selected from:

(1) a $C_1$–$C_6$ alkyl group substituted by 1, 2 or 3 hydroxy groups;

(2) $SO_3R_4$ in which $R_4$ is hydrogen or $C_1$–$C_6$ alkyl unsubstituted or substituted by 1, 2 or 3 hydroxy groups;

(3) $SO_2NHR_5$ in which $R_5$ is as $R_4$ defined above or a —$(CH_2)_n$—$N(C_1$–$C_6$ alkyl$)_2$ group in which n is 2 or 3;

(4) $COOR_6$ in which $R_6$ is $C_1$–$C_6$ alkyl unsubstituted or substituted by phenyl or by 1, 2 or 3 hydroxy groups or phenyl;

(5) $CONHR_7$ in which $R_7$ is hydrogen, phenyl or $C_1$–$C_6$ alkyl substituted by 1, 2 or 3 hydroxy groups or by phenyl;

(6) $NHSO_2R_8$ in which $R_8$ is $C_1$–$C_6$ alkyl or phenyl unsubstituted or substituted by halogen or by $C_1$–$C_4$ alkyl;

(7) $N(R_9)_2$, $NHR_9$ or $OR_9$ wherein $R_9$ is $C_2$–$C_6$ alkyl substituted by 1, 2 or 3 hydroxy groups;

(8) $NHCOR_{10}$, $OOCR_{10}$ or $CH_2OOCR_{10}$ in which $R_{10}$ is $C_1$–$C_6$ alkyl substituted by 1, 2 or 3 hydroxy groups;

(9) $NHCONH_2$; NH—$C(NH_2)$=NH; $C(NH_2)$=NH; $CH_2NHC(NH_2)$=NH; $CH_2NH_2$; $OPO(OH)_2$; $CH_2OPO(OH)_2$; $PO(OH)_2$; or a

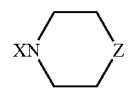

group wherein X is selected from the group consisting of $CH_2$, $SO_2$, CO, or $NHCO(CH_2)_p$ in which p is 1, 2, or 3 and Z is CH2, O or N—$R_{11}$ in which $R_{11}$ is hydrogen or is as $R_9$ defined above.

The term "alkanoyl" refers to a chemical moiety with formula —$(R)_n$—CO—R', where R and R' are selected from the group consisting of alkyl or aryl and n is 0 or 1.

Inhibitors of protein kinase catalytic activity are known in the art. Small molecule inhibitors typically block the binding of substrates by tightly interacting with the protein kinase active-site. Indolinone compounds, for example, can bind to the active-site of a protein kinase and inhibit the molecule effectively, as measured by inhibition constants on the order of $10^{-6}$ M.

A preferred embodiment of the invention relates to an hydrosoluble indolinone compound that inhibits the catalytic activity of a FLK protein kinase. The indolinone preferably inhibits the catalytic activity of the FLK protein kinase with an $IC_{50}$ less than 50 μM, more preferably with an $IC_{50}$ less than 5 μM, and most preferably with an $IC_{50}$ less than 0.5 μM.

In another aspect, the invention features a method of synthesizing a hydrosoluble indolinone compound, where the method comprises the steps of:
(a) reacting an aldehyde of formula XVI with an oxindole of formula XVII,

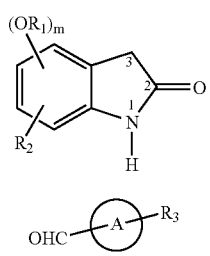

XVI

XVII where
(a) A is a five or six membered ring comprised of atoms selected from the group consisting of oxygen, carbon, sulfer and nitrogen
(b) m is zero, 1, or 2;
(c) $R_1$ is hydrogen, $C_1$–$C_6$ alkyl or $C_2$–$C_6$ alkanoyl;
(d) one of $R_2$ and $R_3$ independently is hydrogen and the other is a substituent selected from:
  (1) a $C_1$–$C_6$ alkyl group substituted by 1, 2 or 3 hydroxy groups;
  (2) $SO_3R_4$ in which $R_4$ is hydrogen or $C_1$–$C_6$ alkyl unsubstituted or substituted by 1, 2 or 3 hydroxy groups;
  (3) $SO_2NHR_5$ in which $R_5$ is as $R_4$ defined above or a —$(CH_2)_n$—$N(C_1$–$C_6$ alkyl$)_2$ group in which n is 2 or 3;
  (4) $COOR_6$ in which $R_6$ is $C_1$–$C_6$ alkyl unsubstituted or substituted by phenyl or by 1, 2 or 3 hydroxy groups or phenyl;
  (5) $CONHR_7$ in which $R_7$ is hydrogen, phenyl or $C_1$–$C_6$ alkyl substituted by 1, 2 or 3 hydroxy groups or by phenyl;
  (6) $NHSO_2R_8$ in which $R_8$ is $C_1$–$C_6$ alkyl or phenyl unsubstituted or substituted by halogen or by $C_1$–$C_4$ alkyl;
  (7) $N(R_9)_2$, $NHR_9$ or $OR_9$ wherein $R_9$ is $C_2$–$C_6$ alkyl substituted by 1, 2 or 3 hydroxy groups;
  (8) $NHCOR_{10}$, $OOCR_{10}$ or $CH_2OOCR_{10}$ in which $R_{10}$ is $C_1$–$C_6$ alkyl substituted by 1, 2 or 3 hydroxy groups;
  (9) $NHCONH_2$; $NH$—$C(NH_2)$=$NH$; $C(NH)$=$NH$; $CH_2NHC(NH_2)$=$NH$; $CH_2NH_2$; $OPO(OH)_2$; $CH_2OPO(OH)_2$; $PO(OH)_2$; or a

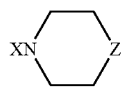

group wherein X is selected from the group consisting of $CH_2$, $SO_2$, $CO$, or $NHCO(CH_2)_p$ in which p is 1,2, or 3 and Z is CH2, O or N—$R_{11}$ in which $R_{11}$ is hydrogen or is as $R_9$ defined above; and
(b) separating the indolinone compound from the aldehyde and oxindole reactants.

Another aspect of the invention features a pharmaceutical composition comprising an oxidolinone compound of the invention and a physiologically acceptable carrier or diluent.

In the embodiments set forth below, several preferred subclasses of compounds having activity against Flk are set forth. Thus, in one embodiment, the invention provides compounds having the formula:

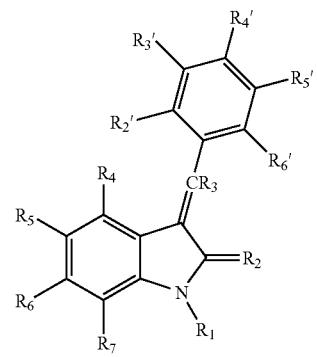

wherein
$R_1$ is hydrogen or alkyl (preferably lower alkyl, more preferably methyl);
$R_2$ is oxygen or sulfur;
$R_3$ is hydrogen or methyl;
$R_4$, $R_5$, $R_6$, and $R_7$ are each independently selected from the group consisting of hydrogen (preferably at least two or three of $R_4$, $R_5$, $R_6$ and R 7 are hydrogen), alkyl (preferably lower alkyl, more preferably methyl), halogen, $NO_2$, and NRR';
$R_{2'}$, $R_{3'}$, $R_{4'}$, $R_{5'}$, and $R_6$, are each independently selected from the group consisting of hydrogen, alkyl, halogen, $NO_2$, NRR' (where taken together $NRR^1$ may form a five or six member non-aromatic heterocyc optionally substituted with COH), OH, $ORNRR^1$, and OR;
R is hydrogen, alkyl or aryl; and
R' is hydrogen, alkyl or aryl.

In another embodiment, the invention provides compounds having the formula:

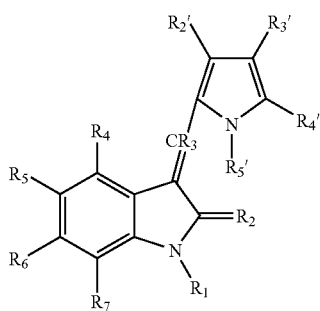

wherein
$R_1$ is hydrogen or alkyl (preferably lower alkyl, more preferably methyl);
$R_2$ is oxygen or sulfer;
$R_3$ is hydrogen or methyl;
$R_4$, $R_5$, $R_6$, and $R_7$ are each independently selected from the group consisting of hydrogen, alkyl (preferably lower alkyl, more preferably methyl), halogen, and NRR';
$R_{2'}$, $R_{3'}$, $R_{4'}$, and $R_{5'}$, are each independently selected from the group consisting of hydrogen, alkyl, halogen, and (alkyl)$_n$ $CO_2R$;

R is hydrogen, alkyl or aryl; and

R' is hydrogen, alkyl or aryl.

In another embodiment, the invention provides compounds having the formula:

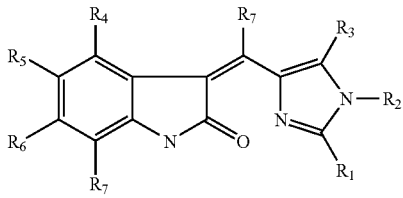

wherein $R_1$, $R_2$, and $R_3$, are each independently selected from the group consisting of hydrogen, alkyl, halogen, and (alkyl)$_n$ CO$_2$R;

$R_4$, $R_5$, $R_6$, and $R_7$ are each independently selected from the group consisting of hydrogen, alkyl (preferably lower alkyl, more preferably methyl), halogen, and NRR';

$R_8$ and $R_9$ are independently hydrogen or alkyl;

R is hydrogen, alkyl or aryl; and

R' is hydrogen, alkyl or aryl.

In another embodiment, the invention provides compounds having the formula:

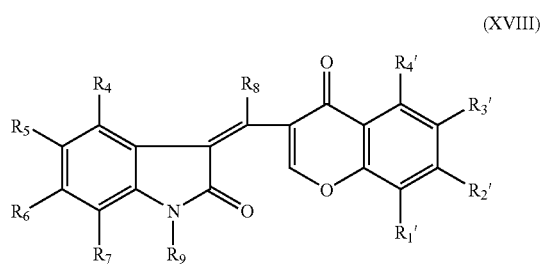

(XVIII)

wherein $R_{1'}$, $R_{2'}$, $R_{3'}$, $R_{4'}$ and $R_7$ are each independently selected from the group consisting of hydrogen, alkyl (preferably lower alkyl, more preferably methyl), halogen and NRR';

$R_8$ and $R_9$ are independently hydrogen or alkyl;

R is hydrogen, alkyl or aryl; and

R' is hydrogen, alkyl or aryl.

In another aspect, the invention features a method of synthesizing an indolinone compound, where the method comprises the steps of:

(a) reacting an appropriate aldehyde with an appropriate oxindole, (b) separating the indolinone compound from the aldehyde and oxindole reactants.

In another aspect, the invention features an indolinone compound, salt, ester, amide, prodrug, isomer, or metabolite thereof that modulates the catalytic activity of a protein kinase.

The term "modulates" refers to the ability of a compound to alters the catalytic activity of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "protein kinase" defines a class of proteins that regulate a variety of cellular functions. Protein kinases regulate cellular functions by reversibly phosphorylating protein substrates which thereby changes the conformation of the substrate protein. The conformational change modulates catalytic activity of the substrate or its ability to interact with other binding partners.

The term "catalytic activity", in the context of the invention, defines the rate at which a protein kinase phosphorylates a substrate. Catalytic activity can be measured, for example, by determining the amount of a substrate converted to a product as a function of time. Phosphorylation of a substrate occurs at the active-site of a protein kinase. The active-site is normally a cavity in which the substrate binds to the protein kinase and is phosphorylated.

A preferred embodiment of the invention relates to an indolinone compound that inhibits the catalytic activity of a FLK protein kinase. The indolinone preferably inhibits the catalytic activity of the FLK protein kinase with an IC50 less than 50 µM, more preferably with an IC50 less than 5 µM, and most preferably with an IC50 less than 0.5 µM.

The term "FLK" refers to a protein kinase that phosphorylates protein substrates on tyrosine residues. The FLK protein kinase regulates cellular functions in response to the VEGF growth factor. These cellular functions include, but are not limited to, cellular proliferation, and in particular, blood vessel proliferation in tissues.

The term "IC$_{50}$", in the context of the invention, refers to a parameter that describes the concentration of a particular indolinone required to inhibit 50% of the FLK protein kinase catalytic activity. The IC$_{50}$ parameter can be measured using an assay described herein and by varying the concentration of a particular indolinone compound.

Another aspect of the invention features a pharmaceutical composition comprising, consisting essentially of, or consisting of an indolinone compound, salt, ester, amide, prodrug, isomer, or metabolite thereof of the invention and a physiologically acceptable carrier or diluent.

The term "pharmaceutical composition" refers to a mixture of an indolinone compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "physiologically acceptable" defines a carrier or diluent that does not cause significant irritation to an organism and does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

Another aspect of the invention features a method of preventing or treating an abnormal condition in an organism. The abnormal condition is associated with an aberration in a signal transduction pathway characterized by an interaction between a protein kinase and a natural binding partner. The method comprises the following steps: (a) administering a compound of the invention to an organism; and (b) promoting or disrupting the abnormal interaction.

The term "preventing" refers to a method of barring the organism from acquiring the abnormal condition.

The term "treating" refers to a method of alleviating or abrogating the abnormal condition in the organism.

The term "organism" relates to any living entity comprised of at least one cell. An organism can be as simple as one eukaryotic cell or as complex as a mammal.

The term "abnormal condition" refers to a function in the cells or tissues of an organism that deviates from their normal functions in that organism. An abnormal condition can relate to cell proliferation, cell differentiation, or cell survival.

Aberrant cell proliferative conditions include cancers such as fibrotic and mesangial disorders, abnormal angiogenesis and vasculogenesis, wound healing, psoriasis, diabetes mellitus, and inflammation.

Aberrant differentiation conditions include, but are not limited to neurodegenerative disorders, slow wound healing rates, and tissue grafting techniques.

Aberrant cell survival conditions relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

Cell proliferation, differentiation, and survival are phenomena simply measured by methods in the art. These methods can involve observing the number of cells or the appearance of cells under a microscope with respect to time (days).

The term "administering" relates to a method of incorporating a compound into cells or tissues of an organism. The abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to) oral, parenteral, dermal, injection, and aerosol applications. For cells outside of the organism, multiple techniques exist in the art to administer the compounds, including (but not limited to) cell microinjection techniques, transformation techniques, and carrier techniques.

The aberrant condition can also be prevented or treated by administering a group of cells having an aberration in a signal transduction process to an organism. The effect of administering a compound on organism function can then be monitored. The art contains multiple methods of introducing a group of cells to an organism as well as methods of administering a compound to an organism. The organism is preferably a frog, more preferably a mouse, rat, rabbit, guinea pig, or goat, and most preferably a monkey or ape.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein kinases, receptor and non-receptor protein phosphatases, nucleotide exchange factors, and transcription factors.

The term "aberration", in conjunction with a signal transduction process, refers to a protein kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "natural binding partner" refers to a polypeptide that normally binds to the intracellular region of a protein kinase in a cell. These natural binding partners can play a role in propagating a signal in a protein kinase signal transduction process. The natural binding partner can bind to a protein kinase intracellular region with high affinity. High affinity represents an equilibrium binding constant on the order of $10^{-6}$ M or less. However, a natural binding partner can also transiently interact with a protein kinase intracellular region and chemically modify it. Protein kinase natural binding partners are chosen from a group consisting of, but not limited to, src homology 2 (SH2) or 3 (SH3) domains, other phosphoryl tyrosine binding (PTB) domains, and other protein kinases or, protein phosphatases.

The term "promoting or disrupting the abnormal interaction" refers to a method that can be accomplished by administering a compound of the invention to cells or tissues in an organism. A compound can promote an interaction between a protein kinase and natural binding partners by forming favorable interactions with multiple amino acids at the complex interface. Alternatively, a compound can inhibit an interaction between a protein kinase and natural binding partners by compromising favorable interactions formed between amino acids at the complex interface.

A preferred embodiment of the invention relates to the method of treating an abnormal condition in an organism, where the organism is a mammal.

The term "mammal" refers preferably to such organisms as mice, rats, rabbits, guinea pigs, and goats, more preferably to monkeys and apes, and most preferably to humans.

Another preferred embodiment of the invention relates to a method of treating or preventing an abnormal condition associated with the FLK protein kinase.

Another preferred embodiment of the invention relates to an indolinone compound that inhibits the catalytic activity of a platelet derived growth factor protein kinase. The indolinone preferably inhibits the catalytic activity of the platelet derived growth factor protein kinase with an $IC_{50}$ less than 50 µM, more preferably with an $IC_{50}$ less than 5 µM, and most preferably with an $IC_{50}$ less than 0.5 µM.

The term "platelet derived growth factor" refers to a protein kinase that phosphorylates substrates on tyrosine residues. The platelet derived growth factor protein kinase regulates cellular functions in response to the PDGF growth factor. These cellular functions include, but are not limited to, cellular proliferation.

The chemical formulae referred herein may exhibit the phenomena of tautomerism or structural isomerism. For example, the compounds described herein may be adopt a cis or trans conformation about the double bond connecting the indolinone 3-substituent to the indolinone ring, or may be mixtures of cis and trans isomers. As the formulae drawing within this specification can only represent one possible tautomeric or structural isomeric form, it should be understood that the invention encompasses any tautomeric or structural isomeric form, or mixtures thereof, which possesses the ability to regulate, inhibit and/or modulate tyrosine kinase signal transduction or cell proliferation and is not limited to any one tautomeric or structural isomeric form utilized within the formulae drawing.

In addition to the above-described compounds, the invention is further directed, where applicable, to solvated as well as unsolvated forms of the compounds (e.g. hydrated forms) having the ability to regulate and/or modulate cell proliferation.

The compounds described herein may be prepared by any process known to be applicable to the preparation of chemically-related compounds. Suitable processes are illustrated in the examples. Necessary starting materials may be obtained by standard procedures of organic chemistry.

An individual compound's relevant activity and efficacy as an agent to affect receptor tyrosine kinase mediated signal transduction may be determined using available techniques. Preferentially, a compound is subjected to a series of screens to determine the compound's ability to modulate, regulate and/or inhibit cell proliferation. These screens, in the order in which they are conducted, include biochemical assays, cell growth assays and in vivo experiments.

The summary of the invention described above is not limiting and other features and advantages of the invention will be apparent from the following detailed description of the invention, and from the claims.

BRIEF DESCRIPTION OF THE TABLES

Table 1 depicts examples of compounds of the invention. The table illustrates the molecular structure of each indolinone, the molecular weight of the compound, and the chemical formula of the compound.

Table 2 depicts the biological activity of select compounds of the invention. Listed are the chemical structure of the compound with $IC_{50}$ values measured in FLK-1 biological inhibition assays.

Table 3 shows preferred indole based aldehydes that can be used in the present invention.

Table 4 shows preferred oxindoles that can be used in the present invention.

Table 5 depicts examples of compounds of the invention. The table illustrates the molecular structure of each indolinone, the molecular weight of the compound, and the chemical formula of the compound.

Tables 6 and 7 depicts the biological activity of select compounds of the invention. Listed are the chemical structure of the compound with $IC_{50}$ values measured in FLK-1 and platelet derived growth factor protein kinase (PDGFR) biological inhibition assays.

Table 8 depicts examples of compounds of the invention. The table illustrates the molecular structure of exemplary indolinones and the biological activity of select compounds of the invention. Listed are the chemical structure of the compound with $IC_{50}$ values measured in FLK-1 biological inhibition assays.

Table 9 lists exemplary compounds of the invention.

Table 10 shows FLK activity data for illustrative compounds of the invention.

Table 11 shows type A oxindols.

Table 12 shows type B aldehydes.

Table 13 shows the names of several indolinone compounds of the present invention.

Table 14 shows kinase data for the compounds listed in Table 13 as determined using the assays described herein.

DETAILED DESCRIPTION OF THE INVENTION

The invention is directed in part towards designing protein kinase inhibitors that obliterate tumors by severing their sources of sustenance. The inhibitors are designed to specifically bind protein kinases over-expressed in the vasculature that supply tumors with sustenance. One such protein kinase target is FLK-1, which is over-expressed in the proliferating endothelial cells of a growing tumor, but not in the surrounding quiescent endothelial cells. Plate et al., 1992, *Nature* 359:845–848.

FLK-1 is activated upon binding VEGF, a strong regulator for endothelial cell proliferation as well as normal and pathological angiogenesis. Klagsburn and Soker, 1993, *Current Biology* 3:699–702. Thus, compounds that specifically inhibit the FLK protein kinase are potential anti-cancer agents as they may decrease the vasculature that nourishes tumors. These inhibitors will most likely result in minimizing and even obliterating solid tumors. In addition, compounds that specifically inhibit FLK will potentially represent a new generation of cancer therapeutics as they will most likely cause few side effects. These potential properties are a welcome improvement over the currently utilized cancer therapeutics that cause multiple side effects and deleteriously weaken patients.

Synthesis of Indolinone Compounds

The indolinone compounds of the invention are synthesized by reacting an aldehyde with an oxindol as shown in the examples provided herein. Descriptions of methods for synthesizing indolinone compounds are provided in the examples described herein. The examples fully describe the solvents, temperatures, separation techniques, and other conditions utilized for the invention. Other synthetic techniques, such as those described in International patent publications WO 96/22976, published Aug. 1, 1996 by Ballinari et al., and WO 96/40116, published Dec. 19, 1996 by Tang et al. may also be used or adapted by those skilled in the art to make the compounds of the present invention. Descriptions of the methods used to specifically synthesize the indolinone compounds of the invention, are disclosed herein.

Biological Activity of Indolinone Compounds

Indolinone compounds of the invention can be tested for their ability to activate or inhibit protein kinases in biological assays. The methods used to measure indolinone modulation of protein kinase function are described herein. Indolinone compounds of the invention were tested for their ability to inhibit the FLK protein kinase. The biological assay and results of these inhibition studies are reported herein.

Target Diseases to be Treated by Indolinone Compounds

Protein kinases are essential regulatory molecules that control a variety of cellular functions. For this reason, any alteration in the function of a protein kinase can cause an abnormal condition in an organism. One of the many functions controlled by protein kinases is cell proliferation.

Alterations in the function of a protein kinase that normally regulates cell proliferation can lead to enhanced or decreased cell proliferative conditions evident in certain diseases. Aberrant cell proliferative conditions include cancers such as fibrotic and mesangial disorders, abnormal angiogenesis and vasculogenesis, wound healing, psoriasis, restenosis, diabetes mellitus, and inflammation.

Fibrotic disorders and mesangial cell proliferative disorders are described in International Patent Publication No. WO 96/40116, published Dec. 19, 1996 by Tang et al.

Angiogenic and vasculogenic disorders result from excess proliferation of blood vessels. Blood vessel proliferation is necessary in a variety of normal physiological processes such as embryonic development, corpus luteum formation, wound healing and organ regeneration. However, blood vessel proliferation is also essential in cancer tumor development. Other examples of blood vessel proliferative disorders include arthritis, where new capillary blood vessels invade the joint and destroy cartilage. In addition, blood vessel proliferative diseases include ocular diseases, such as diabetic retinopathy, where new capillaries in the retina invade the vitreous, bleed and cause blindness. Conversely, disorders related to the shrinkage, contraction or closing of blood vessels, such as restenosis, are also implicated in adverse regulation of RPKs or RPPs.

Moreover, vasculogenesis and angiogenesis are associated with the growth of malignant solid tumors and metastasis. A vigorously growing-cancer tumor requires a nutrient and oxygen rich blood supply to continue growing. As a consequence, an abnormally large number of capillary blood vessels often grow in concert with the tumor and act as supply lines to the tumor. In addition to supplying nutrients to the tumor, the new blood vessels embedded in a tumor provide a gateway for tumor cells to enter the circulation and metastasize to distant sites in the organism. Folkman, 1990, *J. Natl. Cancer Inst.* 82:4–6.

Angiogenic and vasculogenic disorders are closely linked to the FLK protein kinase. FLK-1 is activated upon binding VEGF, a strong regulator for endothelial cell proliferation as well as normal and pathological angiogenesis. Klagsburn and Soker, 1993, *Current Biology* 3:699–702. Thus, compounds that specifically inhibit the FLK protein kinase are potential anti-cancer agents as they may decrease the vasculature that nourishes tumors. These inhibitors will most likely result in minimizing and even obliterating solid tumors. In addition, compounds that specifically inhibit FLK will potentially represent a new generation of cancer therapeutics as they will most likely cause few side effects. These potential properties are a significant improvement over the currently utilized cancer therapeutics that cause multiple side effects and deleteriously weaken patients.

In addition to cell proliferation, some RPKs and RPPs regulate the penultimate cellular functions, cell survival and cell death. Glial derived growth factor (GDNF) activates c-ret, for example, by bringing multiple c-ret receptors together into close proximity and promoting cross phosphorylation of the intracellular regions. Signal transduction molecules that form a complex with c-ret as a result of these phosphoryl moieties, such as grb-2, sos, ras, and raf, propagate a signal in the cell that promotes neural survival. Thus, compounds that promote the interactions of these stimulatory molecules of c-ret would enhance the activity of c-ret. Alternatively, protein phosphatases can remove the phosphoryl moieties placed on the intracellular region of c-ret in response to GDNF, and thus inhibit the signaling capability of c-ret. Thus compounds that inhibit phosphatases of c-ret will enhance the signaling capacity of c-ret. In the context of the present invention, the c-ret protein kinase could be activated by indolinone compounds that are modified with substituents, particularly at the 5 position of the oxindole ring.

c-ret is implicated in the development and survival of enteric, synaptic, and sensory neurons and neurons of the renal system upon stimulation by GDNF. Lack of function mutations in c-ret can lead to Hirschsprung's disease, for example, which manifests itself as a decrease in intestinal tract innervation in patients. Thus, compounds that activate c-ret are potential therapeutic agents for the treatment of neurodegenerative disorders, including, but not limited to, Hirschsprung's disease, Parkinson's disease, Alzheimer's disease, and amyotrophic lateral sclerosis. Compounds that inhibit c-ret function are possible anti-cancer agents as over-expression of ret in cells is implicated in cancers, such as cancer of the thyroid.

Pharmaceutical Compositions and Administration of Indolinone Compounds

Methods of preparing pharmaceutical formulations of the compounds, methods of determining the amounts of compounds to be administered to a patient, and modes of administering compounds to an organism are disclosed in International Patent Publication No. WO 96/22976, published Aug. 1, 1996 by Ballinari et al., which is incorporated herein by reference in its entirety, including any drawings. Those skilled in the art will appreciate that such descriptions are applicable to the present invention and can be easily adapted to it. The mechanism of such action and possible uses for such compounds are described in International Patent Publication WO 96/40116, published Dec. 19, 1996 by Tang et al.

The compounds described herein can be administered to a human patient per se, or in pharmaceutical compositions where it is mixed with suitable carriers or excipient(s). Techniques for formulation and administration of the compounds of the instant application may be found in "Remington's Pharmaceutical Sciences," Mack Publishing Co., Easton, Pa., latest edition or in International Patent Publication No. WO 96/40116, published Dec. 19, 1996 by Tang et al.

Effective Dosage

Pharmaceutical compositions suitable for use in the present invention include compositions wherein the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein and in International Patent Publication No. WO 96/40116, published Dec. 19, 1996 by Tang et al.

Packaging

The compositions may, if desired, be presented in a pack or dispenser device which may contain one or more unit dosage forms containing the active ingredient according to the description provided in International Patent Publication No. WO 96/40116, published Dec. 19, 1996 by Tang et al.

EXAMPLES

The examples below are not limiting and are merely representative of various aspects and features of the present invention. The examples demonstrate methods of synthesizing indolinone compounds of the invention. The examples also demonstrate the specificity as well as the potency with which these compounds inhibit protein kinase function in cells.

Example 1

Compound Synthesis

The compounds of the present invention may be synthesized according to known techniques such as those described in International Patent Publication No. WO 96/40116, published Dec. 19, 1996 by Tang et al. The following represent preferred methods for synthesizing the compounds of the claimed invention.

(a) Preparation of 4-Methyl-2-oxindole. Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternatively with 10% sodium hydroxide and 30% hydrogen peroxide until the dark color was no longer present. The solid was filtered off and the filtrate acidified with 6N hydrochloric acid. The resulting precipitate was collected by vacuum filtration, washed with water, and dried under vacuum to give 9.8 g (45% yield) of 1-methyl-6-nitrophenylacetic acid as an off-white solid. The sold was hydrogenated in methanol over 10% palladium on carbon to give 9.04 g of the title compound as a white solid.

(b) Preparation of 5—Nitro-2-oxindole. The 2-oxindole (6.5 g) was dissolved in 25 mL of concentrated sulfuric acid and the mixture maintained at −10–15° C. while 2.1 mL of fuming nitric acid was added dropwise. After the addition of the nitric acid the reaction mixture was stirred at 0° C. for 0.5 hr and poured into ice water. The precipitate was collected by filtration, washed with water and crystallized from 50% of the acetic acid. The final crystal was then filtered, washed with water and dried under vacuum to give 6.3 g (70%) of 5-nitro-2-oxindole.

(c) Preparation of 5-Amino-2-oxindole. The 5-nitro-2-oxindole (6.3 g) was hydrogenated in methanol over 10% palladium on carbon to give 3.0 g (60% yield) of the title compound as a white solid.

(d) Preparation of 5-Fluoro-2-oxindole. 5-Fluoroisatin (8.2 g) was dissolved in 50 mL of hydrazine hydrate and refluxed for 1 hr. The reaction mixtures were then poured in ice water. The precipitate was then filtered, washed with water and dried under vacuum oven to give 6.0 g of 5-fluoro-2-oxindole (79% yield).

(e) Preparation of 5-Bromo-2-oxindole. 2-Oxindole (1.3 g) in 20 mL of acetonitrile was cooled to −10° C. and 2.0 g of N-bromosuccinimide was slowly added with stirring. The reaction was stirred for 1 hour at −10° C. and 2 hours at 0° C. The precipitate was collected, washed with water and dried to give 1.9 g (90% yield) of the title compound.

(f) Preparation 5-Carboxy-2-oxindole

Step 1. Synthesis of 5-Methoxycarbonyl-2-oxindole. 5-Iodo-2-oxindole (17 g) was refluxed with 2 g of palladium diacetate, 18.15 g of triethylamine, 150 mL of methanol, 15 mL of dimethylsulfoxide and 2.6 g of DPPP in an atmosphere saturated with carbon monoxide. After 24 hours, the reaction was filtered to remove the catalyst and the filtrate concentrated. The concentrate was chromatographed on a silica gel in 30% ethyl acetate in hexane. The fractions containing product were concentrated and allowed to stand. The precipitated product was collected by vacuum filtration to give 0.8 g (7%) of the title compound as an off-white solid.

Step 2: Synthesis of 5-Carboxy-2-oxindole. 5-Methoxycarbonyl-2-oxindole (1 g) and 1 g of sodium hydroxide in 20 mL of methanol was refluxed for 3 hours. The reaction mixture was cooled and concentrated todryness. The residue was dissolved in water and extracted twice with ethyl acetate. The aqueous layer was acidified with 6 N hydrochloric acid and the precipitated solid collected, washed with water, and dried to give 0.7 g (78%) of the title compound as an off-white solid.

(g) Preparation of 5-Carboxyethyl-2-oxindole

Step 1: Synthesis of 5-Chloroacetyl-2-oxindole. Aluminum chloride (30.8 g) and 2-oxindole (5.0 g) were added to 200 ml of carbon disulfide at room temperature and the mixture stirred. Chloroacetyl chloride (3.8 mL) was added and the stirring continued for 1 hour. The mixture was heated to reflux for 3 hours, cooled and the solvent decanted. The residue was stirred in ice water until it became a solid suspension. The solid was collected by vacuum filtration, washed in water, and dried to give 7.0 g (90% yield) of the title compound.

Step 2: Synthesis of 5-Chloroethyl-2-oxindole. 5-Chloroacetyl-2-oxindole (7.0 g) was added to 25 mL of trifluoroacetic acid and the mixture cooled in an ice bath with stirring. Triethylsilane (12.3 mL) was added dropwise over 2 minutes. The reaction was then stirred at room temperature for 4 hours and poured into ice water. Hexane was added, the mixture stirred vigorously, and the solid collected by vacuum siltation and washed with hexane to give 5.9 g (91% yield) of the product as a white solid.

Step 3: Synthesis of 5-Cyanoethyl-2-oxindole. Potassium cyanide (2.02 g) was added to 15 mL of dimethylsulfoxide and heated to 90° C. 5-Chloroethyl-2-oxindole (3.0 g) dissolved in 5mL of dimethylsulfoxide was added slowly with stirring, and the reaction heated to 150° C. for 2 hours. The mixture was cooled, poured into ice water and the precipitate collected by vacuum filtration, washed with water, and dried to give crude product. The crude material was chromatographed on silica gel in 5% methanol in chloroform to give 1.2 g (42% yield) of the title compound.

Step 4: Synthesis of 5-Carboxyethyl-2-oxindole. 5-Cyanoethyl-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

(h) Preparation of 3,5-Dimethylpyrrol-2-carboxaldehyde 5-Cyanoethly-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

(i) Preparation of 3,5-Dimethylpyrrol-2-carboaldehyde

To a solution dimethylformamide (80.4 g) and 1 L of dichloroethane at 0° C. was added phosphorous oxychoride (153.3 g) over a few minutes and the reaction stirred for 1–2 hr at 0° C. 2,4-Dimethylpyrrole (114.6 g) was added dropwise to the above solution at temperature below 5° C. After the addition was complete the reaction was heated and the aqueous layer isolated and saved. The organic layer was extracted again with 300 mL of water and the two aqueous layers combined. The aqueous phase was extracted with 200 mL of dichloroethane and the organic layer discarded. The aqueous phase was cooled to 10° C. and adjusted to pH 10 with 10% sodium hydroxide. The mixture was stirred at 10° C. for 2 hr. The yellow solid was collected by vacuum filtration and washed thoroughly with water. The solid was dried at room temperature under vacuum to give 110.8 g (90% yield of 2,4-dimethyl-5-formylpyrrole).

(j) Preparation of 3,5-Diethylpyrrol-2-carboxaldehyde:

The solution of 25.0 g of 3,5-heptanedione and 42.3 g of diethyl aminomalonate hydrochloride in 200 mL of acetic acid was heated to 95–10° C. for 1.25 hr. Sodium acetate was added and the reaction mixture was stirred for 5.35 hr and cooled down for 4 hr. The salt was filtered and washed with acetic acid. The acetic acid solution was then concentrated and the residue poured into 800 mL of water. The yellow solid was filtered and dried in a vacuum oven overnight to give 36.0 g of ethyl 3,5-diethlypyrrol-2-carboxalate as the orange liquid (92% yield).

Decarboxylation of ethyl 3,5-diethylpyrro-2-carboxalate upon hydrolysis gave 2,4-diethylpyrrole. The title compound was then synthesized via Vilsmeier formulation of 2,4-diethlpyrrole with the same condition used for the preparation of 3,5-dimethylpyrrol-5-carboxaldehyde.

(k) Preparation of 3,5-Diisopropylpyrrol-2-carboxaldehyde

The procedure was the same as the one for the preparation of 3,5-diethylpyrrol-2-carboxaldehyde except starting with 2,6-dimethyl-3,5-heptanedione.

Example 2

FLK Inhibition by Indolinone Compounds of the Invention

An enzyme linked immunosorbent assay (ELISA) was conducted to measure the catalytic activity of the FLK-1 receptor and more specifically, the inhibition or activation of indolinone compounds on the catalytic activity of the FLK-1 receptor. Specifically, the following assay was conducted to measure catalytic activity of the FLK-1 receptor in FLK-1/NIH3T3 cells.

The materials and protocol for the FLK-1 ELISA assay are as described in International Patent Publication No. WO 96/40116, published Dec. 19, 1996 by Tang et al.

Selected compounds were tested in the FLK-1 ELISA assay. IC50 measurements are reported in the tables. Derivatives of 3-[(indole-3-yl)methylene]-2-indolinone compounds with a methyl substituent at the 1' position proved to be the most potent inhibitors of the group of compounds tested in the assay.

Example 3

In Vitro RTK Assays

The following in vitro assays may be used to determine the level of activity and effect of the different compounds of the present invention on one or more of the RTKs. Similar assays can be designed along the same lines for any tyrosine kinase using techniques well known in the art.

(a) Enzyme Linked Immunosorbent Assay (ELISA)

Enzyme linked immunosorbent assays (ELISA) may be used to detect and measure the presence of tyrosine kinase activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. Of Microbiology, Washington, D.C.

The disclosed protocol may be adapted for determining activity with respect to a specific RTK. For example, the preferred protocols for conducting the ELISA experiments for specific RTKs is provided below. Adaptation of these protocols for determining a compound's activity for other members of the RTK family, as well as other receptor and non-receptor tyrosine kinases, are within the scope of those in the art.

(i) FLK-1 ELISA

An ELISA assay was conducted to measure the kinase activity of the FLK-1 receptor and more specifically, the inhibition or activation of protein tyrosine kinase activity on the FLK-1 receptor. Specifically, the following assay was conducted to measure kinase activity of the FLK-1 receptor in FLK-1/NIH3T3 cells.

Materials and Methods.

Materials. The following reagents and supplies were used:
a. Corning 96-well ELISA plates (Corning Catalog No. 25805–96);
b. Cappel goat anti-rabbit IgG (catalog no. 55641);
c. PBS (Gibco Catalog No. 450–1300EB);
d. TBSW Buffer (50 mM Tris (pH 7.2), 150 mM NaCl and 0.1% Tween-20);
e. Ethanolamine stock (10% ethanolamine (pH 7.0), stored at 4° C.);
f. HNTG buffer (20 mM HEPES buffer (pH 7.5), 150 mM NaCl, 0.2% Triton X-100, and 10% glycerol);
g. EDTA (0.5 M (pH 7.0) as a 100× stock);
h. Sodium ortho vanadate (0.5 M as a 100× stock);
i. Sodium pyro phosphate (0.2M as a 100× stock);
j. NUNC 96 well V bottom polypropylene plates (Applied Scientific Catalog No. AS-72092);
k. NIH3T3 C7#3 Cells (FLK-1 expressing cells);
l. DMEM with 1× high glucose L Glutamine (catalog No. 11965-050);
m. FBS, Gibco (catalog no. 16000-028);
n. L-glutamine, Gibco (catalog no. 25030-016);
o. VEGF, PeproTech, Inc. (catalog no. 100-20)(kept as 1 µg/100 µl stock in Milli-Q $dH_2O$ and stored at −20° C.;
p. Affinity purified anti-FLK-1 antiserum which can be obtained or purified as follows:
  1. Prepare a Tresyl-Activated Agarose/Flk-1-D column by incubating 10 ml of Tresyl-Activated Agarose with 20 mg of purified GST-Flk-1-D fusion protein in 100 mM sodium bicarbonate (pH 9.6) buffer overnight at 4° C.
  2. Wash the column once with PBS.
  3. Block the excess sites on the column with 2 M glycine for 2 hours at 4° C.
  4. Wash the column with PBS.
  5. Incubate the column with Rabbit anti-Flk-1D production bleed for 2 hours at 4° C.
  6. Wash the column with PBS.
  7. Elute antiserum with 100 mM Citric Acid, pH3.0 and neutralize the eluate immediately with 2 M Tris, pH 9.0.
  8. Dialyize the eluate against PBS overnight at 4° C. with 3 changes of buffer (sample to buffer ratio is 1:100).
  9. Adjust the dialyized antiserum to 5% glycerol and store at −80° C. in small aliquotes.

q. UB40 monoclonal antibody specific for phosphotyrosine, (see, Fendley, et al., 1990, *Cancer Research* 50:1550–1558);

r. EIA grade Goat anti-mouse IgG-POD (BioRad catalog no. 172-1011);

s. 2,2-azino-bis(3-ethylbenz-thiazoline-6-sulfonic acid (ABTS) solution (100 mM citric acid (anhydrous), 250 mM $Na_2HPO_4$ (pH 4.0), 0.5 mg/ml ABTS (Sigma catalog no. A-1888)), solution should be stored in dark at 4° C. until ready for use;

t. $H_2O_2$ (30% solution) (Fisher catalog no. H325);

u. $ABTS/H_2O_2$ (15 ml ABTS solution, 2 μl $H_2O_2$) prepared 5 minutes before use and left at room temperature;

v. 0.2 M HCl stock in $H_2O$;

w. dimethylsulfoxide (100%) (Sigma Catalog No. D-8418); and x. Trypsin-EDTA (Gibco BRL Catalog No. 25200-049).

Protocol. The following protocol was used for conducting the assay:

1. Coat Corning 96-well elisa plates with 1.0 μg per well Cappel Anti-rabbit IgG antibody in 0.1M $Na_2CO_3$ pH 9.6. Bring final volume to 150 μl per well. Coat plates overnight at 4° C. Plates can be kept up to two weeks when stored at 4° C.

2. Grow cells in Growth media(DMEM, supplemental with 2.0 mM L-Glutamine, 10% FBS) in suitable culture dishes until confluent at 37° C., 5% $CO_2$.

3. Harvest cells by trypsinization and seed in Corning 25850 polystyrene 96-well roundbottom cell plates, 25.000 cells/well in 200 μl of growth media.

4. Grow cells at least one day at 37° C., 5% $CO_2$.

5. Wash cells with D-PBS 1×.

6. Add 200 μl/well of starvation media (DMEM, 2.0 mM 1-Glutamine, 0.1% FBS). Incubate overnight at 37° C., 5% $CO_2$.

7. Dilute Compounds/Extracts 1:20 in polypropylene 96 well plates using starvation media. Dilute dimethylsulfoxide 1:20 for use in control wells.

8. Remove starvation media from 96 well cell culture plates and add 162 μl of fresh starvation media to each well.

9. Add 18 μl of 1:20 diluted Compound/Extract dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% $CO_2$ for two hours.

10. Remove unbound antibody from ELISA plates by inverting plate to remove liquid. Wash 3 times with TBSW+ 0.5% ethanolamine, pH 7.0. Pat the plate on a paper towel to remove excess liquid and bubbles.

11. Block plates with TBSW+0.5% Ethanolamine, pH 7.0, 150 μl per well. Incubate plate thirty minutes while shaking on a microtiter plate shaker.

12. Wash plate 3 times as described in step 10.

13. Add 0.5 μg/well affinity purified anti-FLU-1 polyclonal rabbit antiserum. Bring final volume to 150 μl/well with TBSW+0.5% ethanolamine pH 7.0. Incubate plate for thirty minutes while shaking.

14. Add 180 μl starvation medium to the cells and stimulate cells with 20 μl/well 10.0 mM sodium ortho vanadate and 500 ng/ml VEGF (resulting in a final concentration of 1.0 mM sodium ortho vanadate and 50 ng/ml VEGF per well) for eight minutes at 37° C., 5% $CO_2$. Negative control wells receive only starvation medium.

15. After eight minutes, media should be removed from the cells and washed one time with 200 μl/well PBS.

16. Lyse cells in 150 μl/well HNTG while shaking at room temperature for five minutes. HNTG formulation includes sodium ortho vanadate, sodium pyro phosphate and EDTA.

17. Wash ELISA plate three times as described in step 10.

18. Transfer cell lysates from the cell plate to elisa plate and incubate while shaking for two hours. To transfer cell lysate pipette up and down while scrapping the wells.

19. Wash plate three times as described in step 10.

20. Incubate ELISA plate with 0.02 μg/well UB40 in TBSW+05% ethanolamine. Bring final volume to 150 μl/well. Incubate while shaking for 30 minutes.

21. Wash plate three times as described in step 10.

22. Incubate ELISA plate with 1:10,000 diluted EIA grade goat anti-mouse IgG conjugated horseradish peroxidase in TBSW+0.5% ethanolamine, pH 7.0. Bring final volume to 150 μl/well. Incubate while shaking for thirty minutes.

23. Wash plate as described in step 10.

24. Add 100 μl of $ABTS/H_2O_2$ solution to well. Incubate ten minutes while shaking.

25. Add 100 μl of 0.2 M HCl for 0.1 M HCl final to stop the color development reaction. Shake 1 minute at room temperature. Remove bubbles with slow stream of air and read the ELISA plate in an ELISA plate reader at 410 nm.

(ii) HER-2 ELISA

HER-2 ELISA assays are described in International Patent Publication No. WO 96/40116, published Dec. 19, 1996 by Tang et al.

(iii) PDGF-R ELISA

A PDGF-R ELISA is described in International Patent Publication No. WO 96/40116, published Dec. 19, 1996 by Tang et al.

(iv) IGF-I ELISA

The IGF-I ELISA protocol described in International Patent Publication No. WO 96/40116, published Dec. 19, 1996 by Tang et al. may be used to measure phosphotyrosine level on IGF-I receptor, which indicates IGF-I receptor tyrosine kinase activity.

(v) EGF Receptor ELISA

EGF Receptor kinase activity (EGFR-NIH3T3 assay) in whole cells was measured as described in International Patent Publication No. WO 96/40116, published Dec. 19, 1996 by Tang et al.

(vi) Cellular Insulin Receptor ELISA

The protocol described in International Patent Publication No. WO 96/40116, published Dec. 19, 1996 by Tang et al. was used to determine whether the compounds of the present invention possessed insulin receptor tyrosine kinase activity.

(vii) EGFR ELISA ASSAY

Purpose

To provide a consistent method for measuring the in vitro kinase activity of the EGFR in an Enzyme-linked immunosorbent assay (Elisa).

Scope. The following protocol describes the procedures used to analyze protein tyrosine kinase activity on the EGFR in an Elisa. The procedure also describes the protocol for the initial screening of drugs for inhibition or activation of protein tyrosine kinase activity.

Reagents and Supplies.

1. Corning 96-well Elisa plates

Corning Catalog #25805-96

2. 05-101 monoclonal anti-EGFR antibody (commercially available from UB1)

−80° C., 1 ml aliquots

3. PBS (Dulbecco's Phosphate-Buffered Saline)

Gibco Catalog # 450-1300EB

| Formulation: | 2.7 mM KCL |
| | 1.1 mM KH2PO$_4$ |
| | 0.5 mM MgCl$_2$ (anhydrous) |
| | 138 mM NaCl |
| | 8.1 mM Na2HPO$_4$ |

4. TBST Buffer

| Formulation: | 50 mM Tris pH 7.2 |
| | 150 mM NaCl |
| | 0.1% Triton X-100 |

5. Blocking Buffer

| Formulation: | 5% Carnation Instant Milk in PBS |

6. A431 cell lysate
A431 cells are available from a variety of commercial sources and may be used lysed using conventional methods known to those skilled in the art or as described for lysis of the 3T3 cells in the EGF cellular assay described herein. −80° C., 1 ml aliquots 7. TBS Buffer

| Formulation: | 50 mM Tris pH 7.2 |
| | 150 mM NaCl |

8. TBS+10% DMSO

| Formulation: | 10% DMSO in TBS Buffer |
| | (DMSO from Sigma, Catalog # D-2650) |

9. ATP/MnCl$_2$ phosphorylation mix

| Formulation: | 0.03 mM ATP |
| | (Adenosine-5'-triphosphate, Sigma Catalog #A-5394) |
| | 50 mM MnCl$_2$ |

Make fresh in autoclaved Milli-Q H2O immediately before use
Keep on ice until use
10. NUNC 96-well V bottom polypropylene plates
Applied Scientific Catalog # AS-72092
11. EDTA

| Formulation: | 200 mM EDTA pH 8.0 |

12. Rabbit polyclonal anti-phosphotyrosine serum or UB40 monoclonal antibody specific for phosphotyrosine or UBI's mab 4610, Upstate Biotechnology, Lake Placid, N.Y., Catalog # 05-321
−80° C., 1 ml aliquots
Thaw 1 ml vial and aliquot in smaller volumes to store at −80° C.
Antiserum is stable for weeks when thawed and stored at 4 C
13. Goat anti-rabbit IgG peroxidase conjugate
Biosource Catalog # ALI0404
14. ABTS Solution

| Formulation: | 100 mM Citric Acid (anhydrous) |
| | 250 mM Na$_2$HPO4 pH 4.0 |
| | 0.5 mg/ml ABTS |

(2,2'-azino-bis(3-ethylbenzthiazoline-6-sulfonic acid) (Sigma Catalog # A-1888)
Keep solution in dark at 4 C until ready to use
15. Hydrogen peroxide 30% solution
Fisher Catalog # H325
Store in the dark at 4 C until ready to use
16. ABTS/H$_2$O$_2$

| Formulation: | 15 mls ABTS solution |
| | 2 ul H$_2$O$_2$ |

Prepare 5 minutes before use and room temperature
17. 0.2 M HCL stock in H$_2$O
Procedure.
1. Coat Corning 96-well elisa plates with 0.5 ug per well 05-101 antibody.
Bring final volume to 100 ul per well with PBS.
Coat plates overnight at 40 C.
2. Remove unbound 05-101 from wells by inverting plate to remove liquid.
Wash 1× with distilled H2O by filling wells
Pat the plate on a paper towel to remove excess liquid.
3. Block plates with 5% milk in PBS.
150 ul per well.
Incubate plate 30 minutes while shaking on a microtiter plate shaker.
4. Wash plate 3× with dionized water, then once with TBST
5. Add 7 ug A431 cell lysate per well (EGFR source).
Add PBS to final volume of 100 ul per well
Incubate 30 minutes while shaking.
6. Wash as described in step 4.
7. At this point, drugs or extracts are added to the wells.
Dilute drugs/extracts 1:100 (unless specified otherwise) in TBS+10% DMSO in 96-well polypropylene plates.
Add 120 ul TBS to ELISA plate containing captured EGFR.
Add 13.5 ul diluted drugs/extracts to ELISA plate.
To control wells (wells which do not receive any drug) add 135 ul TBS+1% DMSO.
Incubate plate 30 minutes while shaking.
8. Add 15 ul of 0.03 mM ATP+50 mM MnCl$_2$ phosphorylation mix directly to all wells except negative control well which does not receive ATP/MnCl2 (see diagram).
(150 ul final volume in well with 3 uM ATP/5 mM MnCl2 final concentration in well.)
Incubate 5 minutes while shaking vigorously.
*NOTE: It is critical that ATP/MnCl2 phosphorylates the receptor for 5 minutes only.

It is best to add the ATP/MnCl$_2$ with an 12 channel pipettor 1 row at a time leaving 20 seconds between each row so that the reaction may be stopped with EDTA exactly 5 minutes later (this depends on the number of plates being phosphorylated in one batch). Shake between each addition.

9. After 5 minutes, to stop reaction, add 16.5 ul of 200 mM EDTA pH 8.0 for 20 mM final in well, shaking continuously between each addition. This is done using the same timing method as above. After last row has received EDTA, shake plate an additional minute.

10. Wash 4× with deionized water, twice with TBST.

11. Add rabbit polyclonal anti-phosphotyrosine serum.
Dilute 1:3000 in TBST.
Add 100 ul per well.
Incubate 30–45 minutes while shaking.

12. Wash as described above in step 4.

13. Add BioSource anti-rabbit peroxidase conjugate antibody.
Dilute 1:2000 in TBST.
Add 100 ul per well.
Incubate 30 minutes while shaking.

14. Wash as described in step 4.

15. Add 100 ul of ABTS/H$_2$O$_2$ solution to well.
Incubate 5 to 10 minutes while shaking.
Remove bubbles 16. If necessary stop reaction with the addition of 100 ul of 0.2M HCl per well 17. Read assay on Dynatech MR7000 elisa reader.
Test Filter: 410 nM
Reference Filter: 630 nM (b) Cell Growth Assays The cell growth assays described in International Patent Publication No. WO 96/40116, published Dec. 19, 1996 by Tang et al. may be conducted to measure the effect of the claimed compounds upon cell growth as a result of the compound's interaction with one or more RTKs.

(vi) Assay Measuring Phosphorylating Function of Raf

The following assay reports the amount of RAF-catalyzed phosphorylation of its target protein MEK as well as MEK's target MAPK. The RAF gene sequence is described in Bonner et al., 1985, *Molec. Cell. Biol.* 55: 1400–1407, and is readily accessible in multiple gene sequence data banks. Construction of the nucleic acid vector and cell lines utilized for this portion of the invention are fully described in Morrison et al., 1988, *Proc. Natl. Acad. Sci. USA* 85: 8855–8859.

Materials and Reagents

1. Sf9 (*Spodoptera frugiperda*) cells; GIBCO-BRL, Gaithersburg, Md.

2. RIPA buffer: 20 mM Tris/HCl pH 7.4, 137 mM NaCl, 10% glycerol, 1 mM PMSF, 5 mg/L Aprotenin, 0.5% Triton X-100;

3. Thioredoxin-MEK fusion protein (T-MEK): T-MEK expression and purification by affinity chromatography were performed according to the manufacturer's procedures. Catalog# K 350-01 and R 350-40, Invitrogen Corp., San Diego, Calif.

4. His-MAPK (ERK 2); His-tagged MAPK was expressed in XL1 Blue cells transformed with pUC18 vector encoding His-MAPK. His-MAPK was purified by Ni-affinity chromatography. Cat# 27-4949-01, Pharmacia, Alameda, Calif.

5. Sheep anti mouse IgG: Jackson laboratories, West Grove, Pa. Catalog, # 515-006-008, Lot# 28563

6. RAF-1 protein kinase specific antibody: URP2653 from UBI.

7. Coating buffer: PBS; phosphate buffered saline, GIBCO-BRL, Gaithersburg, Md.

8. Wash buffer: TBST–50 mM Tris/HCL pH 7.2, 150 mM NaCl, 0.1% Triton X-100

9. Block buffer: TBST, 0.1% ethanolamine pH 7.4

10. DMSO, Sigma, St. Louis, Mo.

11. Kinase buffer (KB): 20 mM Hepes/HCl pH 7.2, 150 mM NaCl, 0.1% Triton X-100, 1 mM PMSF, 5 mg/L Aprotenin, 75 µM sodium ortho vanadate, 0.5 mM DTT and 10 mM MgCl$_2$.

12. ATP mix: 100 mM MgCl$_2$, 300 µM ATP, 10 µCi γ-$^{33}$P ATP (Dupont-NEN)/mL.

13. Stop solution: 1% phosphoric acid; Fisher, Pittsburgh, Pa.

14. Wallac Cellulose Phosphate Filter mats; Wallac, Turku, Finland.

15. Filter wash solution: 1% phosphoric acid, Fisher, Pittsburgh, Pa.

16. Tomtec plate harvester, Wallac, Turku, Finland.

17. Wallac beta plate reader # 1205, Wallac, Turku, Finland.

18. NUNC 96-well V bottom polypropylene plates for compounds Applied Scientific Catalog # AS-72092.

Procedure

All of the following steps are conducted at room temperature unless specifically indicated.

1. ELISA plate coating: ELISA wells are coated with 100 µL of Sheep anti mouse affinity purified antiserum (1 µg/100 µL coating buffer) over night at 4° C. ELISA plates can be used for two weeks when stored at 4° C.

2. Invert the plate and remove liquid. Add 100 µL of blocking solution and incubate for 30 min.

3. Remove blocking solution and wash four times with wash buffer. Pat the plate on a paper towel to remove excess liquid.

4. Add 1 µg of purified Sumo 22 to each well and incubate for 1 hour. Wash as described in step 3.

5. Thaw lysates from RAS/RAF infected Sf9 cells and dilute with TBST to 10 µg/100 µL. Add 10 µg of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifugation (5 min at 10 000×g). Aliquots of lysates are frozen in dry ice/ethanol and stored at –80° C. until use.

6. Remove non-bound material and wash as outlined above (step 3).

7. Add 2 µg of T-MEK and 2 µg of His-MAPK per well and adjust the volume to 40 µL with kinase buffer.

8. Predilute compounds (stock solution 10 mg/mL DMSO) or extracts 20 fold in TBST plus 1% DMSO. Add 5 µL of the prediluted compounds/extracts to the wells described in step 6. Incubate for 20 min. Controls receive no drug.

9. Start the kinase reaction by addition of 5 µL ATP mix; Shake the plates on an ELISA plate shaker during incubation.

10. Stop the kinase reaction after 60 min by addition of 30 µL stop solution to each well.

11. Place the phosphocellulose mat and the ELISA plate in the Tomtec plate harvester. Harvest and wash the filter with the filter wash solution according to the manufacturers recommendation. Dry the filter mats. Seal the filter mats and place them in the holder. Insert the holder into radioactive detection apparatus and quantitate the radioactive phosphorous on the filter mats.

Alternatively, 40 µL aliquots from individual wells of the assay plate can be transferred to the corresponding positions on the phosphocellulose filter mat. After air-drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantitate the radioactive phosphorous on the filter mats.

(c) Toxicity and Animal Models

Measurement Of Cell Toxicity and In Vivo Animal Models are described in International Patent Publication No. WO 96/40116, published Dec. 19, 1996 by Tang et al.

(d) MET Biochemical Kinase Assay

A met biochemical kinase assay may be performed for met generally as described above for other kinases by substituting that or the other kinases. In particular, ELISA plates are coated with goat anti-rabbit Fc antibodies, which are used to capture commercially available (from Santa Cruz Biotechnology) rabbit polyclonal antibodies to the cytoplasmic domain of human MET. Lysates are made from 293T cells that have been transiently transfected with a chimeric receptor composed of the extracellular domain of the EGFr and the transmembrane and cytoplasmic domain of the MET receptor, or from NCI-H441 cells (a human lung adenocarcinoma cell line) which express high endogenous levels of MET. The chimeric receptors, or MET, from these lysates are captured on the antibody coated plates. After washing away extraneous proteins, test compounds are added and an in vitro kinase assay is performed by addition of an appropriate kinase buffer (containing ATP, divalent metal ions, etc.). Incorporation of phosphate into the captured receptors is detected with an anti-phosphotyrosine antibody conjugate with horse radish peroxidase using TMB as a substrate for calorimetric detection.

The present invention is not to be limited in scope by the exemplified embodiments which are intended as illustrations of single aspects of the invention. Indeed, various modifications of the invention in addition to those described herein will become apparent to those skilled in the art from the foregoing description and accompanying drawings. Such modifications are intended to fall within the scope of the appended claims.

All references cited herein are hereby incorporated by reference in their entirety.

Other embodiments are within the following claims.

TABLE 1

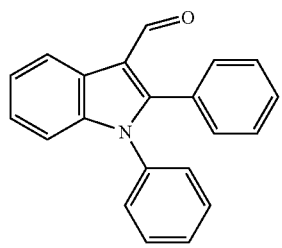

TABLE 1-continued

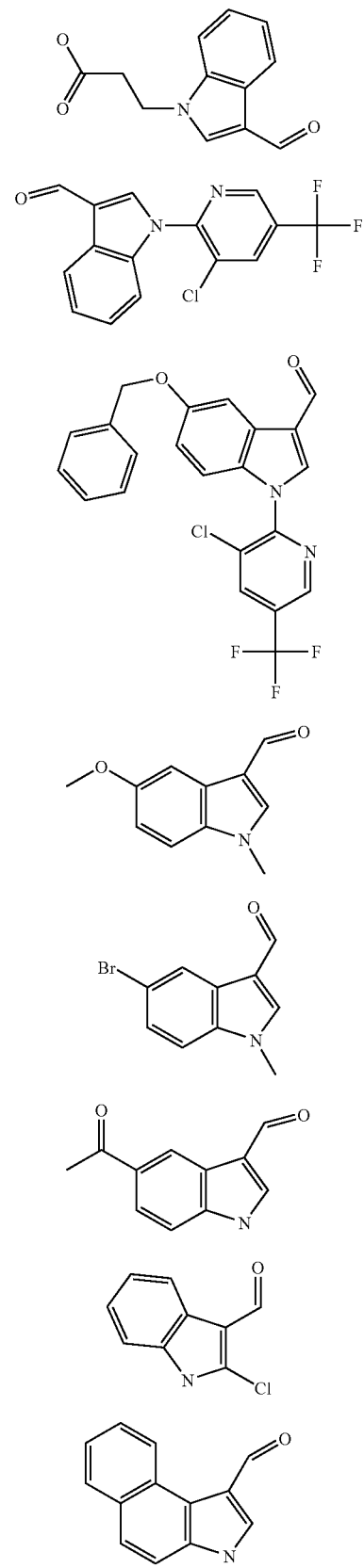

TABLE 1-continued
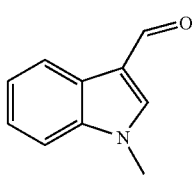
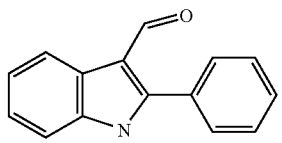
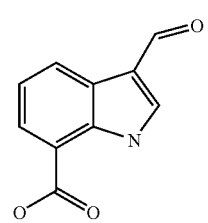
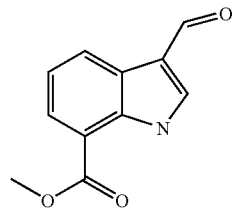
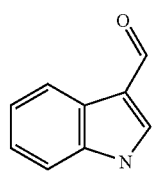
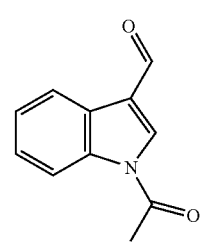
TABLE 1-continued
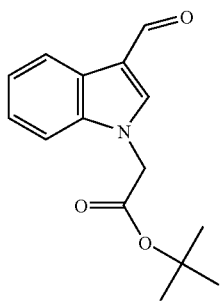
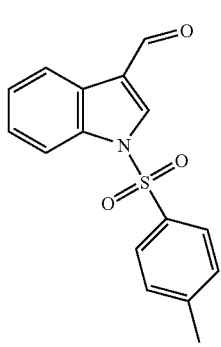
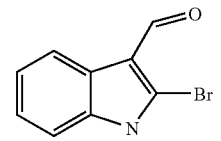
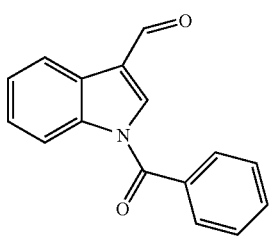
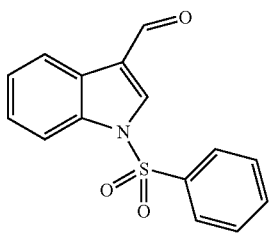
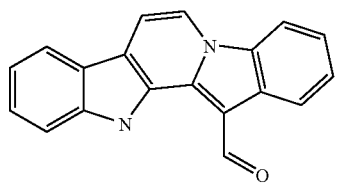

TABLE 1-continued
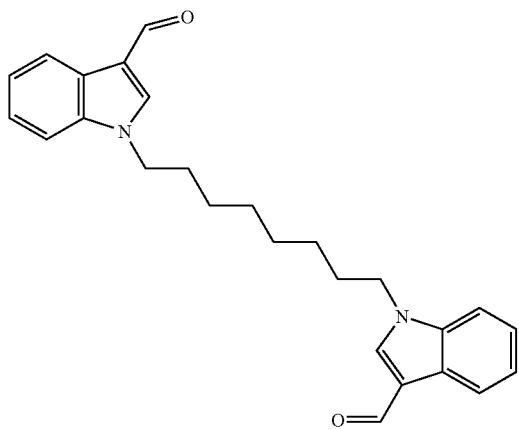
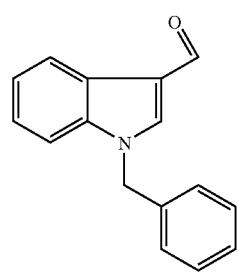
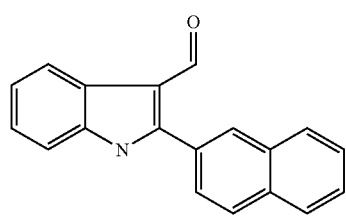
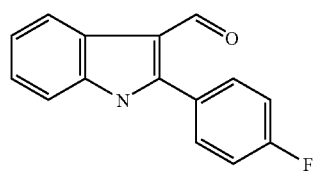
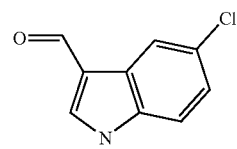
TABLE 1-continued
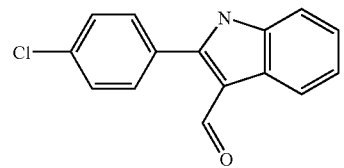
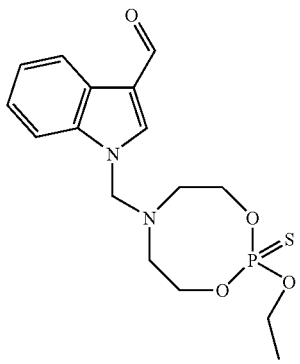
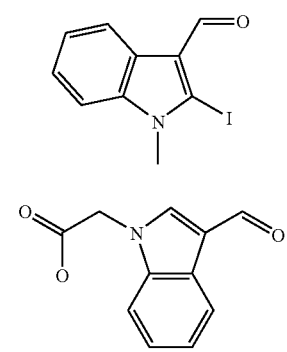
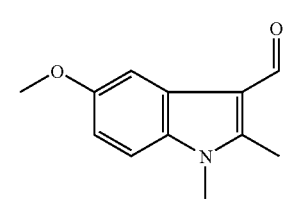
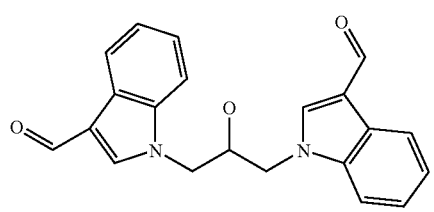
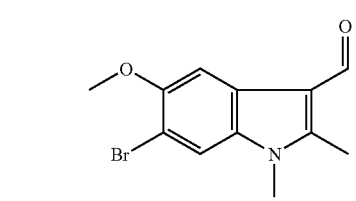

TABLE 1-continued
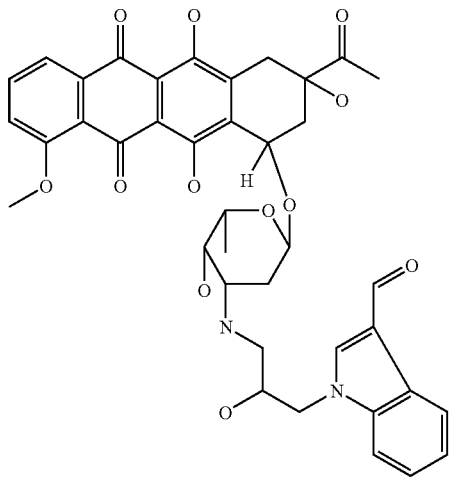
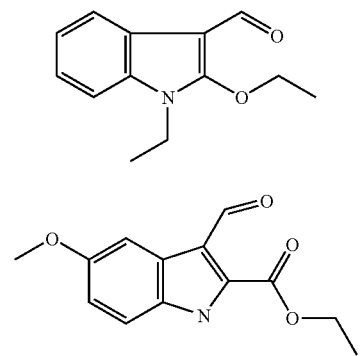
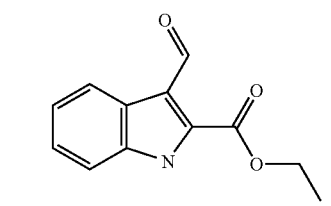
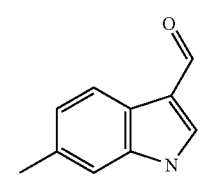
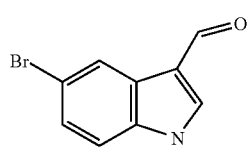
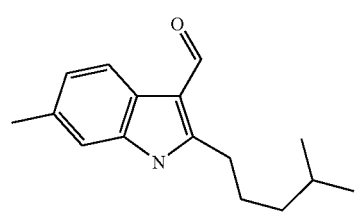
TABLE 1-continued
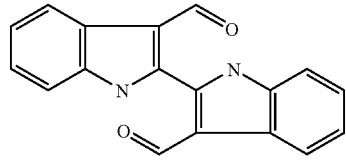
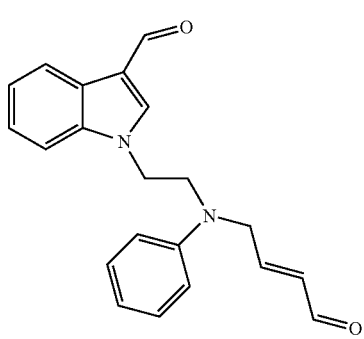
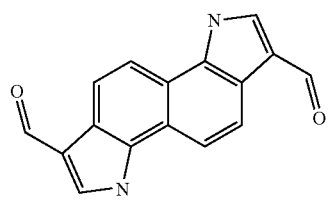
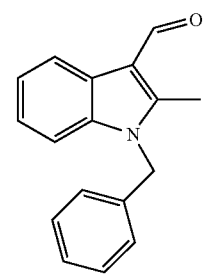
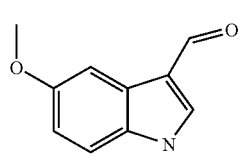
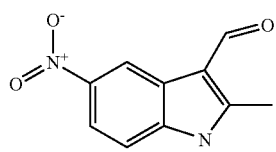
TABLE 2
| FLK Kinase IC50 (μM) | STRUCTURES |
|---|---|
| 0.7 | 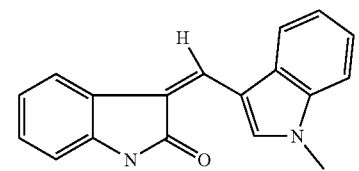 |

TABLE 2-continued

| FLK Kinase IC50 (μM) | STRUCTURES |
|---|---|
| 7.7 | (4-methyl-indolin-2-one linked via =CH to N-methyl indole) |
| 2.5 | (5-amino-indolin-2-one linked via =CH to N-methyl indole) |
| 14 | (5-fluoro-indolin-2-one linked via =CH to N-methyl indole) |
| 13 | (indolin-2-one linked via =CH to 5-methoxy indole) |

TABLE 3

| NUMBER | ID | STRUCTURE |
|---|---|---|
| 1 | ind/ald-001 | 1-(2-carboxyethyl)-1H-indole-3-carbaldehyde |
| 2 | ind/ald-002 | 1-methyl-1H-indole-3-carbaldehyde |
| 3 | ind/ald-003 | 1,2-diphenyl-1H-indole-3-carbaldehyde |
| 4 | ind/ald-004 | 1-benzyl-1H-indole-3-carbaldehyde |
| 5 | ind/ald-005 | 1-benzoyl-1H-indole-3-carbaldehyde |
| 6 | ind/ald-006 | 1-acetyl-1H-indole-3-carbaldehyde |
| 7 | ind/ald-007 | 1-(4-methylphenylsulfonyl)-1H-indole-3-carbaldehyde |
| 8 | ind/ald-008 | 1-[3-chloro-5-(trifluoromethyl)pyridin-2-yl]-1H-indole-3-carbaldehyde |
| 9 | ind/ald-009 | 5-benzyloxy-1-[3-chloro-5-(trifluoromethyl)pyridin-2-yl]-1H-indole-3-carbaldehyde |

TABLE 3-continued
| NUMBER | ID | STRUCTURE |
|---|---|---|
| 10 | ind/ald-010 | 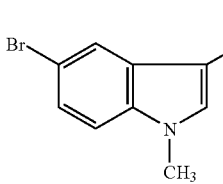 |
| 11 | ind/ald-011 | 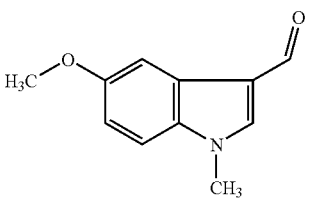 |
| 12 | ind/ald-012 | 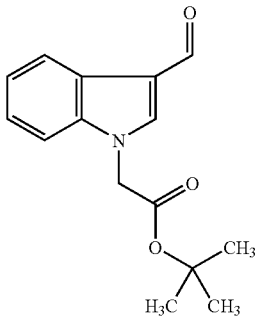 |
| 13 | ind/ald-013 | 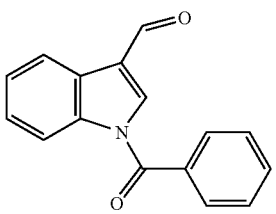 |
| 14 | ind/ald-014 | 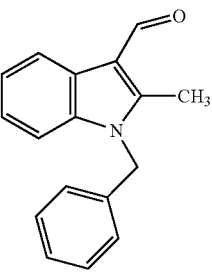 |
| 15 | ind/ald-015 | 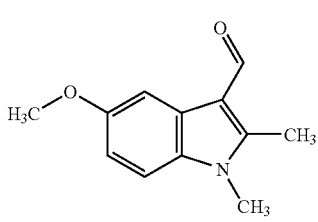 |
TABLE 3-continued
| NUMBER | ID | STRUCTURE |
|---|---|---|
| 16 | ind/ald-016 | 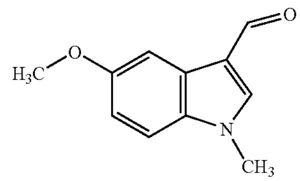 |
| 17 | ind/ald-017 | 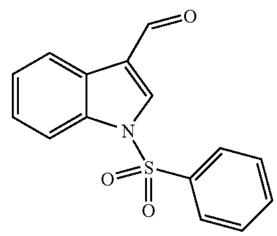 |
| 18 | ind/ald-018 | 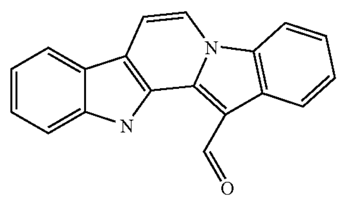 |
| 19 | ind/ald-019 | 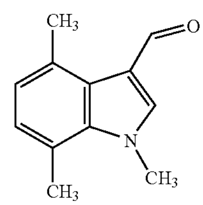 |
| 20 | ind/ald-020 | 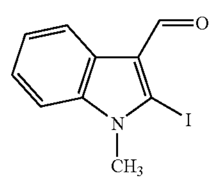 |
| 21 | ind/ald-021 | 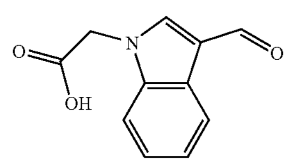 |
| 22 | ind/ald-022 | 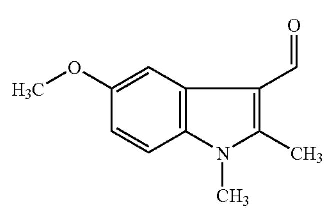 |

TABLE 3-continued

| NUMBER | ID | STRUCTURE |
|---|---|---|
| 23 | ind/ald-023 | (5-methoxy-6-bromo-1,2-dimethyl-1H-indole-3-carbaldehyde) |
| 24 | ind/ald-024 | (2-ethoxy-1-ethyl-1H-indole-3-carbaldehyde) |
| 25 | ind/ald-025 | (1-(phenylsulfonyl)-1H-indole-3-carbaldehyde) |

TABLE 4

| NUMBER | CORP ID | STRUCTURE |
|---|---|---|
| 1 | oxindole-001 | (5-amino-1,3-dihydro-2H-indol-2-one) |
| 2 | oxindole-002 | (5-bromo-1,3-dihydro-2H-indol-2-one) |
| 3 | oxindole-003 | (5-chloro-1,3-dihydro-2H-indol-2-one) |
| 4 | oxindole-004 | (4,6-dimethyl-1,3-dihydro-2H-indol-2-one) |
| 5 | oxindole-005 | (5,6-dimethoxy-1,3-dihydro-2H-indol-2-one) |
| 6 | oxindole-006 | (1,3-dihydro-2H-indol-2-one) |

TABLE 4-continued

| NUMBER | CORP ID | STRUCTURE |
|---|---|---|
| 7 | oxindole-007 | 4-methyl oxindole |
| 8 | oxindole-008 | 5,7-dibromo oxindole |
| 9 | oxindole-009 | 5-chloro-7-bromo oxindole |
| 10 | oxindole-010 | 5-fluoro oxindole |
| 11 | oxindole-011 | 5-nitro oxindole |
| 12 | oxindole-012 | 5-iodo oxindole |
| 13 | oxindole-013 | 5-chloro-7-methyl oxindole |
| 14 | oxindole-014 | 5-methyl oxindole |
| 15 | oxindole-015 | 5-bromo-4-methyl oxindole |
| 16 | oxindole-016 | 7-fluoro oxindole |

TABLE 4-continued

| NUMBER | CORP ID | STRUCTURE |
|---|---|---|
| 17 | oxindole-028 | 3-(4-methyl-2-oxoindolin-5-yl)propanoic acid |
| 18 | oxindole-036 | 2-oxoindoline-5-sulfonamide |
| 19 | oxindole-037 | N-methyl-2-oxoindoline-5-sulfonamide |
| 20 | oxindole-038 | 2-oxo-N-(4-(trifluoromethyl)phenyl)indoline-5-sulfonamide |
| 21 | oxindole-039 | 5-(morpholinosulfonyl)indolin-2-one |
| 22 | oxindole-040 | 6-(trifluoromethyl)indolin-2-one |
| 23 | oxindole-041 | 5-(2-chloroethyl)indolin-2-one |
| 24 | oxindole-045 | methyl 2-oxoindoline-5-carboxylate |
| 25 | oxindole-048 | 2-oxoindoline-5-carboxylic acid |

TABLE 4-continued
| NUMBER | CORP ID | STRUCTURE |
|---|---|---|
| 26 | oxindole-050 | 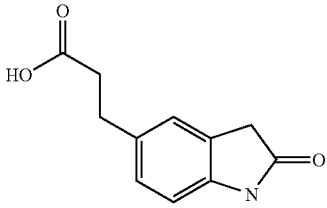 |
| 27 | oxindole-054 | 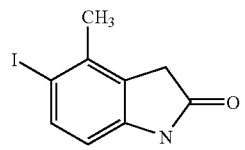 |
| 28 | oxindole-056 | 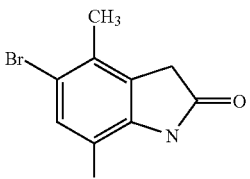 |
| 29 | oxindole-057 | 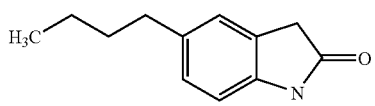 |
| 30 | oxindole-058 | 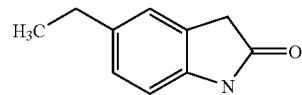 |
| 31 | oxindole-059 | 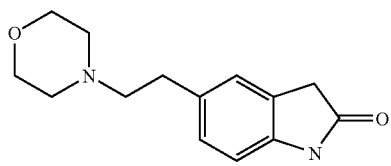 |
| 32 | oxindole-060 | 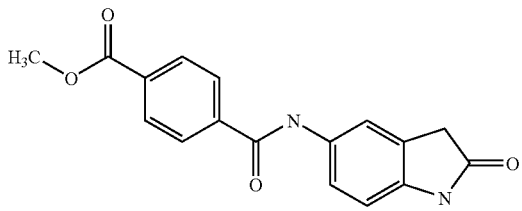 |
| 33 | oxindole-061 | 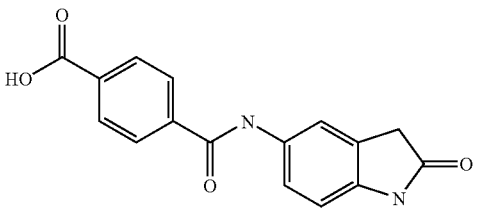 |
| 34 | oxindole-062 | 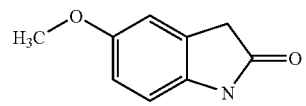 |

TABLE 5

| Structure | |
|---|---|
| (structure) | Formula $C_{17}H_{15}BrN_2O$<br>M.W. 343.2230 |
| (structure) | Formula $C_{17}H_{16}N_2O$<br>M.W. 264.3260 |
| (structure) | Formula $C_{18}H_{18}N_2O$<br>M.W. 278.3530 |

TABLE 6

| FLK Kinase IC50 (µM) | STRUCTURES |
|---|---|
| 1.2 | (structure) |
| 1.4 | (structure) |
| 5 | (structure) |

TABLE 7

| Structure | |
|---|---|
| (structure) | 0128<br>Activity<br>$IC_{50} = 1.7$ µm  FLK Kinase<br>$IC_{50} = 6.8$ µm  PDGF Kinase |
| (structure) | 0129<br>Activity<br>$IC_{50} = 19.6$ µm  FLK Kinase<br>$IC_{50} = 0.6$ µm  PDGF Kinase |

TABLE 8

| Structure | |
|---|---|
| (structure) | SU #<br>Activity<br>$EC_{200} = 2.8$ µm |
| (structure) | SU #<br>Activity<br>$EC_{200} = 2.8$ µm |
| (structure) | SU #<br>Activity<br>$EC_{200} = 10$ µm |

TABLE 8-continued

| Structure | SU # Activity |
|---|---|
| (structure) | EC$_{200}$ = 32 μm |
| (structure) | EC$_{200}$ > 100 μm |
| (structure) | EC$_{200}$ = 46 μm |

TABLE 9

3-[(pyrrol-2-yl)methylidenyl]-5-sulfonyl-2-indolinone
3-[(2,4-dimethylpyrrol-5-yl)methylidenyl]-5-sulfonyl-2-indolinone
3-[(2,4-dimethyl-3-ethoxycarbonylpyrrol-5-yl)methylidenyl]-5-sulfonyl-2-indolinone
3-[(2-methylthien-5-yl)methylidenyl]-5-sulfonyl-2-indolinone
3-[(3-methylthien-2-yl)methylidenyl]-5-sulfonyl-2-indolinone
3-[(4,5,6,7-tetrahydroindol-3-yl)methylidenyl]-5-sulfonyl-2-indolinone
3-[(pyrrol-2-yl)methylidenyl]-5-aminosulfonyl-2-indolinone
3-[(2,4-dimethylpyrrol-5-yl)methylidenyl]-5-aminosulfonyl-2-indolinone
3-[(2,4-dimethyl-3-ethoxycarbonylpyrrol-5-yl)methylidenyl]-5-aminosulfonyl-2-indolinone
3-[(2-methylthien-5-yl)methylidenyl]-5-aminosulfonyl-2-indolinone
3-[(3-methylthien-2-yl)methylidenyl]-5-aminosulfonyl-2-indolinone
3-[(4,5,6,7-tetrahydroindol-3-yl)methylidenyl]-5-aminosulfonyl-2-indolinone
3-[(pyrrol-2-yl)methylidenyl]-5-methoxycarbonyl-2-indolinone
3-[(2,4-dimethylpyrrol-5-yl)methylidenyl]-5-methoxycarbonyl-2-indolinone
3-[(2,4-dimethyl-3-ethoxycarbonylpyrrol-5-yl)methylidenyl]-5-methoxycarbonyl-2-indolinone
3-[(2-methylthien-5-yl)methylidenyl]-5-methoxycarbonyl-2-indolinone
3-[(3-methylthien-2-yl)methylidenyl]-5-methoxycarbonyl-2-indolinone
3-[(4,5,6,7-tetrahydroindol-3-yl)methylidenyl]-5-methoxycarbonyl-2-indolinone
3-[(pyrrol-2-yl)methylidenyl]-5-diethanolamino-2-indolinone
3-[(2,4-dimethylpyrrol-5-yl)methylidenyl]-5-diethanolamino-2-indolinone
3-[(2,4-dimethyl-3-ethoxycarbonylpyrrol-5-yl)methylidenyl]-5-diethanolamino-2-indolinone
3-[(2-methylthien-5-yl)methylidenyl]-5-diethanolamino-2-indolinone
3-[(3-methylthien-2-yl)methylidenyl]-5-diethanolamino-2-indolinone
3-[(4,5,6,7-tetrahydroindol-3-yl)methylidenyl]-5-diethanolamino-2-indolinone
3-[(pyrrol-2-yl)methylidenyl]-5-(2,3-dihydroxypropylamino)-2-indolinone
3-[(2,'4-dimethylpyrrol-5-yl)methylidenyl]-5-(2,3-dihydroxypropylamino)-2-indolinone
3-[(2,4-dimethyl-3-ethoxycarbonylpyrrol-5-yl)methylidenyl]-5-(2,3-dihydroxypropylamino)-2-indolinone
3-[(2-methylthien-5-yl)methylidenyl]-5-(2,3-dihydroxypropylamino)-2-indolinone
3-[(3-methylthien-2-yl)methylidenyl]-5-(2,3-dihydroxypropylamino)-2-indolinone
3-[(4,5,6,7-tetrahydroindol-3-yl)methylidenyl]-5-(2,3-dihydroxypropylamino)-2-
3-[(pyrrol-2-yl)methylidenyl]-5-ureido-2-indolinone
3-[(2,4-dimethylpyrrol-5-yl)methylidenyl]-5-ureido-2-indolinone
3-[(2,4-dimethyl-3-ethoxycarbonylpyrrol-5-yl)methylidenyl]-5-ureido-2-indolinone
3-[(2-methylthien-5-yl)methylidenyl]-5-ureido-2-indolinone
3-[(3-methylthien-2-yl)methylidenyl]-5-ureido-2-indolinone
3-[(4,5,6,7-tetrahydroindol-3-yl)methylidenyl]-5-ureido-2-indolinone
3-[(pyrrol-2-yl)methylidenyl]-5-guanidino-2-indolinone
3-[(2,4-dimethylpyrrol-5-yl)methylidenyl]-5-guanidino-2-indolinone
3-[(2,4-dimethyl-3-ethoxycarbonylpyrrol-5-yl)methylidenyl]-5-guanidino-2-indolinone
3-[(2-methylthien-5-yl)methylidenyl]-5-guanidino-2-indolinone
3-[(3-methylthien-2-yl)methylidenyl]-5-guanidino-2-indolinone
3-[(4,5,6,7-tetrahydroindol-3-yl)methylidenyl]-5-guanidino-2-indolinone
3-[(pyrrol-2-yl)methylidenyl]-5-glyceroylamido-2-indolinone
3-[(2,4-dimethylpyrrol-5-yl)methylidenyl]-5-glyceroylamido-2-indolinone
3-[(2,4-dimethyl-3-ethoxycarbonylpyrrol-5-yl)methylidenyl]-5-glyceroylamido-2-indolinone
3-[(2-methylthien-5-yl)methylidenyl]-5-glyceroylamido-2-indolinone
3-[(3-methylthien-2-yl)methylidenyl]-5-glyceroylamido-2-indolinone
3-[(4,5,6,7-tetrahydroindol-3-yl)methylidenyl]-5-glyceroylamido-2-indolinone
3-[(pyrrol-2-yl)methylidenyl]-5-[(3-piperidinyl)propanoylamino]-2-indolinone
3-[(2,4-dimethylpyrrol-5-yl)methylidenyl]-5-[(3-piperidinyl)propanoylamino]-2-indolinone
3-[(2,4-dimethyl-3-ethoxycarbonylpyrrol-5-yl)methylidenyl]-5-[(3-piperidinyl)propanoylamino]-2-indolinone

TABLE 9-continued

3-[(2-methylthien-5-yl)methylidenyl]-5-[(3-piperidinyl)propanoylamino]-2-indolinone
3-[(3-methylthien-2-yl)methylidenyl]-5-[(3-piperidinyl)propanoylamino]-2-indolinone
3-[(4,5,6,7-tetrahydroindol-3-yl)methylidenyl]-5-[(3-piperidinyl)propanoylamino]-2-indolinone
3-[(pyrrol-2-yl)methylidenyl]-5-mesylamino-2-indolinone
3-[(2,4-dimethylpyrrol-5-yl)methylidenyl]-5-mesylamino-2-indolinone
3-[(2,4-dimethyl-3-ethoxycarbonylpyrrol-5-yl)methylidenyl]-5-mesylamino-2-indolinone
3-[(2-methylthien-5-yl)methylidenyl]-5-mesylamino-2-indolinone
3-[(3-methylthien-2-yl)methylidenyl]-5-mesylamino-2-indolinone
3-[(4,5,6,7-tetrahydroindol-3-yl)methylidenyl]-5-mesylamino-2-indolinone
3-[(pyrrol-2-yl)methylidenyl]-5-glycoloyloxy-2-indolinone
3-[(2,4-dimethylpyrrol-5-yl)methylidenyl]-5-glycoloyloxy-2-indolinone
3-[(2,4-dimethyl-3-ethoxycarbonylpyrrol-5-yl)methylidenyl]-5-glycoloyloxy-2-indolinone
3-[(2-methylthien-5-yl)methylidenyl]-5-glycoloyloxy-2-indolinone
3-[(3-methylthien-2-yl)methylidenyl]-5-glycoloyloxy-2-indolinone
3-[(4,5,6,7-tetrahydroindol-3-yl)methylidenyl]-5-glycoloyloxy-2-indolinone
3-[(pyrrol-2-yl)methylidenyl]-5-(2,3-dihydroxypropoxy)-2-indolinone
3-[(2,4-dimethylpyrrol-5-yl)methylidenyl]-5-(2,3-dihydroxypropoxy)-2-indolinone
3-[(2,4-dimethyl-3-ethoxycarbonylpyrrol-5-yl)methylidenyl]-5-(2,3-dihydroxypropoxy)-2-indolinone
3-[(2-methylthien-5-yl)methylidenyl]-5-(2,3-dihydroxypropoxy)-2-indolinone
3-[(3-methylthien-2-yl)methylidenyl]-5-(2,3-dihydroxypropoxy)-2-indolinone
3-[(4,5,6,7-tetrahydroindol-3-yl)methylidenyl]-5-(2,3-dihydroxypropoxy)-2-indolinone
3-[(pyrrol-2-yl)methylidenyl]-5-aminomethyl-2-indolinone
3-[(2,4-dimethylpyrrol-5-yl)methylidenyl]-5-aminomethyl-2-indolinone
3-[(2,4-dimethyl-3-ethoxycarbonylpyrrol-5-yl)methylidenyl]-5-aminomethyl-2-indolinone
3-[(2-methylthien-5-yl)methylidenyl]-5-aminomethyl-2-indolinone
3-[(3-methylthien-2-yl)methylidenyl]-5-aminomethyl-2-indolinone
3-[(4,5,6,7-tetrahydroindol-3-yl)methylidenyl]-5-aminomethyl-2-indolinone
3-[(pyrrol-2-yl)methylidenyl]-5-amidino-2-indolinone
3-[(2,4-dimethylpyrrol-5-yl)methylidenyl]-5-amidino-2-indolinone
3-[(2,4-dimethyl-3-ethoxycarbonylpyrrol-5-yl)methylidenyl]-5-amidino-2-indolinone
3-[(2-methylthien-5-yl)methylidenyl]-5-amidino-2-indolinone
3-[(3-methylthien-2-yl)methylidenyl]-5-amidino-2-indolinone
3-[(4,5,6,7-tetrahydroindol-3-yl)methylidenyl]-5-amidino-2-indolinone
3-[(pyrrol-2-yl)methylidenyl]-5-hydroxymethyl-2-indolinone
3-[(2,4-dimethylpyrrol-5-yl)methylidenyl] 5-hydroxymethyl-2-indolinone
3-[(2,4-dimethyl-3-ethoxycarbonylpyrrol-5-yl)methylidenyl-5-hydroxymethyl-2-indolinone
3-[(2-methylthien-5-yl)methylidenyl]-5-hydroxymethyl-2-indolinone
3-[(3-methylthien-2-yl)methylidenyl]-5-hydroxymethyl-2-indolinone
3-[(4,5,6,7-tetrahydroindol-3-yl)methylidenyl]-5-hydroxymethyl-2-indolinone
3-[(pyrrol-2-yl)methylidenyl]-5-phosphonooxy-2-indolinone
3-[(2,4-dimethylpyrrol-5-yl)methylidenyl]-5-phosphonooxy-2-indolinone
3-[(2,4-dimethyl-3-ethoxycarbonylpyrrol-5-yl)methylidenyl]-5-phosphonooxy-2-indolinone
3-[(2-methylthien-5-yl)methylidenyl]-5-phosphonooxy-2-indolinone
3-[(3-methylthien-2-yl)methylidenyl]-5-phosphonooxy-2-indolinone
3-[(4,5,6,7-tetrahydroindol-3-yl)methylidenyl]-5-phosphonooxy-2-indolinone
3-[(pyrrol-2-yl)methylidenyl]-5-ethoxycarbonyl-2-indolinone
3-[(2,4-dimethylpyrrol-5-yl)methylidenyl]-5-ethoxycarbonyl-2-indolinone
3-[(2,4-dimethyl-3-ethoxycarbonylpyrrol-5-yl)methylidenyl]-5-ethoxycarbonyl-2-indolinone
3-[(2-methylthien-5-yl)methylidenyl]-5-ethoxycarbonyl-2-indolinone
3-[(3-methylthien-2-yl)methylidenyl]-5-ethoxycarbonyl-2-indolinone
3-[(4,5,6,7-tetrahydroindol-3-yl)methylidenyl]-5-ethoxycarbonyl-2-indolinone
3-[(pyrrol-2-yl)methylidenyl]-5-benzyloxycarbonyl-2-indolinone
3-[(2,4-dimethylpyrrol-5-yl)methylidenyl]-5-benzyloxycarbonyl-2-indolinone
3-[(2,4-dimethyl-3-ethoxycarbonylpyrrol-5-yl)methylidenyl]-5-benzyloxycarbonyl-2-indolinone
3-[(2-methylthien-5-yl)methylidenyl]-5-benzyloxycarbonyl-2-indolinone 5-benzyloxycarbonyl-2-indolinone
3-[(3-methylthien-2-yl)methylidenyl]-5-benzyloxycarbonyl-2-indolinone
3-[(4,5,6,7-tetrahydroindol-3-yl)methylidenyl]-5-benzyloxycarbonyl-2-indolinone
3-[(pyrrol-2-yl)methylidenyl]-5-phenylaminocarbonyl-2-indolinone
3-[(2,4-dimethylpyrrol-5-yl)methylidenyl]-5-phenylaminocarbonyl-2-indolinone
3-[(2,4-dimethyl-3-ethoxycarbonylpyrrol-5-yl)methylidenyl]-5-phenylaminocarbonyl-2-indolinone
3-[(2-methylthien-5-yl)methylidenyl]-5-phenylaminocarbonyl-2-indolinone
3-[(3-methylthien-2-yl)methylidenyl]-5-phenylaminocarbonyl-2-indolinone
3-[(4,5,6,7-tetrahydroindol-3-yl)methylidenyl]-5-phenylaminocarbonyl-2-indolinone
3-[(pyrrol-2-yl)methylidenyl]-5-benzylaminocarbonyl-2-indolinone
3-[(2,4-dimethylpyrrol-5-yl)methylidenyl]-5-benzylaminocarbonyl-2-indolinone
3-[(2,4-dimethyl-3-ethoxycarbonylpyrrol-5-yl)methylidenyl]-5-benzylaminocarbonyl-2-indolinone
3-[(2-methylthien-5-yl)methylidenyl]-5-benzylaminocarbonyl-2-indolinone
3-[(3-methylthien-2-yl)methylidenyl]-5-benzylaminocarbonyl-2-indolinone
3-[(4,5,6,7-tetrahydroindol-3-yl)methylidenyl]-5-benzylaminocarbonyl-2-indolinone

TABLE 10

| FLK Kinase IC50 (μM) | STRUCTURES | METHOD |
|---|---|---|
| 1.6 | 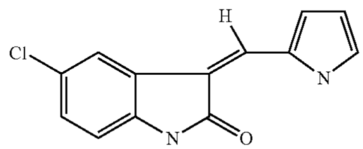 | A |
| 2.6 | 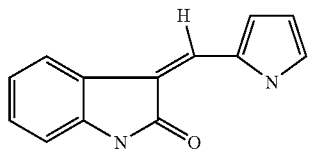 | A |
| 1.9 | 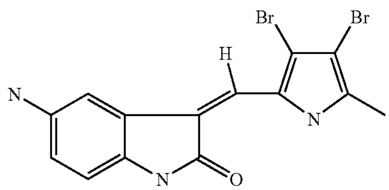 | B |
| 4.7 | 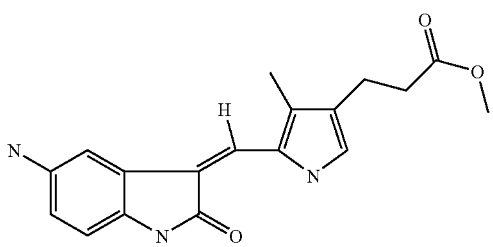 | B |
| 5.6 | 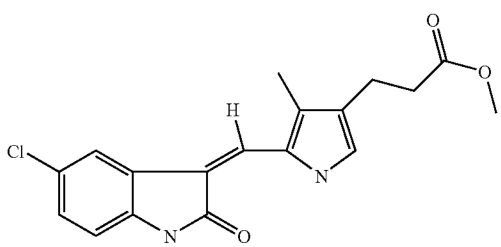 | B |
| 10.8 | 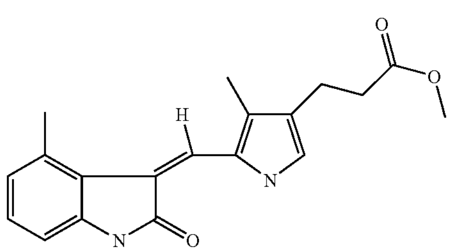 | B |
| 12.5 | 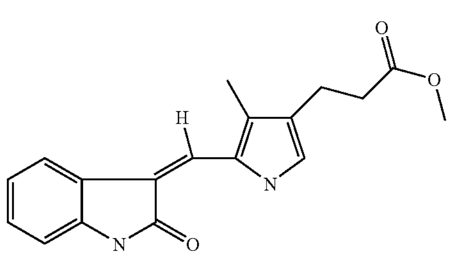 | A |

TABLE 10-continued

| FLK Kinase IC50 (μM) | STRUCTURES | METHOD |
|---|---|---|
| 0.97 | 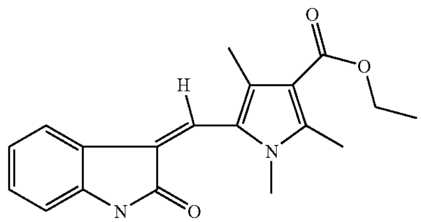 | B |
| 1.5 | 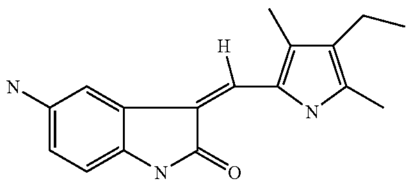 | B |
| 1.1 | 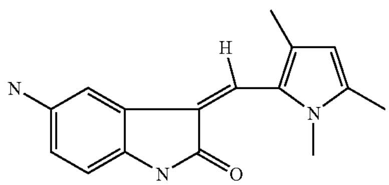 | B |
| 3.5 | 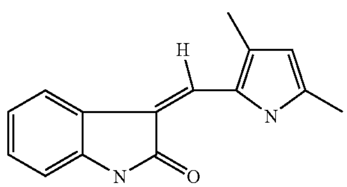 | A |
| 7.3 | 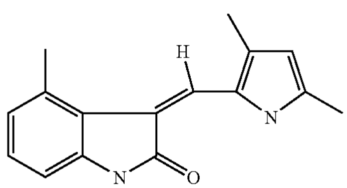 | A |
| 5.6 | 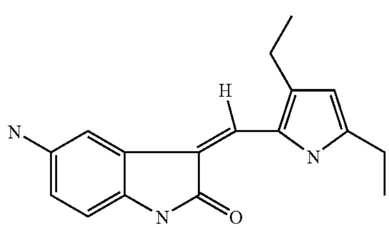 | B |
| 8.1 | 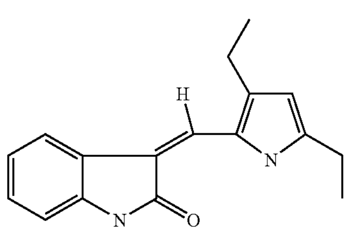 | A |

TABLE 10-continued

| FLK Kinase IC50 (μM) | STRUCTURES | METHOD |
|---|---|---|
| 17.3 | 4-methyl-3-[(3,5-diethyl-1H-pyrrol-2-yl)methylene]-1,3-dihydro-2H-indol-2-one | A |
| 2.9 | 3-[(3-hydroxy-4-methoxyphenyl)methylene]-1,3-dihydro-2H-indol-2-one | B |
| 5.2 | 5-chloro-3-[(3-bromo-4-hydroxyphenyl)methylene]-1,3-dihydro-2H-indol-2-one | B |
| 18.5 | 5-chloro-7-methyl-3-[(3-bromo-4,5-dihydroxyphenyl)methylene]-1,3-dihydro-2H-indol-2-one | B |
| 8.8 | 5-chloro-7-bromo-3-[(3-bromo-4,5-dihydroxyphenyl)methylene]-1,3-dihydro-2H-indol-2-one | B |
| 4 | 3-[(4-(3-dimethylaminopropoxy)phenyl)methylene]-1,3-dihydro-2H-indol-2-one | B |
| 8 | 4-methyl-3-[(4-(3-dimethylaminopropoxy)phenyl)methylene]-1,3-dihydro-2H-indol-2-one | B |

TABLE 10-continued
| FLK Kinase IC50 (μM) | STRUCTURES | METHOD |
|---|---|---|
| 11.5 | 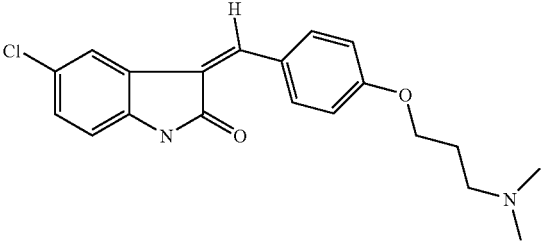 | B |
| 13.7 | 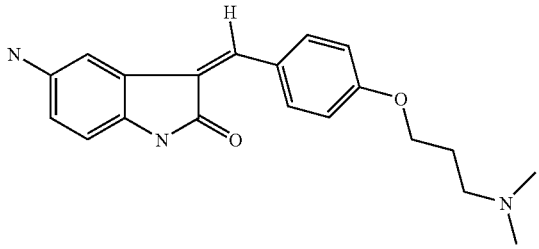 | B |
| 10.4 | 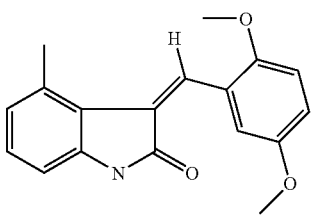 | B |
| 10.7 | 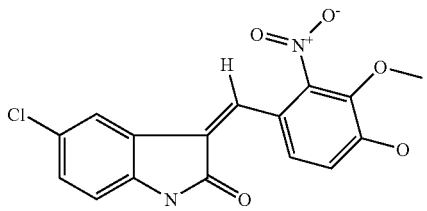 | B |
| 16.4 | 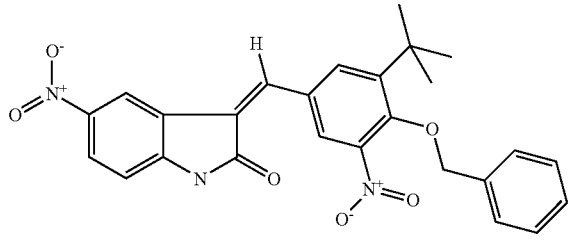 | B |
| 19.9 | 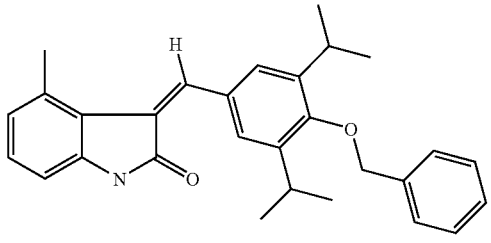 | B |

TABLE 10-continued

| FLK Kinase IC50 (μM) | STRUCTURES | METHOD |
|---|---|---|
| 9.7 | 3-[(4-tert-butylphenyl)methylene]-1,3-dihydro-2H-indol-2-one | B |
| 20.3 | 3-[(4-ethylphenyl)methylene]-1,3-dihydro-2H-indol-2-one | B |
| 4.6 | 4,6-dimethyl-3-(1H-imidazol-4-ylmethylene)-1,3-dihydro-2H-indol-2-one | B |
| 5.6 | 5-chloro-3-(1H-imidazol-4-ylmethylene)-1,3-dihydro-2H-indol-2-one | B |
| 9.9 | 3-[(4-pyrrolidin-1-ylphenyl)methylene]-1,3-dihydro-2H-indol-2-one | A |
| 12.3 | 5-chloro-3-[(4-pyrrolidin-1-ylphenyl)methylene]-1,3-dihydro-2H-indol-2-one | B |
| 18.4 | 5-amino-3-[(4-pyrrolidin-1-ylphenyl)methylene]-1,3-dihydro-2H-indol-2-one | B |
| 5.8 | 5-chloro-3-[(4-(4-formylpiperazin-1-yl)phenyl)methylene]-1,3-dihydro-2H-indol-2-one | B |

TABLE 10-continued

| FLK Kinase IC50 (µM) | STRUCTURES | METHOD |
|---|---|---|
| 6.2 | 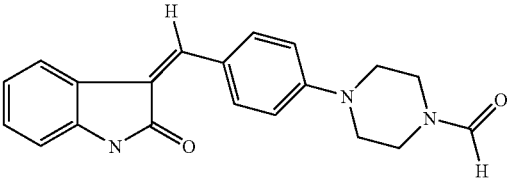 | A |
| 17.1 | 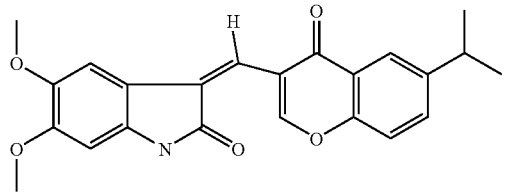 | B |

TABLE 11

| | | |
|---|---|---|
| 5-aminooxindole oxindole-001 | 5-bromooxindole oxindole-002 | 5-chlorooxindole oxindole-003 |
| 4,5-dimethyloxindole oxindole-004 | 5,5-dimethoxyoxindole oxindole-005 | oxindole oxindole-006 |
| 4-methyloxindole oxindole-007 | 5,7-dibromooxindole oxindole-008 | 7-bromo-5-chlorooxindole oxindole-009 |
| 5-fluorooxindole oxindole-010 | 5-nitrooxindole oxindole-011 | 5-iodooxindole oxindole-012 |
| 5-chloro-7-methyloxindole oxindole-013 | 5-methyloxindole oxindole-014 | 5-bromo-4-methyloxindole oxindole-015 |
| 7-fluorooxindole oxindole-016 | 7-chlorooxindole oxindole-017 | 4-fluorooxindole oxindole-018 |
| 6-fluorooxindole oxindole-019 | 4-chlorooxindole oxindole-020 | 5-chlorooxindole oxindole-021 |
| 5-bromo-7-methyloxindole oxindole-022 | 7-chloro-5-cyanooxindole oxindole-023 | 4-bromooxindole oxindole-024 |
| 7-methoxyoxindole oxindole-025 | 4-methyl-5-carboxyoxindole oxindole-026 | 4-methyl-5-carboxymethyloxindole oxindole-027 |
| 4-methyl-5-carboxyethyloxindole oxindole-028 | 4-methyl-5(3-carboxy-n-propyl) oxindole oxindole-029 | 4-methyl-5-hydroxymethyloxindole oxindole-030 |
| 4-methyl-5-methoxymethyloxindole oxindole-031 | 4-methyl-5-(2-hydroxyethyl)oxindole oxindole-032 | 4-methyl-5-(2-methoxyethyl)oxindole oxindole-033 |
| 4-methyl-5-(3-hydroxy-n-propyl) oxindole oxindole-034 | 4-methyl-5-(3-methoxy-n-propyl) oxindole oxindole-035 | 5-aminosulfonyloxindole oxindole-036 |
| 5-methylaminosulfonyloxindole oxindole-037 | 5-(4-trifluoromethylanilinosulfonyl) oxindole oxindole-038 | 5-(morpholin-1-yl-sulfonyl)oxindole oxindole-039 |
| 6-trifluoromethyloxindole oxindole-040 | 5-(2-chloroethyl)oxindole oxindole-041 | 5-carboxymethyloxindole oxindole-042 |
| 6-carboxymethyloxindole oxindole-043 | 4-methoxycarbonyloxindole oxindole-044 | 5-methoxycarbonyloxindole oxindole-045 |
| 6-methoxycarbonyloxindole oxindole-046 | 4-carboxyoxindole oxindole-047 | 5-carboxyoxindole oxindole-048 |
| 6-carboxyoxindole oxindole-049 | 5-carbaxyethyloxindole oxindole-050 | 5-hydroxyethyloxindole oxindole-051 |
| 4-methyl-5-aminooxindole oxindole-052 | 4-methyl-5-nitrooxindole oxindole-053 | 4-methyl-5-iodooxindole oxindole-054 |
| 4-methyl-5-chlorooxindole oxindole-055 | | |

TABLE 12

| | | |
|---|---|---|
| 2-ethoxybenzaldehyde<br>CHO-001 | 2-thiophenecarboxaldehyde<br>CHO-002 | 1-methylpyrrole-2-carboxaldehyde<br>CHO-003 |
| 4-fluorobenzaldehyde<br>CHO-004 | Indole-3-carboxaldehyde<br>CHO-005 | 5-methylthiophene-2-carboxaldehyde<br>CHO-006 |
| 4-bromobenzaldehyde<br>CHO-007 | pyrrole-2-carboxaldehyde<br>CHO-008 | 2-Hydroxy-5-methoxycenzaldehyde<br>CHO-009 |
| 3-methyl-2-thiophenecarboxaldehyde<br>CHO-010 | 3,4-Dibromo-5-methyl-2-pyrrolecarboxaldehyde<br>CHO-011 | Ethyl-2,4-Dimethyl-5-formyl-3-pyrrolecarboxylate<br>CHO-012 |
| 3-Bromo-2-hydroxy-5-methoxybenzaldehyde<br>CHO-013 | 1-Hydroxy-2-naphthaldehyde<br>CHO-014 | Ethyl-2(ethoxycarbonyl)-4-(ethoxycarbonylmethyl)-5-formyl-3-pyrrolepropionate<br>CHO-015 |
| Ethyl-5-formyl-2-methyl-3-furancarboxylate<br>CHO-016 | 4-Formyl-3-methoxycarbonymethyl-5-me-1H-pyrrole-2-carboxylic acid methyl ester<br>CHO-017 | 2-Hydroxy-3-nitrobenzaldehyde<br>CHO-018 |
| 2,4-Dihydroxy-3-methylbenzaldehyde<br>CHO-019 | Methyl5-formyl-4-methy-3-pyrrolepropionate<br>CHO-020 | 2-furaldehyde<br>CHO-021 |
| 5-Nitro-2-furaldehyde<br>CHO-022 | 4-Ethoxy-3-methoxybenzaldehyde<br>CHO-023 | 3,4-Dihydroxybenzaldehyde<br>CHO-024 |
| 2,4-Dimethoxybenzaldehyde<br>CHO-025 | 3,5-Dimethyl-4-ethyl-2-pyrrolcarboxaldehyde<br>CHO-026 | 2,4,6-nmethoxybenzaldehyde<br>CHO-027 |
| 4-Hydroxybenzaldehyde<br>CHO-028 | 4-(Dimethylanino)-benzaldehyde<br>CHO-029 | 2,4-Dimethyl-3-carbenoxypyrrole-5-carboxaldehyde<br>CHO-030 |
| 2-chloro-4-flucrobenzaldehyde<br>CHO-031 | 3-Nitrobenzaldehyde<br>CHO-032 | 4-fluorc-2-(trifluoromethyl)benzaldehyde<br>CHO-033 |
| 2,4,6-Trifluorobenzaldehyde<br>CHO-034 | 4-Hydroxy-2-methoxybenzaldenyde<br>CHO-035 | 3,4-Dimethoxybenzaldehyde<br>CHO-036 |
| Salicylaldehyde<br>CHO-037 | Benzaldehyde<br>CHO-038 | 3,5-diethylpyrrole-2-carboxaldehyde<br>CHO-038 |
| 5-(Methylthio)thiophene-2-carboxaldehyde<br>CHO-039 | 2,4-Dihydroxy-6-methylbenzaldehyde<br>CHO-040 | Methyl-5-formyl-4-methlyl-3-pyrrolepropionate<br>CHO-041 |
| 3-Ethoxy-4-hydroxybenzaldehyde<br>CHO-042 | 2-Hydroxy-5-methoxybenzaldenyde<br>CHO-043 | 2-Imidazolecarboxaldehyde<br>CHO-044 |
| 1-Methyl-2-formylbenzimidazole<br>CHO-045 | 4-Chloro-1-methylpyrazole-3-carboxaldehyde<br>CHO-046 | 2,3-dimethyl-5-formylthiophene<br>CHO-047 |
| 2-Formyl-4,5,6,7-tetrahydroindole<br>CHO-048 | 3-Chloromethyl-5-nitrosalicylaldehyde<br>CHO-049 | 1-(3,5-Dichlorophenyl)pyrrole-2-carboxaldehyde<br>CHO-050 |
| 5-Chlorothiophene-2-carboxaldehyde<br>CHO-051 | 3,5-dimethyl-5-formylpyrrole<br>CHO-052 | 3-t-Butyl-4-hydroxybenzaldehyde<br>CHO-053 |
| 3-t-Butyl-5-bromo-4-hydroxybenzaldehyde<br>CHO-054 | 3,5-Di-tert-butyl-4-hydroxybenzaldehyde hemihydrate<br>CHO-055 | 3-t-Butyl-t-hydroxy-5-nitrobenzaldehyde<br>CHO-056 |
| 2,4,6-Trihydroxybenzaldehyde<br>CHO-057 | 2-formyl-5-nitrothiophene<br>CHO-058 | 4-Carboxybenzaldehyde<br>CHO-059 |
| 2,4-difluorobenzaldehyde<br>CHO-060 | 3,5-Dimethyl-4-hydroxybenzaldehyde<br>CHO-061 | 3-Chloro-4-hydroxy-5-t-butylbenzaldehyde<br>CHO-062 |
| 4-Ethoxy-3-methoxybenzaldehyde<br>CHO-063 | 2-Nitrothiophene-4-carboxaldehyde<br>CHO-064 | 4-(Dibutylamino)benzaldehyde<br>CHO-065 |
| 4-(Trifluromethyl)benzaldehyde<br>CHO-066 | 4,6-Dimethoxy-salicylaldehyde<br>CHO-067 | 2,3,4,-Trihydroxybenzaldehyde<br>CHO-068 |
| 2-Hydroxy-3-methoxybenzaldehyde<br>CHO-069 | 5-Bromo-3,4-dihydroxybenzaldehyde<br>CHO-070 | 3,4-Diacetoxybenzaldehyde<br>CHO-071 |
| 4-Hydroxy-3-methylbenzaldehyde<br>CHO-072 | 2-Bromobenzaldehyde<br>CHO-073 | 2,4-Dihdroxybezaldehyde<br>CHO-074 |
| 2-Hydroxy-4-methoxybenzaldehyde<br>CHO-075 | 3-Bromobenzaldehyde<br>CHO-076 | 3,5-Di-tert-butyl-2-hydroxybenzaldehyde<br>CHO-077 |
| 4-Carboxybenzaldehyde<br>CHO-078 | 4-Dimethylamino-t-napthaldehyde<br>CHO-079 | 4-Hydroxy-3-nitroxybenzaldehyde<br>CHO-080 |
| 2-Hydroxy-4-metroxybenzaldehyde<br>CHO-081 | 3-Hydroxy-4-nitrobenzaldehyde<br>CHO-082 | 4-Bromobenzaldehyde<br>CHO-083 |
| 2,3,6,7-Tetrahydro-8-hydroxy-1 H,5H-benzo[ij]quinolizine.9 carboxaldehyde<br>CHO-084 | 3,5-Diisopropyl-4-hydroxybenzaldehyde<br>CHO-085 | Benzo(b)furan-2-carboxaldehyde<br>CHO-086 |
| 3,5-Diiodo-4-methyl-2-pyrrolecarboxaldehyde<br>CHO-087 | 1-(4-chloropenyl)pyrrole-2-carboxaldehyde<br>CHO-088 | 5-Ethyl-2-furaldehyde<br>CHO-089 |
| 3,4-Dimethylthieno(bi)thiophene-2-carboxaldehyde<br>CHO-090 | 3-Bromothiopnene-2-carboxaldehyde<br>CHO-091 | 6-Bromo-2-hydroxy-3-methoxybenzaldehyde<br>CHO-092 |
| 5-Methylfurfural<br>CHO-093 | 3-methyl-1H-Pyrazole-5-carboxaldehyde<br>CHO-094 | 5-iodo-2-furaldehyde<br>CHO-095 |
| 6-Methoxy-4-methylsalicylaldehyde<br>CHO-096 | Ethyl 2,4-Dimethyl-5-formy-3-pyrrolecarboxylate<br>CHO-097 | 4-Ethyl-5-formy-methyl-2-pyrrolecardoxylic acid<br>CHO-098 |
| Ethyl-5-formy-1,2,4-nmethyl-3-pyrrolecarboxylate | 4-(4-formylpeprazine-1-yl)benzaldehyde | 4-(4-Formylmorphonino-1-yl)benzaldehyde |

TABLE 12-continued

| | | |
|---|---|---|
| CHO-099 | CHO-100 | CHO-101 |
| 5-Chloro-3-methoxycarbonyl-4-methoxycarbonylmethyl-pyrrole-2-carboxaldehyde | 1-(4-chlorobenzyl)-4-bromo-pyrazole-5-carboxaldehyde | Imicazole-4-carboxaidehyde |
| CHO-102 | CHO-103 | CHO-104 |
| 4-Chloro-pyrazole-5-carboxaldehyde | 5-Ethoxycarbonyl-4-methyl-3-methylcarbonyl-pyrrole-2-corboxaldehyde | 5-t-Butyl-4-hydroxy-3-iodobenzaldehyde |
| CHO-105 | CHO-106 | CHO-107 |
| 5-Bromofuran-2-carboxaldehyde | 1,4-Dimethyl-3-formylcarbazole | 1,4-Dihydroxy-2-formyl-5,6,7,8-tetrahydronaphthalene |
| CHO-108 | CHO-109 | CHO-110 |
| 5-fluoroisatin | 3,4-dimethyl-2-formylpyrrole | isatin |
| CHO-111 | CHO-112 | CHO-113 |
| 5-ethyl-2-formylthiophene | 4-methoxybenzaldehyde | 4-diethylaminobenzaldehyde |
| CHO-114 | CHO-115 | CHO-116 |
| 3,5-diethylpyrrole-2-carboxaldehyde | 5-Benzyloxyindole-3-carboxaldehyde | 3-Bromo-5-chloro-2-hydroxybenzaldehyde |
| CHO-117 | CHO-118 | CHO-119 |
| 2-(4-chlorophenylthio)benzaldenyde | 6-Chloropiperonal | Chromone-3-carboxaldehyde |
| CHO-120 | CHO-121 | CHO-122 |
| 3-Cyanobenzaldehyde | 4-Cyanobenzaldehyde | 6,6-Dichlorochromone-3-carboxaldehyde |
| CHC-123 | CHO-124 | CHO-125 |
| 2,5-ethycroxybenzaldehyde | 2,3-Dimethoxybenzaldehyde | 2,4-Dimethoxybenzaldehyde |
| CHO-126 | CHO-127 | CHO-128 |
| 2,5-Dimethoxybenzaldehyde | 2,6-Dimethoxybenzaldehyde | 3,5-Dimethoxybenzaldehyde |
| CHO-129 | CHO-130 | CHO-131 |
| 4-Dimethylamino-2-methoxybenzaldehyde | 3,4-Dimethylbenzaldehyde | 5,7-Dimethylchromone-3-carboxaldehyde |
| CHO-132 | CHO-133 | CHO-134 |
| 5-Ethylfurfural | Ferrocenecarboxaldehyde | Flucrene-2-carboxaldehyde |
| CHO-135 | CHO-136 | CHO-137 |
| 2-Fluoro-3-(trifluoromethyl)benzaldehyde | 2-Fluoro-4-(trifluromethyl)benzaldehyde | 2-Fluoro-5-(trifluoromethyl)benzaldehyde |
| CHO-138 | CHO-139 | CHO-140 |
| 2-Fluouro-6-(trifluoromethyl)benzaldehyde | 2-Formylphenoxyacetic acid | 3-Methoxy-5,-methylenedioxybenzaldehyde |
| CHO-141 | CHO-142 | CHO-143 |
| 2-Methoxy-1-naphthaldehyde | 4-Methoxy-1-naphthaldehyde | 4-(Methylthio)benzaldehyde |
| CHO-144 | CHO-145 | CHO-146 |
| 3-Methylthiophene-2-carboxaldehyde | 5-Methylthiophene-2-carboxaldehyde | pentamethylbenzaldehyde |
| CHO-147 | CHO-148 | CHO-149 |
| 3-Phenoxybenzaldehyde | Pyridine-2-carboxaldehyde | Pyridine-3-carboxaldehyde |
| CHO-150 | CHO-151 | CHO-152 |
| | 4-Pyrrolidinebenzaldehyde | |
| Pyridine-4-carboxaldehyde | 98 + % | 1,2,3,6-Tetrahydrobenzaldehyde |
| CHO-153 | CHO-154 | CHO-155 |
| 2,3,4-Trimethoxybenzaldehyde | 2,4,5-Trimethoxybenzaldehyde | 2,4,6-Trimethoxybenzaldehyde |
| CHO-156 | CHO-157 | CHO-158 |
| 3,4,5-Trimethoxybenzaldehyde | 1-Acetyl-3-indolecarboxaldehyde | 6-Chloro-3-formylchromone |
| CHO-159 | CHO-160 | CHO-161 |
| 6-Chloro-3-formyl-7-methylchromone | 5-(2-Chlorophenyl)furfural | 2-Chloro-3-quinolinecarboxaldehyde |
| CHO-162 | CHO-163 | CHO-164 |
| 6,8-Dibromo-3-formylchromone | 2,5-Dimethoxy-3-tetrahydrofuracarboxaldehyde | 4,5-Dimethyl-2-furaldehyde |
| CHO-165 | CHO-166 | CHO-167 |
| 9-Ethyl-3-carbazolecarboxaldehyde | 3-Formyl-6,7-dimethylchromone | 3-formyl-6,8-dimethylchromone |
| CHO-168 | CHO-169 | CHO-170 |
| 3-formyl-6-isopropylchromone | 3-formyl-6-methylchromone | 3-formyl-6-nitrochromone |
| CHO-171 | CHO-172 | CHO-173 |
| 5-Formyluracil | 5-Methoxyindole-3-carboxaldehyde | 1-Methylisatin |
| CHO-174 | CHO-175 | CHO-176 |
| 5-(2-Nitrophenyl)furfural | (S)-(−)-Perillaldehyde | 2-(Trifluoroacetyl)thiophene |
| CHO-177 | CHO-178 | CHO-179 |
| 3,5-diisopropyl-4-methoxybenzaldehyde | 4-benzyloxy-3,5-diisopropylbenzaldehyde | 3-t-butyl-4-methoxybenzaldehyde |
| CHO-180 | CHO-181 | CHO-182 |
| 4-benzyloxy-3-t-butylbenzaldehyde | 3-bromo-5-t-butyl-4-methoxybenzaldehyde | 4-benzyloxy-3-bromo-5-t-butylbenzaldehyde |
| CHO-183 | CHO-184 | CHO-185 |
| 3-t-butyl-5-chloro-4-methoxybenzaldehyde | 4-benzyloxy-3-t-butyl-5-chlorobenzaldehyde | 3-t-butyl-5-iodo-4-methoxybenzaldehyde |
| CHO-186 | CHO-187 | CHO-188 |
| 4-benzyloxy-3-t-butyl-5-iodobenzaldehyde | 3-t-butyl-4-methoxy-5-nitrobenzaldehyde | 4-benzyloxy-3-t-butyl-5-nitrobenzaldehyde |
| CHO-189 | CHO-190 | CHO-191 |
| 3,5-di-t-butyl-4-methoxybenzaldehyde | 4-benzyloxy-3,5-di-t-butylbenzaldehyde | 3,5-dimethyl-4-methoxybenzaldehyde |
| CHO-192 | CHO-193 | CHO-194 |
| 4-benzyloxy-3,5-dimethylbenzaldehyde | 5-bromo-2-hydroxy-3-methoxy-benzaldehyde | 5-bromosalicyaldehyde 201 |
| CHO-195 | CHO-196 | CHO-197 |
| 2-hydroxy-5-nitrobenzaldehyde | 4-hydroxy-2-nitro-3-methoxybenzaldehyde | 3-ethoxysalicylaldehyde |
| CHO-198 | CHO-199 | CHO-200 |
| 3,5-dichlorosalicylaldehyde | 5-chlorosalicyaldehyde | 4-(diethylamino)salicyaldehyde |
| CHO-201 | CHO-202 | CHO-203 |
| 5-(influoromethoxy)salicylaldehyde | 3,5-dibromosalicylaldehyde | 3-fluorosalicylaldehyde |
| CHO-204 | CHO-205 | CHO-206 |
| 3-bromo-4-hydroxybenzaldehyde | 5-chlorosalicyaldehyde | 2-4,dimethyl-5-formylpyrrole |
| CHO-207 | CHO-208 | CHO-209 |
| 3,5-diisopropyl-2-formylpyrrole | 3,5-dimethylthiophene-2-carboxaldehyde | 3-methyl-5-ethylthiophene-2-carboxaldehyde |
| CHO-210 | CHO-211 | CHO-212 |

TABLE 12-continued

| | | |
|---|---|---|
| 3-methyl-5-isopropylthiophene-2-carboxaldehyde<br>CHO-213 | 3-methyl-5-cyclopentylmethylthiophene-2-carboxaldehyde<br>CHO-214 | 3-methyl-5-cyclopropylthiophene-2-carboxaldehyde<br>CHO-215 |
| 4-methyl-5-ethylthiophene-2-carboxaldehyde<br>CHO-216 | 4-methyl-5-isopropylthiophene-2-carboxaldehyde<br>CHO-217 | 4-methyl-5-cyclopentylmethylthiophene-2-carboxaldehyde<br>CHO-218 |
| 4-methyl-5-cyclopropylmethylthiophene-2-carboxaldehyde<br>CHO-219 | 5-isopropylthiophene-2-carboxaldehyde<br>CHO-220 | 5-phenylmethylthiophene-2-carboxaldehyde<br>CHO-221 |
| 5-cyclohexylmethylthiophene-2-carboxaldehyde<br>CHO-222 | 5-cyclohexylthiophene-2-carboxaldehyde<br>CHO-223 | 5-phenylthiophene-2-carboxaldehyde<br>CHO-224 |
| 3-methyl-5-oropylthlophene-2-carboxaldehyde<br>CHO-225 | 3-methyl-5-cyclohexylmethylthiophene-2-carboxaldehyde<br>CHO-226 | 4-methyl-5-propylthiophene-2-carboxaldehyde<br>CHO-227 |
| 4-methyl-5-cyclohexylmethylthiophene-2-carboxaldehyde<br>CHO-228 | 5-n-butylthiophene-2-carboxaldehyde<br>CHO-229 | 5-cyclopropylmethylthiophene-2-carboxaldehyde<br>CHO-230 |
| 5-cyclopropylthiophene-2-carboxaldehyde<br>CHO-231 | 3-methyl-5-phenylmethylthiophene-2-carboxaldehyde<br>CHO-232 | 4-methyl-5-phenylmethylthiophene-2-carboxaldehyde<br>CHO-233 |
| 5-cyclopentylmethylthiophene-2-carboxaldehyde<br>CHO-234 | 5-cyclopentylthiophene-2-carboxaldehyde<br>CHO-235 | 4,5-dimethylthiophene-2-carboxaldehyde<br>CHO-236 |
| 5-n-propylthiophene-2-carboxaldehyde<br>CHO-237 | | |

TABLE 13

| MASTER BARCODE | PLATE ROW | PLATE COLUMN | NAME |
|---|---|---|---|
| 10717 | A | 2 | 3-(2-ethoxybenzylidenyl)-5,7-dibromo-2-indolinone |
| 10717 | A | 3 | 3-[(thien-2-yl)methylidenyl]-5,7-dibromo-2-indolinone |
| 10717 | A | 4 | 3-[(1-methylpyrrol-2-yl)methylidenyl]-5,7-dibromo-2-indolinone |
| 10717 | A | 5 | 3-(4-fluorobenzylidenyl)-5,7-dibromo-2-indolinone |
| 10717 | A | 6 | 3-[(indol-3-yl)methylidenyl]-5,7-dibromo-2-indolinone |
| 10717 | A | 7 | 3-[(2-methylthien-5-yl)methylidenyl]-5,7-dibromo-2-indolinone |
| 10717 | A | 8 | 3-(4-bromobenzylidenyl)-5,7-dibromo-2-indolinone |
| 10717 | A | 9 | 3-[(pyrrol-2-yl)methylidenyl]-5,7-dibromo-2-indolinone |
| 10717 | A | 10 | 3-(2-hydroxy-6-methoxybenzylidenyl)-5,7-dibromo-2-indolinone |
| 10717 | A | 11 | 3-[(3,4-dibromo-2-methylpyrrol-5-yl)methylidenyl]-5,7-dibromo-2-indolinone |
| 10717 | B | 2 | 3-(2-ethoxybenzylidenyl)-5-iodo-2-indolinone |
| 10717 | B | 3 | 3-[(thien-2-yl)methylidenyl]-5-iodo-2-indolinone |
| 10717 | B | 4 | 3-[(1-methylpyrrol-2-yl)methylidenyl]-5-iodo-2-indolinone |
| 10717 | B | 5 | 3-(4-fluorobenzylidenyl)-5-iodo-2-indolinone |
| 10717 | B | 6 | 3-[(indol-3-yl)methylidenyl]-5-iodo-2-indolinone |
| 10717 | B | 7 | 3-[(2-methylthien-5-yl)methylidenyl]-5-iodo-2-indolinone |
| 10717 | B | 8 | 3-(4-bromobenzylidenyl)-5-iodo-2-indolinone |
| 10717 | B | 9 | 3-[(pyrrol-2-yl)methylidenyl]-5-iodo-2-indolinone |
| 10717 | B | 10 | 3-(2-hydroxy-6-methoxybenzylidenyl)-5-iodo-2-indolinone |
| 10717 | B | 11 | 3-[(3,4-dibromo-2-methylpyrrol-5-yl)methylidenyl]-5-iodo-2-indolinone |
| 10717 | C | 2 | 3-(2-ethoxybenzylidenyl)-5-bromo-4-methyl-2-indolinone |
| 10717 | C | 3 | 3-[(thien-2-yl)methylidenyl]-5-bromo-4-methyl-2-indolinone |
| 10717 | C | 4 | 3-[(1-methylpyrrol-2-yl)methylidenyl]-5-bromo-4-methyl-2-indolinone |
| 10717 | C | 5 | 3-(4-fluorobenzylidenyl)-5-bromo-4-methyl-2-indolinone |
| 10717 | C | 6 | 3-[(indol-3-yl)methylidenyl]-5-bromo-4-methyl-2-indolinone |
| 10717 | C | 7 | 3-[(2-methylthien-5-yl)methylidenyl]-5-bromo-4-methyl-2-indolinone |

TABLE 13-continued

| MASTER BARCODE | PLATE ROW | PLATE COLUMN | NAME |
|---|---|---|---|
| 10717 | C | 8 | 3-(4-bromobenzylidenyl)-5-bromo-4-methyl-2-indolinone |
| 10717 | C | 9 | 3-[(pyrrol-2-yl)methylidenyl]-5-bromo-4-methyl-2-indolinone |
| 10717 | C | 10 | 3-(2-hydroxy-6-methoxybenzylidenyl)-5-bromo-4-methyl-2-indolinone |
| 10717 | C | 11 | 3-[(3,4-dibromo-2-methylpyrrol-5-yl)methylidenyl]-5-bromo-4-methyl-2-indolinone |
| 10717 | D | 2 | 3-(2-ethoxybenzylidenyl)-5-methylaminosulfonyl-2-indolinone |
| 10717 | D | 3 | 3-[(thien-2-yl)methylidenyl]-5-methylaminosulfonyl-2-indolinone |
| 10717 | D | 4 | 3-[(1-methylpyrrol-2-yl)methylidenyl]-5-methylaminosulfonyl-2-indolinone |
| 10717 | D | 5 | 3-(4-fluorobenzylidenyl)-5-methylaminosulfonyl-2-indolinone |
| 10717 | D | 6 | 3-[(indol-3-yl)methylidenyl]-5-methylaminosulfonyl-2-indolinone |
| 10717 | D | 7 | 3-[(2-methylthien-5-yl)methylidenyl]-5-methylaminosulfonyl-2-indolinone |
| 10717 | D | 8 | 3-(4-bromobenzylidenyl)-5-methylaminosulfonyl-2-indolinone |
| 10717 | D | 9 | 3-[(pyrrol-2-yl)methylidenyl]-5-methylaminosulfonyl-2-indolinone |
| 10717 | D | 10 | 3-(2-hydroxy-6-methoxybenzylidenyl)-5-methylaminosulfonyl-2-indolinone |
| 10717 | D | 11 | 3-[(3,4-dibromo-2-methylpyrrol-5-yl)methylidenyl]-5-methylaminosulfonyl-2-indolinone |
| 10717 | E | 2 | 3-(2-ethoxybenzylidenyl)-5-[4-(trifluoromethyl)phenylaminosulfonyl]-2-indolinone |
| 10717 | E | 3 | 3-[(thien-2-yl)methylidenyl]-5-[4-(trifluoromethyl)phenylaminosulfonyl]-2-indolinone |
| 10717 | E | 4 | 3-[(1-methylpyrrol-2-yl)methylidenyl]-5-[4-(trifluoromethyl)phenylaminosulfonyl]-2-indolinone |
| 10717 | E | 5 | 3-(4-fluorobenzylidenyl)-5-[4-(trifluoromethyl)phenylaminosulfonyl]-2-indolinone |
| 10717 | E | 6 | 3-[(indol-3-yl)methylidenyl]-5-[4-(trifluoromethyl)phenylaminosulfonyl]-2-indolinone |
| 10717 | E | 7 | 3-[(2-methylthien-5-yl)methylidenyl]-5-[4-(trifluoromethyl)phenylaminosulfonyl]-2-indolinone |
| 10717 | E | 8 | 3-(4-bromobenzylidenyl)-5-[4-(trifluoromethyl)phenylaminosulfonyl]-2-indolinone |
| 10717 | E | 9 | 3-[(pyrrol-2-yl)methylidenyl]-5-[4-(trifluoromethyl)phenylaminosulfonyl]-2-indolinone |
| 10717 | E | 10 | 3-(2-hydroxy-6-methoxybenzylidenyl)-5-[4-(trifluoromethyl)phenylaminosulfonyl]-2-indolinone |
| 10717 | E | 11 | 3-[(3,4-dibromo-2-methylpyrrol-5-yl)methylidenyl]-5-[4-(trifluoromethyl)phenylaminosulfonyl]-2-indolinone |
| 10717 | F | 2 | 3-(2-ethoxybenzylidenyl)-5-(morpholin-1-yl)sulfonyl-2-indolinone |
| 10717 | F | 3 | 3-[(thien-2-yl)methylidenyl]-5-(morpholin-1-yl)sulfonyl-2-indolinone |
| 10717 | F | 4 | 3-[(1-methylpyrrol-2-yl)methylidenyl]-5-(morpholin-1-yl)sulfonyl-2-indolinone |
| 10717 | F | 5 | 3-(4-fluorobenzylidenyl)-5-(morpholin-1-yl)sulfonyl-2-indolinone |
| 10717 | F | 6 | 3-[(indol-3-yl)methylidenyl]-5-(morpholin-1-yl)sulfonyl-2-indolinone |
| 10717 | F | 7 | 3-[(2-methylthien-5-yl)methylidenyl]-5-(morpholin-1-yl)sulfonyl-2-indolinone |
| 10717 | F | 8 | 3-(4-bromobenzylidenyl)-5-(morpholin-1-yl)sulfonyl-2-indolinone |
| 10717 | F | 9 | 3-[(pyrrol-2-yl)methylidenyl]-5-(morpholin-1-yl)sulfonyl-2-indolinone |
| 10717 | F | 10 | 3-(2-hydroxy-6-methoxybenzylidenyl)-5-(morpholin-1-yl)sulfonyl-2-indolinone |
| 10717 | F | 11 | 3-[(3,4-dibromo-2-methylpyrrol-5-yl)methylidenyl]-5-(morpholin-1-yl)sulfonyl-2-indolinone |
| 10717 | G | 2 | 3-(2-ethoxybenzylidenyl)-5-(2-chloroethyl)-2-indolinone |
| 10717 | G | 3 | 3-[(thien-2-yl)methylidenyl]-5-(2-chloroethyl)-2-indolinone |
| 10717 | G | 4 | 3-[(1-methylpyrrol-2-yl)methylidenyl]-5-(2-chloroethyl)-2-indolinone |

TABLE 13-continued

| MASTER BARCODE | PLATE ROW | PLATE COLUMN | NAME |
|---|---|---|---|
| 10717 | G | 5 | 3-(4-fluorobenzylidenyl)-5-(2-chloroethyl)-2-indolinone |
| 10717 | G | 6 | 3-[(indol-3-yl)methylidenyl]-5-(2-chloroethyl)-2-indolinone |
| 10717 | G | 7 | 3-[(2-methylthien-5-yl)methylidenyl]-5-(2-chloroethyl)-2-indolinone |
| 10717 | G | 8 | 3-(4-bromobenzylidenyl)-5-(2-chloroethyl)-2-indolinone |
| 10717 | G | 9 | 3-[(pyrrol-2-yl)methylidenyl]-5-(2-chloroethyl)-2-indolinone |
| 10717 | G | 10 | 3-(2-hydroxy-6-methoxybenzylidenyl)-5-(2-chloroethyl)-2-indolinone |
| 10717 | G | 11 | 3-[(3,4-dibromo-2-methylpyrrol-5-yl)methylidenyl]-5-(2-chloroethyl)-2-indolinone |
| 10718 | A | 2 | 3-[(2,4-dimethyl-3-ethoxycarbonylpyrrol-5-yl)methylidenyl]-5,7-dibromo-2-indolinone |
| 10718 | A | 3 | 3-(3-bromo-2-hydroxy-5-methoxybenzylidenyl)-5,7-dibromo-2-indolinone |
| 10718 | A | 4 | 3-[(1-hydroxynapth-2-yl)methylidenyl]-5,7-dibromo-2-indolinone |
| 10718 | A | 5 | 3-[[2-ethoxycarbonyl-3-(2-ethoxycarbonyl)ethyl-4-(ethoxycarbonylmethyl)pyrrol-5-yl]methylidenyl]-5,7-dibromo-2-indolinone |
| 10718 | A | 6 | 3-[(2-methyl-3-ethoxycarbonylfuran-5-yl)methylidenyl]-5,7-dibromo-2-indolinone |
| 10718 | A | 7 | 3-[(2,3-dimethoxycarbonyl-5-methylpyrrol-4-yl)methylidenyl]-5,7-dibromo-2-indolinone |
| 10718 | A | 8 | 3-(4-chloro-3-nitrobenzylidenyl)-5,7-dibromo-2-indolinone |
| 10718 | A | 9 | 3-(2,4-dihydroxy-3-methylbenzylidenyl)-5,7-dibromo-2-indolinone |
| 10718 | A | 10 | 3-[(furan-2-yl)methylidenyl]-5,7-dibromo-2-indolinone |
| 10718 | A | 11 | 3-[(2-nitrofuran-5-yl)methylidenyl]-5,7-dibromo-2-indolinone |
| 10718 | B | 2 | 3-[(2,4-dimethyl-3-ethoxycarbonylpyrrol-5-yl)methylidenyl]-5-iodo-2-indolinone |
| 10718 | B | 3 | 3-(3-bromo-2-hydroxy-5-methoxybenzylidenyl)-5-iodo-2-indolinone |
| 10718 | B | 4 | 3-[(1-hydroxynapth-2-yl)methylidenyl]-5-iodo-2-indolinone |
| 10718 | B | 5 | 3-[[2-ethoxycarbonyl-3-(2-ethoxycarbonyl)ethyl-4-(ethoxycarbonylmethyl)pyrrol-5-yl]methylidenyl]-5-iodo-2-indolinone |
| 10718 | B | 6 | 3-[(2-methyl-3-ethoxycarbonylfuran-5-yl)methylidenyl]-5-iodo-2-indolinone |
| 10718 | B | 7 | 3-[(2,3-dimethoxycarbonyl-5-methylpyrrol-4-yl)methylidenyl]-5-iodo-2-indolinone |
| 10718 | B | 8 | 3-(4-chloro-3-nitrobenzylidenyl)-5-iodo-2-indolinone |
| 10718 | B | 9 | 3-(2,4-dihydroxy-3-methylbenzylidenyl)-5-iodo-2-indolinone |
| 10718 | B | 10 | 3-[(furan-2-yl)methylidenyl]-5-iodo-2-indolinone |
| 10718 | B | 11 | 3-[(2-nitrofuran-5-yl)methylidenyl]-5-iodo-2-indolinone |
| 10718 | C | 2 | 3-[(2,4-dimethyl-3-ethoxycarbonylpyrrol-5-yl)methylidenyl]-5-bromo-4-methyl-2-indolinone |
| 10718 | C | 3 | 3-(3-bromo-2-hydroxy-5-methoxybenzylidenyl)-5-bromo-4-methyl-2-indolinone |
| 10718 | C | 4 | 3-[(1-hydroxynapth-2-yl)methylidenyl]-5-bromo-4-methyl-2-indolinone |
| 10718 | C | 5 | 3-[[2-ethoxycarbonyl-3-(2-ethoxycarbonyl)ethyl-4-(ethoxycarbonylmethyl)pyrrol-5-yl]methylidenyl]-5-bromo-4-methyl-2-indolinone |
| 10718 | C | 6 | 3-[(2-methyl-3-ethoxycarbonylfuran-5-yl)methylidenyl]-5-bromo-4-methyl-2-indolinone |
| 10718 | C | 7 | 3-[(2,3-dimethoxycarbonyl-5-methylpyrrol-4-yl)methylidenyl]-5-bromo-4-methyl-2-indolinone |
| 10718 | C | 8 | 3-(4-chloro-3-nitrobenzylidenyl)-5-bromo-4-methyl-2-indolinone |
| 10718 | C | 9 | 3-(2,4-dihydroxy-3-methylbenzylidenyl)-5-bromo-4-methyl-2-indolinone |
| 10718 | C | 10 | 3-[(furan-2-yl)methylidenyl]-5-bromo-4-methyl-2-indolinone |
| 10718 | C | 11 | 3-[(2-nitrofuran-5-yl)methylidenyl]-5-bromo-4-methyl-2-indolinone |

TABLE 13-continued

| MASTER BARCODE | PLATE ROW | PLATE COLUMN | NAME |
|---|---|---|---|
| 10718 | D | 2 | 3-[(2,4-dimethyl-3-ethoxycarbonylpyrrol-5-yl)methylidenyl]-5-methylaminosulfonyl-2-indolinone |
| 10718 | D | 3 | 3-(3-bromo-2-hydroxy-5-methoxybenzylidenyl)-5-methylaminosulfonyl-2-indolinone |
| 10718 | D | 4 | 3-[(1-hydroxynapth-2-yl)methylidenyl]-5-methylaminosulfonyl-2-indolinone |
| 10718 | D | 5 | 3-[[2-ethoxycarbonyl-3-(2-ethoxycarbonyl)ethyl-4-(ethoxycarbonylmethyl)pyrrol-5-yl]methylidenyl]-5-methylaminosulfonyl-2-indolinone |
| 10718 | D | 6 | 3-[(2-methyl-3-ethoxycarbonylfuran-5-yl)methylidenyl]-5-methylaminosulfonyl-2-indolinone |
| 10718 | D | 7 | 3-[(2,3-dimethoxycarbonyl-5-methylpyrrol-4-yl)methylidenyl]-5-methylaminosulfonyl-2-indolinone |
| 10718 | D | 8 | 3-(4-chloro-3-nitrobenzylidenyl)-5-methylaminosulfonyl-2-indolinone |
| 10718 | D | 9 | 3-(2,4-dihydroxy-3-methylbenzylidenyl)-5-methylaminosulfonyl-2-indolinone |
| 10718 | D | 10 | 3-[(furan-2-yl)methylidenyl]-5-methylaminosulfonyl-2-indolinone |
| 10718 | D | 11 | 3-[(2-nitrofuran-5-yl)methylidenyl]-5-methylaminosulfonyl-2-indolinone |
| 10718 | E | 2 | 3-[(2,4-dimethyl-3-ethoxycarbonylpyrrol-5-yl)methylidenyl]-5-[4-(trifluoromethyl)phenylaminosulfonyl]-2-indolinone |
| 10718 | E | 3 | 3-(3-bromo-2-hydroxy-5-methoxybenzylidenyl)-5-[4-(trifluoromethyl)phenylaminosulfonyl]-2-indolinone |
| 10718 | E | 4 | 3-[(1-hydroxynapth-2-yl)methylidenyl]-5-[4-(trifluoromethyl)phenylaminosulfonyl]-2-indolinone |
| 10718 | E | 5 | 3-[(2-ethoxycarbonyl-3-(2-ethoxycarbonyl)ethyl-4-ethoxycarbonylmethyl-pyrrol-5-yl)methylidenyl]-5-[4-(trifluoromethyl)phenylaminosulfonyl]-2-indolinone |
| 10718 | E | 6 | 3-[(2-methyl-3-ethoxycarbonylfuran-5-yl)methylidenyl]-5-[4-(trifluoromethyl)phenylaminosulfonyl]-2-indolinone |
| 10718 | E | 7 | 3-[(2,3-dimethoxycarbonyl-5-methylpyrrol-4-yl)methylidenyl]-5-[4-(trifluoromethyl)phenylaminosulfonyl]-2-indolinone |
| 10718 | E | 8 | 3-(4-chloro-3-nitrobenzylidenyl)-5-[4-(trifluoromethyl)phenylaminosulfonyl]-2-indolinone |
| 10718 | E | 9 | 3-(2,4-dihydroxy-3-methylbenzylidenyl)-5-[4-(trifluoromethyl)phenylaminosulfonyl]-2-indolinone |
| 10718 | E | 10 | 3-[(furan-2-yl)methylidenyl]-5-[4-(trifluoromethyl)phenylaminosulfonyl]-2-indolinone |
| 10718 | E | 11 | 3-[(2-nitrofuran-5-yl)methylidenyl]-5-[4-(trifluoromethyl)phenylaminosulfonyl]-2-indolinone |
| 10718 | F | 2 | 3-[(2,4-dimethyl-3-ethoxycarbonylpyrrol-5-yl)methylidenyl]-5-(morpholin-1-yl)sulfonyl-2-indolinone |
| 10718 | F | 3 | 3-(3-bromo-2-hydroxy-5-methoxybenzylidenyl)-5-(morpholin-1-yl)sulfonyl-2-indolinone |
| 10718 | F | 4 | 3-[(1-hydroxynapth-2-yl)methylidenyl]-5-(morpholin-1-yl)sulfonyl-2-indolinone |
| 10718 | F | 5 | 3-[[2-ethoxycarbonyl-3-(2-ethoxycarbonyl)ethyl-4-(ethoxycarbonylmethyl)pyrrol-5-yl]methylidenyl]-5-(morpholin-1-yl)sulfonyl-2-indolinone |
| 10718 | F | 6 | 3-[(2-methyl-3-ethoxycarbonylfuran-5-yl)methylidenyl]-5-(morpholin-1-yl)sulfonyl-2-indolinone |
| 10718 | F | 7 | 3-[(2,3-dimethoxycarbonyl-5-methyl-pyrrol-4-yl)methylidenyl]-5-(morpholin-1-yl)sulfonyl-2-indolinone |
| 10718 | F | 8 | 3-(4-chloro-3-nitrobenzylidenyl)-5-(morpholin-1-yl)sulfonyl-2-indolinone |
| 10718 | F | 9 | 3-(2,4-dihydroxy-3-methylbenzylidenyl)-5-(morpholin-1-yl)sulfonyl-2-indolinone |
| 10718 | F | 10 | 3-[(furan-2-yl)methylidenyl]-5-(morpholin-1-yl)sulfonyl-2-indolinone |
| 10718 | F | 11 | 3-[(2-nitrofuran-5-yl)methylidenyl]-5-(morpholin-1-yl)sulfonyl-2-indolinone |
| 10718 | G | 2 | 3-[(2,4-dimethyl-3-ethoxycarbonylpyrrol-5-yl)methylidenyl]-5-(2-chloroethyl)-2-indolinone |

TABLE 13-continued

| MASTER BARCODE | PLATE ROW | PLATE COLUMN | NAME |
|---|---|---|---|
| 10718 | G | 3 | 3-(3-bromo-2-hydroxy-5-methoxybenzylidenyl)-5-(2-chloroethyl)-2-indolinone |
| 10718 | G | 4 | 3-[(1-hydroxynapth-2-yl)methylidenyl]-5-(2-chloroethyl)-2-indolinone |
| 10718 | G | 5 | 3-[[2-ethoxycarbonyl-3-(2-ethoxycarbonyl)ethyl-4(ethoxycarbonylmethyl)pyrrol-5-yl]methylidenyl]-5-(2-chloroethyl)-2-indolinone |
| 10718 | G | 6 | 3-[(2-methyl-3-ethoxycarbonylfuran-5-yl)methylidenyl]-5-(2-chloroethyl)-2-indolinone |
| 10718 | G | 7 | 3-[(2,3-dimethoxycarbonyl-5-methylpyrrol-4-yl)methylidenyl]-5-(2-chloroethyl)-2-indolinone |
| 10718 | G | 8 | 3-(4-chloro-3-nitrobenzylidenyl)-5-(2-chloroethyl)-2-indolinone |
| 10718 | G | 9 | 3-(2,4-dihydroxy-3-methylbenzylidenyl)-5-(2-chloroethyl)-2-indolinone |
| 10718 | G | 10 | 3-[(furan-2-yl)methylidenyl]-5-(2-chloroethyl)-2-indolinone |
| 10718 | G | 11 | 3-[(2-nitrofuran-5-yl)methylidenyl]-5-(2-chloroethyl)-2-indolinone |
| 10719 | A | 2 | 3-(4-ethoxy-3-methoxybenzylidenyl)-5,7-dibromo-2-indolinone |
| 10719 | A | 3 | 3-(3,4-dihydoxybenzylidenyl)-5,7-dibromo-2-indolinone |
| 10719 | A | 4 | 3-(2,4-dimethoxybenzylidenyl)-5,7-dibromo-2-indolinone |
| 10719 | A | 5 | 3-[(2,4-dimethyl-3-ethylpyrrol-5-yl)methylidenyl]-5,7-dibromo-2-indolinone |
| 10719 | A | 6 | 3-(2,4,6-trimethoxybenzylidenyl)-5,7-dibromo-2-indolinone |
| 10719 | A | 7 | 3-(4-hydroxybenzylidenyl)-5,7-dibromo-2-indolinone |
| 10719 | A | 8 | 3-(4-dimethylaminobenzylidenyl)-5,7-dibromo-2-indolinone |
| 10719 | A | 9 | 3-(2-chloro-4-fluorobenzylidenyl)-5,7-dibromo-2-indolinone |
| 10719 | A | 10 | 3-(3-nitrobenzylidenyl)-5,7-dibromo-2-indolinone |
| 10719 | A | 11 | 3-[4-fluoro-2-(trifluoromethyl)benzylidenyl]-5,7-dibromo-2-indolinone |
| 10719 | B | 2 | 3-(4-ethoxy-3-methoxybenzylidenyl)-5-iodo-2-indolinone |
| 10719 | B | 3 | 3-(3,4-dihydoxybenzylidenyl)-5-iodo-2-indolinone |
| 10719 | B | 4 | 3-(2,4-dimethoxybenzylidenyl)-5-iodo-2-indolinone |
| 10719 | B | 5 | 3-[(2,4-dimethyl-3-ethylpyrrol-5-yl)methylidenyl]-5-iodo-2-indolinone |
| 10719 | B | 6 | 3-(2,4,6-trimethoxybenzylidenyl)-5-iodo-2-indolinone |
| 10719 | B | 7 | 3-(4-hydroxybenzylidenyl)-5-iodo-2-indolinone |
| 10719 | B | 8 | 3-(4-dimethylaminobenzylidenyl)-5-iodo-2-indolinone |
| 10719 | B | 9 | 3-(2-chloro-4-fluorobenzylidenyl)-5-iodo-2-indolinone |
| 10719 | B | 10 | 3-(3-nitrobenzylidenyl)-5-iodo-2-indolinone |
| 10719 | B | 11 | 3-[4-fluoro-2-(trifluoromethyl)benzylidenyl]-5-iodo-2-indolinone |
| 10719 | C | 2 | 3-(4-ethoxy-3-methoxybenzylidenyl)-5-bromo-4-methyl-2-indolinone |
| 10719 | C | 3 | 3-(3,4-dihydoxybenzylidenyl)-5-bromo-4-methyl-2-indolinone |
| 10719 | C | 4 | 3-(2,4-dimethoxybenzylidenyl)-5-bromo-4-methyl-2-indolinone |
| 10719 | C | 5 | 3-[(2,4-dimethyl-3-ethylpyrrol-5-yl)methylidenyl]-5-bromo-4-methyl-2-indolinone |
| 10719 | C | 6 | 3-(2,4,6-trimethoxybenzylidenyl)-5-bromo-4-methyl-2-indolinone |
| 10719 | C | 7 | 3-(4-hydroxybenzylidenyl)-5-bromo-4-methyl-2-indolinone |
| 10719 | C | 8 | 3-(4-dimethylaminobenzylidenyl)-5-bromo-4-methyl-2-indolinone |
| 10719 | C | 9 | 3-(2-chloro-4-fluorobenzylidenyl)-5-bromo-4-methyl-2-indolinone |
| 10719 | C | 10 | 3-(3-nitrobenzylidenyl)-5-bromo-4-methyl-2-indolinone |
| 10719 | C | 11 | 3-[4-fluoro-2-(trifluoromethyl)benzylidenyl]-5-bromo-4-methyl-2-indolinone |
| 10719 | D | 2 | 3-(4-ethoxy-3-methoxybenzylidenyl)-5-methylaminosulfonyl-2-indolinone |

TABLE 13-continued

| MASTER BARCODE | PLATE ROW | PLATE COLUMN | NAME |
|---|---|---|---|
| 10719 | D | 3 | 3-(3,4-dihydoxybenzylidenyl)-5-methylaminosulfonyl-2-indolinone |
| 10719 | D | 4 | 3-(2,4-dimethoxybenzylidenyl)-5-methylaminosulfonyl-2-indolinone |
| 10719 | D | 5 | 3-[(2,4-dimethyl-3-ethylpyrrol-5-yl)methylidenyl]-5-methylaminosulfonyl-2-indolinone |
| 10719 | D | 6 | 3-(2,4,6-trimethoxybenzylidenyl)-5-methylaminosulfonyl-2-indolinone |
| 10719 | D | 7 | 3-(4-hydroxybenzylidenyl)-5-methylaminosulfonyl-2-indolinone |
| 10719 | D | 8 | 3-(4-dimethylaminobenzylidenyl)-5-methylaminosulfonyl-2-indolinone |
| 10719 | D | 9 | 3-(2-chloro-4-fluorobenzylidenyl)-5-methylaminosulfonyl-2-indolinone |
| 10719 | D | 10 | 3-(3-nitrobenzylidenyl)-5-methylaminosulfonyl-2-indolinone |
| 10719 | D | 11 | 3-[4-fluoro-2-(trifluoromethyl)benzylidenyl]-5-methylaminosulfonyl-2-indolinone |
| 10719 | E | 2 | 3-(4-ethoxy-3-methoxybenzylidenyl)-5-[4-(trifluoromethyl)phenylaminosulfonyl]-2-indolinone |
| 10719 | E | 3 | 3-(3,4-dihydoxybenzylidenyl)-5-[4-(trifluoromethyl)phenylaminosulfonyl]-2-indolinone |
| 10719 | E | 4 | 3-(2,4-dimethoxybenzylidenyl)-5-[4-(trifluoromethyl)phenylaminosulfonyl]-2-indolinone |
| 10719 | E | 5 | 3-[(2,4-dimethyl-3-ethylpyrrol-5-yl)methylidenyl]-5-[4-(trifluoromethyl)phenylaminosulfonyl]-2-indolinone |
| 10719 | E | 6 | 3-(2,4,6-trimethoxybenzylidenyl)-5-[4-(trifluoromethyl)phenylaminosulfonyl]-2-indolinone |
| 10719 | E | 7 | 3-(4-hydroxybenzylidenyl)-5-[4-(trifluoromethyl)phenylaminosulfonyl]-2-indolinone |
| 10719 | E | 8 | 3-(4-dimethylaminobenzylidenyl)-5-[4-(trifluoromethyl)phenylaminosulfonyl]-2-indolinone |
| 10719 | E | 9 | 3-(2-chloro-4-fluorobenzylidenyl)-5-[4-(trifluoromethyl)phenylaminosulfonyl]-2-indolinone |
| 10719 | E | 10 | 3-(3-nitrobenzylidenyl)-5-[4-(trifluoromethyl)phenylaminosulfonyl]-2-indolinone |
| 10719 | E | 11 | 3-[4-fluoro-2-(trifluoromethyl)benzylidenyl]-5-[4-(trifluoromethyl)phenylaminosulfonyl]-2-indolinone |
| 10719 | F | 2 | 3-(4-ethoxy-3-methoxybenzylidenyl)-5-(morpholin-1-yl)sulfonyl-2-indolinone |
| 10719 | F | 3 | 3-(3,4-dihydoxybenzylidenyl)-5-(morpholin-1-yl)sulfonyl-2-indolinone |
| 10719 | F | 4 | 3-(2,4-dimethoxybenzylidenyl)-5-(morpholin-1-yl)sulfonyl-2-indolinone |
| 10719 | F | 5 | 3-[(2,4-dimethyl-3-ethylpyrrol-5-yl)methylidenyl]-5-(morpholin-1-yl)sulfonyl-2-indolinone |
| 10719 | F | 6 | 3-(2,4,6-trimethoxybenzylidenyl)-5-(morpholin-1-yl)sulfonyl-2-indolinone |
| 10719 | F | 7 | 3-(4-hydroxybenzylidenyl)-5-(morpholin-1-yl)sulfonyl-2-indolinone |
| 10719 | F | 8 | 3-(4-dimethylaminobenzylidenyl)-5-(morpholin-1-yl)sulfonyl-2-indolinone |
| 10719 | F | 9 | 3-(2-chloro-4-fluorobenzylidenyl)-5-(morpholin-1-yl)sulfonyl-2-indolinone |
| 10719 | F | 10 | 3-(3-nitrobenzylidenyl)-5-(morpholin-1-yl)sulfonyl-2-indolinone |
| 10719 | F | 11 | 3-[4-fluoro-2-(trifluoromethyl)benzylidenyl]-5-(morpholin-1-yl)sulfonyl-2-indolinone |
| 10719 | G | 2 | 3-(4-ethoxy-3-methoxybenzylidenyl)-5-(2-chloroethyl)-2-indolinone |
| 10719 | G | 3 | 3-(3,4-dihydoxybenzylidenyl)-5-(2-chloroethyl)-2-indolinone |
| 10719 | G | 4 | 3-(2,4-dimethoxybenzylidenyl)-5-(2-chloroethyl)-2-indolinone |
| 10719 | G | 5 | 3-[(2,4-dimethyl-3-ethylpyrrol-5-yl)methylidenyl]-5-(2-chloroethyl)-2-indolinone |
| 10719 | G | 6 | 3-(2,4,6-trimethoxybenzylidenyl)-5-(2-chloroethyl)-2-indolinone |
| 10719 | G | 7 | 3-(4-hydroxybenzylidenyl)-5-(2-chloroethyl)-2-indolinone |
| 10719 | G | 8 | 3-(4-dimethylaminobenzylidenyl)-5-(2-chloroethyl)-2-indolinone |
| 10719 | G | 9 | 3-(2-chloro-4-fluorobenzylidenyl)-5-(2-chloroethyl)-2-indolinone |

TABLE 13-continued

| MASTER BARCODE | PLATE ROW | PLATE COLUMN | NAME |
|---|---|---|---|
| 10719 | G | 10 | 3-(3-nitrobenzylidenyl)-5-(2-chloroethyl)-2-indolinone |
| 10719 | G | 11 | 3-[4-fluoro-2-(trifluoromethyl)benzylidenyl]-5-(2-chloroethyl)-2-indolinone |
| 10720 | A | 2 | 3-(2,4,6-trifluorobenzylidenyl)-5,7-dibromo-2-indolinone |
| 10720 | A | 3 | 3-(4-hydroxy-2-methoxybenzylidenyl)-5,7-dibromo-2-indolinone |
| 10720 | A | 4 | 3-(3,4-dimethoxybenzylidenyl)-5,7-dibromo-2-indolinone |
| 10720 | A | 5 | 3-(2-hydroxybenzylidenyl)-5,7-dibromo-2-indolinone |
| 10720 | A | 6 | 3-benzylidenyl-5,7-dibromo-2-indolinone |
| 10720 | A | 7 | 3-[(2-methylmercaptothien-5-yl)methylidenyl]-5,7-dibromo-2-indolinone |
| 10720 | A | 8 | 3-(2,4-dihydroxy-6-methylbenzylidenyl)-5,7-dibromo-2-indolinone |
| 10720 | A | 9 | 3-(3-ethoxy-4-hydroxybenzylidenyl)-5,7-dibromo-2-indolinone |
| 10720 | A | 10 | 3-(2-hydroxy-5-methoxybenzylidenyl)-5,7-dibromo-2-indolinone |
| 10720 | A | 11 | 3-[(imidazol-2-yl)methylidenyl]-5,7-dibromo-2-indolinone |
| 10720 | B | 2 | 3-(2,4,6-trifluorobenzylidenyl)-5-iodo-2-indolinone |
| 10720 | B | 3 | 3-(4-hydroxy-2-methoxybenzylidenyl)-5-iodo-2-indolinone |
| 10720 | B | 4 | 3-(3,4-dimethoxybenzylidenyl)-5-iodo-2-indolinone |
| 10720 | B | 5 | 3-(2-hydroxybenzylidenyl)-5-iodo-2-indolinone |
| 10720 | B | 6 | 3-benzylidenyl-5-iodo-2-indolinone |
| 10720 | B | 7 | 3-[(2-methylmercaptothien-5-yl)methylidenyl]-5-iodo-2-indolinone |
| 10720 | B | 8 | 3-(2,4-dihydroxy-6-methylbenzylidenyl)-5-iodo-2-indolinone |
| 10720 | B | 9 | 3-(3-ethoxy-4-hydroxybenzylidenyl)-5-iodo-2-indolinone |
| 10720 | B | 10 | 3-(2-hydroxy-5-methoxybenzylidenyl)-5-iodo-2-indolinone |
| 10720 | B | 11 | 3-[(imidazol-2-yl)methylidenyl]-5-iodo-2-indolinone |
| 10720 | C | 2 | 3-(2,4,6-trifluorobenzylidenyl)-5-bromo-4-methyl-2-indolinone |
| 10720 | C | 3 | 3-(4-hydroxy-2-methoxybenzylidenyl)-5-bromo-4-methyl-2-indolinone |
| 10720 | C | 4 | 3-(3,4-dimethoxybenzylidenyl)-5-bromo-4-methyl-2-indolinone |
| 10720 | C | 5 | 3-(2-hydroxybenzylidenyl)-5-bromo-4-methyl-2-indolinone |
| 10720 | C | 6 | 3-benzylidenyl-5-bromo-4-methyl-2-indolinone |
| 10720 | C | 7 | 3-[(2-methylmercaptothien-5-yl)methylidenyl]-5-bromo-4-methyl-2-indolinone |
| 10720 | C | 8 | 3-(2,4-dihydroxy-6-methylbenzylidenyl)-5-bromo-4-methyl-2-indolinone |
| 10720 | C | 9 | 3-(3-ethoxy-4-hydroxybenzylidenyl)-5-bromo-4-methyl-2-indolinone |
| 10720 | C | 10 | 3-(2-hydroxy-5-methoxybenzylidenyl)-5-bromo-4-methyl-2-indolinone |
| 10720 | C | 11 | 3-[(imidazol-2-yl)methylidenyl]-5-bromo-4-methyl-2-indolinone |
| 10720 | D | 2 | 3-(2,4,6-trifluorobenzylidenyl)-5-methylaminosulfonyl-2-indolinone |
| 10720 | D | 3 | 3-(4-hydroxy-2-methoxybenzylidenyl)-5-methylaminosulfonyl-2-indolinone |
| 10720 | D | 4 | 3-(3,4-dimethoxybenzylidenyl)-5-methylaminosulfonyl-2-indolinone |
| 10720 | D | 5 | 3-(2-hydroxybenzylidenyl)-5-methylaminosulfonyl-2-indolinone |
| 10720 | D | 6 | 3-benzylidenyl-5-methylaminosulfonyl-2-indolinone |
| 10720 | D | 7 | 3-[(2-methylmercaptothien-5-yl)methylidenyl]-5-methylaminosulfonyl-2-indolinone |
| 10720 | D | 8 | 3-(2,4-dihydroxy-6-methylbenzylidenyl)-5-methylaminosulfonyl-2-indolinone |
| 10720 | D | 9 | 3-(3-ethoxy-4-hydroxybenzylidenyl)-5-methylaminosulfonyl-2-indolinone |
| 10720 | D | 10 | 3-(2-hydroxy-5-methoxybenzylidenyl)-5-methylaminosulfonyl-2-indolinone |
| 10720 | D | 11 | 3-[(imidazol-2-yl)methylidenyl]-5-methylaminosulfonyl-2-indolinone |

TABLE 13-continued

| MASTER BARCODE | PLATE ROW | PLATE COLUMN | NAME |
|---|---|---|---|
| 10720 | E | 2 | 3-(2,4,6-trifluorobenzylidenyl)-5-[4-(trifluoromethyl)phenylaminosulfonyl]-2-indolinone |
| 10720 | E | 3 | 3-(4-hydroxy-2-methoxybenzylidenyl)-5-[4-(trifluoromethyl)phenylaminosulfonyl]-2-indolinone |
| 10720 | E | 4 | 3-(3,4-dimethoxybenzylidenyl)-5-[4-(trifluoromethyl)phenylaminosulfonyl]-2-indolinone |
| 10720 | E | 5 | 3-(2-hydroxybenzylidenyl)-5-[4-(trifluoromethyl)phenylaminosulfonyl]-2-indolinone |
| 10720 | E | 6 | 3-benzylidenyl-5-[4-(trifluoromethyl)phenylaminosulfonyl]-2-indolinone |
| 10720 | E | 7 | 3-[(2-methylmercaptothien-5-yl)methylidenyl]-5-[4-(trifluoromethyl)phenylaminosulfonyl]-2-indolinone |
| 10720 | E | 8 | 3-(2,4-dihydroxy-6-methylbenzylidenyl)-5-[4-(trifluoromethyl)phenylaminosulfonyl]-2-indolinone |
| 10720 | E | 9 | 3-(3-ethoxy-4-hydroxybenzylidenyl)-5-[4-(trifluoromethyl)phenylaminosulfonyl]-2-indolinone |
| 10720 | E | 10 | 3-(2-hydroxy-5-methoxybenzylidenyl)-5-[4-(trifluoromethyl)phenylaminosulfonyl]-2-indolinone |
| 10720 | E | 11 | 3-[(imidazol-2-yl)methylidenyl]-5-[4-(trifluoromethyl)phenylaminosulfonyl]-2-indolinone |
| 10720 | F | 2 | 3-(2,4,6-trifluorobenzylidenyl)-5-(morpholin-1-yl)sulfonyl-2-indolinone |
| 10720 | F | 3 | 3-(4-hydroxy-2-methoxybenzylidenyl)-5-(morpholin-1-yl)sulfonyl-2-indolinone |
| 10720 | F | 4 | 3-(3,4-dimethoxybenzylidenyl)-5-(morpholin-1-yl)sulfonyl-2-indolinone |
| 10720 | F | 5 | 3-(2-hydroxybenzylidenyl)-5-(morpholin-1-yl)sulfonyl-2-indolinone |
| 10720 | F | 6 | 3-benzylidenyl-5-(morpholin-1-yl)sulfonyl-2-indolinone |
| 10720 | F | 7 | 3-[(2-methylmercaptothien-5-yl)methylidenyl]-5-(morpholin-1-yl)sulfonyl-2-indolinone |
| 10720 | F | 8 | 3-(2,4-dihydroxy-6-methylbenzylidenyl)-5-(morpholin-1-yl)sulfonyl-2-indolinone |
| 10720 | F | 9 | 3-(3-ethoxy-4-hydroxybenzylidenyl)-5-(morpholin-1-yl)sulfonyl-2-indolinone |
| 10720 | F | 10 | 3-(2-hydroxy-5-methoxybenzylidenyl)-5-(morpholin-1-yl)sulfonyl-2-indolinone |
| 10720 | F | 11 | 3-[(imidazol-2-yl)methylidenyl]-5-(morpholin-1-yl)sulfonyl-2-indolinone |
| 10720 | G | 2 | 3-(2,4,6-trifluorobenzylidenyl)-5-(2-chloroethyl)-2-indolinone |
| 10720 | G | 3 | 3-(4-hydroxy-2-methoxybenzylidenyl)-5-(2-chloroethyl)-2-indolinone |
| 10720 | G | 4 | 3-(3,4-dimethoxybenzylidenyl)-5-(2-chloroethyl)-2-indolinone |
| 10720 | G | 5 | 3-(2-hydroxybenzylidenyl)-5-(2-chloroethyl)-2-indolinone |
| 10720 | G | 6 | 3-benzylidenyl-5-(2-chloroethyl)-2-indolinone |
| 10720 | G | 7 | 3-[(2-methylmercaptothien-5-yl)methylidenyl]-5-(2-chloroethyl)-2-indolinone |
| 10720 | G | 8 | 3-(2,4-dihydroxy-6-methylbenzylidenyl)-5-(2-chloroethyl)-2-indolinone |
| 10720 | G | 9 | 3-(3-ethoxy-4-hydroxybenzylidenyl)-5-(2-chloroethyl)-2-indolinone |
| 10720 | G | 10 | 3-(2-hydroxy-5-methoxybenzylidenyl)-5-(2-chloroethyl)-2-indolinone |
| 10720 | G | 11 | 3-[(imidazol-2-yl)methylidenyl]-5-(2-chloroethyl)-2-indolinone |
| 10721 | A | 2 | 3-[(1-methylbenzimidazol-2-yl)methylidenyl]-5,7-dibromo-2-indolinone |
| 10721 | A | 3 | 3-[(4-chloro-1-methylpyrazol-3-yl)methylidenyl]-5,7-dibromo-2-indolinone |
| 10721 | A | 4 | 3-[(2,3-dimethylthien-5-yl)methylidenyl]-5,7-dibromo-2-indolinone |
| 10721 | A | 5 | 3-[(4,5,6,7-tetrahydroindol-2-yl)methylidenyl]-5,7-dibromo-2-indolinone |
| 10721 | A | 6 | 3-(3-chloromethyl-2-hydroxy-5-nitrobenzylidenyl)-5,7-dibromo-2-indolinone |
| 10721 | A | 7 | 3-[(2-chlorothien-5-yl)methylidenyl]-5,7-dibromo-2-indolinone |
| 10721 | A | 8 | 3-[(2,4-dimethylpyrrol-5-yl)methylidenyl]-5,7-dibromo-2-indolinone |
| 10721 | A | 9 | 3-(3-t-butyl-4-hydroxybenzylidenyl)-5,7-dibromo-2-indolinone |

TABLE 13-continued

| MASTER BARCODE | PLATE ROW | PLATE COLUMN | NAME |
|---|---|---|---|
| 10721 | A | 10 | 3-(3-bromo-5-t-butyl-4-hydroxybenzylidenyl)-5,7-dibromo-2-indolinone |
| 10721 | A | 11 | 3-(3,5-di-t-butyl-4-hydroxybenzylidenyl)-5,7-dibromo-2-indolinone |
| 10721 | B | 2 | 3-[(1-methylbenzimidazol-2-yl)methylidenyl]-5-iodo-2-indolinone |
| 10721 | B | 3 | 3-[(4-chloro-1-methylpyrazol-3-yl)methylidenyl]-5-iodo-2-indolinone |
| 10721 | B | 4 | 3-[(2,3-dimethylthien-5-yl)methylidenyl]-5-iodo-2-indolinone |
| 10721 | B | 5 | 3-[(4,5,6,7-tetrahydroindol-2-yl)methylidenyl]-5-iodo-2-indolinone |
| 10721 | B | 6 | 3-(3-chloromethyl-2-hydroxy-5-nitrobenzylidenyl)-5-iodo-2-indolinone |
| 10721 | B | 7 | 3-[(2-chlorothien-5-yl)methylidenyl]-5-iodo-2-indolinone |
| 10721 | B | 8 | 3-[(2,4-dimethylpyrrol-5-yl)methylidenyl]-5-iodo-2-indolinone |
| 10721 | B | 9 | 3-(3-t-butyl-4-hydroxybenzylidenyl)-5-iodo-2-indolinone |
| 10721 | B | 10 | 3-(3-bromo-5-t-butyl-4-hydroxybenzylidenyl)-5-iodo-2-indolinone |
| 10721 | B | 11 | 3-(3,5-di-t-butyl-4-hydroxybenzylidenyl)-5-iodo-2-indolinone |
| 10721 | C | 2 | 3-[(1-methylbenzimidazol-2-yl)methylidenyl]-5-bromo-4-methyl-2-indolinone |
| 10721 | C | 3 | 3-[(4-chloro-1-methylpyrazol-3-yl)methylidenyl]-5-bromo-4-methyl-2-indolinone |
| 10721 | C | 4 | 3-[(2,3-dimethylthien-5-yl)methylidenyl]-5-bromo-4-methyl-2-indolinone |
| 10721 | C | 5 | 3-[(4,5,6,7-tetrahydroindol-2-yl)methylidenyl]-5-bromo-4-methyl-2-indolinone |
| 10721 | C | 6 | 3-(3-chloromethyl-2-hydroxy-5-nitrobenzylidenyl)-5-bromo-4-methyl-2-indolinone |
| 10721 | C | 7 | 3-[(2-chlorothien-5-yl)methylidenyl]-5-bromo-4-methyl-2-indolinone |
| 10721 | C | 8 | 3-[(2,4-dimethylpyrrol-5-yl)methylidenyl]-5-bromo-4-methyl-2-indolinone |
| 10721 | C | 9 | 3-(3-t-butyl-4-hydroxybenzylidenyl)-5-bromo-4-methyl-2-indolinone |
| 10721 | C | 10 | 3-(3-bromo-5-t-butyl-4-hydroxybenzylidenyl)-5-bromo-4-methyl-2-indolinone |
| 10721 | C | 11 | 3-(3,5-di-t-butyl-4-hydroxybenzylidenyl)-5-bromo-4-methyl-2-indolinone |
| 10721 | D | 2 | 3-[(1-methylbenzimidazol-2-yl)methylidenyl]-5-methylaminosulfonyl-2-indolinone |
| 10721 | D | 3 | 3-[(4-chloro-1-methylpyrazol-3-yl)methylidenyl]-5-methylaminosulfonyl-2-indolinone |
| 10721 | D | 4 | 3-[(2,3-dimethylthien-5-yl)methylidenyl]-5-methylaminosulfonyl-2-indolinone |
| 10721 | D | 5 | 3-[(4,5,6,7-tetrahydroindol-2-yl)methylidenyl]-5-methylaminosulfonyl-2-indolinone |
| 10721 | D | 6 | 3-(3-chloromethyl-2-hydroxy-5-nitrobenzylidenyl)-5-methylaminosulfonyl-2-indolinone |
| 10721 | D | 7 | 3-[(2-chlorothien-5-yl)methylidenyl]-5-methylaminosulfonyl-2-indolinone |
| 10721 | D | 8 | 3-[(2,4-dimethylpyrrol-5-yl)methylidenyl]-5-methylaminosulfonyl-2-indolinone |
| 10721 | D | 9 | 3-(3-t-butyl-4-hydroxybenzylidenyl)-5-methylaminosulfonyl-2-indolinone |
| 10721 | D | 10 | 3-(3-bromo-5-t-butyl-4-hydroxybenzylidenyl)-5-methylaminosulfonyl-2-indolinone |
| 10721 | D | 11 | 3-(3,5-di-t-butyl-4-hydroxybenzylidenyl)-5-methylaminosulfonyl-2-indolinone |
| 10721 | E | 2 | 3-[(1-methylbenzimidazol-2-yl)methylidenyl]-5-[4-(trifluoromethyl)phenylaminosulfonyl]-2-indolinone |
| 10721 | E | 3 | 3-[(4-chloro-1-methylpyrazol-3-yl)methylidenyl]-5-[4-(trifluoromethyl)phenylaminosulfonyl]-2-indolinone |
| 10721 | E | 4 | 3-[(2,3-dimethylthien-5-yl)methylidenyl]-5-[4-(trifluoromethyl)phenylaminosulfonyl]-2-indolinone |
| 10721 | E | 5 | 3-[(4,5,6,7-tetrahydroindol-2-yl)methylidenyl]-5-[4-(trifluoromethyl)phenylaminosulfonyl]-2-indolinone |
| 10721 | E | 6 | 3-(3-chloromethyl-2-hydroxy-5-nitrobenzylidenyl)-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10721 | E | 7 | 3-[(2-chlorothien-5-yl)methylidenyl]-5-[4-(trifluoromethyl)phenylaminosulfonyl]-2-indolinone |
| 10721 | E | 8 | 3-[(2,4-dimethylpyrrol-5-yl)methylidenyl]-5-[4-(trifluoromethyl)phenylaminosulfonyl]-2-indolinone |
| 10721 | E | 9 | 3-(3-t-butyl-4-hydroxybenzylidenyl)-5-[4-(trifluoromethyl)phenylaminosulfonyl]-2-indolinone |
| 10721 | E | 10 | 3-(3-bromo-5-t-butyl-4-hydroxybenzylidenyl)-5-[4-(trifluoromethyl)phenylaminosulfonyl]-2-indolinone |
| 10721 | E | 11 | 3-(3,5-di-t-butyl-4-hydroxybenzylidenyl)-5-[4-(trifluoromethyl)phenylaminosulfonyl]-2-indolinone |
| 10721 | F | 2 | 3-[(1-methylbenzimidazol-2-yl)methylidenyl]-5-(morpholin-1-yl)sulfonyl]-2-indolinone |
| 10721 | F | 3 | 3-[(4-chloro-1-methylpyrazol-3-yl)methylidenyl]-5-(morpholin-1-yl)sulfonyl]-2-indolinone |
| 10721 | F | 4 | 3-[(2,3-dimethylthien-5-yl)methylidenyl]-5-(morpholin-1-yl)sulfonyl]-2-indolinone |
| 10721 | F | 5 | 3-[(4,5,6,7-tetrahydroindol-2-yl)methylidenyl]-5-(morpholin-1-yl)sulfonyl]-2-indolinone |
| 10721 | F | 6 | 3-(3-chloromethyl-2-hydroxy-5-nitrobenzylidenyl)-5-(morpholin-1-yl)sulfonyl]-2-indolinone |
| 10721 | F | 7 | 3-[(2-chlorothien-5-yl)methylidenyl]-5-(morpholin-1-yl)sulfonyl]-2-indolinone |
| 10721 | F | 8 | 3-[(2,4-dimethylpyrrol-5-yl)methylidenyl]-5-(morpholin-1-yl)sulfonyl]-2-indolinone |
| 10721 | F | 9 | 3-(3-t-butyl-4-hydroxybenzylidenyl)-5-(morpholin-1-yl)sulfonyl]-2-indolinone |
| 10721 | F | 10 | 3-(3-bromo-5-t-butyl-4-hydroxybenzylidenyl)-5-(morpholin-1-yl)sulfonyl]-2-indolinone |
| 10721 | F | 11 | 3-(3,5-di-t-butyl-4-hydroxybenzylidenyl)-5-(morpholin-1-yl)sulfonyl]-2-indolinone |
| 10721 | G | 2 | 3-[(1-methylbenzimidazol-2-yl)methylidenyl]-5-(2-chloroethyl)-2-indolinone |
| 10721 | G | 3 | 3-[(4-chloro-1-methylpyrazol-3-yl)methylidenyl]-5-(2-chloroethyl)-2-indolinone |
| 10721 | G | 4 | 3-[(2,3-dimethylthien-5-yl)methylidenyl]-5-(2-chloroethyl)-2-indolinone |
| 10721 | G | 5 | 3-[(4,5,6,7-tetrahydroindol-2-yl)methylidenyl]-5-(2-chloroethyl)-2-indolinone |
| 10721 | G | 6 | 3-(3-chloromethyl-2-hydroxy-5-nitrobenzylidenyl)-5-(2-chloroethyl)-2-indolinone |
| 10721 | G | 7 | 3-[(2-chlorothien-5-yl)methylidenyl]-5-(2-chloroethyl)-2-indolinone |
| 10721 | G | 8 | 3-[(2,4-dimethylpyrrol-5-yl)methylidenyl]-5-(2-chloroethyl)-2-indolinone |
| 10721 | G | 9 | 3-(3-t-butyl-4-hydroxybenzylidenyl)-5-(2-chloroethyl)-2-indolinone |
| 10721 | G | 10 | 3-(3-bromo-5-t-butyl-4-hydroxybenzylidenyl)-5-(2-chloroethyl)-2-indolinone |
| 10721 | G | 11 | 3-(3,5-di-t-butyl-4-hydroxybenzylidenyl)-5-(2-chloroethyl)-2-indolinone |
| 10722 | A | 2 | 3-(3-t-butyl-4-hydroxy-5-nitrobenzylidenyl)-5,7-dibromo-2-indolinone |
| 10722 | A | 3 | 3-(2,4,6-trihydroxybenzylidenyl)-5,7-dibromo-2-indolinone |
| 10722 | A | 4 | 3-[(2-nitrothien-5-yl)methylidenyl]-5,7-dibromo-2-indolinone |
| 10722 | A | 5 | 3-(4-carboxybenzylidenyl)-5,7-dibromo-2-indolinone |
| 10722 | A | 6 | 3-(2,4-difluorobenzylidenyl)-5,7-dibromo-2-indolinone |
| 10722 | A | 7 | 3-(3,5-dimethyl-4-hydroxybenzylidenyl)-5,7-dibromo-2-indolinone |
| 10722 | A | 8 | 3-(3-t-butyl-5-chloro-4-hydroxybenzylidenyl)-5,7-dibromo-2-indolinone |
| 10722 | A | 9 | 3-[(2-nitrothien-4-yl)methylidenyl]-5,7-dibromo-2-indolinone |
| 10722 | A | 10 | 3-(4-di-n-butylaminobenzylidenyl)-5,7-dibromo-2-indolinone |
| 10722 | A | 11 | 3-[4-(trifluoromethyl)benzylidenyl]-5,7-dibromo-2-indolinone |
| 10722 | B | 2 | 3-(3-t-butyl-4-hydroxy-5-nitrobenzylidenyl)-5-iodo-2-indolinone |
| 10722 | B | 3 | 3-(2,4,6-trihydroxybenzylidenyl)-5-iodo-2-indolinone |
| 10722 | B | 4 | 3-[(2-nitrothien-5-yl)methylidenyl]-5-iodo-2-indolinone |
| 10722 | B | 5 | 3-(4-carboxybenzylidenyl)-5-iodo-2-indolinone |
| 10722 | B | 6 | 3-(2,4-difluorobenzylidenyl)-5-iodo-2-indolinone |

TABLE 13-continued

| MASTER BARCODE | PLATE ROW | PLATE COLUMN | NAME |
|---|---|---|---|
| 10722 | B | 7 | 3-(3,5-dimethyl-4-hydroxybenzylidenyl)-5-iodo-2-indolinone |
| 10722 | B | 8 | 3-(3-t-butyl-5-chloro-4-hydroxybenzylidenyl)-5-iodo-2-indolinone |
| 10722 | B | 9 | 3-[(2-nitrothien-4-yl)methydenyl]-5-iodo-2-indolinone |
| 10722 | B | 10 | 3-(4-di-n-butylaminobenzylidenyl)-5-iodo-2-indolinone |
| 10722 | B | 11 | 3-[4-(trifluoromethyl)benzylidenyl]-5-iodo-2-indolinone |
| 10722 | C | 2 | 3-(3-t-butyl-4-hydroxy-5-nitrobenzylidenyl)-5-dibromo-4-methyl-2-indolinone |
| 10722 | C | 3 | 3-(2,4,6-trihydroxybenzylidenyl)-5-dibromo-4-methyl-2-indolinone |
| 10722 | C | 4 | 3-[(2-nitrothien-5-yl)methylidenyl]-5-dibromo-4-methyl-2-indolinone |
| 10722 | C | 5 | 3-(4-carboxybenzylidenyl)-5-dibromo-4-methyl-2-indolinone |
| 10722 | C | 6 | 3-(2,4-difluorobenzylidenyl)-5-dibromo-4-methyl-2-indolinone |
| 10722 | C | 7 | 3-(3,5-dimethyl-4-hydroxybenzylidenyl)-5-dibromo-4-methyl-2-indolinone |
| 10722 | C | 8 | 3-(3-t-butyl-5-chloro-4-hydroxybenzylidenyl)-5-dibromo-4-methyl-2-indolinone |
| 10722 | C | 9 | 3-[(2-nitrothien-4-yl)methylidenyl]-5-dibromo-4-methyl-2-indolinone |
| 10722 | C | 10 | 3-(4-di-n-butylaminobenzylidenyl)-5-dibromo-4-methyl-2-indolinone |
| 10722 | C | 11 | 3-[4-(trifluoromethyl)benzylidenyl]-5-dibromo-4-methyl-2-indolinone |
| 10722 | D | 2 | 3-(3-t-butyl-4-hydroxy-5-nitrobenzylidenyl)-5-methylaminosulfonyl-2-indolinone |
| 10722 | D | 3 | 3-(2,4,6-trihydroxybenzylidenyl)-5-methylaminosulfonyl-2-indolinone |
| 10722 | D | 4 | 3-[(2-nitrothien-5-yl)methylidenyl]-5-methylaminosulfonyl-2-indolinone |
| 10722 | D | 5 | 3-(4-carboxybenzylidenyl)-5-methylaminosulfonyl-2-indolinone |
| 10722 | D | 6 | 3-(2,4-difluorobenzylidenyl)-5-methylaminosulfonyl-2-indolinone |
| 10722 | D | 7 | 3-(3,5-dimethyl-4-hydroxybenzylidenyl)-5-methylaminosulfonyl-2-indolinone |
| 10722 | D | 8 | 3-(3-t-butyl-5-chloro-4-hydroxybenzylidenyl)-5-methylaminosulfonyl-2-indolinone |
| 10722 | D | 9 | 3-[(2-nitrothien-4-yl)methylidenyl]-5-methylaminosulfonyl-2-indolinone |
| 10722 | D | 10 | 3-(4-di-n-butylaminobenzylidenyl)-5-methylaminosulfonyl-2-indolinone |
| 10722 | D | 11 | 3-[4-(trifluoromethyl)benzylidenyl]-5-methylaminosulfonyl-2-indolinone |
| 10722 | E | 2 | 3-(3-t-butyl-4-hydroxy-5-nitrobenzylidenyl)-5-[4-(trifluoromethyl)phenylaminosulfonyl]-2-indolinone |
| 10722 | E | 3 | 3-(2,4,6-trihydroxybenzylidenyl)-5-[4-(trifluoromethyl)phenylaminosulfonyl]-2-indolinone |
| 10722 | E | 4 | 3-[(2-nitrothien-5-yl)methylidenyl]-5-[4-(trifluoromethyl)phenylaminosulfonyl]-2-indolinone |
| 10722 | E | 5 | 3-(4-carboxybenzylidenyl)-5-[4-(trifluoromethyl)phenylaminosulfonyl]-2-indolinone |
| 10722 | E | 6 | 3-(2,4-difluorobenzylidenyl)-5-[4-(trifluoromethyl)phenylaminosulfonyl]-2-indolinone |
| 10722 | E | 7 | 3-(3,5-dimethyl-4-hydroxybenzylidenyl)-5-[4-(trifluoromethyl)phenylaminosulfonyl]-2-indolinone |
| 10722 | E | 8 | 3-(3-t-butyt-5-chloro-4-hydroxybenzylidenyl)-5-[4-(trifluoromethyl)phenylaminosulfonyl]-2-indolinone |
| 10722 | E | 9 | 3-[(2-nitrothien-4-yl)methylidenyl]-5-[4-(trifluoromethyl)phenylaminosulfonyl]-2-indolinone |
| 10722 | E | 10 | 3-(4-di-n-butylaminobenzylidenyl)-5-[4-(trifluoromethyl)phenylaminosulfonyl]-2-indolinone |
| 10722 | E | 11 | 3-[4-(trifluoromethyl)benzylidenyl]-5-[4-(trifluoromethyl)phenylaminosulfonyl]-2-indolinone |
| 10722 | F | 2 | 3-(3-t-butyl-4-hydroxy-5-nitrobenzylidenyl)-5-(morpholin-1-yl)aminosulfonyl-2-indolinone |
| 10722 | F | 3 | 3-(2,4,6-trihydroxybenzylidenyl)-5-(morpholin-1-yl)aminosulfonyl-2-indolinone |
| 10722 | F | 4 | 3-[(2-nitrothien-5-yl)methylidenyl]-5-(morpholin-1-yl)aminosulfonyl-2-indolinone |

TABLE 13-continued

| MASTER BARCODE | PLATE ROW | PLATE COLUMN | NAME |
|---|---|---|---|
| 10722 | F | 5 | 3-(4-carboxybenzylidenyl)-5-(morpholin-1-yl)aminosulfonyl-2-indolinone |
| 10722 | F | 6 | 3-(2,4-difluorobenzylidenyl)-5-(morpholin-1-yl)aminosulfonyl-2-indolinone |
| 10722 | F | 7 | 3-(3,5-dimethyl-4-hydroxybenzylidenyl)-5-(morpholin-1-yl)aminosulfonyl-2-indolinone |
| 10722 | F | 8 | 3-(3-t-butyl-5-chloro-4-hydroxybenzylidenyl)-5-(morpholin-1-yl)aminosulfonyl-2-indolinone |
| 10722 | F | 9 | 3-[(2-nitrothien-4-yl)methylidenyl]-5-(morpholin-1-yl)aminosulfonyl-2-indolinone |
| 10722 | F | 10 | 3-(4-di-n-butylaminobenzylidenyl)-5-(morpholin-1-yl)aminosulfonyl-2-indolinone |
| 10722 | F | 11 | 3-[4-(trifluoromethyl)benzylidenyl]-5-(morpholin-1-yl)aminosulfonyl-2-indolinone |
| 10722 | G | 2 | 3-(3-t-butyl-4-hydroxy-5-nitrobenzylidenyl)-5-(2-chloroethyl)-2-indolinone |
| 10722 | G | 3 | 3-(2,4,6-trihydroxybenzylidenyl)-5-(2-chloroethyl)-2-indolinone |
| 10722 | G | 4 | 3-[(2-nitrothien-5-yl)methylideflyl]-5-(2-chloroethyl)-2-indolinone |
| 10722 | G | 5 | 3-(4-carboxybenzylidenyl)-5-(2-chloroethyl)-2-indolinone |
| 10722 | G | 6 | 3-(2,4-difluorobenzylidenyl)-5-(2-chloroethyl)-2-indolinone |
| 10722 | G | 7 | 3-(3,5-dimethyl-4-hydroxybenzylidenyl)-5-(2-chloroethyl)-2-indolinone |
| 10722 | G | 8 | 3-(3-t-butyl-5-chloro-4-hydroxybenzylidenyl)-5-(2-chloroethyl)-2-indolinone |
| 10722 | G | 9 | 3-[(2-nitrothien-4-yl)methylidenyl]-5-(2-chloroethyl)-2-indolinone |
| 10722 | G | 10 | 3-(4-di-n-butylaminobenzylidenyl)-5-(2-chloroethyl)-2-indolinone |
| 10722 | G | 11 | 3-[4-(trifluoromethyl)benzylidenyl)]-5-(2-chloroethyl)-2-indolinone |
| 10723 | A | 2 | 3-(2,3,4-trihydroxybenzylidenyl)-5,7-dibromo-2-indolinone |
| 10723 | A | 3 | 3-(2-hydroxy-3-methoxybenzylidenyl)-5,7-dibromo-2-indolinone |
| 10723 | A | 4 | 3-(3-bromo-4,5-dihydroxybenzylidenyl)-5,7-dibromo-2-indolinone |
| 10723 | A | 5 | 3-(3,4-diacetoxybenzylidenyl)-5,7-dibromo-2-indolinone |
| 10723 | A | 6 | 3-(4-hydroxy-3-methylbenzylidenyl)-5,7-dibromo-2-indolinone |
| 10723 | A | 7 | 3-(2-bromobenzylidenyl)-5,7-dibromo-2-indolinone |
| 10723 | A | 8 | 3-(2,4-dihydroxybenzylidenyl)-5,7-dibromo-2-indolinone |
| 10723 | A | 9 | 3-(2-hydroxy-4-methoxybenzylidenyl)-5,7-dibromo-2-indolinone |
| 10723 | A | 10 | 3-(3-bromobenzylidenyl)-5,7-dibromo-2-indolinone |
| 10723 | A | 11 | 3-(3,5-di-t-butyl-2-hydroxybenzylidenyl)-5,7-dibromo-2-indolinone |
| 10723 | B | 2 | 3-(2,3,4-trihydroxybenzylidenyl)-5-iodo-2-indolinone |
| 10723 | B | 3 | 3-(2-hydroxy-3-methoxybenzylidenyl)-5-iodo-2-indolinone |
| 10723 | B | 4 | 3-(3-bromo-4,5-dihydroxybenzylidenyl)-5-iodo-2-indolinone |
| 10723 | B | 5 | 3-(3,4-diacetoxybenzylidenyl)-5-iodo-2-indolinone |
| 10723 | B | 6 | 3-(4-hydroxy-3-methylbenzylidenyl)-5-iodo-2-indolinone |
| 10723 | B | 7 | 3-(2-bromobenzylidenyl)-5-iodo-2-indolinone |
| 10723 | B | 8 | 3-(2,4-dihydroxybenzylidenyl)-5-iodo-2-indolinone |
| 10723 | B | 9 | 3-(2-hydroxy-4-methoxybenzylidenyl)-5-iodo-2-indolinone |
| 10723 | B | 10 | 3-(3-bromobenzylidenyl)-5-iodo-2-indolinone |
| 10723 | B | 11 | 3-(3,5-di-t-butyl-2-hydroxybenzylidenyl)-5-iodo-2-indolinone |
| 10723 | C | 2 | 3-(2,3,4-trihydroxybenzylidenyl)-5-bromo-4-methyl-2-indolinone |
| 10723 | C | 3 | 3-(2-hydroxy-3-methoxybenzylidenyl)-5-bromo-4-methyl-2-indolinone |
| 10723 | C | 4 | 3-(3-bromo-4,5-dihydroxybenzylidenyl)-5-bromo-4-methyl-2-indolinone |
| 10723 | C | 5 | 3-(3,4-diacetoxybenzylidenyl)-5-bromo-4-methyl-2-indolinone |

TABLE 13-continued

| MASTER BARCODE | PLATE ROW | PLATE COLUMN | NAME |
|---|---|---|---|
| 10723 | C | 6 | 3-(4-hydroxy-3-methylbenzylidenyl)-5-bromo-4-methyl-2-indolinone |
| 10723 | C | 7 | 3-(2-bromobenzylidenyl)-5-bromo-4-methyl-2-indolinone |
| 10723 | C | 8 | 3-(2,4-dihydroxybenzylidenyl)-5-bromo-4-methyl-2-indolinone |
| 10723 | C | 9 | 3-(2-hydroxy-4-methoxybenzylidenyl)-5-bromo-4-methyl-2-indolinone |
| 10723 | C | 10 | 3-(3-bromobenzylidenyl)-5-bromo-4-methyl-2-indolinone |
| 10723 | C | 11 | 3-(3,5-di-t-butyl-2-hydroxybenzylidenyl)-5-bromo-4-methyl-2-indolinone |
| 10723 | D | 2 | 3-(2,3,4-trihydroxybenzylidenyl)-5-methylaminosulfonyl-2-indolinone |
| 10723 | D | 3 | 3-(2-hydroxy-3-methoxybenzylidenyl)-5-methylaminosulfonyl-2-indolinone |
| 10723 | D | 4 | 3-(3-bromo-4,5-dihydroxybenzylidenyl)-5-methylaminosulfonyl-2-indolinone |
| 10723 | D | 5 | 3-(3,4-diacetoxybenzylidenyl)-5-methylaminosulfonyl-2-indolinone |
| 10723 | D | 6 | 3-(4-hydroxy-3-methylbenzylidenyl)-5-methylaminosulfonyl-2-indolinone |
| 10723 | D | 7 | 3-(2-bromobenzylidenyl)-5-methylaminosulfonyl-2-indolinone |
| 10723 | D | 8 | 3-(2,4-dihydroxybenzylidenyl)-5-methylaminosulfonyl-2-indolinone |
| 10723 | D | 9 | 3-(2-hydroxy-4-methoxybenzylidenyl)-5-methylaminosulfonyl-2-indolinone |
| 10723 | D | 10 | 3-(3-bromobenzylidenyl)-5-methylaminosulfonyl-2-indolinone |
| 10723 | D | 11 | 3-(3,5-di-t-butyl-2-hydroxybenzylidenyl)-5-methylaminosulfonyl-2-indolinone |
| 10723 | E | 2 | 3-(2,3,4-trihydroxybenzylidenyl)-5-[4-(trifluoromethyl)phenylaminosulfonyl]-2-indolinone |
| 10723 | E | 3 | 3-(2-hydroxy-3-methoxybenzylidenyl)-5-[4-(trifluoromethyl)phenylaminosulfonyl]-2-indolinone |
| 10723 | E | 4 | 3-(3-bromo-4,5-dihydroxybenzylidenyl)-5-[4-(trifluoromethyl)phenylaminosulfonyl]-2-indolinone |
| 10723 | E | 5 | 3-(3,4-diacetoxybenzylidenyl)-5-[4-(trifluoromethyl)phenylaminosulfonyl]-2-indolinone |
| 10723 | E | 6 | 3-(4-hydroxy-3-methylbenzylidenyl)-5-[4-(trifluoromethyl)phenylaminosulfonyl]-2-indolinone |
| 10723 | E | 7 | 3-(2-bromobenzylidenyl)-5-[4-(trifluoromethyl)phenylaminosulfonyl]-2-indolinone |
| 10723 | E | 8 | 3-(2,4-dihydroxybenzylidenyl)-5-[4-(trifluoromethyl)phenylaminosulfonyl]-2-indolinone |
| 10723 | E | 9 | 3-(2-hydroxy-4-methoxybenzylidenyl)-5[4-(trifluoromethyl)phenylaminosulfonyl]-2-indolinone |
| 10723 | E | 10 | 3-(3-bromobenzylidenyl)-5-[4-(trifluoromethyl)phenylaminosulfonyl]-2-indolinone |
| 10723 | E | 11 | 3-(3,5-di-t-butyl-2-hydroxybenzylidenyl)-5-[4-(trifluoromethyl)phenylaminosulfonyl]-2-indolinone |
| 10723 | F | 2 | 3-(2,3,4-trihydroxybenzylidenyl)-5-(morpholin-1-yl)aminosulfonyl-2-indolinone |
| 10723 | F | 3 | 3-(2-hydroxy-3-methoxybenzylidenyl)-5-(morpholin-1-yl)aminosulfonyl-2-indolinone |
| 10723 | F | 4 | 3-(3-bromo-4,5-dihydroxybenzylidenyl)-5-(morpholin-1-yl)aminosulfonyl-2-indolinone |
| 10723 | F | 5 | 3-(3,4-diacetoxybenzylidenyl)-5-(morpholin-1-yl)aminosulfonyl-2-indolinone |
| 10723 | F | 6 | 3-(4-hydroxy-3-methylbenzylidenyl)-5-(morpholin-1-yl)aminosulfonyl-2-indolinone |
| 10723 | F | 7 | 3-(2-bromobenzylidenyl)-5-(morpholin-1-yl)aminosulfonyl-2-indolinone |
| 10723 | F | 8 | 3-(2,4-dihydroxybenzylidenyl)-5-(morpholin-1-yl)aminosulfonyl-2-indolinone |
| 10723 | F | 9 | 3-(2-hydroxy-4-methoxybenzylidenyl)-5-(morpholin-1-yl)aminosulfonyl-2-indolinone |
| 10723 | F | 10 | 3-(3-bromobenzylidenyl)-5-(morpholin-1-yl)aminosulfonyl-2-indolinone |
| 10723 | F | 11 | 3-(3,5-di-t-butyl-2-hydroxybenzylidenyl)-5-(morpholin-1-yl)aminosulfonyl-2-indolinone |
| 10723 | G | 2 | 3-(2,3,4-trihydroxybenzylidenyl)-5-(2-chloroethyl)-2-indolinone |
| 10723 | G | 3 | 3-(2-hydroxy-3-methoxybenzylidenyl)-5-(2-chloroethyl)-2-indolinone |

TABLE 13-continued

| MASTER BARCODE | PLATE ROW | PLATE COLUMN | NAME |
|---|---|---|---|
| 10723 | G | 4 | 3-(3-bromo-4,5-dihydroxybenzylidenyl)-5-(2-chloroethyl)-2-indolinone |
| 10723 | G | 5 | 3-(3,4-diacetoxybenzylidenyl)-5-(2-choloroethyl)-2-indolinone |
| 10723 | G | 6 | 3-(4-hydroxy-3-methylbenzylidenyl)-5-(2-chloroethyl)-2-indolinone |
| 10723 | G | 7 | 3-(2-bromobenzylidenyl)-5-(2-chloroethyl)-2-indolinone |
| 10723 | G | 8 | 3-(2,4-dihydroxybenzylidenyl)-5-(2-chloroethyl)-2-indolinone |
| 10723 | G | 9 | 3-(2-hydroxy-4-methoxybenzylidenyl)-5-(2-chloroethyl)-2-indolinone |
| 10723 | G | 10 | 3-(3-bromobenzylidenyl)-5-(2-chloroethyl)-2-indolinone |
| 10723 | G | 11 | 3-(3,5-di-t-butyl-2-hydroxybenzylidenyl)-5-(2-chloroethyl)-2-indolinone |
| 10724 | A | 2 | 3-[(1-dimethylaminonapth-4-yl)methylidenyl]-5,7-dibromo-2-indolinone |
| 10724 | A | 3 | 3-(4-hydroxy-3-nitrobenzylidenyl)-5,7-dibromo-2-indolinone |
| 10724 | A | 4 | 3-(3-hydroxy-4-nitrobenzylidenyl)-5,7-dibromo-2-indolinone |
| 10724 | A | 5 | 3-[(8-hydroxy-2,3,6,7-tetrahydro-1H,5H-benzo[ij]quinolizin-9-yl)methylidenyl]-5,7-dibromo-2-indolinone |
| 10724 | A | 6 | 3-(3,5-diisopropyl-4-hydroxybenzylidenyl)-5,7-dibromo-2-indolinone |
| 10724 | A | 7 | 3-[(benzo[b]furan-2-yl)methylidenyl]-5,7-dibromo-2-indolinone |
| 10724 | A | 9 | 3-[[1-(4-chlorophenyl)pyrrol-2-yl]methylidenyl]-5,7-dibromo-2-indolinone |
| 10724 | A | 10 | 3-[(2-ethylfuran-5-yl)methylidenyl]-5,7-dibromo-2-indolinone |
| 10724 | A | 11 | 3-[(3,4-dimethylthieno[2,3-b]thien-2-yl)methylidenyl]-5,7-dibromo-2-indolinone |
| 10724 | B | 2 | 3-[(1-dimethylaminonapth-4-yl)methylidenyl]-5-iodo-2-indolinone |
| 10724 | B | 3 | 3-(4-hydroxy-3-nitrobenzylidenyl)-5-iodo-2-indolinone |
| 10724 | B | 4 | 3-(3-hydroxy-4-nitrobenzylidenyl)-5-iodo-2-indolinone |
| 10724 | B | 5 | 3-[(8-hydroxy-2,3,6,7-tetrahydro-1H,5H-benzo[ij]quinolizin-9-yl)methylidenyl]-5-iodo-2-indolinone |
| 10724 | B | 6 | 3-(3,5-diisopropyl-4-hydroxybenzylidenyl)-5-iodo-2-indolinone |
| 10724 | B | 7 | 3-[(benzo[b]fura-2-yl)methylidenyl]-5-iodo-2-indolinone |
| 10724 | B | 9 | 3-[[1-(4-chlorophenyl)pyrrol-2-yl]methylidenyl]-5-iodo-2-indolinone |
| 10724 | B | 10 | 3-[(2-ethylfuran-5-yl)methylidenyl]-5-iodo-2-indolinone |
| 10724 | B | 11 | 3-[(3,4-dimethylthieno[2,3-b]thien-2-yl)methylidenyl]-5-iodo-2-indolinone |
| 10724 | C | 2 | 3-[(1-dimethylaminonapth-4-yl)methylidenyl]-5-bromo-4-methyl-2-indolinone |
| 10724 | C | 3 | 3-(4-hydroxy-3-nitrobenzylidenyl)-5-bromo-4-methyl-2-indolinone |
| 10724 | C | 4 | 3-(3-hydroxy-4-nitrobenzylidenyl)-5-bromo-4-methyl-2-indolinone |
| 10724 | C | 5 | 3-[(8-hydroxy-2,3,6,7-tetrahydro-1H,5H-benzo[ij]quinolizin-9-yl)methylidenyl]-5-bromo-4-methyl-2-indolinone |
| 10724 | C | 6 | 3-(3,5-diisopropyl-4-hydroxybenzylidenyl)-5-bromo-4-methyl-2-indolinone |
| 10724 | C | 7 | 3-[(benzo[b]furan-2-yl)methylidenyl]-5-bromo-4-methyl-2-indolinone |
| 10724 | C | 9 | 3-[[1-(4-chlorophenyl)pyrrol-2-yl]methylidenyl]-5-bromo-4-methyl-2-indolinone |
| 10724 | C | 10 | 3-[(2-ethylfuran-5-yl)methylidenyl]-5-bromo-4-methyl-2-indolinone |
| 10724 | C | 11 | 3-[(3,4-dimethylthieno[2,3-b]thien-2-yl)methylidenyl]-5-bromo-4-methyl-2-indolinone |
| 10724 | D | 2 | 3-[(1-dimethylaminonapth-4-yl)methylidenyl]-5-methylaminosulfonyl-2-indolinone |

TABLE 13-continued

| MASTER BARCODE | PLATE ROW | PLATE COLUMN | NAME |
|---|---|---|---|
| 10724 | D | 3 | 3-(4-hydroxy-3-nitrobenzylidenyl)-5-methylaminosulfonyl-2-indolinone |
| 10724 | D | 4 | 3-(3-hydroxy-4-nitrobenzylidenyl)-5-methylaminosulfonyl-2-indolinone |
| 10724 | D | 5 | 3-[(8-hydroxy-2,3,6,7-tetrahydro-1H,5H-benzo[ij]quinolizin-9-yl)methylidenyl]-5-methylaminosulfonyl-2-indolinone |
| 10724 | D | 6 | 3-(3,5-diisopropyl-4-hydroxybenzylidenyl)-5-methylaminosulfonyl-2-indolinone |
| 10724 | D | 7 | 3-[(benzo[b]furan-2-yl)methylidenyl]-5-methylaminosulfonyl-2-indolinone |
| 10724 | D | 9 | 3-[1-(4-chlorophenyl)pyrrol-2-yl]methylidenyl]-5-methylaminosulfonyl-2-indolinone |
| 10724 | D | 10 | 3-[(2-ethylfuran-5-yl)methylidenyl]-5-methylaminosulfonyl-2-indolinone |
| 10724 | D | 11 | 3-[(3,4-dimethylthieno[2,3-b]thien-2-yl)methylidenyl]-5-methylaminosulfonyl-2-indolinone |
| 10724 | E | 2 | 3[(1-dimethylaminonapth-4-yl)methylidenyl]-5-[4-(trifluoromethyl)phenylaminosulfonyl]-2-indolinone |
| 10724 | E | 3 | 3-(4-hydroxy-3-nitrobenzylidenyl)-5-[4-(trifluoromethyl)phenylaminosulfonyl]-2-indolinone |
| 10724 | E | 4 | 3-(3-hydroxy-4-nitrobenzylidenyl)-5-[4-(trifluoromethyl)phenylaminosulfonyl]-2-indolinone |
| 10724 | E | 5 | 3-[(8-hydroxy-2,3,6,7-tetrahydro-1H,5H-benzo[ij]quinolizin-9-yl)methylidenyl]-5-[4-(trifluoromethyl)phenylaminosulfonyl]-2-indolinone |
| 10724 | E | 6 | 3-(3,5-diisopropyl-4-hydroxybenzylidenyl)-5-[4-(trifluoromethyl)phenylaminosulfonyl]-2-indolinone |
| 10724 | E | 7 | 3-[(benzo[b]furan-2-yl)methylidenyl]-5-[4-(trifluoromethyl)phenylaminosulfonyl]-2-indolinone |
| 10724 | E | 9 | 3-[[1-(4-chlorophenyl)pyrrol-2-yl]methylidenyl]-5-[4-(trifluoromethyl)phenylaminosulfonyl]-2-indolinone |
| 10724 | E | 10 | 3-[(2-ethylfuran-5-yl)methylidenyl]-5-[4-(trifluoromethyl)phenylaminosulfonyl]-2-indolinone |
| 10724 | E | 11 | 3-[(3,4-dimethylthieno[2,3-b]thien-2-yl)methylidenyl]-5-[4-(trifluoromethyl)phenylaminosulfonyl]-2-indolinone |
| 10724 | F | 2 | 3-[(1-dimethylaminonapth-4-yl)methylidenyl]-5-(morpholin-1yl)aminosulfonyl-2-indolinone |
| 10724 | F | 3 | 3-(4-hydroxy-3-nitrobenzylidenyl)-5-(morpholin-1yl)aminosulfonyl-2-indolinone |
| 10724 | F | 4 | 3-(3-hydroxy-4-nitrobenzylidenyl)-5-(morpholin-1yl)aminosulfonyl-2-indolinone |
| 10724 | F | 5 | 3-[(8-hydroxy-2,3,6,7-tetrahydro-1H,5H-benzo[ij]quinolizin-9-yl)methylidenyl]-5-(morpholin-1yl)aminosulfonyl-2-indolinone |
| 10724 | F | 6 | 3-(3,5-diisopropyl-4-hydroxybenzylidenyl)-5-(morpholin-1yl)aminosulfonyl-2-indolinone |
| 10724 | F | 7 | 3-[(benzo[b]furan-2-yl)methylidenyl]-5-(morpholin-1yl)aminosulfonyl-2-indolinone |
| 10724 | F | 9 | 3-[[1-(4-chlorophenyl)pyrrol-2-yl]methylidenyl]-5-(morpholin-1yl)aminosulfonyl-2-indolinone |
| 10724 | F | 10 | 3-[(2-ethylfuran-5-yl)methylidenyl]-5-(morpholin-1yl)aminosulfonyl-2-indolinone |
| 10724 | F | 11 | 3-[(3,4-dimethylthieno[2,3-b]thien-2-yl)methylidenyl]-5-(morpholin-1yl)aminosulfonyl-2-indolinone |
| 10724 | G | 2 | 3-[(1-dimethylaminonapth-4-yl)methylidenyl]-5-(2-chloroethyl)-2-indolinone |
| 10724 | G | 3 | 3-(4-hydroxy-3-nitrobenzylidenyl)-5-(2-chloroethyl)-2-indolinone |
| 10724 | G | 4 | 3-(3-hydroxy-4-nitrobenzylidenyl)-5-(2-chloroethyl)-2-indolinone |
| 10724 | G | 5 | 3-[(8-hydroxy-2,3,6,7-tetrahydro-1H,5H-benzo[ij]quinolizin-9-yl)methylidenyl]-5-(2-chloroethyl)-2-indolinone |
| 10724 | G | 6 | 3-(3,5-diisopropyl-4-hydroxybenzylidenyl)-5-(2-chloroethyl)-2-indolinone |
| 10724 | G | 7 | 3-[(benzo[b]furan-2-yl)methylidenyl]-5-(2-chloroethyl)-2-indolinone |
| 10724 | G | 9 | 3-[[1-(4-chlorophenyl)pyrrol-2-yl]methylidenyl]-5-(2-chloroethyl)-2-indolinone |
| 10724 | G | 10 | 3-[(2-ethylfuran-5-yl)methylidenyl]-5-(2-chloroethyl)-2-indolinone |
| 10724 | G | 11 | 3-[(3,4-dimethylthieno[2,3-b]thien-2-yl)methylidenyl]-5-(2-chloroethyl)-2-indolinone |

TABLE 13-continued

| MASTER BARCODE | PLATE ROW | PLATE COLUMN | NAME |
|---|---|---|---|
| 10725 | A | 2 | 3-[(3-bromothien-2-yl)methylidenyl]-5,7-dibromo-2-indolinone |
| 10725 | A | 3 | 3-(2-bromo-6-hydroxy-5-methoxybenzylidenyl)-5,7-dibromo-2-indolinone |
| 10725 | A | 4 | 3-[(2-methylfuran-5-yl)methylidenyl]-5,7-dibromo-2-indolinone |
| 10725 | A | 5 | 3-[(3-methylpyrazol-5-yl)methylidenyl]-5,7-dibromo-2-indolinone |
| 10725 | A | 6 | 3-(2-hydroxy-6-methoxy-4-methylbenzylidenyl)-5,7-dibromo-2-indolinone |
| 10725 | A | 7 | 3-[4-(4-formylpiperazin-1-yl)benzylidenyl]-5,7-dibromo-2-indolinone |
| 10725 | A | 8 | 3-[4-(morpholin-1-yl)benzylidenyl]-5,7-dibromo-2-indolinone |
| 10725 | A | 9 | 3-[[2-chloro-4-methoxycarbonyl-3-(methoxycarbonylmethyl)pyrrol-5-yl]methylidenyl]-5,7-dibromo-4-methyl-2-indolinone |
| 10725 | A | 10 | 3-[[4-bromo-2-(4-chlorophenyl)pyrazol-3-yl]methylidenyl]-5,7-dibromo-4-methyl-2-indolinone |
| 10725 | A | 11 | 3-[(imidazol-4-yl)methylidenyl]-5,7-dibromo-4-methyl-2-indolinone |
| 10725 | B | 2 | 3-[(3-bromothien-2-yl)methylidenyl]-5-iodo-2-indolinone |
| 10725 | B | 3 | 3-(2-bromo-6-hydroxy-5-methoxybenzylidenyl)-5-iodo-2-indolinone |
| 10725 | B | 4 | 3-[(2-methylfuran-5-yl)methylidenyl]-5-iodo-2-indolinone |
| 10725 | B | 5 | 3-[(3-methylpyrazol-5-yl)methylidenyl]-5-iodo-2-indolinone |
| 10725 | B | 6 | 3-(2-hydroxy-6-methoxy-4-methylbenzylidenyl)-5-iodo-2-indolinone |
| 10725 | B | 7 | 3-[4-(4-formylpiperazin-1-yl)benzylidenyl]-5-iodo-2-indolinone |
| 10725 | B | 8 | 3-[4-(morpholin-1-yl)benzylidenyl]-5-iodo-2-indolinone |
| 10725 | B | 9 | 3-[[2-chloro-4-methoxycarbonyl-3-(methoxycarbonylmethyl)pyrrol-5-yl]methylidenyl]-5-iodo-2-indolinone |
| 10725 | B | 10 | 3-[[4-bromo-2-(4-chlorophenyl)pyrazol-3-yl]methylidenyl]-5-iodo-2-indolinone |
| 10725 | B | 11 | 3-[(imidazol-4-yl)methylidenyl]-5-iodo-2-indolinone |
| 10725 | C | 2 | 3-[(3-bromothien-2yl)methylidenyl]-5-bromo-4-methyl-2-indolinone |
| 10725 | C | 3 | 3-(2-bromo-6-hydroxy-5-methoxybenzylidenyl)-5-bromo-4-methyl-2-indolinone |
| 10725 | C | 4 | 3-[(2-methylfuran-5-yl)methylidenyl]-5-bromo-4-methyl-2-indolinone |
| 10725 | C | 5 | 3-[(3-methylpyrazol-5-yl)methylidenyl]-5-bromo-4-methyl-2-indolinone |
| 10725 | C | 6 | 3-(2-hydroxy-6-methoxy-4-methylbenzylidenyl)-5-bromo-4-methyl-2-indolinone |
| 10725 | C | 7 | 3-[4-(4-formylpiperazin-1-yl)benzylidenyl]-5-bromo-4-methyl-2-indolinone |
| 10725 | C | 8 | 3-[4-(morpholin-1-yl)benzylidenyl]-5-bromo-4-methyl-2-indolinone |
| 10725 | C | 9 | 3-[[2-chloro-4-methoxycarbonyl-3-(methoxycarbonylmethyl)pyrrol-5-yl]methylidenyl]-5-bromo-4-methyl-2-indolinone |
| 10725 | C | 10 | 3-[[4-bromo-2-(4-chlorophenyl)pyrazol-3-yl]methylidenyl]-5-bromo-4-methyl-2-indolinone |
| 10725 | C | 11 | 3-[(imidazol-4-yl)methylidenyl]-5-bromo-4-methyl-2-indolinone |
| 10725 | D | 2 | 3-[(3-bromothien-2-yl)methylidenyl]-5-methylaminosulfonyl-2-indolinone |
| 10725 | D | 3 | 3-(2-bromo-6-hydroxy-5-methoxybenzylidenyl)-5-methylaminosulfonyl-2-indolinone |
| 10725 | D | 4 | 3-[(2-methylfuran-5-yl)methylidenyl]-5-methylaminosulfonyl-2-indolinone |
| 10725 | D | 5 | 3-[(3-methylpyrazol-5-yl)methylidenyl]-5-methylaminosulfonyl-2-indolinone |
| 10725 | D | 6 | 3-(2-hydroxy-6-methoxy-4-methylbenzylidenyl)-5-methylaminosulfonyl-2-indolinone |
| 10725 | D | 7 | 3-[4-(4-formylpiperazin-1-yl)benzylidenyl]-5-methylaminosulfonyl-2-indolinone |
| 10725 | D | 8 | 3-[4-(morpholin-1-yl)benzylidenyl]-5-methylaminosulfonyl-2-indolinone |

TABLE 13-continued

| MASTER BARCODE | PLATE ROW | PLATE COLUMN | NAME |
|---|---|---|---|
| 10725 | D | 9 | 3-[[2-chloro-4-methoxycarbonyl-3-(methoxycarbonylmethyl)pyrrol-5-yl]methylidenyl]-5-methylaminosulfonyl-2-indolinone |
| 10725 | D | 10 | 3-[[4-bromo-2-(4-chlorophenyl)pyrazol-3-yl]methylidenyl]-5-methylaminosulfonyl-2-indolinone |
| 10725 | D | 11 | 3-[(imidazol-4-yl)methylidenyl]-5-methylaminosulfonyl-2-indolinone |
| 10725 | E | 2 | 3-[(3-bromothien-2-yl)methylidenyl]-5-[4-(trifluoromethyl)phenylaminosulfonyl]-2-indolinone |
| 10725 | E | 3 | 3-(2-bromo-6-hydroxy-5-methoxybenzylidenyl)-5-[4-(trifluoromethyl)phenylaminosulfonyl]-2-indolinone |
| 10725 | E | 4 | 3-[(2-methylfuran-5-yl)methylidenyl]-5-[4-(trifluoromethyl)phenylaminosulfonyl]-2-indolinone |
| 10725 | E | 5 | 3-[(3-methylpyrazol-5-yl)methylidenyl]-5-[4-(trifluoromethyl)phenylaminosulfonyl]-2-indolinone |
| 10725 | E | 6 | 3-(2-hydroxy-6-methoxy-4-methylbenzylidenyl)-5-[4-(trifluoromethyl)phenylaminosulfonyl]-2-indolinone |
| 10725 | E | 7 | 3-[4-(4-formylpiperazin-1-yl)benzylidenyl]-5-[4-(trifluoromethyl)phenylaminosulfonyl]-2-indolinone |
| 10725 | E | 8 | 3-[4-(morpholin-1-yl)benzylidenyl]-5-[4-(trifluoromethyl)phenylaminosulfonyl]-2-indolinone |
| 10725 | E | 9 | 3-[[2-chloro-4-methoxycarbonyl-3-(methoxycarbonylmethyl)pyrrol-5-yl]methylidenyl]-5-[4-(trifluoromethyl)phenylaminosulfonyl]-2-indolinone |
| 10725 | E | 10 | 3-[[4-bromo-2-(4-chlorophnenyl)pyrazol-3-yl]methylidenyl]-5-[4-(trifluoromethyl)phenylaminosulfonyl]-2-indolinone |
| 10725 | E | 11 | 3-[(imidazol-4-yl)methylidenyl]-5-[4-(trifluoromethyl)phenylaminosulfonyl]-2-indolinone |
| 10725 | F | 2 | 3-[(3-bromothien-2-yl)methylidenyl]-5-(morpholin-1-yl)sulfonyl-2-indolinone |
| 10725 | F | 3 | 3-(2-bromo-6-hydroxy-5-methoxybenzylidenyl)-5-(morpholin-1-yl)sulfonyl-2-indolinone |
| 10725 | F | 4 | 3-[(2-methylfuran-5-yl)methylidenyl]-5-(morpholin-1-yl)sulfonyl-2-indolinone |
| 10725 | F | 5 | 3-[(3-methylpyrazol-5-yl)methylidenyl]-5-(morpholin-1-yl)sulfonyl-2-indolinone |
| 10725 | F | 6 | 3-(2-hydroxy-6-methoxy-4-methylbenzylidenyl)-5-(morpholin-1-yl)sulfonyl-2-indolinone |
| 10725 | F | 7 | 3-[4-(4-formylpiperazin-1-yl)benzylidenyl]-5-(morpholin-1-yl)sulfonyl-2-indolinone |
| 10725 | F | 8 | 3-[4-(morpholin-1-yl)benzylidenyl]-5-(morpholin-1-yl)sulfonyl-2-indolinone |
| 10725 | F | 9 | 3-[[2-chloro-4-methoxycarbonyl-3-(methoxycarbonylmethyl)pyrrol-5-yl]methylidenyl]-5-(morpholin-1-yl)sulfonyl-2-indolinone |
| 10725 | F | 10 | 3-[[4-bromo-2-(4-chlorophenyl)pyrazol-3-yl]methylidenyl]-5-(morpholin-1-yl)sulfonyl-2-indolinone |
| 10725 | F | 11 | 3-[(imidazol-4-yl)methylidenyl]-5-(morpholin-1-yl)sulfonyl-2-indolinone |
| 10725 | G | 2 | 3-[(3-bromothien-2-yl)methylidenyl]-5-(2-chloroethyl)-2-indolinone |
| 10725 | G | 3 | 3-(2-bromo-6-hydroxy-5-methoxybenzylidenyl)-5-(2-chloroethyl)-2-indolinone |
| 10725 | G | 4 | 3-[(2-methylfuran-5-yl)methylidenyl]-5-(2-chloroethyl)-2-indolinone |
| 10725 | G | 5 | 3-[(3-methylpyrazol-5-yl)methylidenyl]-5-(2-chloroethyl)-2-indolinone |
| 10725 | G | 6 | 3-(2-hydroxy-6-methoxy-4-methylbenzylidenyl)-5-(2-chloroethyl)-2-indolinone |
| 10725 | G | 7 | 3-[4-(4-formylpiperazin-1-yl)benzylidenyl]-5-(2-chloroethyl)-2-indolinone |
| 10725 | G | 8 | 3-[4-(morpholin-1-yl)benzylidenyl]-5-(2-chloroethyl)-2-indolinone |
| 10725 | G | 9 | 3-[[2-chloro-4-methoxycarbonyl-3-(methoxycarbonylmethyl)pyrrol-5-yl]methylidenyl]-5-(2-chloroethyl)-2-indolinone |
| 10725 | G | 10 | 3-[[4-bromo-2-(4-chlorophenyl)pyrazol-3-yl]methylidenyl]-5-(2-chloroethyl)-2-indolinone |
| 10725 | G | 11 | 3-[(imidazol-4-yl)methylidenyl]-5-(2-Chloroethyl)-2-indolinone |

TABLE 13-continued

| MASTER BARCODE | PLATE ROW | PLATE COLUMN | NAME |
|---|---|---|---|
| 10726 | A | 3 | 3-[(2-ethoxycarbonyl-4-methoxycarbonyl-3-methylpyrrol-5-yl)methylidenyl]-5,7-dibromo-2-indolinone |
| 10726 | A | 4 | 3-(3-t-butyl-4-hydroxy-5-methylbenzylidenyl)-5,7-dibromo-2-indolinone |
| 10726 | A | 5 | 3-[(2-bromofuran-5-yl)methylidenyl]-5,7-dibromo-2-indolinone |
| 10726 | A | 6 | 3-[(1,3-dimethylpyrrol-4-yl)methylidenyl]-5,7-dibromo-2-indolinone |
| 10726 | A | 7 | 3-[(5,8-dihydroxy-1,2,3,4-tetrahydronapth-6-yl)methylidenyl]-5,7-dibromo-2-indolinone |
| 10726 | A | 8 | 3-(5-fluoro-2-oxindol-3-idenyl)-5,7-dibromo-2-indolinone |
| 10726 | A | 9 | 3-(2-oxindol-3-idenyl)-5,7-dibromo-2-indolinone |
| 10726 | A | 10 | 3-[(2-ethylthien-5-yl)methylidenyl]-5,7-dibromo-2-indolinone |
| 10726 | A | 11 | 3-(4-methoxybenzylidenyl)-5,7-dibromo-2-indolinone |
| 10726 | B | 3 | 3-[(2-ethoxycarbonyl-4-methoxycarbonyl-3-methylpyrrol-5-yl)methylidenyl]-5-iodo-2-indolinone |
| 10726 | B | 4 | 3-(3-t-butyl-4-hydroxy-5-methylbenzylidenyl)-5-iodo-2-indolinone |
| 10726 | B | 5 | 3-[(2-bromofuran-5-yl)methylidenyl]-5-iodo-2-indolinone |
| 10726 | B | 6 | 3-[(1,3-dimethylpyrrol-4-yl)methylidenyl]-5-iodo-2-indolinone |
| 10726 | B | 7 | 3-[(5,8-dihydroxy-1,2,3,4-tetrahydronapth-6-yl)methylidenyl]-5-iodo-2-indolinone |
| 10726 | B | 8 | 3-(5-fluoro-2-oxindol-3-idenyl)-5-iodo-2-indolinone |
| 10726 | B | 9 | 3-[(2-oxindol-3-idenyl)methylidenyl]-5-iodo-2-indolinone |
| 10726 | B | 10 | 3-[(2-ethylthien-5-yl)methylidenyl]-5-iodo-2-indolinone |
| 10726 | B | 11 | 3-(4-methoxybenzylidenyl)-5-iodo-2-indolinone |
| 10726 | C | 3 | 3-[(2-ethoxycarbonyl-4-methoxycarbonyl-3-methylpyrrol-5-yl)methylidenyl]-5-bromo-4-methyl-2-indolinone |
| 10726 | C | 4 | 3-(3-t-butyl-4-hydroxy-5-methylbenzylidenyl)-5-bromo-4-methyl-2-indolinone |
| 10726 | C | 5 | 3-[(2-bromofuran-5-yl)methylidenyl]-5-bromo-4-methyl-2-indolinone |
| 10726 | C | 6 | 3-[(1,3-dimethylpyrrol-4-yl)methylidenyl]-5-bromo-4-methyl-2-indolinone |
| 10726 | C | 7 | 3-[(5,8-dihydroxy-1,2,3,4-tetrahydronapth-6-yl)methylidenyl]-5-bromo-4-methyl-2-indolinone |
| 10726 | C | 8 | 3-(5-fluoro-2-oxindol-3-idenyl)-5-bromo-4-methyl-2-indolinone |
| 10726 | C | 9 | 3-(2-oxindol-3-idenyl)-5-bromo-4-methyl-2-indolinone |
| 10726 | C | 10 | 3-[(2-ethylthien-5-yl)methylidenyl]-5-bromo-4-methyl-2-indolinone |
| 10726 | C | 11 | 3-(4-methoxybenzylidenyl)-5-bromo-4-methyl-2-indolinone |
| 10726 | D | 3 | 3-[(2-ethoxycarbonyl-4-methoxycarbonyl-3-methylpyrrol-5-yl)methylidenyl]-5-methylaminosulfonyl-2-indolinone |
| 10726 | D | 4 | 3-(3-t-butyl-4-hydroxy-5-methylbenzylidenyl)-5-methylaminosulfonyl-2-indolinone |
| 10726 | D | 5 | 3-[(2-bromofuran-5-yl)methylidenyl]-5-methylaminosulfonyl-2-indolinone |
| 10726 | D | 6 | 3-[(1,3-dimethylpyrrol-4-yl)methylidenyl]-5-methylaminosulfonyl-2-indolinone |
| 10726 | D | 7 | 3-[(5,8-dihydroxy-1,2,3,4-tetrahydronapth-6-yl)methylidenyl]-5-methylaminosulfonyl-2-indolinone |
| 10726 | D | 8 | 3-(5-fluoro-2-oxindol-3-idenyl)-5-methylaminosulfonyl-2-indolinone |
| 10726 | D | 9 | 3-(2-oxindol-3-idenyl)-5-methylaminosulfonyl-2-indolinone |
| 10726 | D | 10 | 3-[(2-ethylthien-5-yl)methylidenyl]-5-methylaminosulfonyl-2-indolinone |
| 10726 | D | 11 | 3-(4-methoxybenzylidenyl)-5-methylaminosulfonyl-2-indolinone |
| 10726 | E | 3 | 3-[(2-ethoxycarbonyl-4-methoxycarbonyl-3-methylpyrrol-5-yl)methylidenyl]-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10726 | E | 4 | 3-(3-t-butyl-4-hydroxy-5-methylbenzylidenyl)-5-[4-(trifluoromethyl)phenylaminosulfonyl]-2-indolinone |
| 10726 | E | 5 | 3-[(2-bromofuran-5-yl)methylidenyl]-5-[4-(trifluoromethyl)phenylaminosulfonyl)-2-indolinone |
| 10726 | E | 6 | 3-[(1,3-dimethylpyrrol-4-yl)methylidenyl]-5-[4-(trifluoromethyl)phenylaminosulfonyl]-2-indolinone |
| 10726 | E | 7 | 3-[(5,8-dihydroxy-1,2,3,4-tetrahydronapth-6-yl)methylidenyl]-5-[4-(trifluoromethyl)phenylaminosulfonyl]-2-indolinone |
| 10726 | E | 8 | 3-(5-fluoro-2-oxindol-3-idenyl)-5-[4-(trifluoromethyl)phenylaminosulfonyl]-2-indolinone |
| 10726 | E | 9 | 3-(2-oxindol-3-idenyl)-5-[4-(trifluoromethyl)phenylaminosulfonyl]-2-indolinone |
| 10726 | E | 10 | 3-[(2-ethylthien-5-yl)methylidenyl]-5-[4-(trifluoromethyl)phenylaminosulfonyl]-2-indolinone |
| 10726 | E | 11 | 3-(4-methoxybenzylidenyl)-5-[4-(trifluoromethyl)phenylaminosulfonyl]-2-indolinone |
| 10726 | F | 3 | 3-[(2-ethoxycarbonyl-4-methoxycarbonyl-3-methylpyrrol-5-yl)methylidenyl]-5-(morpholin-1-yl)sulfonyl-2-indolinone |
| 10726 | F | 4 | 3-(3-t-butyl-4-hydroxy-5-methylbenzylidenyl)-5-(morpholin-1-yl)sulfonyl-2-indolinone |
| 10726 | F | 5 | 3-[(2-bromofuran-5-yl)methylidenyl]-5-(morpholin-1-yl)sulfonyl-2-indolinone |
| 10726 | F | 6 | 3-[(1,3-dimethylpyrrol-4-yl)methylidenyl]-5-(morpholin-1-yl)sulfonyl-2-indolinone |
| 10726 | F | 7 | 3-[(5,8-dihydroxy-1,2,3,4-tetrahydronapth-6-yl)methylidenyl]-5-(morpholin-1-yl)sulfonyl-2-indolinone |
| 10726 | F | 8 | 3-(5-fluoro-2-oxindol-3-idenyl)-5-(morpholin-1-yl)sulfonyl-2-indolinone |
| 10726 | F | 9 | 3-(2-oxindol-3-idenyl)-5-(morpholin-1-yl)sulfonyl-2-indolinone |
| 10726 | F | 10 | 3-[(2-ethylthien-5-yl)methylidenyl]-5-(morpholin-1-yl)sulfonyl-2-indolinone |
| 10726 | F | 11 | 3-(4-methoxybenzylidenyl)-5-(morpholin-1-yl)sulfonyl-2-indolinone |
| 10726 | G | 3 | 3-[(2-ethoxycarbonyl-4-methoxycarbonyl-3-methylpyrrol-5-yl)methylidenyl]-5-(2-chloroethyl)-2-indolinone |
| 10726 | G | 4 | 3-(3-t-butyl-4-hydroxy-5-methylbenzylidenyl)-5-(2-chloroethyl)-2-indolinone |
| 10726 | G | 5 | 3-[(2-bromofuran-5-yl)methylidenyl]-5-(2-chloroethyl)-2-indolinone |
| 10726 | G | 6 | 3-[(1,3-dimethylpyrrol-4-yl)methylidenyl]-5-(2-chloroethyl)-2-indolinone |
| 10726 | G | 7 | 3-[(5,8-dihydroxy-1,2,3,4-tetrahydronapth-6-yl)methylidenyl]-5-(2-chloroethyl)-2-indolinone |
| 10726 | G | 8 | 3-(5-fluoro-2-oxindol-3-idenyl)-5-(2-chloroethyl)-2-indolinone |
| 10726 | G | 9 | 3-(2-oxindol-3-idenyl)-5-(2-chloroethyl)-2-indolinone |
| 10726 | G | 10 | 3-[(2-ethylthien-5-yl)methylidenyl]-5-(2-chloroethyl)-2-indolinone |
| 10726 | G | 11 | 3-(4-methoxybenzylidenyl)-5-(2-chloroethyl)-2-indolinone |
| 10727 | A | 2 | 3-(4-diethylaminobenzylidenyl)-5,7-dibromo-2-indolinone |
| 10727 | A | 3 | 3-[(2,4-diethylpyrrol-5-yl)methylidenyl]-5,7-dibromo-2-indolinone |
| 10727 | A | 4 | 3-(3-bromo-5-chloro-2-hydroxybenzylidenyl)-5,7-dibromo-2-indolinone |
| 10727 | A | 5 | 3-[2-(4-chlorophenylmercapto)benzylidenyl]-5,7-dibromo-2-indolinone |
| 10727 | A | 6 | 3-[(5-chlorobenzodioxolan-6 yl)methylidenyl]-5,7-dibromo-2-indolinone |
| 10727 | A | 7 | 3-[(1,4-benzopyranon-3 yl)methylidenyl]-5,7-dibromo-2-indolinone |
| 10727 | A | 8 | 3-(3-cyanobenzylidenyl)-5,7-dibromo-2-indolinone |
| 10727 | A | 9 | 3-(4-cyanobenzylidenyl)-5,7-dibromo-2-indolinone |
| 10727 | A | 10 | 3-(2,5-dihydroxybenzylidenyl)-5,7-dibromo-2-indolinone |
| 10727 | A | 11 | 3-(2,3-dimethoxybenzylidenyl)-5,7-dibromo-2-indolinone |
| 10727 | B | 2 | 3-(4-diethylaminobenzylidenyl)-5-iodo-2-indolinone |
| 10727 | B | 3 | 3-[(2,4-diethylpyrrol-5-yl)methylidenyl]-5-iodo-2-indolinone |

TABLE 13-continued

| MASTER BARCODE | PLATE ROW | PLATE COLUMN | NAME |
|---|---|---|---|
| 10727 | B | 4 | 3-(3-bromo-5-chloro-2-hydroxybenzylidenyl)-5-iodo-2-indolinone |
| 10727 | B | 5 | 3-[2-(4-chlorophenylmercapto)benzylidenyl]-5-iodo 2-indolinone |
| 10727 | B | 6 | 3-[(5-chlorobenzodioxolan-6-yl)methylidenyl]-5-iodo-2-indolinone |
| 10727 | B | 7 | 3-[(1,4-benzopyranon-3-yl)methylidenyl]-5-iodo-2-indolinone |
| 10727 | B | 8 | 3-(3-cyanobenzylidenyl)-5-iodo-2-indolinone |
| 10727 | B | 9 | 3-(4-cyanobenzylidenyl)-5-iodo-2-indolinone |
| 10727 | B | 10 | 3-(2,5-dihydroxybenzylidenyl)-5-iodo-2-indolinone |
| 10727 | B | 11 | 3-(2,3-dimethoxybenzylidenyl)-5-iodo-2-indolinone |
| 10727 | C | 2 | 3-(4-diethylaminobenzylidenyl)-5-bromo-4-methyl-2-indolinone |
| 10727 | C | 3 | 3-[(2,4-diethylpyrrol-5-yl)methylidenyl]-5-bromo-4-methyl-2-indolinone |
| 10727 | C | 4 | 3-(3-bromo-5-chloro-2-hydroxybenzylidenyl)-5-bromo-4-methyl-2-indolinone |
| 10727 | C | 5 | 3-[2-(4-chlorophenylmercapto)benzylidenyl]-5-bromo-4-methyl-2-indolinone |
| 10727 | C | 6 | 3-[(5-chlorobenzodioxolan-6-yl)methylidenyl]-5-bromo-4-methyl-2-indolinone |
| 10727 | C | 7 | 3-[(1,4-benzopyranon-3-yl)methylidenyl]-5-bromo-4-methyl-2-indolinone |
| 10727 | C | 8 | 3-(3-cyanobenzylidenyl)-5-bromo-4-methyl-2-indolinone |
| 10727 | C | 9 | 3-(4-cyanobenzylidenyl)-5-bromo-4-methyl-2-indolinone |
| 10727 | C | 10 | 3-(2,5-dihydroxybenzylidenyl)-5-bromo-4-methyl-2-indolinone |
| 10727 | C | 11 | 3-(2,3-dimethoxybenzylidenyl)-5-bromo-4-methyl-2-indolinone |
| 10727 | D | 2 | 3-(4-diethylaminobenzylidenyl)-5-methylaminosulfonyl-2-indolinone |
| 10727 | D | 3 | 3-[(2,4-diethylpyrrol-5-yl)methylidenyl]-5-methylaminosulfonyl-2-indolinone |
| 10727 | D | 4 | 3-(3-bromo-5-chloro-2-hydroxybenzylidenyl)-5-methylaminosulfonyl-2-indolinone |
| 10727 | D | 5 | 3-[2-(4-chlorophenylmercapto)benzylidenyl]-5-methylaminosulfonyl-2-indolinone |
| 10727 | D | 6 | 3-[(5-chlorobenzodioxolan-6-yl)methylidenyl]-5-methylaminosulfonyl-2-indolinone |
| 10727 | D | 7 | 3-[(1,4-benzopyranon-3-yl)methylidenyl]-5-methylaminosulfonyl-2-indolinone |
| 10727 | D | 8 | 3-(3-cyanobenzylidenyl)-5-methylaminosulfonyl-2-indolinone |
| 10727 | D | 9 | 3-(4-cyanobenzylidenyl)-5-methylaminosulfonyl-2-indolinone |
| 10727 | D | 10 | 3-(2,5-dihydroxybenzylidenyl)-5-methylaminosulfonyl-2-indolinone |
| 10727 | D | 11 | 3-(2,3-dimethoxybenzylidenyl)-5-methylaminosulfonyl-2-indolinone |
| 10727 | E | 2 | 3-(4-diethylaminobenzylidenyl)-5-[4-(trifluoromethyl)phenylaminosulfonyl]-2-indolinone |
| 10727 | E | 3 | 3-[(2,4-diethylpyrrol-5-yl)methylidenyl]-5-[4-(trifluoromethyl)phenylaminosulfonyl]-2-indolinone |
| 10727 | E | 4 | 3-(3-bromo-5-chloro-2-hydroxybenzylidenyl)-5-[4-(trifluoromethyl)phenylaminosulfonyl]-2-indolinone |
| 10727 | E | 5 | 3-[2-(4-chlorophenylmercapto)benzylidenyl]-5-[4-(trifluoromethyl)phenylaminosulfonyl]-2-indolinone |
| 10727 | E | 6 | 3-[(5-chlorobenzodioxolan-6-yl)methylidenyl]-5-[4-(trifluoromethyl)phenylaminosulfonyl]-2-indolinone |
| 10727 | E | 7 | 3-[(1,4-benzopyranon-3-yl)methylidenyl]-5-[4-(trifluoromethyl)phenylaminosulfonyl]-2-indolinone |
| 10727 | E | 8 | 3-(3-cyanobenzylidenyl)-5-[4-(trifluoromethyl)phenylaminosulfonyl]-2-indolinone |
| 10727 | E | 9 | 3-(4-cyanobenzylidenyl)-5-[4-(trifluoromethyl)phenylaminosulfonyl]-2-indolinone |
| 10727 | E | 10 | 3-(2,5-dihydroxybenzylidenyl)-5-[4-(trifluoromethyl)phenylaminosulfonyl]-2-indolinone |
| 10727 | E | 11 | 3-(2,3-dimethoxybenzylidenyl)-5-[4-(trifluoromethyl)phenylaminosulfonyl]-2-indolinone |
| 10727 | F | 2 | 3-(4-diethylaminobenzylidenyl)-5-(morpholin-1-yl)sulfonyl-2-indolinone |
| 10727 | F | 3 | 3-[(2,4-diethylpyrrol-5-yl)methylidenyl]-5-(morpholin-1-yl)sulfonyl-2-indolinone |

TABLE 13-continued

| MASTER BARCODE | PLATE ROW | PLATE COLUMN | NAME |
|---|---|---|---|
| 10727 | F | 4 | 3-(3-bromo-5-chloro-2-hydroxybenzylidenyl)-5-(morpholin-1-yl)sulfonyl-2-indolinone |
| 10727 | F | 5 | 3-[2-(4-chlorophenylmercapto)benzylidenyl]-5-(morpholin-1-yl)sulfonyl-2-indolinone |
| 10727 | F | 6 | 3-[(5-chlorobenzodioxolan-6-yl)methylidenyl]-5-(morpholin-1-yl)sulfonyl-2-indolinone |
| 10727 | F | 7 | 3-[(1,4-benzopyranon-3-yl)methylidenyl]-5-(morpholin-1-yl)sulfonyl-2-indolinone |
| 10727 | F | 8 | 3-(3-cyanobenzylidenyl)-5-(morpholin-1-yl)sulfonyl-2-indolinone |
| 10727 | F | 9 | 3-(4-cyanobenzylidenyl)-5-(morpholin-1-yl)sulfonyl-2-indolinone |
| 10727 | F | 10 | 3-(2,5-dihydroxybenzylidenyl)-5-(morpholin-1-yl)sulfonyl-2-indolinone |
| 10727 | F | 11 | 3-(2,3-dimethoxybenzylidenyl)-5-(morpholin-1-yl)sulfonyl-2-indolinone |
| 10727 | G | 2 | 3-(4-diethylaminobenzylidenyl)-5-(2-chloroethyl)-2-indolinone |
| 10727 | G | 3 | 3-[(2,4-diethylpyrrol-5-yl)methylidenyl]-5-(2-chloroethyl)-2-indolinone |
| 10727 | G | 4 | 3-(3-bromo-5-chloro-2-hydroxybenzylidenyl)-5-(2-chloroethyl)-2-indolinone |
| 10727 | G | 5 | 3-[2-(4-chlorophenylmercapto)benzylidenyl]-5-(2-chloroethyl)-2-indolinone |
| 10727 | G | 6 | 3-[(5-chlorobenzodioxolan-6-yl)methylidenyl]-5-(2-chloroethyl)-2-indolinone |
| 10727 | G | 7 | 3-[(1,4-benzopyranon-3-yl)methylidenyl]-5-(2-chloroethyl)-2-indolinone |
| 10727 | G | 8 | 3-(3-cyanobenzylidenyl)-5-(2-chloroethyl)-2-indolinone |
| 10727 | G | 9 | 3-(4-cyanobenzylidenyl)-5-(2-chloroethyl)-2-indolinone |
| 10727 | G | 10 | 3-(2,5-dihydroxybenzylidenyl)-5-(2-chloroethyl)-2-indolinone |
| 10727 | G | 11 | 3-(2,3-dimethoxybenzylidenyl)-5-(2-chloroethyl)-2-indolinone |
| 10728 | A | 2 | 3-(2,5-dimethoxybenzylidenyl)-5,7-dibromo-2-indolinone |
| 10728 | A | 3 | 3-(2,6-dimethoxybenzylidenyl)-5,7-dibromo-2-indolinone |
| 10728 | A | 4 | 3-(3,5-dimethoxybenzylidenyl)-5,7-dibromo-2-indolinone |
| 10728 | A | 5 | 3-(4-dimethylamino-2-methoxybenzylidenyl)-5,7-dibromo-2-indolinone |
| 10728 | A | 6 | 3-[(fluoren-2-yl)methylidenyl]-5,7-dibromo-2-indolinone |
| 10728 | A | 7 | 3-[2-fluoro-3-(trifluoromethyl)benzylidenyl]-5,7-dibromo-2-indolinone |
| 10728 | A | 8 | 3-[2-fluoro-5-(trifluoromethyl)benzylidenyl]-5,7-dibromo-2-indolinone |
| 10728 | A | 9 | 3-[2-fluoro-6-(trifluoromethyl)benzylidenyl]-5,7-dibromo-2-indolinone |
| 10728 | A | 10 | 3-(2-carboxymethoxybenzylidenyl)-5,7-dibromo-2-indolinone |
| 10728 | A | 11 | 3-[(4-methoxybenzodioxolan-6-yl)methylidenyl]-5,7-dibromo-2-indolinone |
| 10728 | B | 2 | 3-(2,5-dimethoxybenzylidenyl)-5-iodo-2-indolinone |
| 10728 | B | 3 | 3-(2,6-dimethoxybenzylidenyl)-5-iodo-2-indolinone |
| 10728 | B | 4 | 3-(3,5-dimethoxybenzylidenyl)-5-iodo-2-indolinone |
| 10728 | B | 5 | 3-(4-dimethylamino-2-methoxybenzylidenyl)-5-iodo-2-indolinone |
| 10728 | B | 6 | 3-[(fluoren-2-yl)methylidenyl]-5-iodo-2-indolinone |
| 10728 | B | 7 | 3-[2-fluoro-3-(trifluoromethyl)benzylidenyl]-5-iodo-2-indolinone |
| 10728 | B | 8 | 3-[2-fluoro-5-(trifluoromethyl)benzylidenyl]-5-iodo-2-indolinone |
| 10728 | B | 9 | 3-[2-fluoro-6-(trifluoromethyl)benzylidenyl]-5-iodo-2-indolinone |
| 10728 | B | 10 | 3-(2-carboxymethoxybenzylidenyl)-5-iodo-2-indolinone |
| 10728 | B | 11 | 3-[(4-methoxybenzodioxolan-6-yl)methylidenyl]-5-iodo-2-indolinone |
| 10728 | C | 2 | 3-(2,5-dimethoxybenzylidenyl)-5-bromo-4-methyl-2-indolinone |
| 10728 | C | 3 | 3-(2,6-dimethoxybenzylidenyl)-5-bromo-4-methyl-2-indolinone |

TABLE 13-continued

| MASTER BARCODE | PLATE ROW | PLATE COLUMN | NAME |
|---|---|---|---|
| 10728 | C | 4 | 3-(3,5-dimethoxybenzylidenyl)-5-bromo-4-methyl-2-indolinone |
| 10728 | C | 5 | 3-(4-dimethylamino-2-methoxybenzylidenyl)-5-bromo-4-methyl-2-indolinone |
| 10728 | C | 6 | 3-[(fluoren-2-yl)methylidenyl]-5-bromo-4-methyl-2-indolinone |
| 10728 | C | 7 | 3-[2-fluoro-3-(trifluoromethyl)benzylidenyl]-5-bromo-4-methyl-2-indolinone |
| 10728 | C | 8 | 3-[2-fluoro-5-(trifluoromethyl)benzylidenyl]-5-bromo-4-methyl-2-indolinone |
| 10728 | C | 9 | 3-[2-fluoro-6-(trifluoromethyl)benzylidenyl]-5-bromo-4-methyl-2-indolinone |
| 10728 | C | 10 | 3-(2-carboxymethoxybenzylidenyl)-5-bromo-4-methyl-2-indolinone |
| 10728 | C | 11 | 3-[(4-methoxybenzodioxolan-6-yl)methylidenyl]-5-bromo-4-methyl-2-indolinone |
| 10728 | D | 2 | 3-(2,5-dimethoxybenzylidenyl)-5-methylaminosulfonyl-2-indolinone |
| 10728 | D | 3 | 3-(2,6-dimethoxybenzylidenyl)-5-methylaminosulfonyl-2-indolinone |
| 10728 | D | 4 | 3-(3,5-dimethoxybenzylidenyl)-5-methylaminosulfonyl-2-indolinone |
| 10728 | D | 5 | 3-(4-dimethylamino-2-methoxybenzylidenyl)-5-methylaminosulfonyl-2-indolinone |
| 10728 | D | 6 | 3-[(fluoren-2-yl)methylidenyl]-5-methylaminosulfonyl-2-indolinone |
| 10728 | D | 7 | 3-[2-fluoro-3-(trifluoromethyl)benzylidenyl]-5-methylaminosulfonyl-2-indolinone |
| 10728 | D | 8 | 3-[2-fluoro-5-(trifluoromethyl)benzylidenyl]-5-methylaminosulfonyl-2-indolinone |
| 10728 | D | 9 | 3-[2-fluoro-6-(trifluoromethyl)benzylidenyl]-5-methylaminosulfonyl-2-indolinone |
| 10728 | D | 10 | 3-(2-carboxymethoxybenzylidenyl)-5-methylaminosulfonyl-2-indolinone |
| 10728 | D | 11 | 3-[(4-methoxybenzodioxolan-6-yl)methylidenyl]-5-methylaminosulfonyl-2-indolinone |
| 10728 | E | 2 | 3-(2,5-dimethoxybenzylidenyl)-5-[4-(trifluoromethyl)phenylaminosulfonyl]-2-indolinone |
| 10728 | E | 3 | 3-(2,6-dimethoxybenzylidenyl)-5-[4-(trifluoromethyl)phenylaminosulfonyl]-2-indolinone |
| 10728 | E | 4 | 3-(3,5-dimethoxybenzylidenyl)-5-[4-(trifluoromethyl)phenylaminosulfonyl]-2-indolinone |
| 10728 | E | 5 | 3-(4-dimethylamino-2-methoxybenzylidenyl)-5-[4-(trifluoromethyl)phenylaminosulfonyl]-2-indolinone |
| 10728 | E | 6 | 3-[(fluoren-2-yl)methylidenyl]-5-[4-(trifluoromethyl)phenylaminosulfonyl]-2-indolinone |
| 10728 | E | 7 | 3-[2-fluoro-3-(trifluoromethyl)benzylidenyl]-5-[4-(trifluoromethyl)phenylaminosulfonyl]-2-indolinone |
| 10728 | E | 8 | 3-[2-fluoro-5-(trifluoromethyl)benzylidenyl]-5-[4-(trifluoromethyl)phenylaminosulfonyl]-2-indolinone |
| 10728 | E | 9 | 3-[2-fluoro-6-(trifluoromethyl)benzylidenyl]-5-[4-(trifluoromethyl)phenylaminosulfonyl]-2-indolinone |
| 10728 | E | 10 | 3-(2-carboxymethoxybenzylidenyl)-5-[4-(trifluoromethyl)phenylaminosulfonyl]-2-indolinone |
| 10728 | E | 11 | 3-[(4-methoxybenzodioxolan-6-yl)methylidenyl]-5-[4-(trifluoromethyl)phenylaminosulfonyl]-2-indolinone |
| 10728 | F | 2 | 3-(2,5-dimethoxybenzylidenyl)-5-(morpholin-1-yl)aminosulfonyl-2-indolinone |
| 10728 | F | 3 | 3-(2,6-dimethoxybenzylidenyl)-5-(morpholin-1-yl)aminosulfonyl-2-indolinone |
| 10728 | F | 4 | 3-(3,5-dimethoxybenzylidenyl)-5-(morpholin-1-yl)aminosulfonyl-2-indolinone |
| 10728 | F | 5 | 3-(4-dimethylamino-2-methoxybenzylidenyl)-5-(morpholin-1-yl)aminosulfonyl-2-indolinone |
| 10728 | F | 6 | 3-[(fluoren-2-yl)methylidenyl]-5-(morpholin-1-yl)aminosulfonyl-2-indolinone |
| 10728 | F | 7 | 3-[2-fluoro-3-(trifluoromethyl)benzylidenyl]-5-(morpholin-1-yl)aminosulfonyl-2-indolinone |
| 10728 | F | 8 | 3-[2-fluoro-5-(trifluoromethyl)benzylidenyl]-5-(morpholin-1-yl)aminosulfonyl-2-indolinone |
| 10728 | F | 9 | 3-[2-fluoro-6-(trifluoromethyl)benzylidenyl]-5-(morpholin-1-yl)aminosulfonyl-2-indolinone |
| 10728 | F | 10 | 3-(2-carboxymethoxybenzylidenyl)-5-(morpholin-1-yl)aminosulfonyl-2-indolinone |

TABLE 13-continued

| MASTER BARCODE | PLATE ROW | PLATE COLUMN | NAME |
|---|---|---|---|
| 10728 | F | 11 | 3-[(4-methoxybenzodioxolan-6-yl)methylidenyl]-5-(morpholin-1-yl)aminosulfonyl-2-indolinone |
| 10728 | G | 2 | 3-(2,5-dimethoxybenzylidenyl)-5-(2-chloroethyl)-2-indolinone |
| 10728 | G | 3 | 3-(2,6-dimethoxybenzylidenyl)-5-(2-chloroethyl)-2-indolinone |
| 10728 | G | 4 | 3-(3,5-dimethoxybenzylidenyl)-5-(2-chloroethyl)-2-indolinone |
| 10728 | G | 5 | 3-(4-dimethylamino-2-methoxybenzylidenyl)-5-(2-chloroethyl)-2-indolinone |
| 10728 | G | 6 | 3-[(fluoren-2-yl)methylidenyl]-5-(2-chloroethyl)-2-indolinone |
| 10728 | G | 7 | 3-[2-fluoro-3-(trifluoromethyl)benzylidenyl]-5-(2-chloroethyl)-2-indolinone |
| 10728 | G | 8 | 3-[2-fluoro-5-(trifluoromethyl)benzylidenyl]-5-(2-chloroethyl)-2-indolinone |
| 10728 | G | 9 | 3-[2-fluoro-6-(trifluoromethyl)benzylidenyl]-5-(2-chloroethyl)-2-indolinone |
| 10728 | G | 10 | 3-(2-carboxymethoxybenzylidenyl)-5-(2-chloroethyl)-2-indolinone |
| 10728 | G | 11 | 3-[(4-methoxybenzodioxolan-6-yl)methylidenyl]-5-(2-chloroethyl)-2-indolinone |
| 10729 | A | 2 | 3-[(2-methoxynapth-1-yl)methylidenyl]-5,7-dibromo-2-indolinone |
| 10729 | A | 3 | 3-[(1-methoxynapth-4-yl)methylidenyl]-5,7-dibromo-2-indolinone |
| 10729 | A | 4 | 3-(4-methylmercaptobenzylidenyl)-5,7-dibromo-2-indolinone |
| 10729 | A | 5 | 3-[(3-methylthien-2-yl)methylidenyl]-5,7-dibromo-2-indolinone |
| 10729 | A | 6 | 3-(3-phenoxybenzylidenyl)-5,7-dibromo-2-indolinone |
| 10729 | A | 7 | 3-[(pyrid-2-yl)methylidenyl]-5,7-dibromo-2-indolinone |
| 10729 | A | 8 | 3-[(pyrid-3-yl)methylidenyl]-5,7-dibromo-2-indolinone |
| 10729 | A | 9 | 3-[(pyrid-4-yl)methylidenyl]-5,7-dibromo-2-indolinone |
| 10729 | A | 10 | 3-[4-(pyrrolidin-1-yl)benzylidenyl]-5,7-dibromo-2-indolinone |
| 10729 | A | 11 | 3-[(cyclohexen-3-yl)methylidenyl]-5,7-dibromo-2-indolinone |
| 10729 | B | 2 | 3-[(2-methoxynapth-1-yl)methylidenyl]-5-iodo-2-indolinone |
| 10729 | B | 3 | 3-[(1-methoxynapth-4-yl)methylidenyl]-5-iodo-2-indolinone |
| 10729 | B | 4 | 3-(4-methylmercaptobenzylidenyl)-5-iodo-2-indolinone |
| 10729 | B | 5 | 3-[(3-methylthien-2-yl)methylidenyl]-5-iodo-2-indolinone |
| 10729 | B | 6 | 3-(3-phenoxybenzylidenyl)-5-iodo-2-indolinone |
| 10729 | B | 7 | 3-[(pyrid-2-yl)methylidenyl]-5-iodo-2-indolinone |
| 10729 | B | 8 | 3-[(pyrid-3-yl)methylidenyl]-5-iodo-2-indolinone |
| 10729 | B | 9 | 3-[(pyrid-4-yl)methylidenyl]-5-iodo-2-indolinone |
| 10729 | B | 10 | 3-[4-(pyrrolidin-1-yl)benzylidenyl]-5-iodo-2-indolinone |
| 10729 | B | 11 | 3-[(cyclohexen-3-yl)methylidenyl]-5-iodo-2-indolinone |
| 10729 | C | 2 | 3-[(2-methoxynapth-1-yl)methylidenyl]-5-bromo-4-methyl-2-indolinone |
| 10729 | C | 3 | 3-[(1-methoxynapth-4-yl)methylidenyl]-5-bromo-4-methyl-2-indolinone |
| 10729 | C | 4 | 3-(4-methylmercaptobenzylidenyl)-5-bromo-4-methyl-2-indolinone |
| 10729 | C | 5 | 3-[(3-methylthien-2-yl)methylidenyl]-5-bromo-4-methyl-2-indolinone |
| 10729 | C | 6 | 3-(3-phenoxybenzylidenyl)-5-bromo-4-methyl-2-indolinone |
| 10729 | C | 7 | 3-[(pyrid-2-yl)methylidenyl]-5-bromo-4-methyl-2-indolinone |
| 10729 | C | 8 | 3-[(pyrid-3-yl)methylidenyl]-5-bromo-4-methyl-2-indolinone |
| 10729 | C | 9 | 3-[(pyrid-4-yl)methylidenyl]-5-bromo-4-methyl-2-indolinone |
| 10729 | C | 10 | 3-[4-(pyrrolidin-1-yl)benzylidenyl]-5-bromo-4-methyl-2-indolinone |

TABLE 13-continued

| MASTER BARCODE | PLATE ROW | PLATE COLUMN | NAME |
|---|---|---|---|
| 10729 | C | 11 | 3-[(cyclohexen-3-yl)methylidenyl]-5-bromo-4-methyl-2-indolinone |
| 10729 | D | 2 | 3-[(2-methoxynapth-1-yl)methylidenyl]-5-methylaminosulfonyl-2-indolinone |
| 10729 | D | 3 | 3-[(1-methoxynapth-4-yl)methylidenyl]-5-methylaminosulfonyl-2-indolinone |
| 10729 | D | 4 | 3-(4-methylmercaptobenzylidenyl)-5-methylaminosulfonyl-2-indolinone |
| 10729 | D | 5 | 3-[(3-methylthien-2-yl)methylidenyl]-5-methylaminosulfonyl-2-indolinone |
| 10729 | D | 6 | 3-(3-phenoxybenzylidenyl)-5-methylaminosulfonyl-2-indolinone |
| 10729 | D | 7 | 3-[(pyrid-2-yl)methylidenyl]-5-methylaminosulfonyl-2-indolinone |
| 10729 | D | 8 | 3-[(pyrid-3-yl)methylidenyl]-5-methylaminosulfonyl-2-indolinone |
| 10729 | A | 7 | 3-[(pyrid-2-yl)methylidenyl]-5,7-dibromo-2-indolinone |
| 10729 | A | 8 | 3-[(pyrid-3-yl)methylidenyl]-5,7-dibromo-2-indolinone |
| 10729 | A | 9 | 3-[(pyrid-4-yl)methylidenyl]-5,7-dibromo-2-indolinone |
| 10729 | A | 10 | 3-[4-(pyrrolidin-1-yl)benzylidenyl]-5,7-dibromo-2-indolinone |
| 10729 | A | 11 | 3-[(cyclohexen-3-yl)methylidenyl]-5,7-dibromo-2-indolinone |
| 10729 | B | 2 | 3-[(2-methoxynapth-1-yl)methylidenyl]-5-iodo-2-indolinone |
| 10729 | B | 3 | 3-[(1-methoxynapth-4-yl)methylidenyl]-5-iodo-2-indolinone |
| 10729 | B | 4 | 3-(4-methylmercaptobenzylidenyl)-5-iodo-2-indolinone |
| 10729 | B | 5 | 3-[(3-methylthien-2-yl)methylidenyl]-5-iodo-2-indolinone |
| 10729 | B | 6 | 3-(3-phenoxybenzylidenyl)-5-iodo-2-indolinone |
| 10729 | B | 7 | 3-[(pyrid-2-yl)methylidenyl]-5-iodo-2-indolinone |
| 10729 | B | 8 | 3-[(pyrid-3-yl)methylidenyl]-5-iodo-2-indolinone |
| 10729 | B | 9 | 3-[(pyrid-4-yl)methylidenyl]-5-iodo-2-indolinone |
| 10729 | B | 10 | 3-[4-(pyrrolidin-1-yl)benzylidenyl]-5-iodo-2-indolinone |
| 10729 | B | 11 | 3-[(cyclohexen-3-yl)methylidenyl]-5-iodo-2-indolinone |
| 10729 | C | 2 | 3-[(2-methoxynapth-1-yl)methylidenyl]-5-bromo-4-methyl-2-indolinone |
| 10729 | C | 3 | 3-[(1-methoxynapth-4-yl)methylidenyl]-5-bromo-4-methyl-2-indolinone |
| 10729 | C | 4 | 3-(4-methylmercaptobenzylidenyl)-5-bromo-4-methyl-2-indolinone |
| 10729 | C | 5 | 3-[(3-methylthien-2-yl)methylidenyl]-5-bromo-4-methyl-2-indolinone |
| 10729 | C | 6 | 3-(3-phenoxybenzylidenyl)-5-bromo-4-methyl-2-indolinone |
| 10729 | C | 7 | 3-[(pyrid-2-yl)methylidenyl]-5-bromo-4-methyl-2-indolinone |
| 10729 | C | 8 | 3-[(pyrid-3-yl)methylidenyl]-5-bromo-4-methyl-2-indolinone |
| 10729 | C | 9 | 3-[(pyrid-4-yl)methylidenyl]-5-bromo-4-methyl-2-indolinone |
| 10729 | C | 10 | 3-[4-(pyrrolidin-1-yl)benzylidenyl]-5-bromo-4-methyl-2-indolinone |
| 10729 | C | 11 | 3-[(cyclohexen-3-yl)methylidenyl]-5-bromo-4-methyl-2-indolinone |
| 10729 | D | 2 | 3-[(2-methoxynapth-1-yl)methylidenyl]-5-methylaminosulfonyl-2-indolinone |
| 10729 | D | 3 | 3-[(1-methoxynapth-4-yl)methylidenyl]-5-methylaminosulfonyl-2-indolinone |
| 10729 | D | 4 | 3-(4-methylmercaptobenzylidenyl)-5-methylaminosulfonyl-2-indolinone |
| 10729 | D | 5 | 3-[(3-methylthien-2-yl)methylidenyl]-5-methylaminosulfonyl-2-indolinone |
| 10729 | D | 6 | 3-(3-phenoxybenzylidenyl)-5-methylaminosulfonyl-2-indolinone |
| 10729 | D | 7 | 3-[(pyrid-2-yl)methylidenyl]-5-methylaminosulfonyl-2-indolinone |
| 10729 | D | 8 | 3-[(pyrid-3-yl)methylidenyl]-5-methylaminosulfonyl-2-indolinone |

TABLE 13-continued

| MASTER BARCODE | PLATE ROW | PLATE COLUMN | NAME |
|---|---|---|---|
| 10729 | D | 9 | 3-[(pyrid-4-yl)methylidenyl]-5-methylaminosulfonyl-2-indolinone |
| 10729 | D | 10 | 3-[4-(pyrrolidin-1-yl)benzylidenyl]-5-methylaminosulfonyl-2-indolinone |
| 10729 | D | 11 | 3-[(cyclohexen-3-yl)methylidenyl]-5-methylaminosulfonyl-2-indolinone |
| 10729 | E | 2 | 3-[(2-methoxynapth-1-yl)methylidenyl]-5-[4-(trifluoromethyl)phenylaminosulfonyl]-2-indolinone |
| 10729 | E | 3 | 3-[(1-methoxynapth-4-yl)methylidenyl]-5-[4-(trifluoromethyl)phenylaminosulfonyl]-2-indolinone |
| 10729 | E | 4 | 3-(4-methylmercaptobenzylidenyl)-5-[4-(trifluoromethyl)phenylaminosulfonyl]-2-indolinone |
| 10729 | E | 5 | 3-[(3-methylthien-2-yl)methylidenyl]-5-[4-(trifluoromethyl)phenylaminosulfonyl]-2-indolinone |
| 10729 | E | 6 | 3-(3-phenoxybenzylidenyl)-5-[4-(trifluoromethyl)phenylaminosulfonyl]-2-indolinone |
| 10729 | E | 7 | 3-[(pyrid-2-yl)methylidenyl]-5-[4-(trifluoromethyl)phenylaminosulfonyl]-2-indolinone |
| 10729 | E | 8 | 3-[(pyrid-3-yl)methylidenyl]-5-[4-(trifluoromethyl)phenylaminosulfonyl]-2-indolinone |
| 10729 | E | 9 | 3-[(pyrid-4-yl)methylidenyl]-5-[4-(trifluoromethyl)phenylaminosulfonyl]-2-indolinone |
| 10729 | E | 10 | 3-[4-(pyrrolidin-1-yl)benzylidenyl]-5-[4-(trifluoromethyl)phenylaminosulfonyl]-2-indolinone |
| 10729 | E | 11 | 3-[(cyclohexen-3-yl)methylidenyl]-5-[4-(trifluoromethyl)phenylaminosulfonyl]-2-indolinone |
| 10729 | F | 2 | 3-[(2-methoxynapth-1-yl)methylidenyl]-5-(morpholin-1-yl)aminosulfonyl-2-indolinone |
| 10729 | F | 3 | 3-[(1-methoxynapth-4-yl)methylidenyl]-5-(morpholin-1-yl)aminosulfonyl-2-indolinone |
| 10729 | F | 4 | 3-(4-methylmercaptobenzylidenyl)-5-(morpholin-1-yl)aminosulfonyl-2-indolinone |
| 10729 | F | 5 | 3-[(3-methylthien-2-yl)methylidenyl]-5-(morpholin-1-yl)aminosulfonyl-2-indolinone |
| 10729 | F | 6 | 3-(3-phenoxybenzylidenyl)-5-(morpholin-1-yl)aminosulfonyl-2-indolinone |
| 10729 | F | 7 | 3-[(pyrid-2-yl)methylidenyl]-5-(morpholin-1-yl)aminosulfonyl-2-indolinone |
| 10729 | F | 8 | 3-[(pyrid-3-yl)methylidenyl]-5-(morpholin-1-yl)aminosulfonyl-2-indolinone |
| 10729 | F | 9 | 3-[(pyrid-4-yl)methylidenyl]-5-(morpholin-1-yl)aminosulfonyl-2-indolinone |
| 10729 | F | 10 | 3-[4-(pyrrolidin-1-yl)benzylidenyl]-5-(morpholin-1-yl)aminosulfonyl-2-indolinone |
| 10729 | F | 11 | 3-[(cyclohexen-3-yl)methylidenyl]-5-(morpholin-1-yl)aminosulfonyl-2-indolinone |
| 10729 | G | 2 | 3-[(2-methoxynapth-1-yl)methylidenyl]-5-(2-chloroethyl)-2-indolinone |
| 10729 | G | 3 | 3-[(1-methoxynapth-4-yl)methylidenyl]-5-(2-chloroethyl)-2-indolinone |
| 10729 | G | 4 | 3-(4-methylmercaptobenzylidenyl)-5-(2-chloroethyl)-2-indolinone |
| 10729 | G | 5 | 3-[(3-methylthien-2-yl)methylidenyl]-5-(2-chloroethyl)-2-indolinone |
| 10729 | G | 6 | 3-(3-phenoxybenzylidenyl)-5-(2-chloroethyl)-2-indolinone |
| 10729 | G | 7 | 3-[(pyrid-2-yl)methylidenyl]-5-(2-chloroethyl)-2-indolinone |
| 10729 | G | 8 | 3-[(pyrid-3-yl)methylidenyl]-5-(2-chloroethyl)-2-indolinone |
| 10729 | G | 9 | 3-[(pyrid-4-yl)methylidenyl]-5-(2-chloroethyl)-2-indolinone |
| 10729 | G | 10 | 3-[4-(pyrrolidin-1-yl)benzylidenyl]-5-(2-chloroethyl)-2-indolinone |
| 10729 | G | 11 | 3-[(cyclohexen-3-yl)methylidenyl]-5-(2-chloroethyl)-2-indolinone |
| 10730 | A | 2 | 3-(2,3,4-trimethoxybenzylidenyl)-5,7-dibromo-2-indolinone |
| 10730 | A | 3 | 3-(2,4,5-trimethoxybenzylidenyl)-5,7-dibromo-2-indolinone |
| 10730 | A | 4 | 3-(3,4,5-trimethoxybenzylidenyl)-5,7-dibromo-2-indolinone |
| 10730 | A | 5 | 3-[(1-acetylindol-3-yl)methylidenyl]-5,7-dibromo-2-indolinone |
| 10730 | A | 6 | 3-[(6-chloro-1,4-benzofuranon-3-yl)methylidenyl]-5,7-dibromo-2-indolinone |

TABLE 13-continued

| MASTER BARCODE | PLATE ROW | PLATE COLUMN | NAME |
|---|---|---|---|
| 10730 | A | 7 | 3-[2-[(2-chlorophenyl)furan-5-yl]methylidenyl]-5,7-dibromo-2-indolinone |
| 10730 | A | 8 | 3-[(2-chloroquinolin-3-yl)methylidenyl]-5,7-dibromo-2-indolinone |
| 10730 | A | 9 | 3-[(6,8-dibromo-1,4-benzofuranon-3-yl)methylidenyl]-5,7-dibromo-2-indolinone |
| 10730 | A | 10 | 3-[(2,5-dimethoxytetrahydrofuran-3-yl)methylidenyl]-5,7-dibromo-2-indolinone |
| 10730 | A | 11 | 3-[(2,3-dimethylfuran-5-yl)methylidenyl]-5,7-dibromo-2-indolinone |
| 10730 | B | 2 | 3-(2,3,4-trimethoxybenzylidenyl)-5-iodo-2-indolinone |
| 10730 | B | 3 | 3-(2,4,5-trimethoxybenzylidenyl)-5-iodo-2-indolinone |
| 10730 | B | 4 | 3-(3,4,5-trimethoxybenzylidenyl)-5-iodo-2-indolinone |
| 10730 | B | 5 | 3-[(1-acetylindol-3-yl)methylidenyl]-5-iodo-2-indolinone |
| 10730 | B | 6 | 3-[(6-chloro-1,4-benzofuranon-3-yl)methylidenyl]-5-iodo-2-indolinone |
| 10730 | B | 7 | 3-[2-[(2-chlorophenyl)furan-5-yl]methylidenyl]-5-iodo-2-indolinone |
| 10730 | B | 8 | 3-[(2-chloroquinolin-3-yl)methylidenyl]-5-iodo-2-indolinone |
| 10730 | B | 9 | 3-[(6,8-dibromo-1,4-benzofuranon-3-yl)methylidenyl]-5-iodo-2-indolinone |
| 10730 | B | 10 | 3-[(2,5-dimethoxytetrahydrofuran-3-yl)methylidenyl]-5-iodo-2-indolinone |
| 10730 | B | 11 | 3-[(2,3-dimethylfuran-5-yl)methylidenyl]-5-iodo-2-indolinone |
| 10730 | C | 2 | 3-(2,3,4-trimethoxybenzylidenyl)-5-bromo-4-methyl-2-indolinone |
| 10730 | C | 3 | 3-(2,4,5-trimethoxybenzylidenyl)-5-bromo-4-methyl-2-indolinone |
| 10730 | C | 4 | 3-(3,4,5-trimethoxybenzylidenyl)-5-bromo-4-methyl-2-indolinone |
| 10730 | C | 5 | 3-[(1-acetylindol-3-yl)methylidenyl]-5-bromo-4-methyl-2-indolinone |
| 10730 | C | 6 | 3-[(6-chloro-1,4-benzofuranon-3-yl)methylidenyl]-5-bromo-4-methyl-2-indolinone |
| 10730 | C | 7 | 3-[2-[(2-chlorophenyl)furan-5-yl]methylidenyl]-5-bromo-4-methyl-2-indolinone |
| 10730 | C | 8 | 3-[(2-chloroquinolin-3-yl)methylidenyl]-5-bromo-4-methyl-2-indolinone |
| 10730 | C | 9 | 3-[(6,8-dibromo-1,4-benzofuranon-3-yl)methylidenyl]-5-bromo-4-methyl-2-indolinone |
| 10730 | C | 10 | 3-[(2,5-dimethoxytetrahydrofuran-3-yl)methylidenyl]-5-bromo-4-methyl-2-indolinone |
| 10730 | C | 11 | 3-[(2,3-dimethylfuran-5-yl)methylidenyl]-5-bromo-4-methyl-2-indolinone |
| 10730 | D | 2 | 3-(2,3,4-trimethoxybenzylidenyl)-5-methylaminosulfonyl-2-indolinone |
| 10730 | D | 3 | 3-(2,4,5-trimethoxybenzylidenyl)-5-methylaminosulfonyl-2-indolinone |
| 10730 | D | 4 | 3-(3,4,5-trimethoxybenzylidenyl)-5-methylaminosulfonyl-2-indolinone |
| 10730 | D | 5 | 3-[(1-acetylindol-3-yl)methylidenyl]-5-methylaminosulfonyl-2-indolinone |
| 10730 | D | 6 | 3-[(6-chloro-1,4-benzofuranon-3-yl)methylidenyl]-5-methylaminosulfonyl-2-indolinone |
| 10730 | D | 7 | 3-[2-[(2-chlorophenyl)furan-5-yl]methylidenyl]-5-methylaminosulfonyl-2-indolinone |
| 10730 | D | 8 | 3-[(2-chloroquinolin-3-yl)methylidenyl]-5-methylaminosulfonyl-2-indolinone |
| 10730 | D | 9 | 3-[(6,8-dibromo-1,4-benzofuranon-3-yl)methylidenyl]-5-methylaminosulfonyl-2-indolinone |
| 10730 | D | 10 | 3-[(2,5-dimethoxytetrahydrofuran-3-yl)methylidenyl]-5-methylaminosulfonyl-2-indolinone |
| 10730 | D | 11 | 3-[(2,3-dimethylfuran-5-yl)methylidenyl]-5-methylaminosulfonyl-2-indolinone |
| 10730 | E | 2 | 3-(2,3,4-trimethoxybenzylidenyl)-5-[4-(trifluoromethyl)phenylaminosulfonyl]-2-indolinone |
| 10730 | E | 3 | 3-(2,4,5-trimethoxybenzylidenyl)-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10730 | E | 4 | 3-(3,4,5-trimethoxybenzylidenyl)-5-[4-(trifluoromethyl)phenylaminosulfonyl]-2-indolinone |
| 10730 | E | 5 | 3-[(1-acetylindol-3-yl)methylidenyl]-5-[4-(trifluoromethyl)phenylaminosulfonyl]-2-indolinone |
| 10730 | E | 6 | 3-[(6-chloro-1,4-benzofuranon-3-yl)methylidenyl]-5-[4-(trifluoromethyl)phenylaminosulfonyl]-2-indolinone |
| 10730 | E | 7 | 3-[2-[(2-chlorophenyl)furan-5-yl]methylidenyl]-5-[4-(trifluoromethyl)phenylaminosulfonyl]-2-indolinone |
| 10730 | E | 8 | 3-[(2-chloroquinolin-3-yl)methylidenyl]-5-[4-(trifluoromethyl)phenylaminosulfonyl]-2-indolinone |
| 10730 | E | 9 | 3-[(6,8-dibromo-1,4-benzofuranon-3-yl)methylidenyl]-5-[4-(trifluoromethyl)phenylaminosulfonyl]-2-indolinone |
| 10730 | E | 10 | 3-[(2,5-dimethoxytetrahydrofuran-3-yl)methylidenyl]-5-[4-(trifluoromethyl)phenylaminosulfonyl]-2-indolinone |
| 10730 | E | 11 | 3-[(2,3-dimethylfuran-5-yl)methylidenyl]-5-[4-(trifluoromethyl)phenylaminosulfonyl]-2-indolinone |
| 10730 | F | 2 | 3-(2,3,4-trimethoxybenzylidenyl)-5-(morpholin-1-yl)sulfonyl-2-indolinone |
| 10730 | F | 3 | 3-(2,4,5-trimethoxybenzylidenyl)-5-(morpholin-1-yl)sulfonyl-2-indolinone |
| 10730 | F | 4 | 3-(3,4,5-trimethoxybenzylidenyl)-5-(morpholin-1-yl)sulfonyl-2-indolinone |
| 10730 | F | 5 | 3-[(1-acetylindol-3-yl)methylidenyl]-5-(morpholin-1-yl)sulfonyl-2-indolinone |
| 10730 | F | 6 | 3-[(6-chloro-1,4-benzofuranon-3-yl)methylidenyl]-5-(morpholin-1-yl)sulfonyl-2-indolinone |
| 10730 | F | 7 | 3-[2-[(2-chlorophenyl)furan-5-yl]methylidenyl]-5-(morpholin-1-yl)sulfonyl-2-indolinone |
| 10730 | F | 8 | 3-[(2-chloroquinolin-3-yl)methylidenyl]-5-(morpholin-1-yl)sulfonyl-2-indolinone |
| 10730 | F | 9 | 3-[(6,8-dibromo-1,4-benzofuranon-3-yl)methylidenyl]-5-(morpholin-1-yl)sulfonyl-2-indolinone |
| 10730 | F | 10 | 3-[(2,5-dimethoxytetrahydrofuran-3-yl)methylidenyl]-5-(morpholin-1-yl)sulfonyl-2-indolinone |
| 10730 | F | 11 | 3-[(2,3-dimethylfuran-5-yl)methylidenyl]-5-(morpholin-1-yl)sulfonyl-2-indolinone |
| 10730 | G | 2 | 3-(2,3,4-trimethoxybenzylidenyl)-5-(2-chloroethyl)-2-indolinone |
| 10730 | G | 3 | 3-(2,4,5-trimethoxybenzylidenyl)-5-(2-chloroethyl)-2-indolinone |
| 10730 | G | 4 | 3-(3,4,5-trimethoxybenzylidenyl)-5-(2-chloroethyl)-2-indolinone |
| 10730 | G | 5 | 3-[(1-acetylindol-3-yl)methylidenyl]-5-(2-chloroethyl)-2-indolinone |
| 10730 | G | 6 | 3-[(6-chloro-1,4-benzofuranon-3-yl)methylidenyl]-5-(2-chloroethyl)-2-indolinone |
| 10730 | G | 7 | 3-[2-[(2-chlorophenyl)furan-5-yl]methylidenyl]-5-(2-chloroethyl)-2-indolinone |
| 10730 | G | 8 | 3-[(2-chloroquinolin-3-yl)methylidenyl]-5-(2-chloroethyl)-2-indolinone |
| 10730 | G | 9 | 3-[(6,8-dibromo-1,4-benzofuranon-3-yl)methylidenyl]-5-(2-chloroethyl)-2-indolinone |
| 10730 | G | 10 | 3-[(2,5-dimethoxytetrahydrofuran-3-yl)methylidenyl]-5-(2-chloroethyl)-2-indolinone |
| 10730 | G | 11 | 3-[(2,3-dimethylfuran-5-yl)methylidenyl]-5-(2-chloroethyl)-2-indolinone |
| 10731 | A | 2 | 3-[(9-ethylcarbazol-3-yl)methylidenyl]-5,7-dibromo-2-indolinone |
| 10731 | A | 3 | 3-[(6,7-dimethyl-1,4-benzopyron-3-yl)methylidenyl]-5,7-dibromo-2-indolinone |
| 10731 | A | 4 | 3-[[4-(propen-2-yl)cyclohexen-1-yl]methylidenyl]-5,7-dibromo-2-indolinone |
| 10731 | A | 5 | 3-[(6-isopropyl-1,4-benzopyron-3-yl)methylidenyl]-5,7-dibromo-2-indolinone |
| 10731 | A | 6 | 3-[(6-methyl-1,4-benzopyron-3-yl)methylidenyl]-5,7-dibromo-2-indolinone |
| 10731 | A | 7 | 3-[(6-nitro-1,4-benzopyron-3-yl)methylidenyl]-5,7-dibromo-2-indolinone |
| 10731 | A | 8 | 3-[(pyrimid-2,4-dion-5-yl)methylidenyl]-5,7-dibromo-2-indolinone |

TABLE 13-continued

| MASTER BARCODE | PLATE ROW | PLATE COLUMN | NAME |
|---|---|---|---|
| 10731 | A | 9 | 3-[(5-methoxyindol-3-yl)methylidenyl]-5,7-dibromo-2-indolinone |
| 10731 | A | 10 | 3-(1-methyl-2-oxindol-3-idenyl)-5,7-dibromo-2-indolinone |
| 10731 | A | 11 | 3-[2-[2-(nitrophenyl)furan-5-yl]methylidenyl]-5,7-dibromo-2-indolinone |
| 10731 | B | 2 | 3-[(9-ethylcarbazol-3-yl)methylidenyl]-5-iodo-2-indolinone |
| 10731 | B | 3 | 3-[(6,7-dimethyl-1,4-benzopyron-3-yl)methylidenyl]-5-iodo-2-indolinone |
| 10731 | B | 4 | 3-[[4-(propen-2-yl)cyclohexen-1-yl]methylidenyl]-5-iodo-2-indolinone |
| 10731 | B | 5 | 3-[(6-isopropyl-1,4-benzopyron-3-yl)methylidenyl]-5-iodo-2-indolinone |
| 10731 | B | 6 | 3-[(6-methyl-1,4-benzopyron-3-yl)methylidenyl]-5-iodo-2-indolinone |
| 10731 | B | 7 | 3-[(6-nitro-1,4-benzopyron-3-yl)methylidenyl]-5-iodo-2-indolinone |
| 10731 | B | 8 | 3-[(pyrimid-2,4-dion-5-yl)methylidenyl]-5-iodo-2-indolinone |
| 10731 | B | 9 | 3-[(5-methoxyindol-3-yl)methylidenyl]-5-iodo-2-indolinone |
| 10731 | B | 10 | 3-(1-methyl-2-oxindol-3-idenyl)-5-iodo-2-indolinone |
| 10731 | B | 11 | 3-[2-[2-(nitrophenyl)furan-5-yl]methylidenyl]-5-iodo-2-indolinone |
| 10731 | C | 2 | 3-[(9-ethylcarbazol-3-yl)methylidenyl]-5-bromo-4-methyl-2-indolinone |
| 10731 | C | 3 | 3-[(6,7-dimethyl-1,4-benzopyron-3-yl)methylidenyl]-5-bromo-4-methyl-2-indolinone |
| 10731 | C | 4 | 3-[[4-(propen-2-yl)cyclohexen-1-yl]methylidenyl]-5-bromo-4-methyl-2-indolinone |
| 10731 | C | 5 | 3-[(6-isopropyl-1,4-benzopyron-3-yl)methylidenyl]-5-bromo-4-methyl-2-indolinone |
| 10731 | C | 6 | 3-[(6-methyl-1,4-benzopyron-3-yl)methylidenyl]-5-bromo-4-methyl-2-indolinone |
| 10731 | C | 7 | 3-[(6-nitro-1,4-benzopyron-3-yl)methylidenyl]-5-bromo-4-methyl-2-indolinone |
| 10731 | C | 8 | 3-[(pyrimid-2,4-dion-5-yl)methylidenyl]-5-bromo-4-methyl-2-indolinone |
| 10731 | C | 9 | 3-[(5-methoxyindol-3-yl)methylidenyl]-5-bromo-4-methyl-2-indolinone |
| 10731 | C | 10 | 3-(1-methyl-2-oxindol-3-idenyl)-5-bromo-4-methyl-2-indolinone |
| 10731 | C | 11 | 3-[2-[2-(nitrophenyl)furan-5-yl]methylidenyl]-5-bromo-4-methyl-2-indolinone |
| 10731 | D | 2 | 3-[(9-ethylcarbazol-3-yl)methylidenyl]-5-methylaminosulfonyl-2-indolinone |
| 10731 | D | 3 | 3-[(6,7-dimethyl-1,4-benzopyron-3-yl)methylidenyl]-5-methylaminosulfonyl-2-indolinone |
| 10731 | D | 4 | 3-[[4-(propen-2-yl)cyclohexen-1-yl]methylidenyl]-5-methylaminosulfonyl-2-indolinone |
| 10731 | D | 5 | 3-[(6-isopropyl-1,4-benzopyron-3-yl)methylidenyl]-5-methylaminosulfonyl-2-indolinone |
| 10731 | D | 6 | 3-[(6-methyl-1,4-benzopyron-3-yl)methylidenyl]-5-methylaminosulfonyl-2-indolinone |
| 10731 | D | 7 | 3-[(6-nitro-1,4-benzopyron-3-yl)methylidenyl]-5-methylaminosulfonyl-2-indolinone |
| 10731 | D | 8 | 3-[(pyrimid-2,4-dion-5-yl)methylidenyl]-5-methylaminosulfonyl-2-indolinone |
| 10731 | D | 9 | 3-[(5-methoxyindol-3-yl)methylidenyl]-5-methylaminosulfonyl-2-indolinone |
| 10731 | D | 10 | 3-(1-methyl-2-oxindol-3-idenyl)-5-methylaminosulfonyl-2-indolinone |
| 10731 | D | 11 | 3-[2-[2-(nitrophenyl)furan-5-yl]methylidenyl]-5-methylaminosulfonyl-2-indolinone |
| 10731 | E | 2 | 3-[(9-ethylcarbazol-3-yl)methylidenyl]-5-[4-(trifluoromethyl)phenylaminosulfonyl]-2-indolinone |
| 10731 | E | 3 | 3-[(6,7-dimethyl-1,4-benzopyron-3-yl)methylidenyl]-5-[4-(trifluoromethyl)phenylaminosulfonyl]-2-indolinone |
| 10731 | E | 4 | 3-[[4-(propen-2-yl)cyclohexen-1-yl]methylidenyl]-5-[4-(trifluoromethyl)phenylaminosulfonyl]-2-indolinone |
| 10731 | E | 5 | 3-[(6-isopropyl-1,4-benzopyron-3-yl)methylidenyl]-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10731 | E | 6 | 3-[(6-methyl-1,4-benzopyron-3-yl)methylidenyl]-5-[4-(trifluoromethyl)phenylaminosulfonyl]-2-indolinone |
| 10731 | E | 7 | 3-[(6-nitro-1,4-benzopyron-3-yl)methylidenyl]-5-[4-(trifluoromethyl)phenylaminosulfonyl]-2-indolinone |
| 10731 | E | 8 | 3-[(pyrimid-2,4-dion-5-yl)methylidenyl]-5-[4-(trifluoromethyl)phenylaminosulfonyl]-2-indolinone |
| 10731 | E | 9 | 3-[(5-methoxyindol-3-yl)methylidenyl]-5-[4-(trifluoromethyl)phenylaminosulfonyl]-2-indolinone |
| 10731 | E | 10 | 3-(1-methyl-2-oxindol-3-idenyl)-5-[4-(trifluoromethyl)phenylaminosulfonyl]-2-indolinone |
| 10731 | E | 11 | 3-[2-[2-(nitrophenyl)furan-5-yl]methylidenyl]-5-[4-(trifluoromethyl)phenylaminosulfonyl]-2-indolinone |
| 10731 | F | 2 | 3-[(9-ethylcarbazol-3-yl)methylidenyl]-5-(morpholin-1-yl)sulfonyl-2-indolinone |
| 10731 | F | 3 | 3-[(6,7-dimethyl-1,4-benzopyron-3-yl)methylidenyl]-5-(morpholin-1-yl)sulfonyl-2-indolinone |
| 10731 | F | 4 | 3-[[4-(propen-2-yl)cyclohexen-1-yl]methylidenyl]-5-(morpholin-1-yl)sulfonyl-2-indolinone |
| 10731 | F | 5 | 3-[(6-isopropyl-1,4-benzopyron-3-yl)methylidenyl]-5-(morpholin-1-yl)sulfonyl-2-indolinone |
| 10731 | F | 6 | 3-[(6-methyl-1,4-benzopyron-3-yl)methylidenyl]-5-(morpholin-1-yl)sulfonyl-2-indolinone |
| 10731 | F | 7 | 3-[(6-nitro-1,4-benzopyron-3-yl)methylidenyl]-5-(morpholin-1-yl)sulfonyl-2-indolinone |
| 10731 | F | 8 | 3-[(pyrimid-2,4-dion-5-yl)methylidenyl]-5-(morpholin-1-yl)sulfonyl-2-indolinone |
| 10731 | F | 9 | 3-[(5-methoxyindol-3-yl)methylidenyl]-5-(morpholin-1-yl)sulfonyl-2-indolinone |
| 10731 | F | 10 | 3-(1-methyl-2-oxindol-3-idenyl)-5-(morpholin-1-yl)sulfonyl-2-indolinone |
| 10731 | F | 11 | 3-[2-[2-(nitrophenyl)furan-5-yl]methylidenyl]-5-(morpholin-1-yl)sulfonyl-2-indolinone |
| 10731 | G | 2 | 3-[(9-ethylcarbazol-3-yl)methylidenyl]-5-(2-chloroethyl)-2-indolinone |
| 10731 | G | 3 | 3-[(6,7-dimethyl-1,4-benzopyron-3-yl)methylidenyl]-5-(2-chloroethyl)-2-indolinone |
| 10731 | G | 4 | 3-[[4-(propen-2-yl)cyclohexen-1-yl]methylidenyl]-5-(2-chloroethyl)-2-indolinone |
| 10731 | G | 5 | 3-[(6-isopropyl-1,4-benzopyron-3-yl)methylidenyl]-5-(2-chloroethyl)-2-indolinone |
| 10731 | G | 6 | 3-[(6-methyl-1,4-benzopyron-3-yl)methylidenyl]-5-(2-chloroethyl)-2-indolinone |
| 10731 | G | 7 | 3-[(6-nitro-1,4-benzopyron-3-yl)methylidenyl]-5-(2-chloroethyl)-2-indolinone |
| 10731 | G | 8 | 3-[(pyrimid-2,4-dion-5-yl)methylidenyl]-5-(2-chloroethyl)-2-indolinone |
| 10731 | G | 9 | 3-[(5-methoxyindol-3-yl)methylidenyl]-5-(2-chloroethyl)-2-indolinone |
| 10731 | G | 10 | 3-(1-methyl-2-oxindol-3-idenyl)-5-(2-chloroethyl)-2-indolinone |
| 10731 | G | 11 | 3-[2-[2-(nitrophenyl)furan-5-yl]methylidenyl]-5-(2-chloroethyl)-2-indolinone |
| 10732 | A | 2 | 3-[2-(thien-2-yl)-2-(trifluoromethyl)ethylidenyl]-5,7-dibromo-2-indolinone |
| 10732 | A | 3 | 3-(3,5-diisopropyl-4-methoxybenzylidenyl)-5,7-dibromo-2-indolinone |
| 10732 | A | 4 | 3-(3,5-diisopropyl-4-phenoxybenzylidenyl)-5,7-dibromo-2-indolinone |
| 10732 | A | 5 | 3-(3-t-butyl-4-methoxybenzylidenyl)-5,7-dibromo-2-indolinone |
| 10732 | A | 6 | 3-(4-benzyloxy-3-t-butylbenzylidenyl)-5,7-dibromo-2-indolinone |
| 10732 | A | 7 | 3-(3-bromo-5-t-butyl-4-methoxybenzylidenyl)-5,7-dibromo-2-indolinone |
| 10732 | A | 8 | 3-(4-benzyloxy-3-bromo-5-t-butylbenzylidenyl)-5,7-dibromo-2-indolinone |
| 10732 | A | 9 | 3-(3-t-butyl-5-chloro-4-methoxybenzylidenyl)-5,7-dibromo-2-indolinone |
| 10732 | A | 10 | 3-(4-benzyloxy-5-t-butyl-3-chlorobenzylidenyl)-5,7-dibromo-2-indolinone |
| 10732 | A | 11 | 3-(3-t-butyl-5-iodo-4-methoxybenzylidenyl)-5,7-dibromo-2-indolinone |
| 10732 | B | 2 | 3-[2-(thien-2-yl)-2-(trifluoromethyl)ethylidenyl]-5-iodo-2-indolinone |

TABLE 13-continued

| MASTER BARCODE | PLATE ROW | PLATE COLUMN | NAME |
|---|---|---|---|
| 10732 | B | 3 | 3-(3,5-diisopropyl-4-methoxybenzylidenyl)-5-iodo-2-indolinone |
| 10732 | B | 4 | 3-(3,5-diisopropyl-4-phenoxybenzylidenyl)-5-iodo-2-indolinone |
| 10732 | B | 5 | 3-(3-t-butyl-4-methoxybenzylidenyl)-5-iodo-2-indolinone |
| 10732 | B | 6 | 3-(4-benzyloxy-3-t-butylbenzylidenyl)-5-iodo-2-indolinone |
| 10732 | B | 7 | 3-(3-bromo-5-t-butyl-4-methoxybenzylidenyl)-5-iodo-2-indolinone |
| 10732 | B | 8 | 3-(4-benzyloxy-3-bromo-5-t-butylbenzylidenyl)-5-iodo-2-indolinone |
| 10732 | B | 9 | 3-(3-t-butyl-5-chloro-4-methoxybenzylidenyl)-5-iodo-2-indolinone |
| 10732 | B | 10 | 3-(4-benzyloxy-5-t-butyl-3-chlorobenzylidenyl)-5-iodo-2-indolinone |
| 10732 | B | 11 | 3-(3-t-butyl-5-iodo-4-methoxybenzylidenyl)-5-iodo-2-indolinone |
| 10732 | C | 2 | 3-[2-(thien-2-yl)-2-(trifluoromethyl)ethylidenyl]-5-bromo-4-methyl-2-indolinone |
| 10732 | C | 3 | 3-(3,5-diisopropyl-4-methoxybenzylidenyl)-5-bromo-4-methyl-2-indolinone |
| 10732 | C | 4 | 3-(3,5-diisopropyl-4-phenoxybenzylidenyl)-5-bromo-4-methyl-2-indolinone |
| 10732 | C | 5 | 3-(3-t-butyl-4-methoxybenzylidenyl)-5-bromo-4-methyl-2-indolinone |
| 10732 | C | 6 | 3-(4-benzyloxy-3-t-butylbenzylidenyl)-5-bromo-4-methyl-2-indolinone |
| 10732 | C | 7 | 3-(3-bromo-5-t-butyl-4-methoxybenzylidenyl)-5-bromo-4-methyl-2-indolinone |
| 10732 | C | 8 | 3-(4-benzyloxy-3-bromo-5-t-butylbenzylidenyl)-5-bromo-4-methyl-2-indolinone |
| 10732 | C | 9 | 3-(3-t-butyl-5-chloro-4-methoxybenzylidenyl)-5-bromo-4-methyl-2-indolinone |
| 10732 | C | 10 | 3-(4-benzyloxy-5-t-butyl-3-chlorobenzylidenyl)-5-bromo-4-methyl-2-indolinone |
| 10732 | C | 11 | 3-(3-t-butyl-5-iodo-4-methoxybenzylidenyl)-5-bromo-4-methyl-2-indolinone |
| 10732 | D | 2 | 3-[2-(thien-2-yl)-2-(trifluoromethyl)ethylidenyl]-5-methylaminosulfonyl-2-indolinone |
| 10732 | D | 3 | 3-(3,5-diisopropyl-4-methoxybenzylidenyl)-5-methylaminosulfonyl-2-indolinone |
| 10732 | D | 4 | 3-(3,5-diisopropyl-4-phenoxybenzylidenyl)-5-methylaminosulfonyl-2-indolinone |
| 10732 | D | 5 | 3-(3-t-butyl-4-methoxybenzylidenyl)-5-methylaminosulfonyl-2-indolinone |
| 10732 | D | 6 | 3-(4-benzyloxy-3-t-butylbenzylidenyl)-5-methylaminosulfonyl-2-indolinone |
| 10732 | D | 7 | 3-(3-bromo-5-t-butyl-4-methoxybenzylidenyl)-5-methylaminosulfonyl-2-indolinone |
| 10732 | D | 8 | 3-(4-benzyloxy-3-bromo-5-t-butylbenzylidenyl)-5-methylaminosulfonyl-2-indolinone |
| 10732 | D | 9 | 3-(3-t-butyl-5-chloro-4-methoxybenzylidenyl)-5-methylaminosulfonyl-2-indolinone |
| 10732 | D | 10 | 3-(4-benzyloxy-5-t-butyl-3-chlorobenzylidenyl)-5-methylaminosulfonyl-2-indolinone |
| 10732 | D | 11 | 3-(3-t-butyl-5-iodo-4-methoxybenzylidenyl)-5-methylaminosulfonyl-2-indolinone |
| 10732 | E | 2 | 3-[2-(thien-2-yl)-2-(trifluoromethyl)ethylidenyl]-5-[4-(trifluoromethyl)phenylaminosulfonyl]-2-indolinone |
| 10732 | E | 3 | 3-(3,5-diisopropyl-4-methoxybenzylidenyl)-5-[4-(trifluoromethyl)phenylaminosulfonyl]-2-indolinone |
| 10732 | E | 4 | 3-(3,5-diisopropyl-4-phenoxybenzylideny)]-5-[4-(trifluoromethyl)phenylaminosulfonyl]-2-indolinone |
| 10732 | E | 5 | 3-(3-t-butyl-4-methoxybenzylidenyl)-5-[4-(trifluoromethyl)phenylaminosulfonyl]-2-indolinone |
| 10732 | E | 6 | 3-(4-benzyloxy-3-t-butylbenzylidenyl)-5-[4-(trifluoromethyl)phenylaminosulfonyl]-2-indolinone |
| 10732 | E | 7 | 3-(3-bromo-5-t-butyl-4-methoxybenzylidenyl)-5-[4-(trifluoromethyl)phenylaminosulfonyl]-2-indolinone |
| 10732 | E | 8 | 3-(4-benzyloxy-3-bromo-5-t-butylbenzylidenyl)-5-[4-(trifluoromethyl)phenylaminosulfonyl]-2-indolinone |
| 10732 | E | 9 | 3-(3-t-butyl-5-chloro-4-methoxybenzylidenyl)-5-[4-(trifluoromethyl)phenylaminosulfonyl]-2-indolinone |
| 10732 | E | 10 | 3-(4-benzyloxy-5-t-butyl-3-chlorobenzylidenyl)-5-[4-(trifluoromethyl)phenylaminosulfonyl]-2-indolinone |

TABLE 13-continued

| MASTER BARCODE | PLATE ROW | PLATE COLUMN | NAME |
|---|---|---|---|
| 10732 | E | 11 | 3-(3-t-butyl-5-iodo-4-methoxybenzylidenyl)-5-[4-(trifluoromethyl)phenylaminosulfonyl]-2-indolinone |
| 10732 | F | 2 | 3-[2-(thien-2-yl)-2-(trifluoromethyl)ethylidenyl]-5-(morpholin-1-yl)sulfonyl-2-indolinone |
| 10732 | F | 3 | 3-(3,5-diisopropyl-4-methoxybenzylidenyl)-5-(morpholin-1-yl)sulfonyl-2-indolinone |
| 10732 | F | 4 | 3-(3,5-diisopropyl-4-phenoxybenzylidenyl)-5-(morpholin-1-yl)sulfonyl-2-indolinone |
| 10732 | F | 5 | 3-(3-t-butyl-4-methoxybenzylidenyl)-5-(morpholin-1-yl)sulfonyl-2-indolinone |
| 10732 | F | 6 | 3-(4-benzyloxy-3-t-butylbenzylidenyl)-5-(morpholin-1-yl)sulfonyl-2-indolinone |
| 10732 | F | 7 | 3-(3-bromo-5-t-butyl-4-methoxybenzylidenyl)-5-(morpholin-1-yl)sulfonyl-2-indolinone |
| 10732 | F | 8 | 3-(4-benzyloxy-3-bromo-5-t-butylbenzylidenyl)-5-(morpholin-1-yl)sulfonyl-2-indolinone |
| 10732 | F | 9 | 3-(3-t-butyl-5-chloro-4-methoxybenzylidenyl)-5-(morpholin-1-yl)sulfonyl-2-indolinone |
| 10732 | F | 10 | 3-(4-benzyloxy-5-t-butyl-3-chloro-benzylidenyl)-5-(morpholin-1-yl)sulfonyl-2-indolinone |
| 10732 | F | 11 | 3-(3-t-butyl-5-iodo-4-methoxybenzylidenyl)-5-(morpholin-1-yl)sulfonyl-2-indolinone |
| 10732 | G | 2 | 3-[2-(thien-2-yl)-2-(trifluoromethyl)ethylidenyl]-5-(2-chloroethyl)-2-indolinone |
| 10732 | G | 3 | 3-(3,5-diisopropyl-4-methoxybenzylidenyl]-5-(2-chloroethyl)-2-indolinone |
| 10732 | G | 4 | 3-(3,5-diisopropyl-4-phenoxybenzylidenyl]-5-(2-chloroethyl)-2-indolinone |
| 10732 | G | 5 | 3-(3-t-butyl-4-methoxybenzylidenyl)-5-(2-chloroethyl)-2-indolinone |
| 10732 | G | 6 | 3-(4-benzyloxy-3-t-butylbenzylidenyl)-5-(2-chloroethyl)-2-indolinone |
| 10732 | G | 7 | 3-(3-bromo-5-t-butyl-4-methoxybenzylidenyl)-5-(2-chloroethyl)-2-indolinone |
| 10732 | G | 8 | 3-(4-benzyloxy-3-bromo-5-t-butylbenzylidenyl)-5-(2-chloroethyl)-2-indolinone |
| 10732 | G | 9 | 3-(3-t-butyl-5-chloro-4-methoxybenzylidenyl)-5-(2-chloroethyl)-2-indolinone |
| 10732 | G | 10 | 3-(4-benzyloxy-5-t-butyl-3-chlorobenzylidenyl)-5-(2-chloroethyl)-2-indolinone |
| 10732 | G | 11 | 3-(3-t-butyl-5-iodo-4-methoxybenzylidenyl)-5-(2-chloroethyl)-2-indolinone |
| 10733 | A | 2 | 3-(4-benzyloxy-3-t-butyl-5-iodobenzylidenyl)-5,7-dibromo-2-indolinone |
| 10733 | A | 3 | 3-(3-t-butyl-4-methoxy-5-nitrobenzylidenyl)-5,7-dibromo-2-indolinone |
| 10733 | A | 4 | 3-(3,5-di-t-butyl-4-methoxybenzylidenyl)-5,7-dibromo-2-indolinone |
| 10733 | A | 5 | 3-(4-benzyloxy-3,5-di-t-butylbenzylidenyl)-5,7-dibromo-2-indolinone |
| 10733 | A | 6 | 3-(3,5-dimethyl-4-methoxybenzylidenyl)-5,7-dibromo-2-indolinone |
| 10733 | A | 7 | 3-(4-benzyloxy-3,5-dimethylbenzylidenyl)-5,7-dibromo-2-indolinone |
| 10733 | A | 8 | 3-(5-bromo-2-hydroxy-3-methoxybenzylidenyl)-5,7-dibromo-2-indolinone |
| 10733 | A | 9 | 3-(5-bromo-2-hydroxybenzylidenyl)-5,7-dibromo-2-indolinone |
| 10733 | A | 10 | 3-(2-hydroxy-5-nitrobenzylidenyl)-5,7-dibromo-2-indolinone |
| 10733 | A | 11 | 3-(4-hydroxy-3-methoxy-2-nitrobenzylidenyl)-5,7-dibromo-2-indolinone |
| 10733 | B | 2 | 3-(4-benzyloxy-3-t-butyl-5-iodobenzylidenyl)-5-iodo-2-indolinone |
| 10733 | B | 3 | 3-(3-t-butyl-4-methoxy-5-nitrobenzylidenyl)-5-iodo-2-indolinone |
| 10733 | B | 4 | 3-(3,5-di-t-butyl-4-methoxybenzylidenyl)-5-iodo-2-indolinone |
| 10733 | B | 5 | 3-(4-benzyloxy-3,5-di-t-butylbenzylidenyl)-5-iodo-2-indolinone |
| 10733 | B | 6 | 3-(3,5-dimethyl-4-methoxybenzylidenyl)-5-iodo-2-indolinone |
| 10733 | B | 7 | 3-(4-benzyloxy-3,5-dimethylbenzylidenyl)-5-iodo-2-indolinone |
| 10733 | B | 8 | 3-(5-bromo-2-hydroxy-3-methoxybenzylidenyl)-5-iodo-2-indolinone |

TABLE 13-continued

| MASTER BARCODE | PLATE ROW | PLATE COLUMN | NAME |
|---|---|---|---|
| 10733 | B | 9 | 3-(5-bromo-2-hydroxybenzylidenyl)-5-iodo-2-indolinone |
| 10733 | B | 10 | 3-(2-hydroxy-5-nitrobenzylidenyl)-5-iodo-2-indolinone |
| 10733 | B | 11 | 3-(4-hydroxy-3-methoxy-2-nitrobenzylidenyl)-5-iodo-2-indolinone |
| 10733 | C | 2 | 3-(4-benzyloxy-3-t-butyl-5-iodobenzylidenyl)-5-bromo-4-methyl-2-indolinone |
| 10733 | C | 3 | 3-(3-t-butyl-4-methoxy-5-nitrobenzylidenyl)-5-bromo-4-methyl-2-indolinone |
| 10733 | C | 4 | 3-(3,5-di-t-butyl-4-methoxybenzylidenyl)-5-bromo-4-methyl-2-indolinone |
| 10733 | C | 5 | 3-(4-benzyloxy-3,5-di-t-butylbenzylidenyl)-5-bromo-4-methyl-2-indolinone |
| 10733 | C | 6 | 3-(3,5-dimethyl-4-methoxybenzlidenyl)-5-bromo-4-methyl-2-indolinone |
| 10733 | C | 7 | 3-(4-benzyloxy-3,5-dimethylbenzylidenyl)-5-bromo-4-methyl-2-indolinone |
| 10733 | C | 8 | 3-(5-bromo-2-hydroxy-3-methoxybenlzylidenyl)-5-bromo-4-methyl-2-indolinone |
| 10733 | C | 9 | 3-(5-bromo-2-hydroxybenzylidenyl)-5-bromo-4-methyl-2-indolinone |
| 10733 | C | 10 | 3-(2-hydroxy-5-nitrobenzylidenyl)-5-bromo-4-methyl-2-indolinone |
| 10733 | C | 11 | 3-(4-hydroxy-3-methoxy-2-nitrobenzylidenyl)-5-bromo-4-methyl-2-indolinone |
| 10733 | D | 2 | 3-(4-benzyloxy-3-t-butyl-5-iodobenzylidenyl)-5-methylaminosulfonyl-2-indolinone |
| 10733 | D | 3 | 3-(3-t-butyl-4-methoxy-5-nitrobenzylidenyl)-5-methylaminosulfonyl-2-indolinone |
| 10733 | D | 4 | 3-(3,5-di-t-butyl-4-methoxybenzylidenyl)-5-methylaminosulfonyl-2-indolinone |
| 10733 | D | 5 | 3-(4-benzyloxy-3,5-di-t-butylbenzylidenyl)-5-methylaminosulfonyl-2-indolinone |
| 10733 | D | 6 | 3-(3,5-dimethyl-4-methoxybenzylidenyl)-5-methylaminosulfonyl-2-indolinone |
| 10733 | D | 7 | 3-(4-benzyloxy-3,5-dimethylbenzylidenyl)-5-methylaminosulfonyl-2-indolinone |
| 10733 | D | 8 | 3-(5-bromo-2-hydroxy-3-methoxybenzylidenyl)-5-methylaminosulfonyl-2-indolinone |
| 10733 | D | 9 | 3-(5-bromo-2-hydroxybenzylidenyl)-5-methylaminosulfonyl-2-indolinone |
| 10733 | D | 10 | 3-(2-hydroxy-5-nitrobenzylidenyl)-5-methylaminosulfonyl-2-indolinone |
| 10733 | D | 11 | 3-(4-hydroxy-3-methoxy-2-nitrobenzylidenyl)-5-methylaminosulfonyl-2-indolinone |
| 10733 | E | 2 | 3-(4-benzyloxy-3-t-butyl-5-iodobenzylidenyl)-5-[4-(trifluoromethyl)phenylaminosulfonyl]-2-indolinone |
| 10733 | E | 3 | 3-(3-t-butyl-4-methoxy-5-nitrobenzylidenyl)-5-[4-(trifluoromethyl)phenylaminosulfonyl]-2-indolinone |
| 10733 | E | 4 | 3-(3,5-di-t-butyl-4-methoxybenzylidenyl)-5-[4-(trifluoromethyl)phenylaminosulfonyl]-2-indolinone |
| 10733 | E | 5 | 3-(4-benzyloxy-3,5-di-t-butylbenzylidenyl)-5-[4-(trifluoromethyl)phenylaminosulfonlyl]-2-indolinone |
| 10733 | E | 6 | 3-(3,5-dimethyl-4-methoxybenzylidenyl)-5-[4-(trifluoromethyl)phenylaminosulfonyl]-2-indolinone |
| 10733 | E | 7 | 3-(4-benzyloxy-3,5-dimethylbenzylidenyl)-5-[4-(trifluoromethyl)phenylaminosulfonyl]-2-indolinone |
| 10733 | E | 8 | 3-(5-bromo-2-hydroxy-3-methoxybenzylidenyl)-5-[4-(trifluoromethyl)phenylaminosulfonyl]-2-indolinone |
| 10733 | E | 9 | 3-(5-bromo-2-hydroxybenzylidenyl)-5-[4-(trifluoromethyl)phenylaminosulfonyl]-2-indolinone |
| 10733 | E | 10 | 3-(2-hydroxy-5-nitrobenzylidenyl)-5-[4-(trifluoromethyl)phenylaminosulfonyl]-2-indolinone |
| 10733 | E | 11 | 3-(4-hydroxy-3-methoxy-2-nitrobenzylidenyl)-5-[4-(trifluoromethyl)phenylaminosulfonyl]-2-indolinone |
| 10733 | F | 2 | 3-(4-benzyloxy-3-t-butyl-5-iodobenzylidenyl)-5-(morpholin-1-yl)sulfonyl-2-indolinone |
| 10733 | F | 3 | 3-(3-t-butyl-4-methoxy-5-nitrobenzylidenyl)-5-(morpholin-1-yl)sulfonyl-2-indolinone |
| 10733 | F | 4 | 3-(3,5-di-t-butyl-4-methoxybenzylidenyl)-5-(morpholin-1-yl)sulfonyl-2-indolinone |
| 10733 | F | 5 | 3-(4-benzyloxy-3,5-di-t-butylbenzylidenyl)-5-(morpholin-1-yl)sulfonyl-2-indolinone |
| 10733 | F | 6 | 3-(3,5-dimethyl-4-methoxybenzylidenyl)-5-(morpholin-1-yl)sulfonyl-2-indolinone |

TABLE 13-continued

| MASTER BARCODE | PLATE ROW | PLATE COLUMN | NAME |
|---|---|---|---|
| 10733 | F | 7 | 3-(4-benzyloxy-3,5-dimethylbenzylidenyl)-5-(morpholin-1-yl)sulfonyl-2-indolinone |
| 10733 | F | 8 | 3-(5-bromo-2-hydroxy-3-methoxybenzylidenyl)-5-(morpholin-1-yl)sulfonyl-2-indolinone |
| 10733 | F | 9 | 3-(5-bromo-2-hydroxybenzylidenyl)-5-(morpholin-1-yl)sulfonyl-2-indolinone |
| 10733 | F | 10 | 3-(2-hydroxy-5-nitrobenzylidenyl)-5-(morpholin-1-yl)sulfonyl-2-indolinone |
| 10733 | F | 11 | 3-(4-hydroxy-3-methoxy-2-nitrobenzylidenyl)-5-(morpholin-1-yl)sulfonyl-2-indolinone |
| 10733 | G | 2 | 3-(4-benzyloxy-3-t-butyl-5-iodobenzylidenyl)-5-(2-chloroethyl)-2-indolinone |
| 10733 | G | 3 | 3-(3-t-butyl-4-methoxy-5-nitrobenzylidenyl)-5-(2-chloroethyl)-2-indolinone |
| 10733 | G | 4 | 3-(3,5-di-t-butyl-4-methoxybenzylidenyl)-5-(2-chloroethyl)-2-indolinone |
| 10733 | G | 5 | 3-(4-benzyloxy-3,5-di-t-butylbenzylidenyl)-5-(2-chloroethyl)-2-indolinone |
| 10733 | G | 6 | 3-(3,5-dimethyl-4-methoxybenzylidenyl)-5-(2-chloroethyl)-2-indolinone |
| 10733 | G | 7 | 3-(4-benzyloxy-3,5-dimethylbenzylidenyl)-5-(2-chloroethyl)-2-indolinone |
| 10733 | G | 8 | 3-(5-bromo-2-hydroxy-3-methoxybenzylidenyl)-5-(2-chloroethyl)-2-indolinone |
| 10733 | G | 9 | 3-(5-bromo-2-hydroxybenzylidenyl)-5-(2-chloroethyl)-2-indolinone |
| 10733 | G | 10 | 3-(2-hydroxy-5-nitrobenzylidenyl)-5-(2-chloroethyl)-2-indolinone |
| 10733 | G | 11 | 3-(4-hydroxy-3-methoxy-2-nitrobenzylidenyl)-5-(2-chloroethyl)-2-indolinone |
| 10734 | A | 2 | 3-(3-ethoxy-2-hydroxybenzylidenyl)-5,7-dibromo-2-indolinone |
| 10734 | A | 3 | 3-(3,5-dichloro-2-hydroxybenzylidenyl)-5,7-dibromo-2-indolinone |
| 10734 | A | 4 | 3-(5-chloro-2-hydroxybenzylidenyl)-5,7-dibromo-2-indolinone |
| 10734 | A | 5 | 3-(4-diethylamino-2-hydroxybenzylidenyl)-5,7-dibromo-2-indolinone |
| 10734 | A | 6 | 3-(4-nitrobenzylidenyl)-5,7-dibromo-2-indolinone |
| 10734 | A | 7 | 3-(3,5-dibromo-2-hydroxybenzylidenyl)-5,7-dibromo-2-indolinone |
| 10734 | A | 8 | 3-(3-fluoro-2-hydroxybenzylidenyl)-5,7-dibromo-2-indolinone |
| 10734 | A | 9 | 3-(3-bromo-4-hydroxybenzylidenyl)-5,7-dibromo-2-indolinone |
| 10734 | A | 10 | 3-(4-t-butylbenzylidenyl)-5,7-dibromo-2-indolinone |
| 10734 | A | 11 | 3-[(2-bromothien-5-yl)methylidenyl]-5,7-dibromo-2-indolinone |
| 10734 | B | 2 | 3-(3-ethoxy-2-hydroxybenzylidenyl)-5-iodo-2-indolinone |
| 10734 | B | 3 | 3-(3,5-dichloro-2-hydroxybenzylidenyl)-5-iodo-2-indolinone |
| 10734 | B | 4 | 3-(5-chloro-2-hydroxybenzylidenyl)-5-iodo-2-indolinone |
| 10734 | B | 5 | 3-(4-diethylamino-2-hydroxybenzylidenyl)-5-iodo-2-indolinone |
| 10734 | B | 6 | 3-(4-nitrobenzylidenyl)-5-iodo-2-indolinone |
| 10734 | B | 7 | 3-(3,5-dibromo-2-hydroxybenzylidenyl)-5-iodo-2-indolinone |
| 10734 | B | 8 | 3-(3-fluoro-2-hydroxybenzylidenyl)-5-iodo-2-indolinone |
| 10734 | B | 9 | 3-(3-bromo-4-hydroxybenzylidenyl)-5-iodo-2-indolinone |
| 10734 | B | 10 | 3-(4-t-butylbenzylidenyl)-5-iodo-2-indolinone |
| 10734 | B | 11 | 3-[(2-bromothien-5-yl)methylidenyl]-5-iodo-2-indolinone |
| 10734 | C | 2 | 3-(3-ethoxy-2-hydroxybenzylidenyl)-5-bromo-4-methyl-2-indolinone |
| 10734 | C | 3 | 3-(3,5-dichloro-2-hydroxybenzylidenyl)-5-bromo-4-methyl-2-indolinone |
| 10734 | C | 4 | 3-(5-chloro-2-hydroxybenzylidenyl)-5-bromo-4-methyl-2-indolinone |
| 10734 | C | 5 | 3-(4-diethylamino-2-hydroxybenzylidenyl)-5-bromo-4-methyl-2-indolinone |
| 10734 | C | 6 | 3-(4-nitrobenzylidenyl)-5-bromo-4-methyl-2-indolinone |

TABLE 13-continued

| MASTER BARCODE | PLATE ROW | PLATE COLUMN | NAME |
|---|---|---|---|
| 10734 | C | 7 | 3-(3,5-dibromo-2-hydroxybenzylidenyl)-5-bromo-4-methyl-2-indolinone |
| 10734 | C | 8 | 3-(3-fluoro-2-hydroxybenzylidenyl)-5-bromo-4-methyl-2-indolinone |
| 10734 | C | 9 | 3-(3-bromo-4-hydroxybenzylidenyl)-5-bromo-4-methyl-2-indolinone |
| 10734 | C | 10 | 3-(4-t-butylbenzylidenyl)-5-bromo-4-methyl-2-indolinone |
| 10734 | C | 11 | 3-[(2-bromothien-5-yl)methylidenyl]-5-bromo-4-methyl-2-indolinone |
| 10734 | D | 2 | 3-(3-ethoxy-2-hydroxybenzylidenyl)-5-methylaminosulfonyl-2-indolinone |
| 10734 | D | 3 | 3-(3,5-dichloro-2-hydroxybenzylidenyl)-5-methylaminosulfonyl-2-indolinone |
| 10734 | D | 4 | 3-(5-chloro-2-hydroxybenzylidenyl)-5-methylaminosulfonyl-2-indolinone |
| 10734 | D | 5 | 3-(4-diethylamino-2-hydroxybenzylidenyl)-5-methylaminosulfonyl-2-indolinone |
| 10734 | D | 6 | 3-(4-nitrobenzylidenyl)-5-methylaminosulfonyl-2-indolinone |
| 10734 | D | 7 | 3-(3,5-dibromo-2-hydroxybenzylidenyl)-5-methylaminosulfonyl-2-indolinone |
| 10734 | D | 8 | 3-(3-fluoro-2-hydroxybenzylidenyl)-5-methylaminosulfonyl-2-indolinone |
| 10734 | D | 9 | 3-(3-bromo-4-hydroxybenzylidenyl)-5-methylaminosulfonyl-2-indolinone |
| 10734 | D | 10 | 3-(4-t-butylbenzylidenyl)-5-methylaminosulfonyl-2-indolinone |
| 10734 | D | 11 | 3-[(2-bromothien-5-yl)methylidenyl]-5-methylaminosulfonyl-2-indolinone |
| 10734 | E | 2 | 3-(3-ethoxy-2-hydroxybenzylidenyl)-5-[4-(trifluoromethyl)phenylaminosulfonyl]-2-indolinone |
| 10734 | E | 3 | 3-(3,5-dichloro-2-hydroxybenzylidenyl)-5-[4-(trifluoromethyl)phenylaminosulfonyl]-2-indolinone |
| 10734 | E | 4 | 3-(5-chloro-2-hydroxybenzylidenyl)-5-[4-(trifluoromethyl)phenylaminosulfonyl]-2-indolinone |
| 10734 | E | 5 | 3-(4-diethylamino-2-hydroxybenzylidenyl)-5-[4-(trifluoromethyl)phenylaminosulfonyl]-2-indolinone |
| 10734 | E | 6 | 3-(4-nitrobenzylidenyl)-5-[4-(trifluoromethyl)phenylaminosulfonyl]-2-indolinone |
| 10734 | E | 7 | 3-(3,5-dibromo-2-hydroxybenzylidenyl)-5-[4-(trifluoromethyl)phenylaminosulfonyl]-2-indolinone |
| 10734 | E | 8 | 3-(3-fluoro-2-hydroxybenzylidenyl)-5-[4-(trifluoromethyl)phenylaminosulfonyl]-2-indolinone |
| 10734 | E | 9 | 3-(3-bromo-4-hydroxybenzylidenyl)-5-[4-(trifluoromethyl)phenylaminosulfonyl]-2-indolinone |
| 10734 | E | 10 | 3-(4-t-butylbenzylidenyl)-5-[4-(trifluoromethyl)phenylaminosulfonyl]-2-indolinone |
| 10734 | E | 11 | 3-[(2-bromothien-5-yl)methylidenyl]-5-[4-(trifluoromethyl)phenylaminosulfonyl]-2-indolinone |
| 10734 | F | 2 | 3-(3-ethoxy-2-hydroxybenzylidenyl)-5-(morpholin-1-yl)sulfonyl-2-indolinone |
| 10734 | F | 3 | 3-(3,5-dichloro-2-hydroxybenzylidenyl)-5-(morpholin-1-yl)sulfonyl-2-indolinone |
| 10734 | F | 4 | 3-(5-chloro-2-hydroxybenzylidenyl)-5-(morpholin-1-yl)sulfonyl-2-indolinone |
| 10734 | F | 5 | 3-(4-diethylamino-2-hydroxybenzylidenyl)-5-(morpholin-1-yl)sulfonyl-2-indolinone |
| 10734 | F | 6 | 3-(4-nitrobenzylidenyl)-5-(morpholin-1-yl)sulfonyl-2-indolinone |
| 10734 | F | 7 | 3-(3,5-dibromo-2-hydroxybenzylidenyl)-5-(morpholin-1-yl)sulfonyl-2-indolinone |
| 10734 | F | 8 | 3-(3-fluoro-2-hydroxybenzylidenyl)-5-(morpholin-1-yl)sulfonyl-2-indolinone |
| 10734 | F | 9 | 3-(3-bromo-4-hydroxybenzylidenyl)-5-(morpholin-1-yl)sulfonyl-2-indolinone |
| 10734 | F | 10 | 3-(4-t-butylbenzylidenyl)-5-(morpholin-1-yl)sulfonyl-2-indolinone |
| 10734 | F | 11 | |
| 10734 | G | 2 | 3-(3-ethoxy-2-hydroxybenzylidenyl)-5-(2-chloroethyl)-2-indolinone |
| 10734 | G | 3 | 3-(3,5-dichloro-2-hydroxybenzylidenyl)-5-(2-chloroethyl)-2-indolinone |
| 10734 | G | 4 | 3-(5-chloro-2-hydroxybenzylidenyl)-5-(2-chloroethyl)-2-indolinone |

TABLE 13-continued

| MASTER BARCODE | PLATE ROW | PLATE COLUMN | NAME |
|---|---|---|---|
| 10734 | G | 5 | 3-(4-diethylamino-2-hydroxybenzylidenyl)-5-(2-chloroethyl)-2-indolinone |
| 10734 | G | 6 | 3-(4-nitrobenzylidenyl)-5-(2-chloroethyl)-2-indolinone |
| 10734 | G | 7 | 3-(3,5-dibromo-2-hydroxybenzylidenyl)-5-(2-chloroethyl)-2-indolinone |
| 10734 | G | 8 | 3-(3-fluoro-2-hydroxybenzylidenyl)-5-(2-chloroethyl)-2-indolinone |
| 10734 | G | 9 | 3-(3-bromo-4-hydroxybenzylidenyl)-5-(2-chloroethyl)-2-indolinone |
| 10734 | G | 10 | 3-(4-t-butylbenzylidenyl)-5-(2-chloroethyl)-2-indolinone |
| 10734 | G | 11 | 3-[(2-bromothien-5-yl)methylidenyl]-5-(2-chloroethyl)-2-indolinone |

TABLE 14

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10717/A02 | 0.1 | 24.3 |  | 46.1 |
| 10717/A03 | 2.9 | 1.0 |  | 54.6 |
| 10717/A04 | −4.5 | 29.0 |  | 37.4 |
| 10717/A05 | −2.6 | 16.6 |  | 35.6 |
| 10717/A06 | −10.8 | −7.8 |  | 31.7 |
| 10717/A07 | −6.4 | 20.2 |  | 29.2 |
| 10717/A08 | −5.2 | 39.1 |  | 21.7 |
| 10717/A09 | −3.9 | 37.7 |  | 9.4 |
| 10717/A10 | −3.3 | 8.1 |  | 71.6 |
| 10717/A11 | −5.8 | 59.9 |  | 64.8 |
| 10717/B02 | 5.0 | 31.7 |  | 87.5 |
| 10717/B03 | −8.8 | 7.3 |  | 90.5 |
| 10717/B04 | −18.3 | 10.3 |  | 70.0 |
| 10717/B05 | 1.0 | 31.7 |  | 87.4 |
| 10717/B06 | 5.4 | −30.8 |  | 89.5 |
| 10717/B07 | −18.3 | 58.3 |  | 90.0 |
| 10717/B08 | −0.9 | 60.5 |  | 88.8 |
| 10717/B09 | −40.7 | 78.3 |  | 88.8 |
| 10717/B10 | −2.3 | 16.1 |  | 56.1 |
| 10717/B11 | 11.4 | 82.7 |  | 91.0 |
| 10717/C02 | 4.1 | −0.4 |  | 29.7 |
| 10717/C03 | −7.7 | 18.0 |  | 25.3 |
| 10717/C04 | −0.8 | 14.4 |  | 25.0 |
| 10717/C05 | −2.3 | 13.1 |  | 44.6 |
| 10717/C06 | 7.6 | −49.7 |  | 44.1 |
| 10717/C07 | 1.6 | 28.7 |  | 16.5 |
| 10717/C08 | 7.0 | 24.3 |  | 27.3 |
| 10717/C09 | 77.1 | 8.1 |  | 47.7 |
| 10717/C10 | −8.0 | 17.5 |  | 22.8 |
| 10717/C11 | 4.6 | 67.3 |  | 71.8 |
| 10717/D02 | 5.1 | 10.1 |  | 28.6 |
| 10717/D03 | 1.1 | −1.4 |  | 11.1 |
| 10717/D04 | −2.1 | 4.9 |  | 21.0 |
| 10717/D05 | −3.8 | −2.8 |  | 23.8 |
| 10717/D06 | 1.0 | −23.4 |  | 33.8 |
| 10717/D07 | −8.4 | −4.5 |  | 16.8 |
| 10717/D08 | 6.8 | −7.8 |  | 16.0 |
| 10717/D09 | −55.0 | 6.8 |  | 29.1 |
| 10717/D10 | −6.0 | 3.5 |  | 15.6 |
| 10717/D11 | 11.6 | 59.1 |  | 55.3 |
| 10717/E02 | 17.9 | 17.2 |  | 24.0 |
| 10717/E03 | 19.0 | 11.7 |  | 52.2 |
| 10717/E04 | 6.1 | −28.3 |  | 29.4 |
| 10717/E05 | 13.2 | 22.4 |  | 39.1 |
| 10717/E06 | 7.5 | −26.1 |  | 24.8 |
| 10717/E07 | 15.3 | −7.8 |  | 41.0 |
| 10717/E08 | 13.2 | 28.2 |  | 51.7 |
| 10717/E09 | −1.1 | −5.8 |  | 19.2 |
| 10717/E10 | 4.7 | −6.1 |  | 35.9 |
| 10717/E11 | 8.9 | 44.9 |  | 75.1 |
| 10717/F02 | 2.2 | 6.2 |  | 30.4 |
| 10717/F03 | 0.5 | −4.7 |  | 42.8 |
| 10717/F04 | −0.1 | −15.7 |  | 11.4 |
| 10717/F05 | 3.2 | −20.1 |  | 21.5 |
| 10717/F06 | 8.9 | −22.8 |  | 49.0 |
| 10717/F07 | 2.0 | −14.3 |  | 37.6 |
| 10717/F08 | −0.7 | −23.4 |  | 64.0 |
| 10717/F09 | −13.3 | 1.8 |  | 41.4 |
| 10717/F10 | −4.4 | −26.4 |  | 54.6 |
| 10717/F11 | 1.4 | 91.2 |  | 81.5 |
| 10717/G02 | 14.9 | 32.3 |  | 30.7 |
| 10717/G03 | 1.8 | 18.8 |  | 4.5 |
| 10717/G04 | 0.8 | 6.0 |  | 10.9 |
| 10717/G05 | 5.3 | −0.1 |  | 4.7 |
| 10717/G06 | 4.3 | −3.4 |  | 34.0 |
| 10717/G07 | −17.0 | 13.1 |  | 7.5 |
| 10717/G08 | 1.9 | 36.4 |  | 10.9 |
| 10717/G09 | −29.7 | 24.9 |  | 19.1 |
| 10717/G10 | 4.8 | 2.4 |  | 30.9 |
| 10717/G11 | 16.4 | 71.7 |  | 73.8 |
| 10718/A02 | 3.0 | 11.3 |  | 54.6 |
| 10718/A03 | 7.6 | −6.1 |  | 92.7 |
| 10718/A04 | 6.9 | 27.3 |  | 81.7 |
| 10718/A05 | 3.2 | −6.9 |  | 36.1 |
| 10718/A06 | 7.8 | 19.4 |  | 61.3 |
| 10718/A07 | 16.2 | −10.6 |  | 58.6 |
| 10718/A08 | 3.2 | 5.8 |  | 36.8 |
| 10718/A09 | −18.4 | −4.1 |  | 67.7 |
| 10718/A10 | 23.4 | 41.5 |  | 77.9 |
| 10718/A11 | 2.7 | 21.2 |  | 58.9 |
| 10718/B02 | 7.0 | 24.9 |  | 52.9 |
| 10718/B03 | 1.7 | −0.2 |  | 77.9 |
| 10718/B04 | 11.8 | 8.5 |  | 63.9 |
| 10718/B05 | 11.5 | 56.3 |  | 76.0 |
| 10718/B06 | 16.5 | 28.5 |  | 78.4 |
| 10718/B07 | 17.7 | 9.9 |  | 53.7 |
| 10718/B08 | 5.4 | 28.9 |  | 63.4 |
| 10718/B09 | −14.7 | −0.8 |  | 52.9 |
| 10718/B10 | 20.1 | 13.7 |  | 83.6 |
| 10718/B11 | 4.5 | 30.3 |  | 69.6 |
| 10718/C02 | 26.2 | −21.9 |  | 29.6 |
| 10718/C03 | −13.9 | 41.3 |  | 95.7 |
| 10718/C04 | 15.3 | 14.8 |  | 93.1 |
| 10718/C05 | 20.5 | 10.9 |  | 8.7 |
| 10718/C06 | 16.8 | 5.6 |  | 3.9 |
| 10718/C07 | 6.3 | −4.9 |  | 29.6 |
| 10718/C08 | 19.6 | 13.1 |  | 22.7 |
| 10718/C09 | 5.3 | 26.5 |  | 38.2 |
| 10718/C10 | −11.9 | −18.7 |  | 4.4 |
| 10718/C11 | 11.4 | −0.2 |  | 10.1 |
| 10718/D02 | 13.3 | 14.4 |  | 32.0 |
| 10718/D03 | 1.1 | 61.9 |  | 92.9 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10718/D04 | 6.4 | 52.0 | | 92.9 |
| 10718/D05 | 11.5 | 2.8 | | 10.6 |
| 10718/D06 | 15.8 | 20.0 | | 11.1 |
| 10718/D07 | 7.8 | 5.6 | | 26.1 |
| 10718/D08 | 3.9 | 3.0 | | 2.3 |
| 10718/D09 | −9.1 | 6.0 | | 9.9 |
| 10718/D10 | 15.0 | 12.3 | | 55.3 |
| 10718/D11 | 13.3 | 5.4 | | 11.3 |
| 10718/E02 | 19.7 | 1.0 | | 46.3 |
| 10718/E03 | 10.0 | 50.4 | | 95.3 |
| 10718/E04 | 15.1 | 16.4 | | 87.7 |
| 10718/E05 | 16.1 | −3.1 | | 32.2 |
| 10718/E06 | 15.4 | 2.0 | | 33.4 |
| 10718/E07 | 15.6 | 13.9 | | 80.5 |
| 10718/E08 | 9.2 | 9.3 | | 69.6 |
| 10718/E09 | 0.9 | 17.0 | | 80.8 |
| 10718/E10 | 15.2 | −7.5 | | 60.8 |
| 10718/E11 | 12.1 | −15.2 | | 37.5 |
| 10718/F02 | 20.1 | 17.8 | | 66.7 |
| 10718/F03 | −0.2 | 22.5 | | 87.9 |
| 10718/F04 | 9.4 | 1.2 | | 78.1 |
| 10718/F05 | 19.5 | −4.9 | | 53.7 |
| 10718/F06 | 18.3 | −9.1 | | 42.5 |
| 10718/F07 | 16.5 | −6.3 | | 67.9 |
| 10718/F08 | 15.3 | −8.7 | | 28.4 |
| 10718/F09 | −3.0 | −9.5 | | 52.7 |
| 10718/F10 | 17.9 | −12.0 | | 23.7 |
| 10718/F11 | 10.1 | −3.9 | | 31.3 |
| 10718/G02 | −2.5 | 49.2 | | 67.7 |
| 10718/G03 | −4.7 | 57.3 | | 77.9 |
| 10718/G04 | 1.8 | 15.8 | | 78.1 |
| 10718/G05 | 3.7 | 2.8 | | 60.3 |
| 10718/G06 | 9.8 | −18.7 | | 61.0 |
| 10718/G07 | 11.4 | −21.3 | | 52.0 |
| 10718/G08 | 6.1 | −8.3 | | 17.5 |
| 10718/G09 | −12.8 | −15.4 | | 27.0 |
| 10718/G10 | 7.1 | −7.5 | | 10.8 |
| 10718/G11 | 15.6 | −4.9 | | 3.0 |
| 10719/A02 | 21.4 | 43.0 | | 40.9 |
| 10719/A03 | 3.9 | 67.7 | | 84.1 |
| 10719/A04 | 19.2 | 43.7 | | 22.9 |
| 10719/A05 | 10.0 | 23.1 | | 39.6 |
| 10719/A06 | 14.0 | 18.2 | | −7.0 |
| 10719/A07 | 21.3 | 15.5 | | 68.1 |
| 10719/A08 | 11.9 | 47.3 | | 75.5 |
| 10719/A09 | 12.3 | 2.2 | | 47.0 |
| 10719/A10 | 10.9 | 8.2 | | 13.4 |
| 10719/A11 | 7.4 | 10.5 | | 34.9 |
| 10719/B02 | 11.5 | 29.0 | | 47.0 |
| 10719/B03 | 14.2 | 59.5 | | 85.8 |
| 10719/B04 | 24.9 | 29.9 | | 38.4 |
| 10719/B05 | 17.7 | 35.9 | | 33.6 |
| 10719/B06 | 21.3 | −0.5 | | 22.5 |
| 10719/B07 | 12.5 | 23.7 | | 52.2 |
| 10719/B08 | 4.0 | 42.3 | | 33.2 |
| 10719/B09 | 11.3 | −17.7 | | 23.5 |
| 10719/B10 | 1.1 | −1.2 | | 53.4 |
| 10719/B11 | 11.2 | −23.9 | | 36.5 |
| 10719/C02 | 4.1 | 10.2 | | 41.3 |
| 10719/C03 | 15.3 | 60.6 | | 69.1 |
| 10719/C04 | 59.9 | 14.4 | | 14.7 |
| 10719/C05 | 25.6 | 27.4 | | 35.5 |
| 10719/C06 | 47.7 | −14.3 | | 18.4 |
| 10719/C07 | 31.2 | 14.4 | | 7.7 |
| 10719/C08 | 15.0 | −10.2 | | 57.5 |
| 10719/C09 | 23.5 | −0.1 | | 8.9 |
| 10719/C10 | 11.8 | 10.7 | | 7.9 |
| 10719/C11 | 9.9 | −25.7 | | −5.1 |
| 10719/D02 | 9.7 | 9.8 | | 27.5 |
| 10719/D03 | 4.8 | 95.7 | | 93.2 |
| 10719/D04 | 27.8 | 15.3 | | 28.9 |
| 10719/D05 | 16.3 | 18.5 | | 71.8 |
| 10719/D06 | 25.8 | −12.2 | | 11.2 |
| 10719/D07 | −123.5 | 13.7 | | 41.5 |
| 10719/D08 | 8.2 | −12.2 | | 45.2 |
| 10719/D09 | 7.8 | −3.1 | | 13.0 |
| 10719/D10 | 8.3 | −11.8 | | 22.3 |
| 10719/D11 | −8.7 | −11.1 | | 12.8 |
| 10719/E02 | 26.1 | 40.0 | | 35.7 |
| 10719/E03 | 17.1 | 73.0 | | 87.2 |
| 10719/E04 | 31.2 | −7.4 | | 3.1 |
| 10719/E05 | 21.5 | 21.2 | | 39.0 |
| 10719/E06 | 17.1 | −42.0 | | −4.5 |
| 10719/E07 | 26.7 | −18.4 | | 55.5 |
| 10719/E08 | 21.8 | 36.8 | | 80.0 |
| 10719/E09 | 13.5 | −33.1 | | 36.1 |
| 10719/E10 | 17.6 | −32.4 | | 40.2 |
| 10719/E11 | 26.3 | −51.8 | | 28.5 |
| 10719/F02 | 28.6 | 14.8 | | 28.1 |
| 10719/F03 | 11.2 | −30.8 | | 89.5 |
| 10719/F04 | 26.6 | −6.0 | | 3.3 |
| 10719/F05 | 20.7 | 35.0 | | 63.1 |
| 10719/F06 | 13.5 | −26.0 | | −22.0 |
| 10719/F07 | 18.7 | 20.1 | | 36.7 |
| 10719/F08 | 15.1 | 90.9 | | 75.7 |
| 10719/F09 | −6.5 | −17.7 | | 19.2 |
| 10719/F10 | 10.4 | −17.7 | | 30.8 |
| 10719/F11 | 11.6 | −66.3 | | 8.7 |
| 10719/G02 | 27.3 | −12.2 | | −2.4 |
| 10719/G03 | −25.8 | 89.5 | | 87.6 |
| 10719/G04 | 11.5 | −4.7 | | −8.2 |
| 10719/G05 | 18.0 | 4.0 | | 15.9 |
| 10719/G06 | 23.2 | −45.7 | | −18.1 |
| 10719/G07 | 20.1 | −8.1 | | 24.0 |
| 10719/G08 | 3.2 | 65.4 | | 39.4 |
| 10719/G09 | 18.1 | −32.8 | | 1.3 |
| 10719/G10 | 9.7 | −27.6 | | 35.5 |
| 10719/G11 | 6.9 | −44.1 | | 24.0 |
| 10720/A02 | 4.7 | 11.3 | | 45.2 |
| 10720/A03 | 17.7 | −5.3 | | 58.2 |
| 10720/A04 | 12.3 | −1.8 | | 62.3 |
| 10720/A05 | 8.0 | −4.4 | | 43.4 |
| 10720/A06 | 5.6 | 44.7 | | 63.6 |
| 10720/A07 | 6.6 | 42.5 | | 57.2 |
| 10720/A08 | −2.2 | −23.2 | | 77.9 |
| 10720/A09 | 8.1 | 8.6 | | 75.4 |
| 10720/A10 | −5.2 | −2.7 | | 68.4 |
| 10720/A11 | −0.6 | −23.2 | | 58.7 |
| 10720/B02 | 6.5 | 18.4 | | 38.8 |
| 10720/B03 | 6.4 | 32.3 | | 53.3 |
| 10720/B04 | 9.8 | 50.5 | | 61.8 |
| 10720/B05 | 11.6 | 58.4 | | 51.8 |
| 10720/B06 | 7.3 | 21.2 | | 55.1 |
| 10720/B07 | 12.0 | 52.0 | | 61.5 |
| 10720/B08 | 3.6 | −12.6 | | 27.7 |
| 10720/B09 | 10.1 | 37.6 | | 57.4 |
| 10720/B10 | −5.5 | 50.2 | | 45.2 |
| 10720/B11 | −20.3 | 22.4 | | 42.1 |
| 10720/C02 | 18.0 | 23.5 | | 63.6 |
| 10720/C03 | 15.1 | 0.9 | | 50.3 |
| 10720/C04 | 15.3 | −13.1 | | 29.0 |
| 10720/C05 | −36.1 | −15.3 | | 72.5 |
| 10720/C06 | 12.2 | −9.7 | | 36.7 |
| 10720/C07 | 20.7 | −25.4 | | 26.7 |
| 10720/C08 | 10.9 | −1.1 | | 65.6 |
| 10720/C09 | 12.1 | 44.7 | | 47.5 |
| 10720/C10 | −21.1 | 2.0 | | 62.6 |
| 10720/C11 | 52.5 | −21.9 | | 30.0 |
| 10720/D02 | 12.1 | 11.1 | | 17.8 |
| 10720/D03 | 17.0 | 0.9 | | 61.5 |
| 10720/D04 | 15.6 | −7.7 | | 23.6 |
| 10720/D05 | 4.8 | −24.1 | | 9.8 |
| 10720/D06 | 10.1 | −35.0 | | 31.8 |
| 10720/D07 | 11.8 | 14.8 | | 36.2 |
| 10720/D08 | 3.3 | −13.3 | | 42.1 |
| 10720/D09 | 5.8 | 2.4 | | 62.8 |
| 10720/D10 | −6.6 | −10.2 | | 51.0 |
| 10720/D11 | 9.8 | −5.5 | | 23.9 |
| 10720/E02 | 5.7 | 25.2 | | 18.0 |
| 10720/E03 | 34.3 | 54.4 | | 54.9 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10720/E04 | 18.4 | -2.7 | | 46.7 |
| 10720/E05 | -13.8 | 40.7 | | 55.4 |
| 10720/E06 | 25.5 | 30.1 | | 33.1 |
| 10720/E07 | 18.8 | 55.1 | | 30.3 |
| 10720/E08 | 2.5 | 37.4 | | 55.1 |
| 10720/E09 | 11.5 | 56.4 | | 43.4 |
| 10720/E10 | -4.1 | 49.1 | | 23.1 |
| 10720/E11 | 9.3 | -65.5 | | -10.4 |
| 10720/F02 | 9.1 | -19.3 | | 17.8 |
| 10720/F03 | 10.6 | 7.1 | | 44.1 |
| 10720/F04 | 10.6 | -11.7 | | 43.1 |
| 10720/F05 | -3.6 | -14.2 | | 39.8 |
| 10720/F06 | 11.9 | -24.3 | | 21.9 |
| 10720/F07 | 4.6 | 35.2 | | 64.6 |
| 10720/F08 | -4.1 | -39.6 | | 36.2 |
| 10720/F09 | 5.9 | 6.4 | | 49.2 |
| 10720/F10 | -2.6 | 6.0 | | 42.8 |
| 10720/F11 | 5.0 | -61.1 | | 1.6 |
| 10720/G02 | 5.0 | -13.1 | | 20.1 |
| 10720/G03 | 2.6 | 10.0 | | 42.1 |
| 10720/G04 | 2.4 | -34.1 | | 5.0 |
| 10720/G05 | -2.9 | 27.0 | | 37.0 |
| 10720/G06 | -3.4 | -10.4 | | 21.6 |
| 10720/G07 | 5.1 | -8.0 | | 12.9 |
| 10720/G08 | -17.9 | -9.5 | | 26.7 |
| 10720/G09 | 2.1 | -19.7 | | 49.5 |
| 10720/G10 | -36.6 | 20.4 | | 55.9 |
| 10720/G11 | -18.0 | -56.7 | | 36.2 |
| 10721/A02 | 10.6 | 17.8 | | 41.1 |
| 10721/A03 | 11.4 | 25.5 | | 56.2 |
| 10721/A04 | 6.5 | 59.0 | | 85.0 |
| 10721/A05 | 12.5 | 41.4 | | 52.9 |
| 10721/A06 | 6.4 | 32.7 | | 81.3 |
| 10721/A07 | -4.7 | 35.2 | | 29.7 |
| 10721/A08 | 4.8 | 24.0 | | 29.9 |
| 10721/A09 | 10.9 | 28.0 | | 23.0 |
| 10721/A10 | 5.2 | 31.1 | | 68.9 |
| 10721/A11 | 4.8 | 24.6 | | 23.9 |
| 10721/B02 | 19.5 | 58.6 | | 82.6 |
| 10721/B03 | 19.9 | 38.9 | | 70.8 |
| 10721/B04 | 13.8 | 79.3 | | 93.1 |
| 10721/B05 | 45.9 | 76.8 | | 70.8 |
| 10721/B06 | 3.4 | 71.5 | | 92.4 |
| 10721/B07 | 11.2 | 47.6 | | 47.1 |
| 10721/B08 | 18.5 | 64.0 | | 64.5 |
| 10721/B09 | 9.0 | 38.9 | | 28.3 |
| 10721/B10 | 20.9 | 42.9 | | 30.4 |
| 10721/B11 | -2.1 | 34.6 | | 6.7 |
| 10721/C02 | 9.7 | 68.3 | | 59.2 |
| 10721/C03 | 16.5 | 64.6 | | 6.2 |
| 10721/C04 | 21.8 | 77.7 | | 88.7 |
| 10721/C05 | 56.4 | 68.1 | | 48.7 |
| 10721/C06 | 14.4 | 80.2 | | 56.4 |
| 10721/C07 | 10.9 | 24.6 | | 25.7 |
| 10721/C08 | 55.8 | 38.3 | | 24.8 |
| 10721/C09 | 17.5 | 39.8 | | -4.7 |
| 10721/C10 | 21.1 | 17.4 | | 44.6 |
| 10721/C11 | 13.9 | 14.1 | | 3.7 |
| 10721/D02 | 15.1 | 21.5 | | 22.5 |
| 10721/D03 | 17.8 | 11.6 | | 19.5 |
| 10721/D04 | 15.2 | 5.0 | | 35.3 |
| 10721/D05 | -25.1 | 47.0 | | 91.9 |
| 10721/D06 | 1.6 | 44.5 | | 9.0 |
| 10721/D07 | 6.4 | 23.0 | | -6.8 |
| 10721/D08 | 3.9 | 31.7 | | 45.3 |
| 10721/D09 | 17.6 | 15.3 | | -4.9 |
| 10721/D10 | 23.7 | 3.3 | | 13.4 |
| 10721/D11 | 20.6 | 22.2 | | 23.2 |
| 10721/E02 | 17.2 | -9.5 | | 38.8 |
| 10721/E03 | 10.9 | 25.1 | | 12.3 |
| 10721/E04 | 16.0 | 48.5 | | 87.3 |
| 10721/E05 | 10.8 | 61.3 | | 69.9 |
| 10721/E06 | 40.4 | 91.5 | | 81.0 |
| 10721/E07 | 15.6 | 37.7 | | 43.6 |
| 10721/E08 | 15.7 | 29.8 | | 39.5 |
| 10721/E09 | 36.9 | 42.5 | | 0.7 |
| 10721/E10 | 9.3 | 19.9 | | 55.7 |
| 10721/E11 | 0.7 | 32.1 | | 31.3 |
| 10721/F02 | 17.0 | 11.0 | | 27.8 |
| 10721/F03 | 9.1 | 7.0 | | 40.6 |
| 10721/F04 | 7.4 | 0.0 | | 26.0 |
| 10721/F05 | 8.1 | 20.5 | | 67.8 |
| 10721/F06 | 2.2 | 21.7 | | 80.3 |
| 10721/F07 | 4.8 | 3.5 | | 55.7 |
| 10721/F08 | -6.4 | 37.3 | | 76.1 |
| 10721/F09 | 65.2 | 7.0 | | 52.5 |
| 10721/F10 | 49.6 | 7.5 | | 79.9 |
| 10721/F11 | 29.7 | 95.9 | | 78.2 |
| 10721/G02 | 16.4 | 23.6 | | 7.9 |
| 10721/G03 | 12.1 | 23.4 | | 25.3 |
| 10721/G04 | 3.2 | 64.6 | | 90.3 |
| 10721/G05 | -15.1 | 7.7 | | 8.6 |
| 10721/G06 | 18.9 | 23.2 | | 39.5 |
| 10721/G07 | 3.3 | 14.7 | | 10.0 |
| 10721/G08 | 5.4 | 12.8 | | -2.4 |
| 10721/G09 | 20.4 | 14.9 | | 5.1 |
| 10721/G10 | 24.4 | 2.1 | | 12.0 |
| 10721/G11 | -7.1 | 0.4 | | -0.0 |
| 10722/A02 | 0.8 | 23.7 | 28.9 | 44.9 |
| 10722/A03 | 6.7 | 0.8 | 29.5 | 90.3 |
| 10722/A04 | 13.4 | 21.0 | -0.9 | 51.4 |
| 10722/A05 | 10.5 | 22.4 | 33.5 | 90.5 |
| 10722/A06 | 9.6 | 28.4 | 19.8 | 71.6 |
| 10722/A07 | 9.4 | 29.9 | 23.8 | 64.1 |
| 10722/A08 | 13.7 | 23.9 | 15.2 | 70.5 |
| 10722/A09 | 7.3 | 16.8 | 21.5 | 86.5 |
| 10722/A10 | 6.6 | -4.2 | 15.2 | 79.0 |
| 10722/A11 | 6.7 | -0.1 | 21.5 | 68.6 |
| 10722/B02 | 10.1 | 16.3 | 28.9 | 44.3 |
| 10722/B03 | 13.6 | 19.6 | 3.7 | 40.1 |
| 10722/B04 | 14.7 | 10.6 | 3.1 | 53.4 |
| 10722/B05 | 18.5 | 9.3 | 21.5 | 67.2 |
| 10722/B06 | 13.9 | -4.9 | 21.5 | 72.6 |
| 10722/B07 | 6.6 | 6.2 | 20.9 | 48.2 |
| 10722/B08 | 11.2 | 0.5 | 27.8 | 72.0 |
| 10722/B09 | 8.7 | 7.8 | 14.6 | 59.7 |
| 10722/B10 | -0.9 | -11.3 | 20.3 | 56.4 |
| 10722/B11 | 5.2 | -15.5 | 25.5 | 83.0 |
| 10722/C02 | 29.1 | 32.1 | 30.6 | 34.5 |
| 10722/C03 | 16.7 | 42.3 | 22.6 | 73.6 |
| 10722/C04 | 10.7 | 26.7 | 8.9 | 70.7 |
| 10722/C05 | 23.5 | 19.1 | 26.6 | 44.9 |
| 10722/C06 | 24.5 | -11.0 | 24.9 | 45.1 |
| 10722/C07 | 15.8 | -15.5 | 31.2 | 61.2 |
| 10722/C08 | 17.8 | 14.8 | 31.2 | 80.1 |
| 10722/C09 | 25.9 | -3.1 | 32.4 | 45.1 |
| 10722/C10 | 2.3 | 22.8 | 18.0 | 33.9 |
| 10722/C11 | 13.8 | -14.2 | 36.4 | 52.6 |
| 10722/D02 | 30.7 | 26.1 | 31.8 | 26.4 |
| 10722/D03 | 15.0 | 31.0 | -9.4 | 52.8 |
| 10722/D04 | 23.5 | 20.3 | 15.7 | 63.4 |
| 10722/D05 | 21.4 | -3.8 | 22.0 | 35.8 |
| 10722/D06 | 21.9 | -2.5 | 8.9 | 32.4 |
| 10722/D07 | 14.1 | -2.8 | 25.5 | 42.6 |
| 10722/D08 | 29.1 | -2.6 | 41.5 | 60.5 |
| 10722/D09 | 14.7 | -17.2 | 30.6 | 52.2 |
| 10722/D10 | 8.2 | -0.6 | 41.5 | 40.5 |
| 10722/D11 | 9.6 | -10.1 | 15.2 | 41.0 |
| 10722/E02 | 17.0 | 22.2 | 23.2 | 71.1 |
| 10722/E03 | 10.7 | 33.0 | -7.2 | 88.4 |
| 10722/E04 | 38.6 | 1.4 | 30.6 | 52.6 |
| 10722/E05 | 19.2 | -7.0 | 19.2 | 73.0 |
| 10722/E06 | 21.4 | 7.6 | 32.9 | 71.6 |
| 10722/E07 | 24.3 | 28.7 | 40.9 | 71.6 |
| 10722/E08 | 18.6 | 10.4 | 38.7 | 82.8 |
| 10722/E09 | 16.2 | 4.1 | 26.6 | 55.1 |
| 10722/E10 | 3.1 | -13.3 | 31.8 | 86.6 |
| 10722/E11 | 15.3 | 4.2 | 28.3 | 84.0 |
| 10722/F02 | 5.3 | 9.2 | 12.9 | 33.9 |
| 10722/F03 | 12.0 | 13.7 | -14.0 | 59.7 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10722/F04 | 27.5 | 16.8 | −2.0 | 58.9 |
| 10722/F05 | 15.0 | −2.8 | 6.0 | 6.4 |
| 10722/F06 | 11.0 | 6.5 | 2.6 | 6.0 |
| 10722/F07 | 15.5 | −3.7 | −6.6 | 63.0 |
| 10722/F08 | 66.3 | −5.4 | 25.5 | 89.3 |
| 10722/F09 | 15.3 | −35.8 | 26.6 | 65.7 |
| 10722/F10 | 3.3 | 10.7 | 24.9 | 67.8 |
| 10722/F11 | 4.5 | −6.5 | 15.7 | 73.2 |
| 10722/G02 | 15.1 | 27.3 | 14.6 | 43.0 |
| 10722/G03 | 5.3 | 4.1 | −3.7 | 52.2 |
| 10722/G04 | 7.2 | −13.3 | 11.7 | 63.2 |
| 10722/G05 | 10.8 | −9.0 | −6.0 | 9.7 |
| 10722/G06 | 7.4 | −5.2 | −6.0 | 12.2 |
| 10722/G07 | 8.0 | −32.5 | −3.7 | 41.2 |
| 10722/G08 | 8.2 | −8.5 | 12.9 | 66.1 |
| 10722/G09 | 6.1 | −5.9 | 0.9 | 51.0 |
| 10722/G10 | −1.7 | 3.3 | 16.9 | 27.0 |
| 10722/G11 | 0.6 | −39.4 | 0.3 | 35.3 |
| 10723/A02 | −5.5 | 97.8 | 64.4 | 100.8 |
| 10723/A03 | 1.2 | 38.5 | 11.7 | 76.5 |
| 10723/A04 | 27.2 | 30.8 | 13.1 | 97.9 |
| 10723/A05 | −17.8 | 26.4 | 17.9 | 75.7 |
| 10723/A06 | 8.6 | 20.1 | 43.6 | 79.1 |
| 10723/A07 | −6.1 | 3.9 | 22.1 | 63.2 |
| 10723/A08 | −12.9 | −2.1 | 29.7 | 77.3 |
| 10723/A09 | −1.0 | −4.5 | 42.9 | 85.9 |
| 10723/A10 | −3.1 | −24.8 | 34.6 | 62.1 |
| 10723/A11 | 42.9 | −4.0 | 41.5 | 60.0 |
| 10723/B02 | −0.3 | 91.0 | 29.0 | 100.3 |
| 10723/B03 | 7.1 | −5.0 | 14.5 | 82.5 |
| 10723/B04 | 18.7 | 5.1 | 40.1 | 90.6 |
| 10723/B05 | −15.4 | 36.4 | 15.2 | 85.1 |
| 10723/B06 | 31.8 | 11.9 | 58.8 | 90.6 |
| 10723/B07 | 6.5 | 28.8 | 24.9 | 86.7 |
| 10723/B08 | 1.0 | −0.4 | 56.1 | 82.8 |
| 10723/B09 | 2.7 | −12.0 | 27.6 | 57.7 |
| 10723/B10 | 5.8 | 1.8 | 17.2 | 88.5 |
| 10723/B11 | 6.3 | −26.0 | 22.8 | 62.6 |
| 10723/C02 | 9.6 | 73.6 | 39.4 | 100.6 |
| 10723/C03 | −3.1 | 5.9 | 42.9 | 88.8 |
| 10723/C04 | 8.8 | 23.5 | 36.7 | 91.9 |
| 10723/C05 | 5.6 | 35.2 | 22.8 | 73.1 |
| 10723/C06 | 17.8 | −4.5 | 26.3 | 63.4 |
| 10723/C07 | 20.9 | −4.0 | 27.6 | 44.3 |
| 10723/C08 | −35.5 | 45.0 | 29.0 | 83.0 |
| 10723/C09 | −22.3 | 62.7 | 62.3 | 84.6 |
| 10723/C10 | 9.5 | −7.2 | 25.6 | 43.8 |
| 10723/C11 | 9.5 | −1.1 | 8.9 | 47.0 |
| 10723/D02 | 2.0 | 63.2 | 22.1 | 93.0 |
| 10723/D03 | −14.7 | 33.5 | 8.2 | 69.4 |
| 10723/D04 | 15.2 | 45.1 | 31.8 | 97.7 |
| 10723/D05 | −6.1 | 3.7 | 8.2 | 54.5 |
| 10723/D06 | 17.6 | −7.4 | 6.2 | 60.0 |
| 10723/D07 | 15.8 | 13.4 | 16.6 | 21.9 |
| 10723/D08 | −4.5 | 4.9 | 31.1 | 53.5 |
| 10723/D09 | 50.4 | −3.8 | 21.4 | 62.6 |
| 10723/D10 | 6.5 | −9.3 | 21.4 | 38.1 |
| 10723/D11 | 14.8 | −6.2 | 24.9 | 42.0 |
| 10723/E02 | 8.1 | 91.0 | 46.4 | 97.9 |
| 10723/E03 | 8.7 | 8.3 | 47.1 | 76.8 |
| 10723/E04 | 30.7 | 59.8 | 36.0 | 94.5 |
| 10723/E05 | 8.9 | −15.6 | −4.9 | 63.7 |
| 10723/E06 | 19.3 | 11.5 | 18.6 | 74.4 |
| 10723/E07 | 17.4 | 38.1 | 14.5 | 47.7 |
| 10723/E08 | −0.4 | 52.6 | 26.3 | 89.3 |
| 10723/E09 | 7.9 | 29.1 | 22.1 | 91.7 |
| 10723/E10 | 5.2 | −7.9 | 44.3 | 59.5 |
| 10723/E11 | 8.9 | −44.6 | 32.5 | 50.1 |
| 10723/F02 | 10.3 | 70.4 | 1.3 | 99.0 |
| 10723/F03 | 4.4 | 9.3 | 1.3 | 78.3 |
| 10723/F04 | 12.3 | 17.5 | 21.4 | 94.0 |
| 10723/F05 | −6.4 | −3.8 | −7.7 | 45.6 |
| 10723/F06 | 20.4 | 5.4 | −30.6 | 84.1 |
| 10723/F07 | 20.7 | −4.1 | 6.8 | 26.6 |
| 10723/F08 | −0.5 | 5.7 | 20.7 | 75.5 |
| 10723/F09 | 1.2 | 14.1 | 3.4 | 78.6 |
| 10723/F10 | 9.1 | 4.2 | −2.2 | 74.1 |
| 10723/F11 | −1.2 | −41.3 | 36.7 | 72.3 |
| 10723/G02 | −1.6 | 90.8 | 13.8 | 99.2 |
| 10723/G03 | 4.3 | 18.5 | 6.2 | 74.7 |
| 10723/G04 | 8.7 | 16.7 | 21.4 | 85.9 |
| 10723/G05 | −9.4 | 1.3 | 2.0 | 79.9 |
| 10723/G06 | 14.1 | −26.7 | −0.8 | 64.5 |
| 10723/G07 | 14.2 | 15.5 | −5.6 | 43.0 |
| 10723/G08 | −22.9 | 0.1 | 7.5 | 79.9 |
| 10723/G09 | −1.8 | −32.6 | −2.9 | 80.7 |
| 10723/G10 | 3.5 | −4.1 | −27.8 | 40.7 |
| 10723/G11 | −4.1 | −35.0 | −7.7 | 39.4 |
| 10724/A02 | 1.8 | 36.7 | 6.3 | 61.7 |
| 10724/A03 | −7.8 | 17.2 | 0.1 | 30.7 |
| 10724/A04 | −15.9 | 15.4 | 5.0 | 62.6 |
| 10724/A05 | −15.2 | 20.3 | 5.0 | 68.4 |
| 10724/A06 | −3.7 | 1.4 | 30.7 | 46.8 |
| 10724/A07 | 3.7 | 18.3 | 16.1 | 58.7 |
| 10724/A09 | −5.2 | 1.6 | 19.6 | 37.5 |
| 10724/A10 | 1.6 | 40.0 | 28.6 | 83.8 |
| 10724/A11 | 12.8 | −16.6 | 29.3 | 27.2 |
| 10724/B02 | −6.2 | 34.9 | −21.5 | 48.8 |
| 10724/B03 | −48.9 | 14.9 | 14.7 | 51.0 |
| 10724/B04 | −20.5 | 50.2 | 42.5 | 81.2 |
| 10724/B05 | −2.2 | 21.2 | 12.6 | 45.6 |
| 10724/B06 | 13.4 | 30.9 | 43.2 | 52.1 |
| 10724/B07 | −1.8 | 44.0 | 27.2 | 57.9 |
| 10724/B09 | 3.5 | 8.7 | 25.8 | 43.8 |
| 10724/B10 | 8.5 | 76.2 | 9.8 | 95.0 |
| 10724/B11 | 9.0 | −23.2 | 23.0 | 43.0 |
| 10724/C02 | −0.3 | 53.6 | −9.0 | 40.7 |
| 10724/C03 | −20.3 | 16.5 | 4.3 | 68.7 |
| 10724/C04 | −18.6 | 13.2 | 24.4 | 84.3 |
| 10724/C05 | −18.6 | −0.8 | 20.3 | 67.7 |
| 10724/C06 | −1.5 | −2.4 | 34.9 | 15.4 |
| 10724/C07 | −1.2 | 9.4 | 22.3 | 14.2 |
| 10724/C09 | 9.3 | 1.0 | 20.3 | 5.3 |
| 10724/C10 | −2.3 | 13.8 | 27.2 | 91.2 |
| 10724/C11 | 10.3 | 0.7 | 23.0 | 4.9 |
| 10724/D02 | 12.4 | 40.5 | −9.6 | 37.5 |
| 10724/D03 | 0.1 | 2.5 | −15.2 | 18.2 |
| 10724/D04 | 0.5 | 5.4 | −1.3 | 70.5 |
| 10724/D05 | −1.6 | −8.4 | 35.6 | 36.1 |
| 10724/D06 | 12.4 | −12.4 | 40.4 | 23.0 |
| 10724/D07 | −2.6 | 25.6 | 7.0 | 38.1 |
| 10724/D09 | 0.9 | −15.3 | 18.9 | 16.1 |
| 10724/D10 | 3.7 | 12.7 | 38.3 | 59.6 |
| 10724/D11 | 14.9 | 12.9 | 29.3 | 20.3 |
| 10724/E02 | 17.7 | 39.8 | −54.2 | 55.4 |
| 10724/E03 | 10.6 | 33.1 | 14.7 | 85.8 |
| 10724/E04 | 55.2 | 8.9 | −32.6 | 93.3 |
| 10724/E05 | 13.8 | 0.5 | −7.6 | 70.3 |
| 10724/E06 | 8.3 | 1.6 | 6.3 | 25.8 |
| 10724/E07 | −3.6 | 9.4 | 0.1 | 46.8 |
| 10724/E09 | 14.3 | 6.3 | 21.0 | 27.0 |
| 10724/E10 | 7.3 | 41.4 | 34.9 | 84.0 |
| 10724/E11 | 5.1 | −26.8 | S.0 | 39.3 |
| 10724/F02 | 9.7 | 27.4 | 0.8 | 73.0 |
| 10724/F03 | −12.5 | 9.8 | −45.8 | 44.2 |
| 10724/F04 | 10.2 | 2.9 | −52.1 | 81.9 |
| 10724/F05 | −7.2 | −16.4 | −0.6 | 67.0 |
| 10724/F06 | 13.8 | −3.5 | −5.5 | 51.2 |
| 10724/F07 | −6.0 | 8.9 | −6.2 | 47.3 |
| 10724/F09 | 17.1 | −14.6 | −17.3 | 20.5 |
| 10724/F10 | 2.7 | −10.4 | 1.5 | 55.6 |
| 10724/F11 | 4.5 | 3.8 | −6.9 | 49.3 |
| 10724/G02 | 15.1 | 42.5 | −7.6 | 44.9 |
| 10724/G03 | −8.4 | 7.8 | −2.7 | 36.7 |
| 10724/G04 | −7.9 | 12.9 | −12.4 | 71.0 |
| 10724/G05 | −0.1 | −20.8 | −10.3 | 61.0 |
| 10724/G06 | 0.1 | 3.2 | −6.9 | 20.3 |
| 10724/G07 | −1.9 | −11.7 | −41.6 | 2.3 |
| 10724/G09 | 9.1 | −21.7 | −18.0 | −2.8 |
| 10724/G10 | 7.0 | −10.6 | −15.9 | 62.8 |

TABLE 14-continued

| Barcode/<br>Plate Row-<br>Plate Column | Flk Kinase<br>% Inhibition | Biochem<br>EGFR<br>% Inhibition | PDGF<br>Kinase<br>% Inhibition | Met Kinase<br>% Inhibition |
|---|---|---|---|---|
| 10724/G11 | 6.8 | −29.5 | −29.1 | 11.2 |
| 10725/A02 | −2.0 | 3.9 | −14.2 | 46.6 |
| 10725/A03 | 3.6 | −38.2 | 5.9 | 68.0 |
| 10725/A04 | −8.6 | 26.2 | −3.2 | 55.3 |
| 10725/A05 | −13.9 | 7.9 | 13.1 | 47.5 |
| 10725/A06 | −7.3 | −9.5 | 40.9 | 71.7 |
| 10725/A07 | −12.3 | 18.2 | 17.9 | 59.3 |
| 10725/A08 | −2.9 | 10.9 | 14.1 | 45.3 |
| 10725/A09 | −13.9 | 4.9 | 29.4 | 44.3 |
| 10725/A10 | −3.2 | 14.0 | 33.7 | 43.2 |
| 10725/A11 | −21.9 | 14.6 | 18.9 | 49.1 |
| 10725/B02 | −2.8 | 2.5 | −7.5 | 66.9 |
| 10725/B03 | 4.9 | −15.3 | 7.8 | 70.8 |
| 10725/B04 | 1.1 | 76.9 | 9.3 | 90.4 |
| 10725/B05 | −61.0 | 20.4 | 44.7 | 68.3 |
| 10725/B06 | −0.5 | −13.7 | 31.3 | 53.3 |
| 10725/B07 | 24.6 | 45.8 | 100.8 | 74.0 |
| 10725/B08 | −24.1 | 41.8 | 29.4 | 66.7 |
| 10725/B09 | 0.4 | 72.3 | 43.8 | 65.7 |
| 10725/B10 | 5.1 | 53.3 | 26.0 | 69.9 |
| 10725/B11 | −42.3 | 43.0 | 66.3 | 76.3 |
| 10725/C02 | 7.0 | −43.4 | −5.1 | 6.3 |
| 10725/C03 | 2.0 | −12.7 | 19.3 | 72.9 |
| 10725/C04 | −27.3 | 31.8 | 25.1 | 75.9 |
| 10725/C05 | −37.0 | −21.9 | 28.9 | 31.7 |
| 10725/C06 | −9.3 | −11.5 | 46.6 | 54.7 |
| 10725/C07 | 65.0 | −16.5 | 107.0 | 38.8 |
| 10725/C08 | −8.7 | −11.9 | 101.7 | 28.0 |
| 10725/C09 | 11.2 | 23.6 | 34.7 | 24.1 |
| 10725/C10 | 8.7 | 5.3 | 38.5 | −0.6 |
| 10725/C11 | 104.5 | −22.1 | 80.7 | 48.4 |
| 10725/D02 | −3.6 | −23.9 | −8.4 | 14.0 |
| 10725/D03 | −11.3 | −2.5 | 5.4 | 72.9 |
| 10725/D04 | 3.6 | 4.3 | 12.2 | 55.1 |
| 10725/D05 | 2.3 | −19.7 | 10.7 | 24.5 |
| 10725/D06 | −0.5 | −26.4 | 21.7 | 24.7 |
| 10725/D07 | 2.6 | −25.8 | 18.4 | 37.0 |
| 10725/D08 | 1.8 | 20.0 | 38.5 | 39.2 |
| 10725/D09 | −0.9 | 4.3 | 35.6 | 28.0 |
| 10725/D10 | 9.0 | 11.7 | 43.8 | 27.8 |
| 10725/D11 | 13.6 | −12.5 | 23.2 | 100.5 |
| 10725/E02 | −5.6 | 4.3 | −8.9 | 40.2 |
| 10725/E03 | −0.8 | −10.3 | 10.7 | 60.9 |
| 10725/E04 | −38.8 | 31.2 | 3.1 | 59.0 |
| 10725/E05 | −0.2 | −5.5 | 27.5 | 28.2 |
| 10725/E06 | −1.8 | −17.7 | 39.0 | 36.7 |
| 10725/E07 | 9.7 | 12.5 | 28.9 | 45.3 |
| 10725/E08 | 12.1 | 14.2 | 48.6 | 39.7 |
| 10725/E09 | 7.0 | 31.4 | 37.5 | 22.4 |
| 10725/E10 | 9.3 | 6.1 | 28.4 | −4.7 |
| 10725/E11 | 18.9 | −36.0 | 20.8 | 9.6 |
| 10725/F02 | 5.8 | −3.7 | −15.1 | 27.8 |
| 10725/F03 | 4.3 | −36.2 | −27.1 | 63.2 |
| 10725/F04 | −6.9 | −49.6 | −4.6 | 38.1 |
| 10725/F05 | −0.8 | −18.9 | −5.6 | 15.5 |
| 10725/F06 | −1.0 | −37.8 | 14.1 | 41.8 |
| 10725/F07 | 6.9 | 16.4 | 15.0 | 67.8 |
| 10725/F08 | 8.9 | 15.4 | 28.9 | 72.2 |
| 10725/F09 | 6.8 | 32.2 | 28.4 | 48.5 |
| 10725/F10 | 4.8 | 3.7 | 17.9 | 14.2 |
| 10725/F11 | 9.9 | 20.8 | 20.3 | 25.7 |
| 10725/G02 | −3.7 | −20.5 | −11.8 | 30.8 |
| 10725/G03 | −6.9 | −2.5 | −6.5 | 58.6 |
| 10725/G04 | 6.1 | −12.3 | −8.9 | 47.1 |
| 10725/G05 | −18.3 | 68.7 | 7.4 | 15.6 |
| 10725/G06 | 21.7 | −19.9 | 27.5 | 35.8 |
| 10725/G07 | 4.8 | −25.8 | 23.7 | 39.7 |
| 10725/G08 | −14.8 | −13.7 | 8.3 | 47.3 |
| 10725/G09 | 15.2 | 6.5 | 43.8 | 4.7 |
| 10725/G10 | 11.1 | 17.8 | 44.7 | 27.7 |
| 10725/G11 | −28.0 | −32.4 | 22.2 | 25.7 |
| 10726/A03 | −2.6 | −12.5 | 4.3 | 70.1 |
| 10726/A04 | 7.6 | 40.8 | 44.2 | 85.7 |
| 10726/A05 | −7.1 | −28.4 | 22.1 | 75.2 |
| 10726/A06 | −4.6 | 0.2 | 22.1 | 54.7 |
| 10726/A07 | −72.3 | 88.7 | −36.8 | 101.4 |
| 10726/A08 | −4.0 | −28.4 | 10.7 | 63.1 |
| 10726/A09 | −4.5 | −6.3 | 16.4 | 70.8 |
| 10726/A10 | 3.7 | 26.5 | 8.1 | 58.9 |
| 10726/A11 | 0.5 | 6.2 | 23.3 | 70.8 |
| 10726/B03 | 11.1 | 3.5 | 16.4 | 81.1 |
| 10726/B04 | 16.8 | 71.1 | 39.1 | 78.9 |
| 10726/B05 | 13.2 | 49.0 | 27.1 | 96.8 |
| 10726/B06 | 11.3 | 6.6 | 34.1 | 76.1 |
| 10726/B07 | −36.5 | 72.4 | −59.5 | 98.5 |
| 10726/B08 | 12.2 | 23.6 | 24.6 | 60.2 |
| 10726/B09 | 7.5 | 28.9 | 22.7 | 72.3 |
| 10726/B10 | 3.7 | 40.8 | 6.2 | 58.5 |
| 10726/B11 | 7.4 | 39.4 | 23.3 | 64.4 |
| 10726/C03 | 24.9 | 29.8 | 28.4 | 38.9 |
| 10726/C04 | 12.3 | 58.4 | 36.6 | 91.7 |
| 10726/C05 | 4.0 | 16.7 | 25.2 | 58.0 |
| 10726/C06 | 23.8 | −0.9 | 36.0 | 42.6 |
| 10726/C07 | −17.0 | 40.8 | −67.7 | 84.9 |
| 10726/C08 | 3.4 | 7.5 | 21.4 | 46.8 |
| 10726/C09 | 12.9 | −14.3 | 26.5 | 48.5 |
| 10726/C10 | 5.5 | 2.8 | 16.4 | 36.7 |
| 10726/C11 | −32.2 | 4.8 | 51.1 | 34.7 |
| 10726/D03 | 21.6 | −5.4 | 21.4 | 52.1 |
| 10726/D04 | 7.8 | −20.1 | 34.1 | 62.9 |
| 10726/D05 | 8.2 | −8.1 | 39.1 | 51.2 |
| 10726/D06 | 16.3 | −24.4 | 28.4 | 42.8 |
| 10726/D07 | −26.9 | 18.5 | −81.0 | 84.6 |
| 10726/D08 | 12.1 | −11.4 | 22.1 | 39.5 |
| 10726/D09 | 14.4 | −6.5 | 22.1 | 45.7 |
| 10726/D10 | 14.7 | −6.5 | 32.2 | 35.3 |
| 10726/D11 | 10.5 | −6.3 | 30.9 | 9.6 |
| 10726/E03 | −5.5 | −15.9 | 20.2 | 62.4 |
| 10726/E04 | 8.1 | 53.0 | 12.6 | 85.5 |
| 10726/E05 | 8.1 | 5.5 | 4.3 | 71.0 |
| 10726/E06 | 6.2 | −20.6 | 41.7 | −7.4 |
| 10726/E07 | −40.0 | 20.5 | −12.1 | 84.0 |
| 10726/E08 | 4.1 | −8.5 | 34.1 | 58.9 |
| 10726/E09 | 9.9 | 10.0 | 34.7 | 50.3 |
| 10726/E10 | 16.5 | −9.0 | 37.9 | 41.5 |
| 10726/E11 | 16.2 | −14.1 | 30.3 | 34.5 |
| 10726/F03 | 8.3 | −17.4 | 5.6 | 54.1 |
| 10726/F04 | 31.5 | 33.4 | 18.3 | 93.5 |
| 10726/F05 | 8.9 | −26.8 | −17.8 | 51.2 |
| 10726/F06 | 17.7 | −24.1 | 17.0 | 16.2 |
| 10726/F07 | 9.6 | 76.2 | −99.4 | 96.1 |
| 10726/F08 | 15.3 | −21.5 | 28.4 | 67.3 |
| 10726/F09 | 9.6 | −22.8 | −2.6 | 66.8 |
| 10726/F10 | 7.0 | −17.4 | 9.4 | 51.4 |
| 10726/F11 | 13.6 | −16.8 | 25.2 | 57.6 |
| 10726/G03 | 11.3 | −17.2 | 4.3 | 26.8 |
| 10726/G04 | 9.7 | 60.6 | 14.5 | 72.8 |
| 10726/G05 | 14.9 | 5.1 | 6.2 | 81.1 |
| 10726/G06 | 7.0 | −37.5 | −26.6 | 19.9 |
| 10726/G07 | −13.7 | 54.4 | −107.6 | 94.8 |
| 10726/G08 | 2.9 | −2.7 | 14.5 | 39.1 |
| 10726/G09 | 3.6 | 3.3 | 13.2 | 42.4 |
| 10726/G10 | 10.5 | 6.0 | −7.0 | 26.8 |
| 10726/G11 | 9.1 | 1.3 | −7.7 | 11.8 |
| 10727/A02 | −1.3 | 3.2 | −10.3 | 52.0 |
| 10727/A03 | 6.3 | −19.2 | −4.5 | 40.7 |
| 10727/A04 | −4.6 | 28.2 | 12.3 | 80.9 |
| 10727/A05 | 4.2 | −3.0 | 5.7 | 29.0 |
| 10727/A06 | −17.1 | −6.3 | 13.7 | 32.7 |
| 10727/A07 | −10.7 | −3.7 | 12.3 | 61.1 |
| 10727/A08 | −0.6 | 9.7 | 15.2 | 9.7 |
| 10727/A09 | −16.8 | 12.7 | 16.6 | 44.2 |
| 10727/A10 | −6.4 | 89.0 | 18.1 | 95.2 |
| 10727/A11 | 7.4 | 6.2 | 10.8 | 16.5 |
| 10727/B02 | 2.4 | −18.4 | −10.3 | 90.5 |
| 10727/B03 | −13.4 | −2.8 | −7.4 | 84.5 |
| 10727/B04 | 46.0 | 47.4 | 21.0 | 87.1 |
| 10727/B05 | 10.5 | 39.0 | 9.4 | 83.3 |
| 10727/B06 | −3.9 | 40.7 | 6.4 | 91.0 |
| 10727/B07 | 8.4 | 46.5 | 0.6 | 83.5 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10727/B08 | 4.0 | 47.4 | 14.4 | 90.7 |
| 10727/B09 | 6.7 | 31.7 | 18.1 | 81.9 |
| 10727/B10 | 3.9 | 94.0 | 29.7 | 99.2 |
| 10727/B11 | 16.8 | 6.9 | 15.9 | 69.8 |
| 10727/C02 | -2.0 | -28.5 | -12.5 | 73.8 |
| 10727/C03 | -3.2 | 14.6 | 11.5 | 11.9 |
| 10727/C04 | 0.2 | 27.6 | 23.2 | 81.7 |
| 10727/C05 | 13.7 | 11.8 | 7.9 | 8.9 |
| 10727/C06 | 5.2 | 5.6 | 12.3 | 45.2 |
| 10727/C07 | 15.9 | 8.4 | 13.0 | 36.7 |
| 10727/C08 | 4.9 | 3.6 | 23.2 | 47.8 |
| 10727/C09 | -13.5 | 16.6 | 21.7 | 37.9 |
| 10727/C10 | -35.3 | 85.3 | 45.7 | 94.4 |
| 10727/C11 | -25.6 | -15.6 | 22.4 | 14.5 |
| 10727/D02 | 3.2 | 22.6 | 5.7 | 51.6 |
| 10727/D03 | 3.1 | 39.4 | -3.0 | 24.0 |
| 10727/D04 | 25.9 | 39.6 | 6.4 | 76.0 |
| 10727/D05 | 8.5 | 3.4 | -0.1 | 39.9 |
| 10727/D06 | 13.1 | 8.6 | 10.8 | 24.4 |
| 10727/D07 | 19.7 | 10.5 | -14.7 | 50.6 |
| 10727/D08 | 14.1 | -0.5 | 5.0 | 8.5 |
| 10727/D09 | 8.2 | 15.1 | 7.2 | 17.9 |
| 10727/D10 | 11.4 | 86.2 | 9.4 | 79.9 |
| 10727/D11 | 10.5 | -23.7 | 17.4 | 17.3 |
| 10727/E02 | 9.3 | 22.4 | -6.7 | 28.0 |
| 10727/E03 | 11.1 | 35.5 | 5.7 | 28.8 |
| 10727/E04 | 46.1 | 82.1 | -7.4 | 98.4 |
| 10727/E05 | 17.1 | 12.9 | -7.4 | 12.1 |
| 10727/E06 | 14.2 | -9.3 | 9.4 | -2.2 |
| 10727/E07 | 20.1 | 7.1 | 10.1 | 45.2 |
| 10727/E08 | 14.2 | 25.6 | 23.9 | 27.0 |
| 10727/E09 | 9.3 | 15.1 | 15.9 | 28.4 |
| 10727/E10 | 9.7 | 85.1 | 5.0 | 96.6 |
| 10727/E11 | 37.3 | -33.4 | 7.9 | -5.4 |
| 10727/F02 | 15.9 | -0.5 | 11.5 | 52.0 |
| 10727/F03 | 8.9 | 36.8 | -3.7 | 22.0 |
| 10727/F04 | 15.3 | 17.9 | -10.3 | 92.0 |
| 10727/F05 | 21.8 | -9.1 | -3.7 | 6.0 |
| 10727/F06 | 14.5 | 4.9 | 8.6 | 37.7 |
| 10727/F07 | 21.4 | -8.9 | 2.1 | 17.9 |
| 10727/F08 | 12.5 | -5.4 | 10.1 | 36.9 |
| 10727/F09 | -45.2 | -2.0 | 21.7 | 9.3 |
| 10727/F10 | 15.9 | 74.1 | 9.4 | 93.4 |
| 10727/F11 | 17.3 | -2.6 | 18.1 | -3.0 |
| 10727/G02 | 7.1 | 37.5 | -20.5 | 81.5 |
| 10727/G03 | -3.5 | 19.4 | -10.3 | 40.5 |
| 10727/G04 | 27.2 | 80.6 | -27.0 | 94.0 |
| 10727/G05 | 8.0 | 11.2 | -2.3 | 7.1 |
| 10727/G06 | 2.9 | -12.1 | -12.5 | 31.1 |
| 10727/G07 | 7.2 | 5.4 | -24.1 | 29.6 |
| 10727/G08 | 15.7 | -19.6 | -7.4 | 21.8 |
| 10727/G09 | 5.7 | -9.7 | 10.8 | 18.8 |
| 10727/G10 | -5.6 | 85.1 | 10.8 | 99.2 |
| 10727/G11 | 6.9 | -3.5 | 15.9 | -0.8 |
| 10728/A02 | -12.3 | 9.2 | -7.9 | 25.6 |
| 10728/A03 | -7.3 | -25.8 | -7.9 | 29.2 |
| 10728/A04 | -3.5 | 28.0 | 15.6 | 28.5 |
| 10728/A05 | -10.8 | 17.7 | 4.5 | 31.8 |
| 10728/A06 | -10.4 | 17.2 | -3.1 | 19.7 |
| 10728/A07 | -21.6 | 59.6 | 31.1 | 28.5 |
| 10728/A08 | -1.4 | 24.1 | 0.5 | 40.2 |
| 10728/A09 | -5.5 | 19.3 | 10.3 | 53.1 |
| 10728/A10 | -16.3 | -3.4 | 1.8 | 77.2 |
| 10728/A11 | -2.3 | -0.6 | -9.3 | 58.8 |
| 10728/B02 | -11.1 | -10.5 | -0.4 | 61.2 |
| 10728/B03 | -1.3 | -36.6 | 10.3 | 74.4 |
| 10728/B04 | -6.0 | -2.0 | 9.8 | 67.2 |
| 10728/B05 | -12.3 | 26.9 | 9.4 | 60.4 |
| 10728/B06 | 4.7 | 38.1 | 7.6 | 56.0 |
| 10728/B07 | 31.4 | 11.1 | 20.9 | 82.2 |
| 10728/B08 | 14.8 | 34.7 | -6.6 | 77.0 |
| 10728/B09 | 1.7 | 31.7 | -0.4 | 81.7 |
| 10728/B10 | 3.9 | 16.8 | 2.7 | 79.3 |
| 10728/B11 | -1.0 | 48.2 | -12.4 | 80.3 |
| 10728/C02 | -32.1 | -35.4 | 42.3 | 15.5 |
| 10728/C03 | 10.5 | 9.7 | 24.9 | 16.9 |
| 10728/C04 | -0.0 | 16.1 | 27.2 | 33.6 |
| 10728/C05 | -21.7 | 16.1 | 23.2 | 33.7 |
| 10728/C06 | 8.4 | 4.2 | 2.7 | 22.9 |
| 10728/C07 | -7.2 | 8.3 | 8.9 | 46.3 |
| 10728/C08 | -2.2 | 17.5 | 9.4 | 25.5 |
| 10728/C09 | 14.5 | -6.8 | 8.1 | 31.6 |
| 10728/C10 | 6.1 | 4.4 | 11.2 | 28.7 |
| 10728/C11 | -10.1 | 21.8 | 8.5 | 45.2 |
| 10728/D02 | -0.3 | 9.9 | 9.8 | 21.4 |
| 10728/D03 | 10.2 | 10.8 | 32.0 | 13.5 |
| 10728/D04 | 6.8 | -1.1 | 26.7 | 23.1 |
| 10728/D05 | 4.9 | 12.7 | 7.2 | 29.5 |
| 10728/D06 | 10.4 | 5.8 | 5.8 | 23.2 |
| 10728/D07 | 8.1 | 2.4 | 2.3 | 21.8 |
| 10728/D08 | 13.5 | 6.9 | 2.7 | 34.7 |
| 10728/D09 | 10.5 | -2.9 | -3.9 | 27.6 |
| 10728/D10 | 17.9 | 18.6 | -3.9 | 30.5 |
| 10728/D11 | 15.9 | 22.1 | -10.2 | 52.5 |
| 10728/E02 | 5.4 | 7.4 | 15.2 | 5.4 |
| 10728/E03 | 13.2 | 9.5 | 12.0 | 11.9 |
| 10728/E04 | 5.5 | 10.1 | 23.2 | 25.6 |
| 10728/E05 | 17.4 | 7.4 | 5.8 | 53.4 |
| 10728/E06 | 6.6 | -4.7 | 12.0 | 26.4 |
| 10728/E07 | 9.6 | 21.8 | 28.0 | 79.8 |
| 10728/E08 | 15.2 | 5.1 | 29.4 | 46.3 |
| 10728/E09 | 9.0 | 0.1 | 22.3 | 40.0 |
| 10728/E10 | 24.7 | -20.8 | 13.8 | 57.2 |
| 10728/E11 | 16.3 | -5.9 | 8.9 | 53.1 |
| 10728/F02 | 2.9 | 4.4 | 7.2 | 25.6 |
| 10728/F03 | 6.8 | -0.2 | -9.3 | 18.7 |
| 10728/F04 | 14.2 | 5.1 | 7.2 | 47.9 |
| 10728/F05 | 6.0 | -5.9 | -0.4 | 53.3 |
| 10728/F06 | 14.4 | -1.5 | 1.8 | 28.2 |
| 10728/F07 | 2.4 | -2.2 | -0.8 | 62.6 |
| 10728/F08 | 14.5 | -13.5 | 8.9 | 62.8 |
| 10728/F09 | 5.9 | -13.0 | 1.4 | 23.4 |
| 10728/F10 | 18.0 | -6.3 | 4.9 | 48.7 |
| 10728/F11 | 16.7 | 0.8 | -12.4 | 72.5 |
| 10728/G02 | 2.3 | -10.2 | 0.9 | 7.1 |
| 10728/G03 | 14.3 | -2.0 | -8.4 | 8.8 |
| 10728/G04 | 21.8 | -8.2 | 0.5 | 20.9 |
| 10728/G05 | 9.4 | 7.2 | -4.4 | 63.1 |
| 10728/G06 | 13.5 | -14.1 | -13.3 | 25.3 |
| 10728/G07 | 22.6 | -12.3 | -17.3 | 42.4 |
| 10728/G08 | 21.4 | -5.7 | -11.9 | 42.3 |
| 10728/G09 | 6.8 | -8.0 | 6.3 | 22.2 |
| 10728/G10 | 10.4 | -12.5 | -0.8 | 27.9 |
| 10728/G11 | 3.2 | 16.1 | -12.8 | 71.4 |
| 10729/A02 | 15.5 | 10.0 | -25.7 | 28.1 |
| 10729/A03 | 4.7 | 27.0 | 1.9 | 27.5 |
| 10729/A04 | -4.0 | 58.8 | -16.6 | 45.4 |
| 10729/A05 | -17.7 | 23.4 | -6.8 | 38.8 |
| 10729/A06 | -10.9 | 36.5 | -8.6 | 29.8 |
| 10729/A07 | -10.0 | 49.0 | -36.7 | 51.1 |
| 10729/A08 | -13.3 | 37.8 | -23.4 | 48.1 |
| 10729/A09 | 0.4 | 25.7 | 11.0 | 80.3 |
| 10729/A10 | 0.7 | 28.7 | -12.8 | 34.8 |
| 10729/A11 | 4.9 | 15.5 | -11.7 | 49.9 |
| 10729/B02 | 13.8 | 34.9 | -10.2 | 77.2 |
| 10729/B03 | 11.2 | 38.2 | -9.4 | 57.3 |
| 10729/B04 | 0.1 | 63.7 | -22.7 | 43.8 |
| 10729/B05 | -5.2 | 50.6 | -25.7 | 51.0 |
| 10729/B06 | 2.0 | 56.9 | -19.2 | 61.1 |
| 10729/B07 | -13.4 | 69.0 | -33.2 | 58.2 |
| 10729/B08 | -14.7 | 53.2 | -13.6 | 66.0 |
| 10729/B09 | -16.0 | 51.6 | -6.4 | 47.2 |
| 10729/B10 | -0.7 | 68.3 | -13.9 | 32.6 |
| 10729/B11 | 7.8 | 18.8 | 4.2 | 36.6 |
| 10729/C02 | 6.0 | 16.9 | 9.1 | 18.2 |
| 10729/C03 | 11.0 | 25.7 | 13.7 | 13.5 |
| 10729/C04 | -2.5 | 35.9 | 4.2 | 20.7 |
| 10729/C05 | 5.8 | 21.8 | -5.6 | 15.5 |
| 10729/C06 | 3.8 | 38.2 | 3.1 | 15.2 |
| 10729/C07 | -22.4 | 60.8 | -1.8 | 58.4 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10729/C08 | -20.3 | 25.4 | -13.6 | 55.7 |
| 10729/C09 | -26.4 | 33.2 | -34.8 | 60.4 |
| 10729/C10 | 2.5 | 45.7 | 3.5 | 15.8 |
| 10729/C11 | 10.4 | 35.9 | -17.4 | 41.3 |
| 10729/D02 | 12.2 | 5.7 | 15.6 | 31.7 |
| 10729/D03 | 15.3 | 15.5 | 14.1 | 22.6 |
| 10729/D04 | -5.7 | 18.8 | -12.8 | 33.1 |
| 10729/D05 | 2.2 | 22.1 | 2.3 | 28.1 |
| 10729/D06 | 0.2 | 45.7 | 2.7 | 30.2 |
| 10729/D07 | -15.3 | 21.4 | -20.0 | 25.5 |
| 10729/D08 | -26.2 | 10.3 | -21.1 | 27.6 |
| 10729/D09 | -9.6 | 22.1 | -12.1 | 34.8 |
| 10729/D10 | 4.1 | 11.3 | -11.3 | 36.1 |
| 10729/D11 | -2.0 | 19.2 | 0.1 | 18.8 |
| 10729/E02 | 26.6 | 8.0 | 28.4 | 11.7 |
| 10729/E03 | 6.9 | 20.1 | 29.2 | 27.5 |
| 10729/E04 | 9.7 | 19.5 | 26.5 | 9.8 |
| 10729/E05 | 46.8 | 12.6 | 29.9 | 13.4 |
| 10729/E06 | 12.1 | 43.7 | 24.7 | -0.7 |
| 10729/E07 | 4.1 | 26.7 | 29.6 | 21.6 |
| 10729/E08 | 10.9 | 40.1 | 11.0 | 73.7 |
| 10729/E09 | 6.9 | 29.6 | -11.7 | 85.0 |
| 10729/E10 | 5.7 | 50.3 | 11.8 | 7.5 |
| 10729/E11 | 70.9 | 25.7 | 22.4 | 50.8 |
| 10729/F02 | 18.9 | -14.0 | 20.1 | 19.5 |
| 10729/F03 | 30.0 | 10.6 | 33.7 | 27.8 |
| 10729/F04 | 16.0 | 13.3 | 25.4 | 44.9 |
| 10729/F05 | 15.4 | -4.8 | 31.5 | 33.8 |
| 10729/F06 | 36.4 | 15.9 | 29.6 | 44.3 |
| 10729/F07 | -5.8 | 6.7 | 6.1 | 37.3 |
| 10729/F08 | -3.4 | 10.3 | 0.8 | 44.6 |
| 10729/F09 | -2.6 | 13.3 | 8.8 | 38.2 |
| 10729/F10 | 20.0 | 58.5 | 15.2 | 39.0 |
| 10729/F11 | -1.5 | 25.4 | 7.2 | 15.2 |
| 10729/G02 | 18.8 | -4.8 | 16.7 | 31.3 |
| 10729/G03 | 10.4 | 14.6 | 13.7 | 20.1 |
| 10729/G04 | 12.2 | 52.9 | 1.6 | 18.2 |
| 10729/G05 | 8.7 | 4.4 | 9.9 | 22.6 |
| 10729/G06 | 10.9 | 15.2 | 11.8 | 26.0 |
| 10729/G07 | -2.5 | -0.8 | 14.4 | 38.2 |
| 10729/G08 | -1.0 | 6.0 | 0.8 | 39.9 |
| 10729/G09 | -3.3 | 20.8 | 1.9 | 49.6 |
| 10729/G10 | -9.1 | 60.1 | -13.2 | 26.7 |
| 10729/G11 | -0.5 | 23.4 | 3.8 | 15.4 |
| 10730/A02 | -3.7 | 27.5 | -23.1 | 39.5 |
| 10730/A03 | -3.2 | 34.4 | -11.2 | 62.3 |
| 10730/A04 | -9.9 | 37.2 | -5.1 | 70.6 |
| 10730/A05 | -10.8 | 18.6 | 2.8 | 42.7 |
| 10730/A06 | -7.0 | 6.7 | 6.3 | 61.0 |
| 10730/A07 | -18.9 | 10.4 | -23.9 | 55.4 |
| 10730/A08 | -2.9 | 10.4 | -6.0 | 69.0 |
| 10730/A09 | 1.9 | 1.1 | -4.7 | 69.5 |
| 10730/A10 | 0.5 | 56.1 | 1.0 | 68.7 |
| 10730/A11 | 6.8 | 56.4 | -6.4 | 91.0 |
| 10730/B02 | 5.0 | 10.4 | 5.4 | 66.3 |
| 10730/B03 | -0.5 | 46.8 | 17.3 | 78.3 |
| 10730/B04 | 12.8 | 36.5 | 7.2 | 73.2 |
| 10730/B05 | -0.5 | 8.5 | -2.9 | 71.1 |
| 10730/B06 | 2.4 | 25.0 | 7.6 | 71.3 |
| 10730/B07 | 0.6 | 57.1 | 2.4 | 63.1 |
| 10730/B08 | 4.4 | 48.4 | 0.2 | 91.8 |
| 10730/B09 | 9.4 | 14.2 | 15.1 | 70.6 |
| 10730/B10 | 15.2 | 15.8 | 19.0 | 69.5 |
| 10730/B11 | 1.9 | 70.2 | -13.9 | 81.7 |
| 10730/C02 | 48.8 | 2.7 | 26.5 | 31.2 |
| 10730/C03 | 25.5 | -12.1 | 36.5 | 43.2 |
| 10730/C04 | 46.1 | 0.1 | 15.5 | 43.2 |
| 10730/C05 | 11.4 | -9.8 | 8.5 | 46.1 |
| 10730/C06 | 5.3 | 8.5 | 7.6 | 34.7 |
| 10730/C07 | 7.3 | 20.3 | 1.0 | 37.4 |
| 10730/C08 | -2.3 | 24.3 | 8.5 | 56.5 |
| 10730/C09 | 14.0 | 28.2 | 18.1 | 42.9 |
| 10730/C10 | 15.4 | 20.5 | 44.4 | 40.3 |
| 10730/C11 | -8.0 | 38.4 | 16.4 | 66.6 |
| 10730/D02 | 12.4 | 18.6 | 24.3 | 34.7 |
| 10730/D03 | 8.4 | 9.9 | 19.0 | 34.2 |
| 10730/D04 | 9.1 | 10.4 | 20.8 | 33.6 |
| 10730/D05 | 11.9 | 12.6 | -1.6 | 38.1 |
| 10730/D06 | 5.8 | 35.3 | -2.0 | 55.9 |
| 10730/D07 | 8.8 | 43.0 | 5.0 | 52.5 |
| 10730/D08 | 8.6 | 44.9 | 12.9 | -13.6 |
| 10730/D09 | 9.8 | 45.1 | -1.6 | 59.1 |
| 10730/D10 | -15.3 | 16.7 | -3.3 | 18.5 |
| 10730/D11 | 7.7 | 2.0 | -0.7 | 9.7 |
| 10730/E02 | 24.8 | 17.7 | 16.4 | 18.8 |
| 10730/E03 | 34.5 | 65.3 | 14.6 | 53.3 |
| 10730/E04 | 22.1 | 13.5 | 18.6 | 35.2 |
| 10730/E05 | 8.7 | 15.8 | 28.7 | 49.0 |
| 10730/E06 | 11.1 | 1.5 | 26.0 | 52.8 |
| 10730/E07 | 12.0 | 18.8 | 30.0 | 37.1 |
| 10730/E08 | 25.1 | 6.2 | 48.4 | 40.3 |
| 10730/E09 | 21.8 | 21.7 | 20.3 | 33.9 |
| 10730/E10 | 26.0 | 9.3 | 39.6 | 63.6 |
| 10730/E11 | 29.1 | 19.1 | 31.7 | 77.2 |
| 10730/F02 | 18.4 | 2.9 | 20.3 | -6.2 |
| 10730/F03 | 11.7 | 10.4 | 1.5 | -0.6 |
| 10730/F04 | 18.3 | -4.8 | 28.7 | 36.0 |
| 10730/F05 | 19.6 | -16.3 | 19.5 | 23.5 |
| 10730/F06 | 21.9 | -0.6 | 3.2 | 56.5 |
| 10730/F07 | 67.5 | 27.3 | -2.0 | 60.7 |
| 10730/F08 | 2.1 | 0.8 | -0.3 | 46.4 |
| 10730/F09 | 14.4 | 17.9 | 13.3 | 71.1 |
| 10730/F10 | 13.4 | 6.2 | 1.9 | 42.1 |
| 10730/F11 | -1.3 | -24.1 | 4.5 | 53.6 |
| 10730/G02 | 23.3 | 20.8 | 18.1 | 41.1 |
| 10730/G03 | 15.2 | -6.9 | 44.0 | 43.2 |
| 10730/G04 | 7.4 | -6.7 | 21.6 | 47.7 |
| 10730/G05 | 22.3 | -18.2 | 65.0 | 35.8 |
| 10730/G06 | 8.2 | -2.7 | 0.2 | 17.7 |
| 10730/G07 | 8.3 | 6.4 | 19.9 | 26.2 |
| 10730/G08 | 23.3 | 9.5 | 20.3 | 16.6 |
| 10730/G09 | 18.7 | -20.3 | 23.0 | 16.4 |
| 10730/G10 | 11.3 | 3.1 | 22.1 | 42.1 |
| 10730/G11 | -1.4 | 26.2 | -0.3 | 46.1 |
| 10731/A02 | 2.7 | 14.8 | -3.9 | 23.9 |
| 10731/A03 | 2.5 | 10.8 | 7.5 | 54.8 |
| 10731/A04 | 5.0 | 20.2 | 5.1 | 43.6 |
| 10731/A05 | -6.5 | 34.3 | 14.1 | 85.8 |
| 10731/A06 | -5.5 | 30.1 | 1.3 | 53.0 |
| 10731/A07 | -4.3 | 39.4 | 4.6 | 49.5 |
| 10731/A08 | -13.8 | 25.7 | -2.5 | 59.9 |
| 10731/A09 | -2.7 | 21.9 | -14.4 | 46.7 |
| 10731/A10 | -5.3 | 26.3 | -3.5 | 41.2 |
| 10731/A11 | 3.1 | 16.1 | -0.1 | 53.4 |
| 10731/B02 | 6.5 | 15.5 | 13.2 | 71.6 |
| 10731/B03 | 1.9 | 12.3 | 9.9 | 60.9 |
| 10731/B04 | 12.0 | 31.3 | 0.3 | 71.0 |
| 10731/B05 | 3.8 | 35.9 | 17.9 | 86.0 |
| 10731/B06 | 6.2 | 37.5 | 5.6 | 56.2 |
| 10731/B07 | 11.7 | 29.1 | 6.0 | 41.6 |
| 10731/B08 | 6.2 | 37.2 | -23.4 | 57.4 |
| 10731/B09 | -0.5 | 15.0 | 0.3 | 29.6 |
| 10731/B10 | 1.3 | 50.5 | 4.6 | 72.9 |
| 10731/B11 | 6.9 | 55.2 | -13.0 | 58.2 |
| 10731/C02 | 3.1 | -6.9 | -2.5 | 11.1 |
| 10731/C03 | 4.5 | 9.1 | 11.3 | 38.7 |
| 10731/C04 | 10.5 | 31.0 | 15.1 | 32.5 |
| 10731/C05 | 14.9 | 35.5 | 22.7 | 78.3 |
| 10731/C06 | 13.8 | 23.1 | 7.0 | 18.2 |
| 10731/C07 | 70.4 | 35.5 | 31.3 | -11.6 |
| 10731/C08 | 10.2 | 23.6 | -3.0 | 25.8 |
| 10731/C09 | 15.1 | 16.8 | -6.3 | 22.7 |
| 10731/C10 | 19.7 | 20.9 | 6.5 | 23.3 |
| 10731/C11 | 5.5 | 29.6 | -9.2 | 16.2 |
| 10731/D02 | -8.4 | 4.9 | 17.9 | 8.7 |
| 10731/D03 | 17.3 | 16.3 | 28.4 | 40.2 |
| 10731/D04 | 9.3 | 15.8 | 6.5 | 24.5 |
| 10731/D05 | 32.7 | 53.9 | 46.0 | 92.7 |
| 10731/D06 | 16.1 | 23.2 | 8.0 | 59.7 |
| 10731/D07 | 12.3 | 25.9 | 2.7 | 45.9 |

TABLE 14-continued

| Barcode/Plate Row-Plate Column | Flk Kinase % Inhibition | Biochem EGFR % Inhibition | PDGF Kinase % Inhibition | Met Kinase % Inhibition |
|---|---|---|---|---|
| 10731/D08 | 25.8 | 16.8 | −8.7 | 44.2 |
| 10731/D09 | 6.1 | 12.6 | −2.0 | 23.9 |
| 10731/D10 | 13.0 | 15.8 | 9.9 | 21.1 |
| 10731/D11 | 15.2 | 43.6 | 8.4 | 56.6 |
| 10731/E02 | 11.2 | 7.9 | 13.7 | 49.1 |
| 10731/E03 | −1.4 | 10.4 | 15.6 | 20.7 |
| 10731/E04 | 23.8 | 13.6 | 30.8 | 55.6 |
| 10731/E05 | 7.0 | 17.7 | 27.0 | 82.2 |
| 10731/E06 | 2.6 | 10.4 | −12.0 | 37.7 |
| 10731/E07 | 12.6 | 38.4 | 3.7 | 45.9 |
| 10731/E08 | 10.5 | 40.1 | 8.9 | 59.0 |
| 10731/E09 | 52.5 | 17.2 | 23.2 | 27.0 |
| 10731/E10 | 33.1 | 25.1 | 21.7 | 35.5 |
| 10731/E11 | 17.9 | 26.4 | 27.9 | 60.7 |
| 10731/F02 | 11.1 | 17.7 | 14.1 | 47.5 |
| 10731/F03 | 7.9 | 8.4 | 11.8 | 40.6 |
| 10731/F04 | 24.5 | 5.0 | 3.2 | 17.0 |
| 10731/F05 | 17.6 | 19.5 | 20.3 | 84.4 |
| 10731/F06 | 2.2 | 7.2 | −23.4 | 20.9 |
| 10731/F07 | 13.3 | 37.7 | 1.3 | 34.7 |
| 10731/F08 | 9.2 | 7.1 | 4.1 | 23.5 |
| 10731/F09 | 2.3 | −0.7 | 15.6 | 20.5 |
| 10731/F10 | 11.0 | 7.9 | 28.4 | 48.1 |
| 10731/F11 | 19.7 | 42.3 | 20.3 | 60.1 |
| 10731/G02 | 16.8 | 4.7 | −10.1 | 15.2 |
| 10731/G03 | 12.9 | 7.7 | 6.5 | 33.7 |
| 10731/G04 | 14.5 | 7.1 | 0.3 | 23.3 |
| 10731/G05 | 17.5 | 18.5 | 8.0 | 72.4 |
| 10731/G06 | 10.8 | 2.3 | −0.6 | 33.3 |
| 10731/G07 | 31.6 | 0.7 | 40.8 | 10.9 |
| 10731/G08 | 18.2 | 13.3 | −13.9 | 19.5 |
| 10731/G09 | 13.3 | 8.9 | −8.7 | 4.4 |
| 10731/G10 | −9.0 | 5.5 | 5.6 | 10.3 |
| 10731/G11 | 1.5 | 67.2 | 16.0 | 64.3 |
| 10732/A02 | −12.5 | 5.1 | 10.8 | 53.7 |
| 10732/A03 | −9.9 | 0.8 | −3.8 | 37.4 |
| 10732/A04 | −14.1 | −10.6 | −9.4 | 34.8 |
| 10732/A05 | −3.9 | 4.6 | −12.9 | 20.5 |
| 10732/A06 | −0.0 | −1.4 | 12.3 | 5.7 |
| 10732/A07 | −19.8 | −0.3 | 0.7 | 26.1 |
| 10732/A08 | −10.0 | 12.1 | 31.0 | 32.7 |
| 10732/A09 | −11.2 | 39.7 | 8.8 | 60.3 |
| 10732/A10 | 10.2 | 6.1 | 7.3 | 20.3 |
| 10732/A11 | −0.6 | 1.8 | 40.1 | 65.3 |
| 10732/B02 | 2.9 | −26.0 | 23.5 | 78.0 |
| 10732/B03 | 8.2 | −15.3 | 17.4 | 58.1 |
| 10732/B04 | −1.3 | −22.1 | 16.9 | 79.5 |
| 10732/B05 | 2.8 | 17.0 | 21.9 | 71.2 |
| 10732/B06 | 8.1 | 12.8 | −12.4 | 74.3 |
| 10732/B07 | 1.6 | 15.8 | 21.4 | 75.1 |
| 10732/B08 | 8.0 | 7.8 | 16.9 | 64.4 |
| 10732/B09 | 14.0 | 2.0 | 18.4 | 69.2 |
| 10732/B10 | 12.1 | 0.6 | 0.7 | 51.5 |
| 10732/B11 | 9.0 | 9.3 | 70.9 | 73.7 |
| 10732/C02 | 11.9 | −6.5 | 7.3 | 40.1 |
| 10732/C03 | 14.7 | 1.4 | 7.3 | 14.0 |
| 10732/C04 | 12.8 | −14.7 | 3.8 | 30.6 |
| 10732/C05 | 11.2 | −22.8 | −17.0 | 18.5 |
| 10732/C06 | 11.8 | −43.2 | 5.3 | 21.6 |
| 10732/C07 | 15.4 | −28.6 | 4.3 | 26.5 |
| 10732/C08 | 7.6 | 1.6 | 17.9 | 54.5 |
| 10732/C09 | 8.0 | −3.9 | 15.4 | 37.9 |
| 10732/C10 | 15.1 | 1.2 | 5.8 | 43.0 |
| 10732/C11 | 18.2 | −5.0 | 16.4 | 31.9 |
| 10732/D02 | 9.2 | 8.7 | −24.0 | 50.2 |
| 10732/D03 | 22.5 | −18.7 | 26.0 | 24.9 |
| 10732/D04 | 24.6 | −11.4 | 50.7 | 40.7 |
| 10732/D05 | 15.7 | −36.7 | 4.3 | 30.2 |
| 10732/D06 | 16.3 | 3.6 | 16.4 | 24.3 |
| 10732/D07 | 14.7 | −19.1 | −3.8 | 43.2 |
| 10732/D08 | 33.3 | −20.6 | 30.5 | 49.4 |
| 10732/D09 | 15.2 | −9.9 | 15.9 | 40.3 |
| 10732/D10 | 25.5 | −16.6 | 24.5 | 33.1 |
| 10732/D11 | 18.8 | −13.4 | 18.9 | 48.6 |
| 10732/E02 | 13.1 | 0.8 | 4.8 | 33.3 |
| 10732/E03 | 16.7 | −1.6 | 48.7 | 3.9 |
| 10732/E04 | 15.8 | −10.6 | 29.5 | 8.2 |
| 10732/E05 | 18.7 | −17.0 | 41.1 | 2.2 |
| 10732/E06 | 2.8 | −11.0 | 16.9 | −2.1 |
| 10732/E07 | 21.3 | −8.5 | 42.2 | 15.2 |
| 10732/E08 | 13.6 | −21.7 | 32.6 | 29.4 |
| 10732/E09 | 15.3 | −7.2 | 46.7 | 18.1 |
| 10732/E10 | 16.7 | −3.3 | 35.6 | 1.6 |
| 10732/E11 | 16.2 | −32.2 | 47.7 | 41.4 |
| 10732/F02 | 7.0 | 23.1 | −9.4 | 55.6 |
| 10732/F03 | 31.9 | 54.1 | 51.8 | 68.6 |
| 10732/F04 | 16.2 | −0.1 | 23.5 | 57.2 |
| 10732/F05 | 37.3 | −30.7 | 12.8 | 58.9 |
| 10732/F06 | 11.6 | −8.0 | 0.2 | 45.7 |
| 10732/F07 | 31.0 | −12.5 | 38.6 | 65.5 |
| 10732/F08 | 12.6 | −11.9 | 14.9 | 76.6 |
| 10732/F09 | 25.6 | −13.4 | 25.5 | 79.7 |
| 10732/F11 | 14.1 | 0.8 | 15.9 | 65.1 |
| 10732/F11 | 21.9 | −21.5 | 77.5 | 75.2 |
| 10732/G02 | 8.1 | −0.7 | 10.3 | 39.5 |
| 10732/G03 | 0.8 | −20.0 | 36.1 | 38.1 |
| 10732/G04 | 12.6 | 8.0 | 25.0 | 24.9 |
| 10732/G05 | 17.2 | 3.8 | 15.4 | 15.2 |
| 10732/G06 | 26.5 | −12.1 | 0.2 | 16.2 |
| 10732/G07 | 4.6 | −21.9 | 21.4 | 23.9 |
| 10732/G08 | 10.0 | −20.4 | 37.6 | 44.7 |
| 10732/G09 | 16.9 | −34.8 | 9.8 | 33.9 |
| 10732/G10 | 14.0 | −38.2 | 20.4 | 45.7 |
| 10732/G11 | 10.9 | −33.7 | 38.6 | 63.0 |
| 10733/A02 | −5.2 | 25.9 | 11.5 | 74.6 |
| 10733/A03 | 45.0 | 33.6 | 23.2 | 24.9 |
| 10733/A04 | −11.2 | 32.8 | −14.1 | 24.0 |
| 10733/A05 | −23.3 | 55.2 | −4.0 | 18.2 |
| 10733/A06 | −16.6 | 45.1 | −24.3 | 33.7 |
| 10733/A07 | −27.4 | 28.5 | −12.9 | 27.2 |
| 10733/A08 | −17.1 | 19.5 | −10.1 | 27.2 |
| 10733/A09 | −11.9 | 25.9 | −7.6 | 22.1 |
| 10733/A10 | −9.3 | 14.2 | −13.3 | 21.1 |
| 10733/A11 | 15.0 | 23.0 | 4.2 | 43.5 |
| 10733/B02 | −7.4 | 31.6 | 14.7 | 74.6 |
| 10733/B03 | 3.1 | 14.4 | 35.8 | 62.2 |
| 10733/B04 | −3.3 | 28.5 | 24.9 | 56.3 |
| 10733/B05 | −1.1 | 26.7 | 27.3 | 61.3 |
| 10733/B06 | 4.6 | 43.6 | −9.2 | 71.4 |
| 10733/B07 | 1.2 | 32.7 | 4.2 | 73.5 |
| 10733/B08 | −16.0 | 32.5 | −15.7 | 65.5 |
| 10733/B09 | −2.6 | 21.1 | 7.0 | 64.5 |
| 10733/B10 | 5.7 | 11.8 | −59.6 | 65.1 |
| 10733/B11 | 22.5 | 12.5 | 23.7 | 36.6 |
| 10733/C02 | 5.8 | 31.6 | 15.1 | 71.8 |
| 10733/C03 | 17.0 | 14.4 | 28.1 | 29.3 |
| 10733/C04 | 8.4 | 29.0 | 19.2 | 18.4 |
| 10733/C05 | 11.5 | 17.2 | 11.1 | 23.2 |
| 10733/C06 | 4.7 | 22.7 | 20.0 | 4.1 |
| 10733/C07 | 1.2 | 16.7 | 4.6 | 10.2 |
| 10733/C08 | −28.5 | 65.8 | −3.6 | 85.7 |
| 10733/C09 | −18.0 | 46.0 | 91.9 | 16.3 |
| 10733/C10 | −7.6 | 36.0 | −6.4 | 20.5 |
| 10733/C11 | 42.8 | 15.8 | 62.2 | 35.1 |
| 10733/D02 | 3.1 | 12.5 | 17.6 | 63.4 |
| 10733/D03 | 33.2 | 11.2 | 40.7 | 32.8 |
| 10733/D04 | 15.5 | 19.9 | 26.5 | 37.7 |
| 10733/D05 | 16.5 | 10.6 | 16.8 | 25.1 |
| 10733/D06 | 17.9 | 30.8 | 1.3 | −19.4 |
| 10733/D07 | −1.4 | 37.4 | 0.9 | −6.8 |
| 10733/D08 | −8.3 | 38.3 | 42.3 | 80.0 |
| 10733/D09 | 9.8 | 48.3 | 33.8 | 38.7 |
| 10733/D10 | 2.9 | 46.8 | −10.1 | 22.8 |
| 10733/D11 | 1.0 | 33.7 | −4.0 | 31.6 |
| 10733/E02 | 0.8 | −1.3 | 20.8 | 60.5 |
| 10733/E03 | 42.6 | 10.7 | 43.1 | 26.8 |
| 10733/E04 | 2.1 | 45.4 | −13.7 | 17.5 |
| 10733/E05 | 10.6 | 58.3 | −33.2 | 2.9 |
| 10733/E06 | 13.5 | 37.3 | 22.4 | 10.4 |
| 10733/E07 | 13.2 | 19.9 | 29.3 | −10.1 |

TABLE 14-continued

| Barcode/ Plate Row-Plate Column | Flk Kinase % Inhibition | Biochem EGFR % Inhibition | PDGF Kinase % Inhibition | Met Kinase % Inhibition |
|---|---|---|---|---|
| 10733/E08 | −5.1 | 54.2 | 75.2 | 81.1 |
| 10733/E09 | 13.4 | 72.4 | 35.8 | 62.6 |
| 10733/E10 | 5.5 | 31.3 | 10.3 | 52.8 |
| 10733/E11 | 5.5 | 31.6 | 15.9 | 71.8 |
| 10733/F02 | −15.7 | 11.3 | 3.8 | 71.6 |
| 10733/F03 | 17.5 | −3.6 | 24.5 | 24.2 |
| 10733/F04 | 21.4 | 76.3 | −28.7 | 65.1 |
| 10733/F05 | 26.2 | 84.6 | −25.1 | 65.1 |
| 10733/F06 | 19.3 | 17.8 | −4.8 | 20.9 |
| 10733/F07 | 16.4 | 19.2 | 1.7 | −16.4 |
| 10733/F08 | −13.2 | 17.2 | −32.4 | 66.6 |
| 10733/F09 | −2.1 | 30.1 | −0.3 | 52.8 |
| 10733/F10 | 8.5 | 21.9 | −5.6 | 24.4 |
| 10733/F11 | 4.1 | 0.6 | −17.8 | 44.4 |
| 10733/G02 | 8.3 | −6.2 | −7.6 | 64.5 |
| 10733/G03 | 24.7 | 0.7 | 12.7 | 30.5 |
| 10733/G04 | 11.5 | 10.6 | 11.9 | 20.3 |
| 10733/G05 | 19.2 | 1.5 | −1.1 | 1.8 |
| 10733/G06 | 37.0 | 5.2 | 0.1 | 0.8 |
| 10733/G07 | 19.5 | 18.1 | −6.8 | 8.5 |
| 10733/G08 | 2.5 | 44.2 | 68.7 | 79.0 |
| 10733/G09 | 77.8 | 38.7 | −17.0 | 41.4 |
| 10733/G10 | 12.7 | 18.2 | −58.0 | 41.9 |
| 10733/G11 | 3.3 | −1.0 | −4.4 | 32.6 |
| 10734/A02 | 4.1 | 0.0 | −3.8 | 51.1 |
| 10734/A03 | 10.1 | 18.5 | 22.3 | 87.8 |
| 10734/A04 | 0.6 | 11.4 | 11.7 | 68.0 |
| 10734/A05 | 9.1 | 22.6 | 2.9 | 69.9 |
| 10734/A06 | −6.4 | −6.4 | −9.9 | 46.9 |
| 10734/A07 | −9.4 | 15.2 | 21.9 | 89.3 |
| 10734/A08 | 0.1 | 6.8 | 9.1 | 71.5 |
| 10734/A09 | −7.9 | 27.3 | −9.5 | 88.4 |
| 10734/A10 | 4.4 | 27.8 | 26.3 | 55.4 |
| 10734/A11 | 6.3 | 12.5 | 5.5 | 51.9 |
| 10734/B02 | 8.5 | −8.9 | −2.9 | 61.9 |
| 10734/B03 | 21.7 | 45.1 | 13.0 | 90.1 |
| 10734/B04 | 2.8 | 38.7 | 14.4 | 88.4 |
| 10734/B05 | −2.3 | 17.8 | 56.3 | 67.8 |
| 10734/B06 | −0.9 | 54.0 | 0.2 | 91.2 |
| 10734/B07 | 9.1 | 65.5 | 18.8 | 93.2 |
| 10734/B08 | −0.5 | 19.3 | −2.4 | 56.1 |
| 10734/B09 | −32.3 | 34.9 | 12.6 | 94.3 |
| 10734/B10 | 15.7 | 60.7 | 7.7 | 82.6 |
| 10734/B11 | 12.6 | 50.9 | −5.5 | 83.6 |
| 10734/C02 | −3.9 | −6.7 | 36.0 | 78.6 |
| 10734/C03 | −5.6 | 48.6 | 24.5 | 88.2 |
| 10734/C04 | −37.6 | 38.1 | 24.5 | 90.7 |
| 10734/C05 | −10.3 | 9.3 | 3.8 | 52.7 |
| 10734/C06 | −1.7 | 18.4 | −0.2 | 48.3 |
| 10734/C07 | −2.7 | 41.0 | 32.0 | 96.8 |
| 10734/C08 | −34.2 | 35.1 | 5.5 | 93.2 |
| 10734/C09 | −13.3 | 36.2 | 11.3 | 88.6 |
| 10734/C10 | 10.1 | 24.4 | 17.4 | 11.6 |
| 10734/C11 | 6.3 | 18.0 | 9.1 | 23.9 |
| 10734/D02 | −11.5 | 5.2 | 6.4 | 46.0 |
| 10734/D03 | 17.4 | 19.6 | 24.1 | 78.6 |
| 10734/D04 | 6.1 | −10.7 | 13.5 | 46.9 |
| 10734/D05 | 2.4 | −9.6 | 8.2 | 55.0 |
| 10734/D06 | 0.0 | 1.3 | −9.1 | 30.6 |
| 10734/D07 | 14.7 | 51.1 | 28.1 | 92.0 |
| 10734/D08 | 2.5 | −13.7 | 2.0 | 49.8 |
| 10734/D09 | −11.6 | 21.0 | 42.2 | 88.0 |
| 10734/D10 | 11.1 | −4.4 | 9.9 | 20.6 |
| 10734/D11 | 9.8 | 14.6 | 17.0 | 33.9 |
| 10734/E02 | 7.9 | −10.8 | 50.1 | 66.9 |
| 10734/E03 | 26.9 | 55.0 | 27.2 | 99.3 |
| 10734/E04 | 10.7 | −7.8 | 26.7 | 88.9 |
| 10734/E05 | 10.6 | 7.9 | 17.9 | 63.6 |
| 10734/E06 | 28.4 | 6.3 | 13.5 | 50.6 |
| 10734/E07 | 27.9 | 82.4 | 8.2 | 100.8 |
| 10734/E08 | 26.6 | 24.2 | 13.0 | 89.1 |
| 10734/E09 | 8.0 | 73.0 | 1.1 | 96.2 |
| 10734/E10 | 18.5 | −5.0 | 29.8 | 27.9 |
| 10734/E11 | 19.2 | −8.0 | 16.1 | 67.1 |
| 10734/F02 | 6.2 | 0.7 | 10.4 | 55.0 |
| 10734/F03 | 4.2 | 24.8 | −24.1 | 86.8 |
| 10734/F04 | −2.6 | 3.9 | 25.0 | 76.5 |
| 10734/F05 | 9.8 | −15.6 | −1.1 | 73.8 |
| 10734/F06 | 11.0 | −17.1 | −21.4 | 64.2 |
| 10734/F07 | 6.6 | 33.7 | −5.1 | 95.7 |
| 10734/F08 | 4.8 | −23.6 | −6.0 | 66.3 |
| 10734/F09 | −3.7 | 3.1 | −17.4 | 93.9 |
| 10734/F10 | 14.8 | −8.3 | 25.8 | 44.8 |
| 10734/F11 | 13.3 | −15.6 | 16.1 | 47.3 |
| 10734/G02 | 1.5 | 3.4 | 14.8 | 63.6 |
| 10734/G03 | 18.7 | 82.8 | −3.8 | 93.4 |
| 10734/G04 | −1.1 | 62.9 | 16.1 | 72.1 |
| 10734/G05 | 7.4 | −0.3 | 2.9 | 57.7 |
| 10734/G06 | 16.5 | 12.5 | −18.8 | 43.1 |
| 10734/G07 | 21.9 | 51.1 | −25.0 | 96.6 |
| 10734/G08 | 11.6 | 33.7 | 0.2 | 82.2 |
| 10734/G09 | 8.5 | 21.4 | −7.7 | 84.7 |
| 10734/G10 | 10.8 | 3.8 | 9.9 | 19.3 |
| 10734/G11 | 8.7 | 4.1 | −25.4 | 20.2 |

The invention claimed is:

1. A compound of the formula

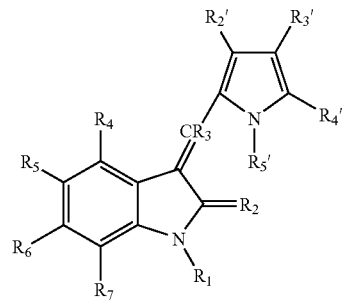

$R_1$ is hydrogen;

$R_2$ is oxygen;

$R_3$ is hydrogen or methyl;

at least one of $R_4$, $R_5$, $R_6$, and $R_7$ is NRR' and the remaining of $R_4$, $R_5$, $R_6$, and $R_7$ are each independently selected from the group consisting of hydrogen, alkyl (preferably lower alkyl, more preferably methyl), and halogen;

$R_2'$, $R_3'$, $R_4'$, and $R_5'$, are each independently selected from the group consisting of hydrogen, alkyl, halogen, and (alkyl)$_n$CO$_2$R;

R is hydrogen, alkyl or aryl; and

R' is hydrogen, alkyl or aryl.

2. The compound of claim 1, wherein the compound is selected from the group consisting of

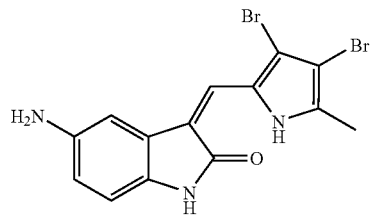

-continued

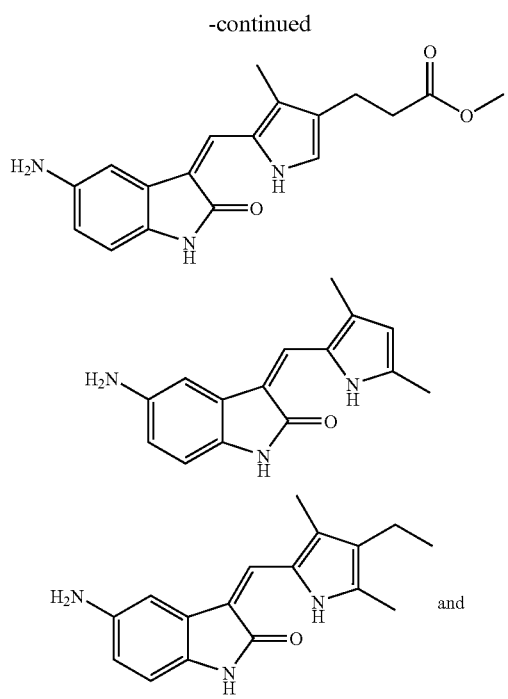

-continued

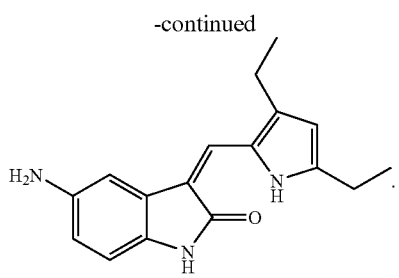

3. A method of making an indolinone compound of claim 1 comprising the steps of reacting an appropriate aldehyde and oxindole and separating the indolinone from the aldehyde and oxindole reactants.

4. A pharmaceutical composition comprising (i) a pharmaceutically acceptable carrier or excipient and (ii) a compound according to claim 1.

5. A method of making an indolinone compound of claim 2 comprising the steps of reacting an appropriate aldehyde and oxindole and separating the indolinone from the aldehyde and oxindole reactants.

6. A pharmaceutical composition comprising (i) a pharmaceutically acceptable carrier or excipient and (ii) a compound according to claim 2.

* * * * *